US011844713B2

(12) United States Patent
Castelli et al.

(10) Patent No.: US 11,844,713 B2
(45) Date of Patent: Dec. 19, 2023

(54) IRIS-STYLE CRIMPERS FOR MEDICAL DEVICES

(71) Applicant: Medtronic, Inc., Minneapolis, MN (US)

(72) Inventors: Brian Castelli, Santa Rosa, CA (US); Nathanael Glucklich, Santa Rosa, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 17/394,025

(22) Filed: Aug. 4, 2021

(65) Prior Publication Data

US 2022/0039979 A1 Feb. 10, 2022

Related U.S. Application Data

(60) Provisional application No. 63/228,208, filed on Aug. 2, 2021, provisional application No. 63/080,978, filed on Sep. 21, 2020, provisional application No. 63/061,874, filed on Aug. 6, 2020.

(51) Int. Cl.
A61F 2/95 (2013.01)

(52) U.S. Cl.
CPC .................. *A61F 2/9524* (2020.05)

(58) Field of Classification Search
CPC ......... A61F 2/9524; A61F 2/95; A61F 2/9522
See application file for complete search history.

(56) References Cited

U.S. PATENT DOCUMENTS

| 5,261,263 | A | * | 11/1993 | Whitesell ........... H01R 43/0424 |
| | | | | 30/90.1 |
| 5,893,867 | A | | 4/1999 | Bagaoisan et al. |
| 6,309,383 | B1 | | 10/2001 | Campbell et al. |
| 6,889,579 | B1 | * | 5/2005 | Brown .................... B25B 27/10 |
| | | | | 81/58 |

(Continued)

FOREIGN PATENT DOCUMENTS

| WO | 01/21076 A1 | 3/2001 |
| WO | 2015179181 A1 | 11/2015 |

(Continued)

OTHER PUBLICATIONS

International Search Report and Written Opinion dated Jan. 27, 2022 in International Application No. PCT/US2021/044721.

*Primary Examiner* — Jacob J Cigna
(74) *Attorney, Agent, or Firm* — MEDLER FERRO WOODHOUSE & MILLS PLLC

(57) ABSTRACT

A crimper for altering an implantable medical device from an uncompressed state to a compressed state. The crimper includes a plurality of crimper elements that define a crimper channel, each of the crimper elements including a non-planar surface that forms a portion of the crimper channel. Each non-planar surface is configured to apply non-uniform radial compression along a length of the implantable medical device during operation of the crimper when altering the implantable medical device from the uncompressed state to the compressed state. The crimper also includes handle configured to operate the crimper. Actuation of the handle decreases a volume of the crimper chamber to transition the implantable medical device from the uncompressed state to the compressed state.

20 Claims, 104 Drawing Sheets

(56) References Cited

U.S. PATENT DOCUMENTS

| | | | |
|---|---|---|---|
| 7,225,518 B2 | 6/2007 | Eidenschink et al. | |
| 7,530,253 B2 * | 5/2009 | Spenser | A61F 2/2412 |
| | | | 72/402 |
| 7,886,569 B2 | 2/2011 | Weber et al. | |
| 8,006,535 B2 * | 8/2011 | Righini | A61F 2/2415 |
| | | | 72/402 |
| 8,099,851 B2 | 1/2012 | Roach et al. | |
| 8,104,321 B2 | 1/2012 | Searrano et al. | |
| 8,151,445 B1 | 4/2012 | Warriner et al. | |
| 8,533,925 B2 | 9/2013 | Austin | |
| 8,539,663 B2 | 9/2013 | Wang et al. | |
| 8,833,209 B2 * | 9/2014 | Brown | B23D 21/08 |
| | | | 81/90.1 |
| 9,757,232 B2 | 9/2017 | Peterson et al. | |
| 10,716,691 B2 * | 7/2020 | Saar | A61F 2/9524 |
| 11,052,521 B2 * | 7/2021 | Van Breda | B21D 39/048 |
| 2002/0138966 A1 | 10/2002 | Mostenbocker | |
| 2005/0183259 A1 | 8/2005 | Eidenschink et al. | |
| 2013/0218139 A1 | 8/2013 | Fargahi | |
| 2016/0270914 A1 | 9/2016 | Krans et al. | |
| 2018/0344490 A1 | 12/2018 | Fox et al. | |
| 2021/0030533 A1 * | 2/2021 | Tamir | A61F 2/2433 |

FOREIGN PATENT DOCUMENTS

| | | | | |
|---|---|---|---|---|
| WO | 2017031412 A1 | 2/2017 | | |
| WO | 20170139421 A1 | 8/2017 | | |
| WO | 2019212812 A1 | 11/2019 | | |
| WO | WO-2019212812 A1 * | 11/2019 | | A61F 2/243 |
| WO | WO-2021194976 A1 * | 9/2021 | | |

* cited by examiner

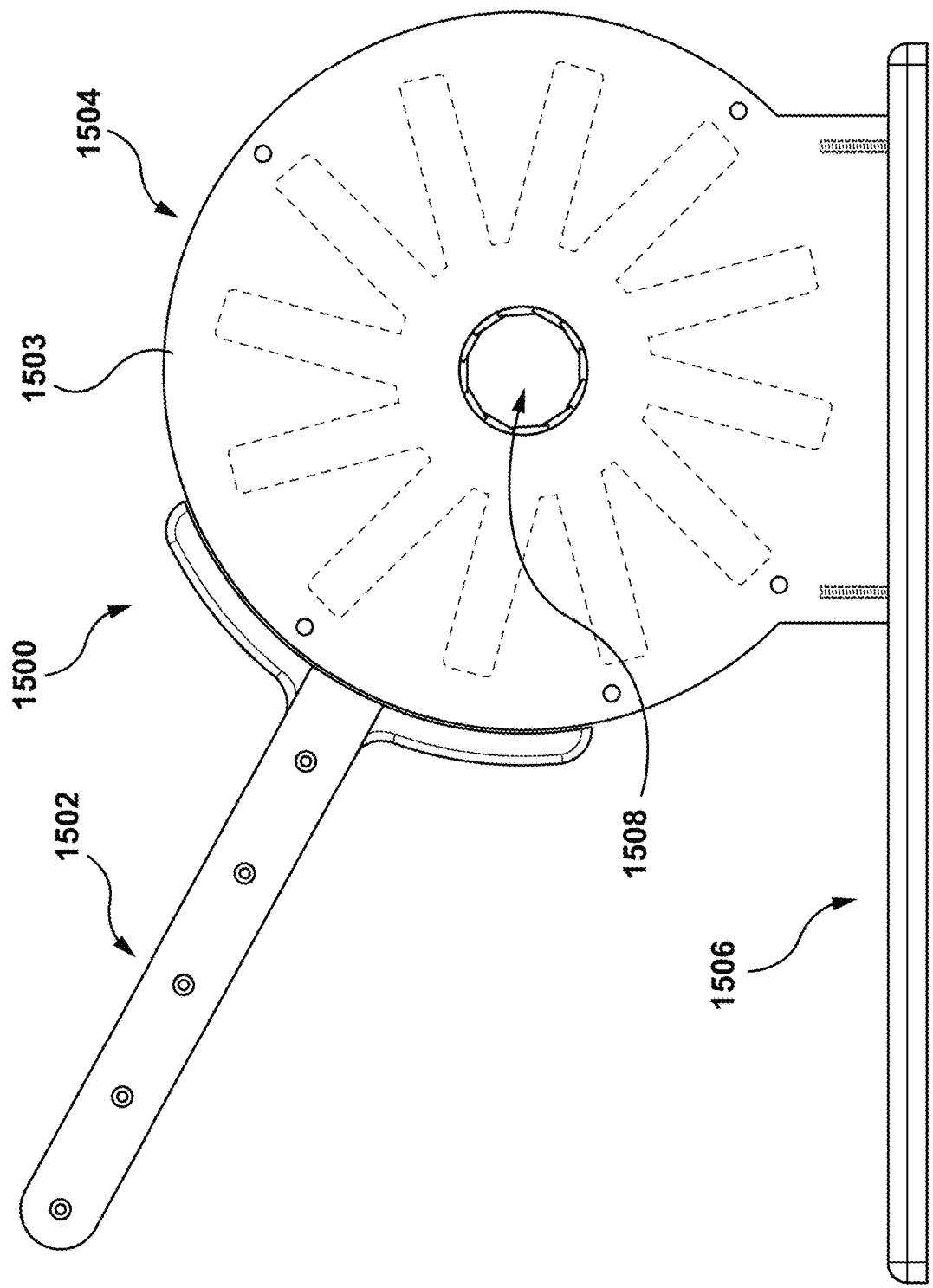

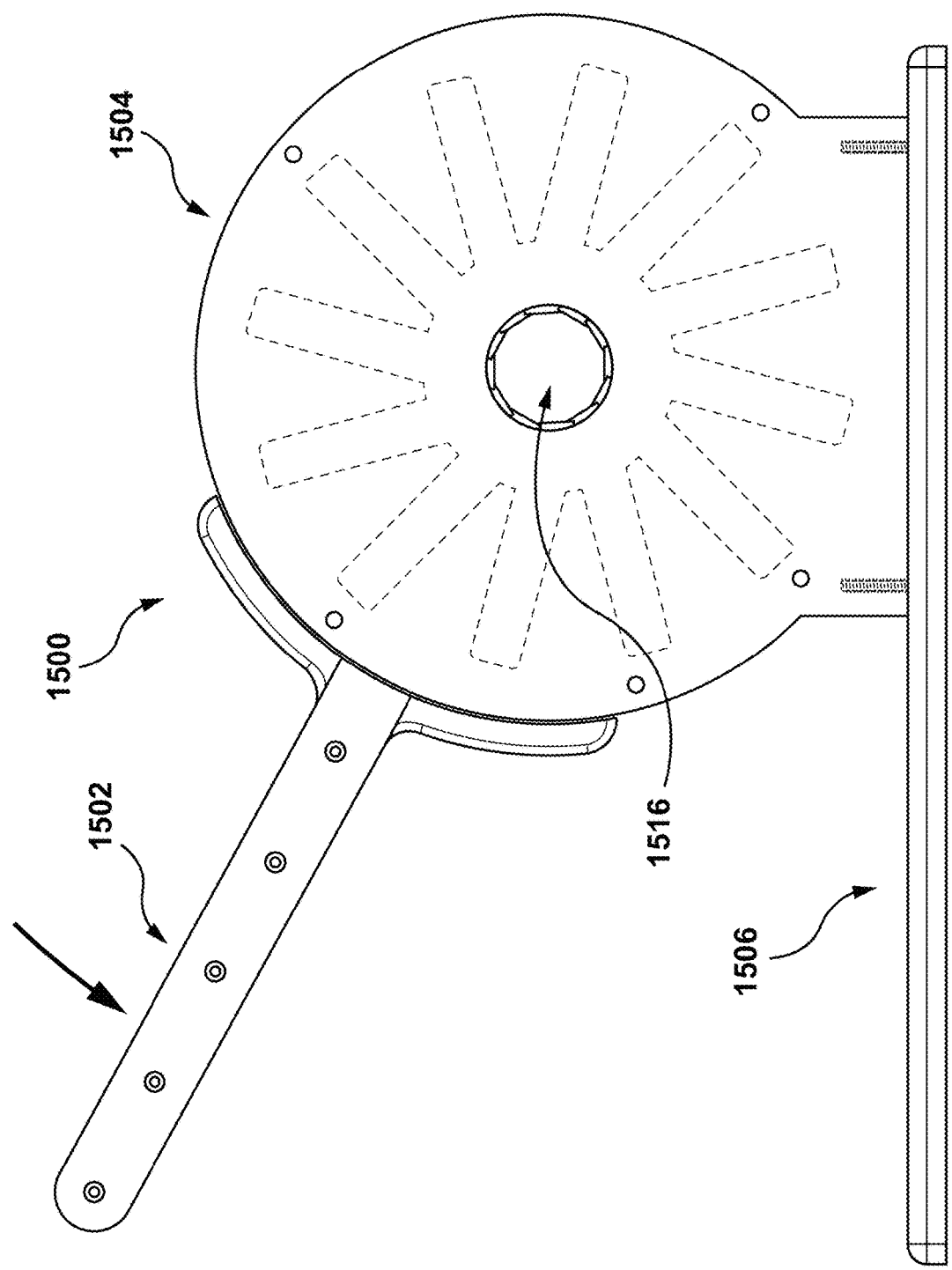

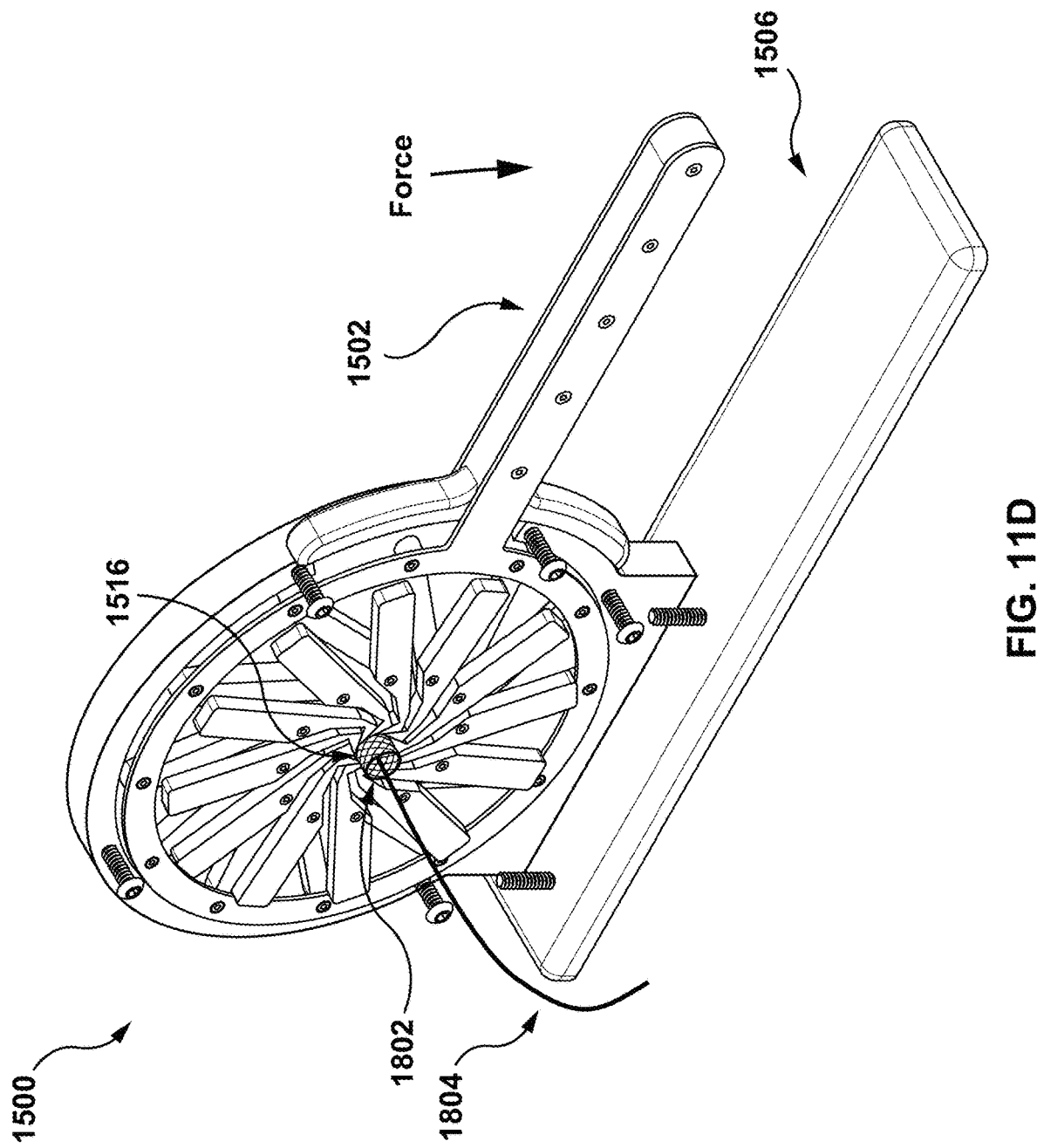

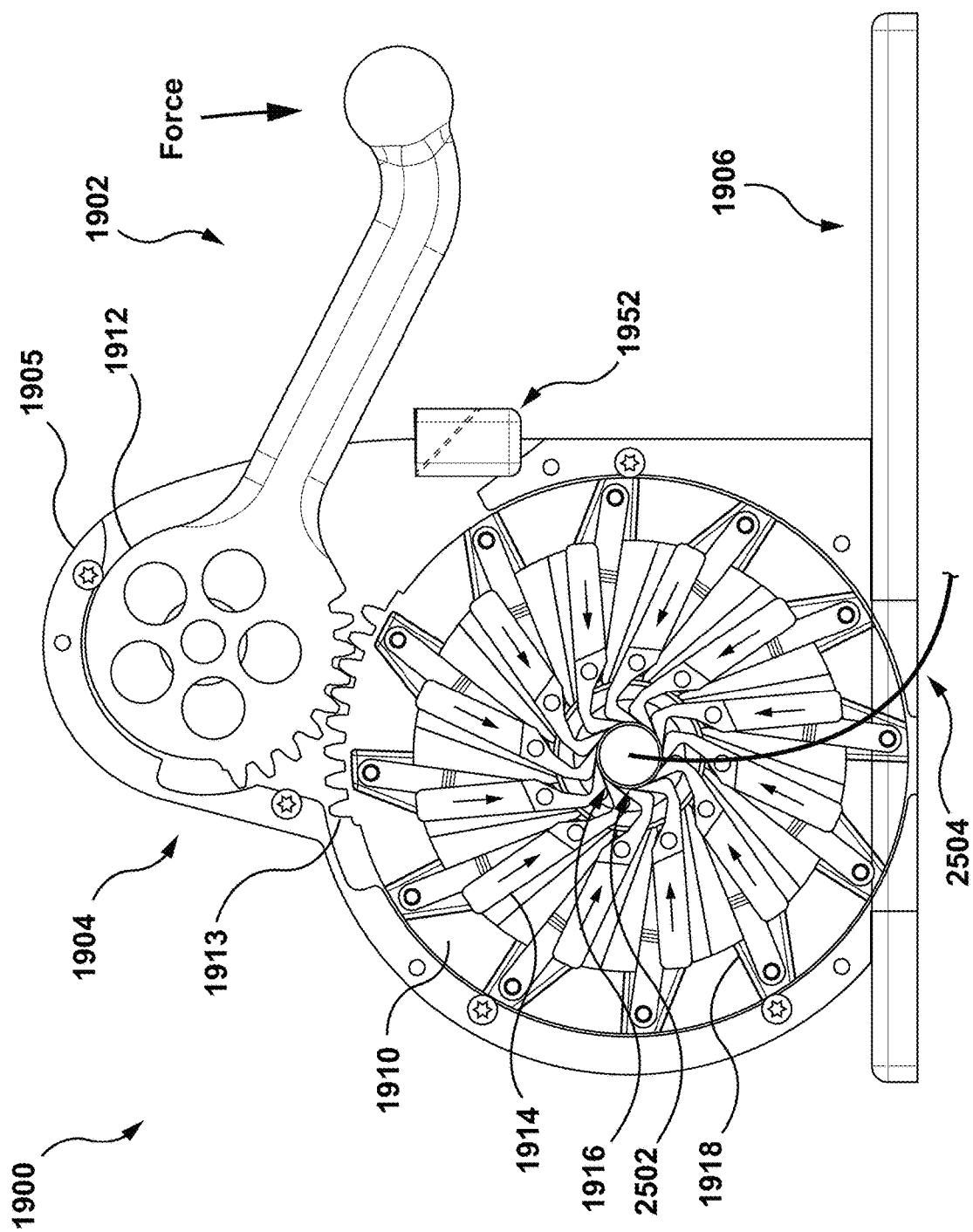

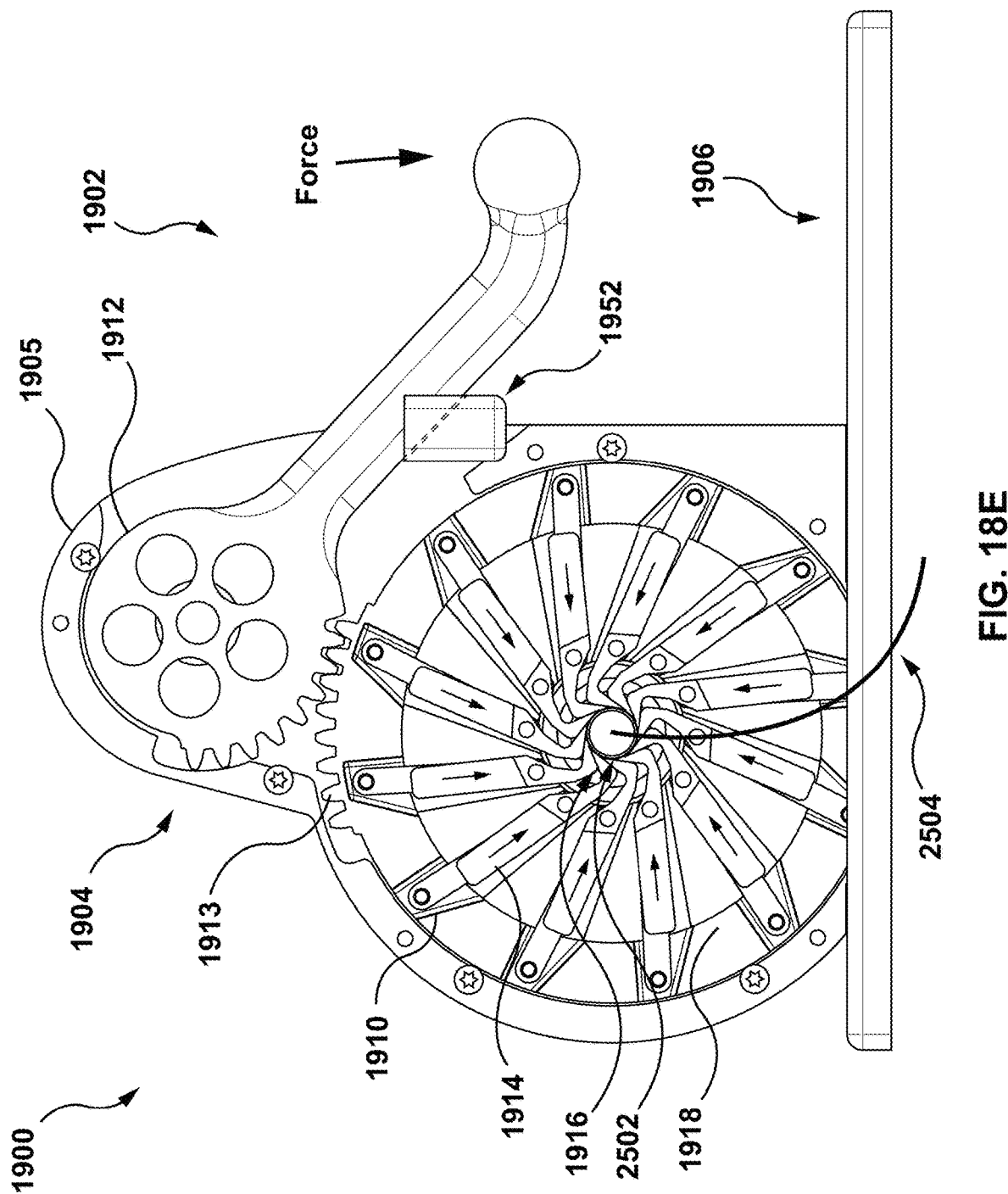

IRIS-STYLE CRIMPERS FOR MEDICAL DEVICES

CROSS-REFERENCE TO RELATED APPLICATIONS

This application claims the benefit of U.S. Provisional Patent Application Ser. No. 63/228,208, filed Aug. 2, 2021; U.S. Provisional Patent Application Ser. No. 63/080,978, filed Sep. 21, 2020; and U.S. Provisional Patent Application Ser. No. 63/061,874, filed Aug. 6, 2020, each of which is hereby incorporated by reference in its entirety for all purposes.

FIELD

The present application is generally related to devices for crimping stents, prosthetic heart valves and other implantable vascular medical devices.

BACKGROUND

Currently, expandable implantable medical devices that include a stent structure and organic tissue, e.g., bovine and porcine, such as prosthetic valves and other cardiac intervention devices, require onsite crimping onto a delivery device at the implantation site, e.g., a catheterization laboratory ("cath lab"). This is due to the need to store the implantable devices in conditions specific to preserve the organic tissue. Typically, iris-style crimpers are utilized in the crimping processes. Current iris-style crimpers experience limitations due to side loading that leads to the difficulty in accurately placing medical devices relative to the delivery device inside of side loading crimpers. With tissue containing implantable devices that need to be crimped by medical personnel immediately before implantation, this difficulty can lead to time delays and damage to the devices by operators not experienced in the processes for crimping the medical device. Given the cost of such devices, the possibility of destroying or damaging such devices can be significant.

SUMMARY

The techniques of this disclosure generally relate to crimpers for loading an implantable medical device onto a delivery device and converting the implantable medical device from an expanded state to a compressed state.

According to a first embodiment hereof, the present disclosure provides a clamshell crimper for altering an expandable medical device from an uncompressed state to a compressed state. The crimper includes a top shell comprising a first plurality of crimper elements, the first plurality of crimper elements defining a top channel and a base shell comprising a second plurality of crimper elements, the second plurality of crimper elements defining a bottom channel. The top shell and the base shell are coupled at a pivot connection. The top shell is configured to rotate about the pivot connection relative to the base shell from an open state to a closed state. When in the open state, the second channel is exposed for loading the expandable medical device, and when in the closed state, the top channel and the bottom channel define a crimper chamber. The crimper also includes a handle configured to operate the clamshell crimper, one or more cams coupled to the handle, and one or more rods coupled to the one or more cams, the first plurality of crimper elements, and the second plurality of crimper elements. When in the closed state, movement of the handle rotates the one or more cams thereby displacing the first plurality of crimper elements and the second plurality of crimper elements via the rods. The displacement of the first plurality of crimper elements and the second plurality of crimper elements decreases a volume of the crimper chamber to transition the expandable medical device from the uncompressed state to the compressed state.

In an aspect of the first embodiment, and in combination with any other aspects herein, the disclosure provides that the top shell or the base shell comprises a first housing and a second housing. Each of the first plurality of crimper elements is movably coupled within the first housing and the second housing.

In an aspect of the first embodiment, and in combination with any other aspects herein, the disclosure provides that one of the first housing or the second housing includes a side plate comprising an interior surface and an exterior surface. One or more crimper channels are formed within the interior surface of the side plate, and the one or more crimper channels are configured to allow the displacement of the first plurality of crimper elements or the second plurality of crimper elements.

In an aspect of the first embodiment, and in combination with any other aspects herein, the disclosure provides that a crimper element from the first plurality of crimper elements or the second plurality of crimper elements includes a crimper lobe, wherein a portion of the crimper lobe forms a portion of the crimper chamber, and a first leg and a second leg coupled to the crimper lobe. A rod from the one or more rods is coupled to the crimper element between the first leg and second leg.

In an aspect of the first embodiment, and in combination with any other aspects herein, the disclosure provides that the crimper lobe includes a crimper space defined by one or more ramps, and at least one of the one or more ramps contacts an adjacent crimper lobe from an adjacent crimper element from the first plurality of crimper elements or the second plurality of crimper elements.

In an aspect of the first embodiment, and in combination with any other aspects herein, the disclosure provides that the handle includes a handle bar and a connection member coupled to the handle bar and configured to couple at least one of the one or more cams.

In an aspect of the first embodiment, and in combination with any other aspects herein, the disclosure provides that the base shell includes one or more base surfaces for supporting the clamshell crimper.

In an aspect of the first embodiment, and in combination with any other aspects herein, the disclosure provides that the top shell further comprises a first locking mechanism. The first locking mechanism prevents movement of the handle to enable movement of the top shell from the closed state to the open state.

In an aspect of the first embodiment, and in combination with any other aspects herein, the disclosure provides that at least one of the top shell or the base shell further comprises a second locking mechanism that locks the top shell and the base shell into the closed state.

In an aspect of the first embodiment, and in combination with any other aspects herein, the disclosure provides that the crimper further includes one or more stops that limit the movement of the handle.

According to a second embodiment hereof, the present disclosure provides a crimper for altering an expandable medical device from an uncompressed state to a compressed state. The crimper includes a crimper housing comprising a plurality of crimper elements which define a crimper channel, a handle configured to operate the crimper, one or more cams coupled to the handle, and one or more rods coupled to the one or more cams and the plurality of crimper elements. Movement of the handle rotates the one or more cams thereby displacing the first plurality of crimper elements and the second plurality of crimper elements via the rods. The displacement of the plurality of crimper elements decreases a volume of the crimper chamber to transition the expandable medical device from the uncompressed state to the compressed state.

In an aspect of the second embodiment, and in combination with any other aspects herein, the disclosure provides that the crimper housing comprises a first side and a second side, and each of the plurality of crimper elements is movably coupled within the first side and the second side.

In an aspect of the second embodiment, and in combination with any other aspects herein, the disclosure provides that one of the first side or the second side includes one or more crimper channels formed within an interior surface of the first side or the second side. The one or more crimper channels are configured to allow the displacement of the plurality of crimper elements.

In an aspect of the second embodiment, and in combination with any other aspects herein, the disclosure provides that the crimper element from the first plurality of crimper elements or the second plurality of crimper elements includes a crimper lobe, a portion of the crimper lobe forming a portion of the crimper chamber, and a first leg and a second leg coupled to the crimper lobe. A rod from the one or more rods is coupled to the crimper element between the first leg and second leg.

In an aspect of the second embodiment, and in combination with any other aspects herein, the disclosure provides that the crimper lobe includes a crimper space defined by one or more ramps. At least one of the one or more ramps contacts an adjacent crimper lobe from an adjacent crimper element from the first plurality of crimper elements or the second plurality of crimper elements.

In an aspect of the second embodiment, and in combination with any other aspects herein, the disclosure provides that the handle includes a handle bar and a connection member coupled to the handle bar and configured to couple at least one of the one or more cams.

In an aspect of the second embodiment, and in combination with any other aspects herein, the disclosure provides that the handle includes a handle bar and a handle cam configured to engage with the one or more cams and to translate the movement of the handle bar to the one or more cams.

In an aspect of the second embodiment, and in combination with any other aspects herein, the disclosure provides that the one or more cams include a first cam coupled to a first portion of the handle and a second cam coupled to a first portion of the handle. The one or more rods are coupled between the first cam and the second cam at one end.

In an aspect of the second embodiment, and in combination with any other aspects herein, the disclosure provides that each of the one or more rods includes a bar and a first leg and a second leg coupled to the bar. The one or more cams is coupled to each of the one or more rods between the first leg and the second leg.

In an aspect of the second embodiment, and in combination with any other aspects herein, the disclosure provides that the crimper further includes a base coupled to the crimper housing for supporting the crimper.

In an aspect of the second embodiment, and in combination with any other aspects herein, the disclosure provides that the crimper further includes one or more stops that limit the movement of the handle.

According to a third embodiment hereof, the present disclosure provides a method for altering an expandable medical device from an uncompressed state to a compressed state. A clamshell crimper is placed in an open state, the clamshell crimper comprising a top iris shell and a base iris shell connected by a pivot connection. When in the open state, a base iris channel of the base iris shell is exposed for loading the expandable medical device. The expandable medical device is loaded into the iris channel of the base iris shell. The crimper is transitioned from the open state to a closed state. When in the closed state, a top iris channel of the top iris shell and the base iris channel of the base iris shell define a crimper chamber. A handle of the clamshell crimper is actuated to decrease a volume of the crimper chamber to transition the expandable medical device from the uncompressed state to the compressed state.

According to a fourth embodiment hereof, the present disclosure provides a clamshell crimper for altering an implantable medical device from an uncompressed state to a compressed state. The crimper includes a top shell including a top cam, a top crimper element housing, and a first plurality of crimper elements, the first plurality of crimper elements defining a top channel. The crimper also includes a base shell including a base cam, a base crimper element housing, and a second plurality of crimper elements, the second plurality of crimper elements defining a bottom channel. The top shell and the base shell are coupled at a pivot connection. The top shell is configured to rotate about the pivot connection relative to the base shell from an open state to a closed state. When in the open state, the second channel is exposed for loading the expandable medical device. When in the closed state, the top channel and the bottom channel define a crimper chamber. The crimper includes a handle configured to operate the clamshell crimper and coupled to at least the top cam of the top shell. When in the closed state, movement of the handle rotates the top cam and the base cam thereby displacing the first plurality of crimper elements and the second plurality of crimper elements, and the displacement of the first plurality of crimper elements and the second plurality of crimper elements decreases a volume of the crimper chamber to transition the implantable medical device from the uncompressed state to the compressed state.

In an aspect of the fourth embodiment, and in combination with any other aspects herein, the disclosure provides that the first plurality of crimper elements is movably coupled within the top crimper element housing and the base crimper element housing.

In an aspect of the fourth embodiment, and in combination with any other aspects herein, the disclosure provides that one of the top crimper element housing or the base crimper element housing includes a side plate comprising an interior surface and an exterior surface. one or more crimper channels are formed within the interior surface of the side plate, and the one or more crimper channels are configured to allow the displacement of the first plurality of crimper elements or the second plurality of crimper elements.

In an aspect of the fourth embodiment, and in combination with any other aspects herein, the disclosure provides that a crimper element from the first plurality of crimper element or the second plurality of crimper elements includes a crimper lobe, wherein a surface of the crimper lobe forms a portion of the crimper chamber, a crimper body coupled to the crimper lobe, and at least one pin coupled to the crimper body. The at least one pin is configured to moveably couple the crimper element one of the top cam or the base cam.

In an aspect of the fourth embodiment, and in combination with any other aspects herein, the disclosure provides that the at least one pin comprises two pin positioned on opposing sides of the crimper body.

In an aspect of the fourth embodiment, and in combination with any other aspects herein, the disclosure provides that the crimper lobe comprises a crimper space defined by one or more ramps. At least one of the one or more ramps contacts an adjacent crimper lobe from an adjacent crimper element from the first plurality of crimper elements or the second plurality of crimper elements.

In an aspect of the fourth embodiment, and in combination with any other aspects herein, the disclosure provides that at least one of the top cam or the base cam includes at least one pin channel formed within a surface of the top cam or the base cam. The pin channel is configured to receive the at least one pin of the crimper element.

In an aspect of the fourth embodiment, and in combination with any other aspects herein, the disclosure provides that the at least one pin channel comprises a plurality of pin channel formed in a spiral pattern.

In an aspect of the fourth embodiment, and in combination with any other aspects herein, the disclosure provides that the handle includes a handle bar and a handle base coupled to the handle bar and configured to couple at least one of the top cam or base cam.

In an aspect of the fourth embodiment, and in combination with any other aspects herein, the disclosure provides that the base shell comprises comprise one or more base surfaces for supporting the clamshell crimper.

In an aspect of the fourth embodiment, and in combination with any other aspects herein, the disclosure provides that the top shell further comprises a first locking mechanism. The first locking mechanism prevents movement of the handle to enable movement of the top shell from the closed state to the open state.

In an aspect of the fourth embodiment, and in combination with any other aspects herein, the disclosure provides that at least one of the top shell or the base shell further comprises a second locking mechanism. The second locking mechanism locks the top shell and the base shell into the closed state.

In an aspect of the fourth embodiment, and in combination with any other aspects herein, the disclosure provides that the crimper further includes one or more stops that limit the movement of the handle.

According to a fifth embodiment hereof, the present disclosure provides a clamshell crimper for altering an implantable medical device from an uncompressed state to a compressed state. The crimper includes a top iris shell comprising a first plurality of crimper elements that define a top iris channel. The crimper also includes a base iris shell coupled to the top iris shell at a pivot connection, the base iris shell including a second plurality of crimper elements that define a base iris channel. The top iris shell is configured to rotate about the pivot connection relative to the base shell from an open state to a closed state. When in the open state, the base iris channel is exposed for loading the expandable medical device. When in the closed state, the top iris channel and the base iris channel define a crimper chamber. The crimper also includes a handle configured to operate the clamshell crimper. Actuation of the handle decreases a volume of the crimper chamber to transition the implantable medical device from the uncompressed state to the compressed state.

In an aspect of the fifth embodiment, and in combination with any other aspects herein, the disclosure provides that the first plurality of crimper elements is movably coupled within the top iris shell and the second plurality of crimper elements are movably coupled within the base iris shell.

In an aspect of the fifth embodiment, and in combination with any other aspects herein, the disclosure provides that the crimper element from the first plurality of crimper element or the second plurality of crimper elements includes a crimper lobe, wherein a surface of the crimper lobe forms a portion of the crimper chamber, a crimper body coupled to the crimper lobe, and at least one pin coupled to the crimper body. The at least one pin is configured to moveably couple the crimper element one of at least one cam of the top iris shell or the base iris shell.

In an aspect of the fifth embodiment, and in combination with any other aspects herein, the disclosure provides that the at least one pin comprises two pin positioned on opposing sides of the crimper body.

In an aspect of the fifth embodiment, and in combination with any other aspects herein, the disclosure provides that the crimper lobe comprises a crimper space defined by one or more ramps. At least one of the one or more ramps contacts an adjacent crimper lobe from an adjacent crimper element from the first plurality of crimper elements or the second plurality of crimper elements.

In an aspect of the fifth embodiment, and in combination with any other aspects herein, the disclosure provides that the at least one cam includes at least one pin channel formed within a surface of the at least one cam. The at least one pin channel is configured to receive the at least one pin of the crimper element.

In an aspect of the fifth embodiment, and in combination with any other aspects herein, the disclosure provides that the at least one pin channel comprises a plurality of pin channel formed in a spiral pattern.

In an aspect of the fifth embodiment, and in combination with any other aspects herein, the disclosure provides that the base iris shell comprises comprise one or more base surfaces for supporting the clamshell crimper.

In an aspect of the fifth embodiment, and in combination with any other aspects herein, the disclosure provides that the top iris shell further comprises a first locking mechanism that prevents movement of the handle to enable movement of the top iris shell from the closed state to the open state.

In an aspect of the fifth embodiment, and in combination with any other aspects herein, the disclosure provides that at least one of the top iris shell or the base iris shell further comprises a second locking mechanism that locks the top iris shell and the base iris shell into the closed state.

In an aspect of the fifth embodiment, and in combination with any other aspects herein, the disclosure provides that the crimper further includes one or more stops that limit the movement of the handle.

According to a sixth embodiment hereof, the present disclosure provides a method for altering an expandable medical device from an uncompressed state to a compressed state. The method includes placing a clamshell crimper in an open state, the clamshell crimper including a top iris shell and a base iris shell connected by a pivot connection. Wherein, when in the open state, a base iris channel of the base iris shell is exposed for loading the expandable medical device. The method also includes loading the expandable medical device into the iris channel of the base iris shell.

Further, the method includes transitioning the crimper from the open state to a closed state. When in the closed state, a top iris channel of the top iris shell and the base iris channel of the base iris shell define a crimper chamber. The method includes actuating a handle of the clamshell crimper, wherein actuation of the handle decreases a volume of the crimper chamber to transition the expandable medical device from the uncompressed state to the compressed state.

According to a seventh embodiment hereof, the present disclosure provides a crimper for altering an implantable medical device from an uncompressed state to a compressed state. The crimper includes a plurality of crimper elements that define a crimper channel, each of the crimper elements including a non-planar surface that forms a portion of the crimper channel. Each non-planar surface is configured to apply non-uniform radial compression along a length of the implantable medical device during operation of the crimper when altering the implantable medical device from the uncompressed state to the compressed state. The crimper also includes handle configured to operate the crimper. Actuation of the handle decreases a volume of the crimper chamber to transition the implantable medical device from the uncompressed state to the compressed state.

In an aspect of the seventh embodiment, and in combination with any other aspects herein, the disclosure provides that each crimper element includes a crimper lobe, wherein the crimper lobe includes the non-planar surface, a crimper body coupled to the crimper lobe, and at least one pin coupled to the crimper body.

In an aspect of the seventh embodiment, and in combination with any other aspects herein, the disclosure provides that the crimper lobe comprises a crimper space defined by one or more ramps. At least one of the one or more ramps contacts an adjacent crimper lobe from an adjacent crimper element from the plurality of crimper elements.

In an aspect of the seventh embodiment, and in combination with any other aspects herein, the disclosure provides that the non-planar surface includes a first longitudinal portion and a second longitudinal portion, the second longitudinal portion being disposed closer to a centerline of the crimper chamber than the first longitudinal portion such that the second longitudinal portion is configured to apply a higher radial force onto the implantable medical device than the first longitudinal portion.

In an aspect of the seventh embodiment, and in combination with any other aspects herein, the disclosure provides that the first longitudinal portion extends between 35% and 45% of a total length of the crimper chamber and the second longitudinal portion 3675B extends between 55% and 65% of the total length of the crimper chamber.

In an aspect of the seventh embodiment, and in combination with any other aspects herein, the disclosure provides that the non-planar surface includes a first longitudinal portion, a second longitudinal portion, and a third longitudinal portion, the second longitudinal portion being disposed between the first and third longitudinal portions, the first and third longitudinal portions being disposed closer to a centerline of the crimper chamber than the second longitudinal portion such that the first and third longitudinal portions are configured to apply a higher radial force onto the implantable medical device than the second longitudinal portion.

In an aspect of the seventh embodiment, and in combination with any other aspects herein, the disclosure provides that each of the first and third longitudinal portions taper along its length to the second longitudinal portion.

In an aspect of the seventh embodiment, and in combination with any other aspects herein, the disclosure provides that each of the first and third longitudinal portions extend between 5% and 15% of a total length of the crimper chamber.

In an aspect of the seventh embodiment, and in combination with any other aspects herein, the disclosure provides that the first longitudinal portion extends between 55% and 65% of a total length of the crimper chamber, the second longitudinal portion extends between 25% and 35% of the total length of the crimper chamber and the third longitudinal portion extends between 5% and 15% of the total length of the crimper chamber.

In an aspect of the seventh embodiment, and in combination with any other aspects herein, the disclosure provides that the third longitudinal portion tapers along its length to the second longitudinal portion.

In an aspect of the seventh embodiment, and in combination with any other aspects herein, the disclosure provides that the non-planar surface includes a first longitudinal portion, a second longitudinal portion, a third longitudinal portion, and a fourth longitudinal portion, the second longitudinal portion being disposed between the first and third longitudinal portions and the third longitudinal portion being disposed between the second and fourth longitudinal portions, the first and fourth longitudinal portions being disposed closer to a centerline of the crimper chamber than each of the second and third longitudinal portions such that the first and fourth longitudinal portions are configured to apply a higher radial force onto the implantable medical device than each of the second and third longitudinal portions, and the second longitudinal portion being disposed closer to the centerline of the crimper chamber than the third longitudinal portion such that the second longitudinal portion is configured to apply a higher radial force onto the implantable medical device than the third longitudinal portion.

In an aspect of the seventh embodiment, and in combination with any other aspects herein, the disclosure provides that the first longitudinal portion tapers along its length to the second longitudinal portion and the fourth longitudinal portion tapers along its length to the third longitudinal portion.

In an aspect of the seventh embodiment, and in combination with any other aspects herein, the disclosure provides that the first longitudinal portion extends between 2% and 8% of a total length of the crimper chamber, the second longitudinal portion extends between 50% and 60% of the total length of the crimper chamber, the third longitudinal portion extends between 25% and 35% of the total length of the crimper chamber, and the fourth longitudinal portion extends between 5% and 15% of the total length of the crimper chamber.

According to an eighth embodiment hereof, the present disclosure provides a method for altering an expandable medical device from an uncompressed state to a compressed state. The method includes loading the expandable medical device into a crimper chamber of a crimper, actuating a handle of the crimper to operate the crimper. The crimper chamber is defined by a plurality of crimper elements, each of the crimper elements including a non-planar surface that forms a portion of the crimper channel. Actuation of the handle decreases a volume of the crimper chamber to transition the expandable medical device from the uncompressed state to the compressed state, and each non-planar surface applies non-uniform radial compression along a length of the implantable medical device during operation of the crimper.

In an aspect of the eighth embodiment, and in combination with any other aspects herein, the disclosure provides that a first radial force is applied onto a first section of the implantable medical device by a first longitudinal portion of the non-planar surface and a second radial force is applied onto a second section of the implantable medical device by a second longitudinal portion of the non-planar surface, the second radial force being greater than the first radial force.

In an aspect of the eighth embodiment, and in combination with any other aspects herein, the disclosure provides that the second section of the implantable medical device is denser than the first section of the implantable medical device.

In an aspect of the eighth embodiment, and in combination with any other aspects herein, the disclosure provides that the second section of the implantable medical device includes a valve.

In an aspect of the eighth embodiment, and in combination with any other aspects herein, the disclosure provides that the first section of the implantable medical device includes a plurality of openings formed in a stent of the implantable medical device, the plurality of openings being configured to allow for coronary access when implanted in situ.

In an aspect of the eighth embodiment, and in combination with any other aspects herein, the disclosure provides that the implantable medical device has a substantially uniform profile in the compressed state.

In an aspect of the eighth embodiment, and in combination with any other aspects herein, the disclosure provides that the second section of the implantable medical device is one of an inflow end of the implantable medical device and an outflow end of the implantable medical device.

In an aspect of the eighth embodiment, and in combination with any other aspects herein, the disclosure provides that the non-planar surface includes a first longitudinal portion and a second longitudinal portion, the second longitudinal portion being disposed closer to a centerline of the crimper chamber than the first longitudinal portion such that the second longitudinal portion is configured to apply a higher radial force onto the implantable medical device than the first longitudinal portion.

In an aspect of the eighth embodiment, and in combination with any other aspects herein, the disclosure provides that the first longitudinal portion extends between 35% and 45% of a total length of the crimper chamber and the second longitudinal portion extends between 55% and 65% of the total length of the crimper chamber.

In an aspect of the eighth embodiment, and in combination with any other aspects herein, the disclosure provides that the non-planar surface includes a first longitudinal portion, a second longitudinal portion, and a third longitudinal portion, the second longitudinal portion being disposed between the first and third longitudinal portions, the first and third longitudinal portions being disposed closer to a centerline of the crimper chamber than the second longitudinal portion such that the first and third longitudinal portions are configured to apply a higher radial force onto the implantable medical device than the second longitudinal portion.

In an aspect of the eighth embodiment, and in combination with any other aspects herein, the disclosure provides that each of the first and third longitudinal portions taper along its length to the second longitudinal portion.

In an aspect of the eighth embodiment, and in combination with any other aspects herein, the disclosure provides that each of the first and third longitudinal portions extend between 5% and 15% of a total length of the crimper chamber.

In an aspect of the eighth embodiment, and in combination with any other aspects herein, the disclosure provides that the first longitudinal portion extends between 55% and 65% of a total length of the crimper chamber, the second longitudinal portion extends between 25% and 35% of the total length of the crimper chamber and the third longitudinal portion extends between 5% and 15% of the total length of the crimper chamber.

In an aspect of the eighth embodiment, and in combination with any other aspects herein, the disclosure provides that the third longitudinal portion tapers along its length to the second longitudinal portion.

In an aspect of the eighth embodiment, and in combination with any other aspects herein, the disclosure provides that the non-planar surface includes a first longitudinal portion, a second longitudinal portion, a third longitudinal portion, and a fourth longitudinal portion, the second longitudinal portion being disposed between the first and third longitudinal portions and the third longitudinal portion being disposed between the second and fourth longitudinal portions, the first and fourth longitudinal portions being disposed closer to a centerline of the crimper chamber than each of the second and third longitudinal portions such that the first and fourth longitudinal portions are configured to apply a higher radial force onto the implantable medical device than each of the second and third longitudinal portions, and the second longitudinal portion being disposed closer to the centerline of the crimper chamber than the third longitudinal portion such that the second longitudinal portion is configured to apply a higher radial force onto the implantable medical device than the third longitudinal portion.

In an aspect of the eighth embodiment, and in combination with any other aspects herein, the disclosure provides that the first longitudinal portion tapers along its length to the second longitudinal portion and the fourth longitudinal portion tapers along its length to the third longitudinal portion.

In an aspect of the eighth embodiment, and in combination with any other aspects herein, the disclosure provides that the first longitudinal portion extends between 2% and 8% of a total length of the crimper chamber, the second longitudinal portion extends between 50% and 60% of the total length of the crimper chamber, the third longitudinal portion extends between 25% and 35% of the total length of the crimper chamber, and the fourth longitudinal portion extends between 5% and 15% of the total length of the crimper chamber.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the present disclosure will be apparent from the following description of embodiments hereof as illustrated in the accompanying drawings. The accompanying drawings, which are incorporated herein and form a part of the specification, further serve to explain the principles of the present disclosure and to enable a person skilled in the pertinent art to make and use the embodiments of the present disclosure. The drawings are not to scale.

FIGS. 8A-8F depict different views of another example of a crimper for use with a medical device, according to an embodiment hereof.

FIGS. 11A-11D depict an operation of the crimper of FIGS. 8A-8F, according to an embodiment hereof.

FIGS. 18A-18E depict an operation of the crimper of FIGS. 12A and 12B, according to an embodiment hereof.

DETAILED DESCRIPTION

Specific embodiments of the present disclosure are now described with reference to the figures. The following detailed description describes examples of embodiments and is not intended to limit the present technology or the application and uses of the present technology. Although the description of embodiments hereof is in the context of a crimper, the present technology may also be used in other devices. Furthermore, there is no intention to be bound by any expressed or implied theory presented in the preceding technical field, background, brief summary or the following detailed description.

Embodiments disclosed herein are directed to crimpers for loading an implantable medical device onto a delivery device and converting the implantable medical device from an expanded state to a compressed state. In some embodiments, a clamshell crimper includes a top iris shell and a base iris shell. The top iris shell can be rotated away from the base iris shell to expose a channel for loading and positioning the implantable medical device and the delivery device. When closed, the channel of the base iris shell and a corresponding channel in the top iris shell form a crimper chamber around the expandable medical device. The clamshell crimper can then be actuated to decrease the volume of the crimper chamber though the process of iris-style displacement of lobes. To decrease the volume of the crimper chamber, a crimper includes a plurality of crimper elements. The plurality of crimper elements form the crimper chamber around the expandable medical device. The crimper can be actuated to decrease the volume of the crimper chamber though the process of iris-style displacement of crimper elements. The displacement of the crimper elements is controlled by a handle that actuates a cam. The cam includes a plurality of spiral channel that are configured to receive connection pin of the crimper elements. The cam operates to translate the rotation motion of the cam to approximate linear motion of the crimper elements.

FIGS. 1A-1E illustrate an example of a clamshell crimper 800 in accordance with an embodiment hereof. One skilled in the art will realize that FIGS. 1A-1E illustrate one example of a crimper and that existing components illustrated in FIGS. 1A-1E may be removed and/or additional components may be added to the clamshell crimper 800.

Figure 1A:
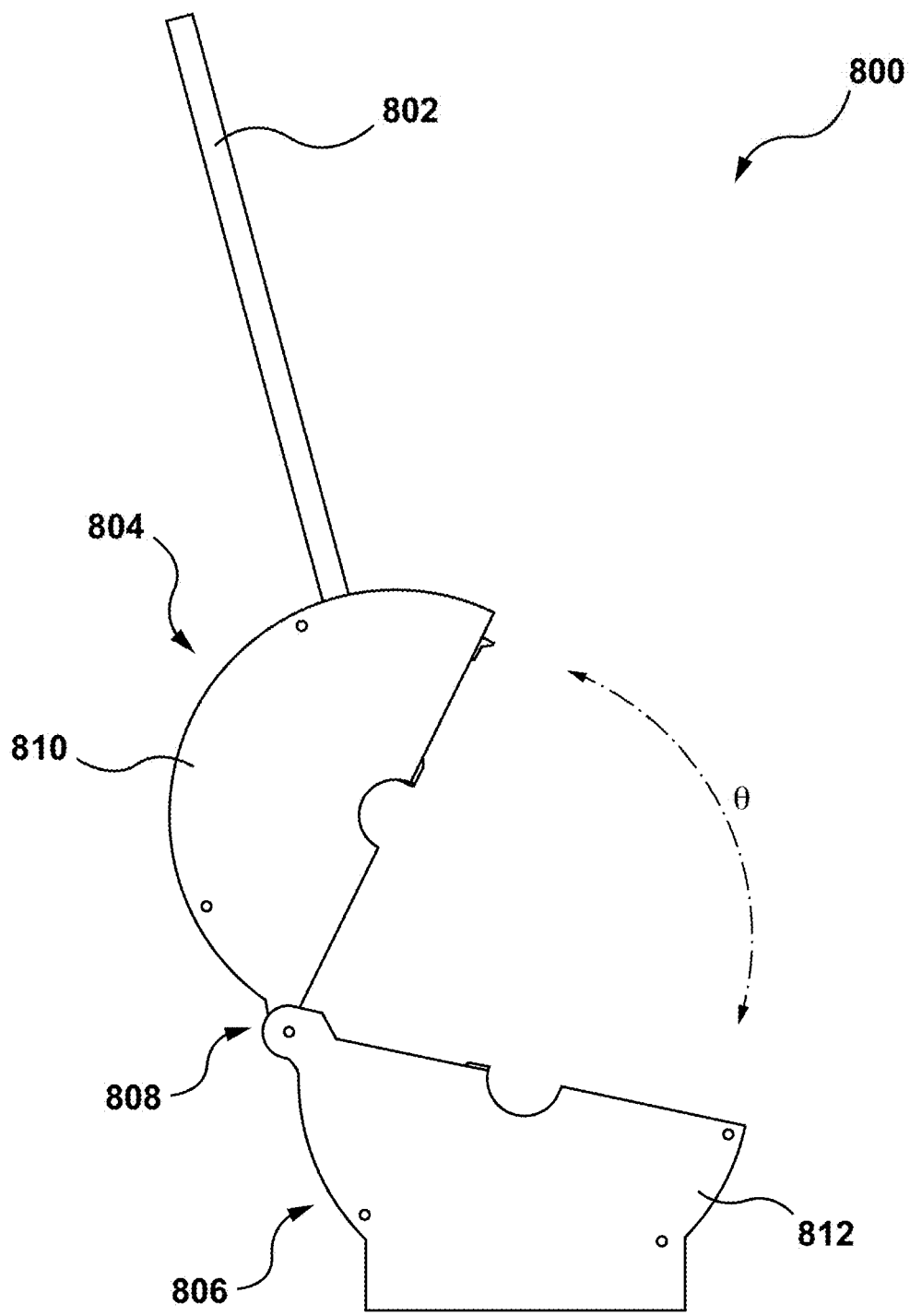
FIGS. 1A-1E depict different views of another example of a clamshell crimper for use with a medical device, according to an embodiment hereof.
Figure 1B:
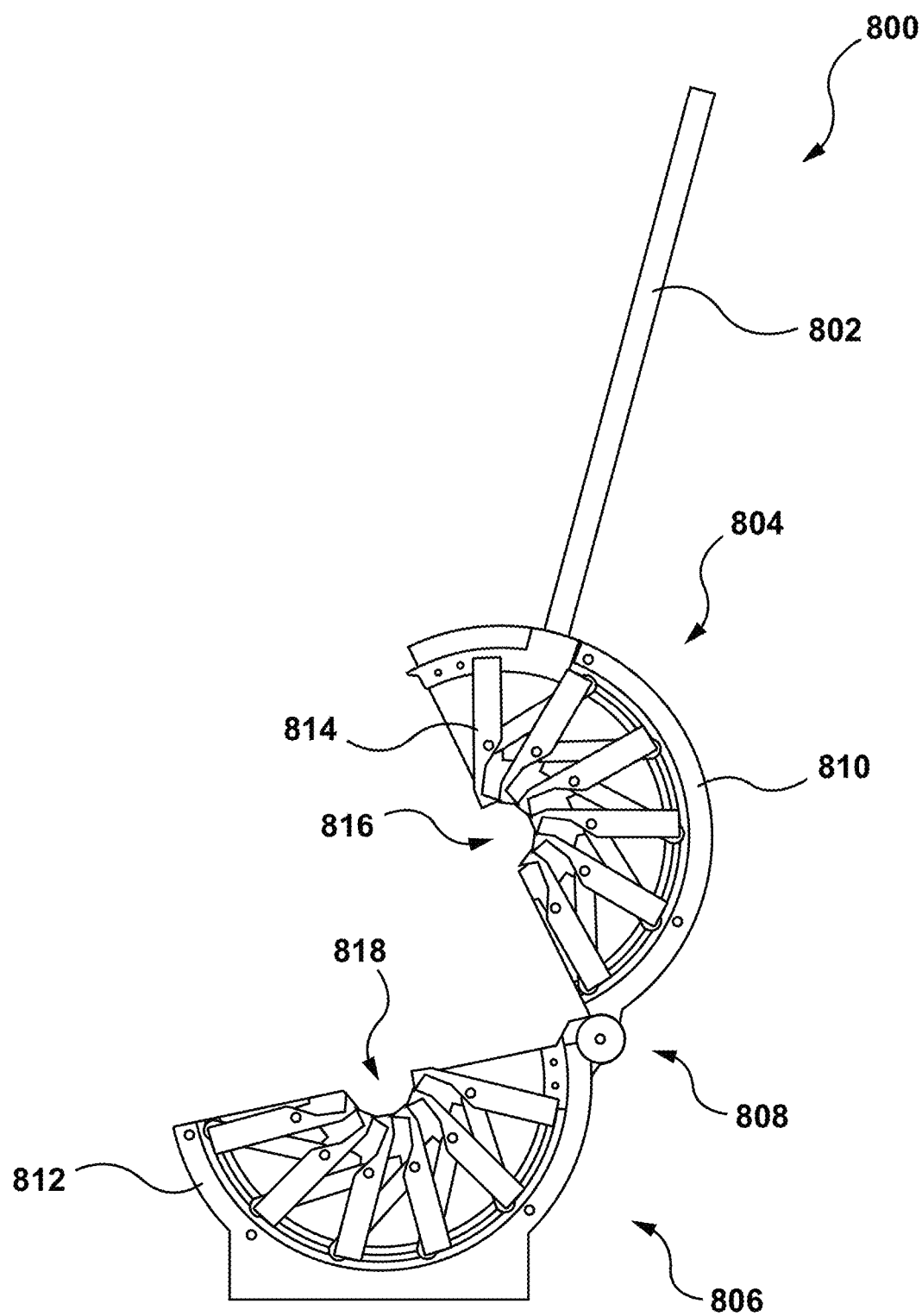
Figure 1C:
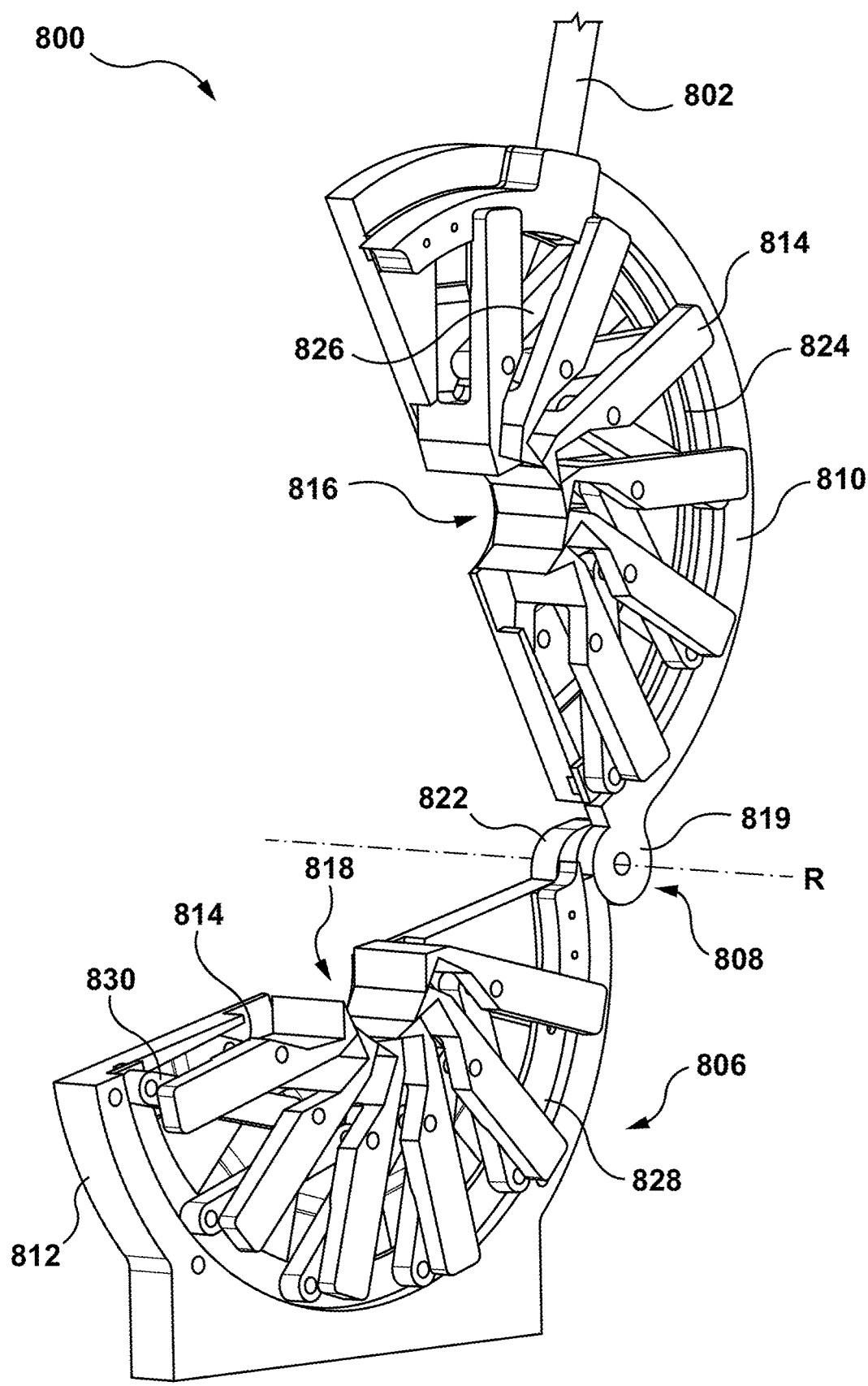
Figure 7:
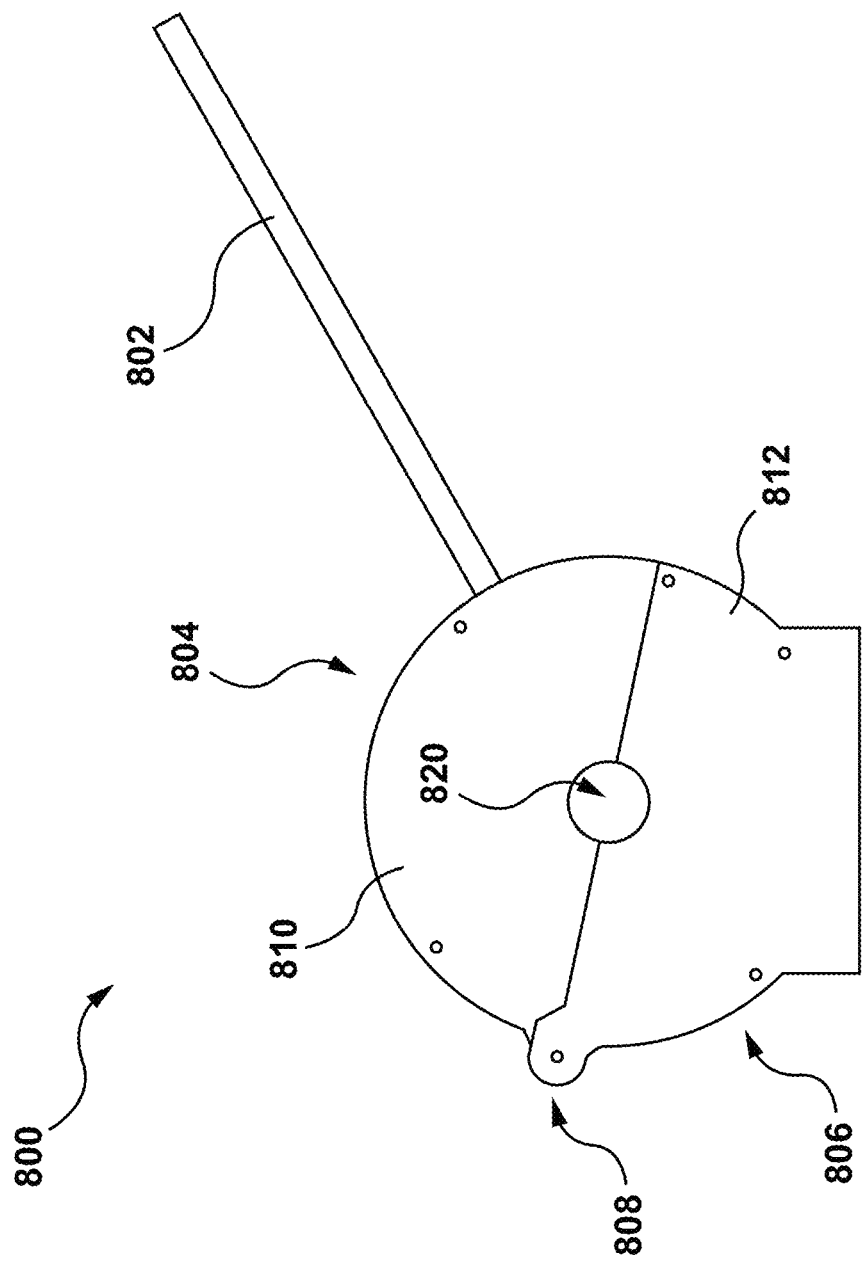
FIG. 7 depicts an operation of the crimper of FIGS. 1A-1E, according to an embodiment hereof.

FIG. 1A is a side view of a first side of the clamshell crimper 800. As illustrated in FIG. 1A, the clamshell crimper 800 includes a handle 802, a top shell 804 (or top iris shell), and a base shell 806 (or base iris shell). The top shell 804 includes a first housing 810, and the base shell 806 includes a first housing 812. The top shell 804 and the base shell 806 are coupled at a pivot connection 808. The pivot connection 808 allows an angle, θ, between the top shell 804 and the base shell 806 to be increased or decreased by rotating the top shell 804 away from the base shell about an axis of rotation, R, (illustrated in FIG. 1C) located at the pivot connection 808. The pivot connection 808 is configured to allow the top shell 804 and the base shell 806 to move relative to each other from an open state (as illustrated in FIGS. 1A-1C) to a closed state (as illustrated in FIG. 7). While not illustrated, the clamshell crimper 800 can be coupled to a base or other structure to provide support to the clamshell crimper 800.

As described herein, an open state for the clamshell crimper 800 defines any angle, θ, between the top shell 804 and the base shell 806 that allows a user to insert an implantable medical device and/or delivery device in the clamshell crimper 800 and that allows a user to view the insertion to properly align the implantable medical device and the delivery device. Likewise, as described herein, the closed state defines any angle, θ, between the top shell 804 and the base shell 806 in which the clamshell crimper 800 is operating to compress the implantable medical device and to crimp or load the implantable medical device onto a delivery device. For example, in an embodiment, the angle, θ, between the top shell 804 and the base shell 806, when in the open state, can range from approximately 45 degrees to approximately 180 degrees. Likewise, for example, in an embodiment, the angle, θ, between the top shell 804 and the base shell 806, when in closed state, can be approximately 0 degrees.

FIG. 1B illustrates a side of a second side of the clamshell crimper 800 that is opposite the first side. In the view of FIG. 1B, housings of the second side of the clamshell crimper 800 are removed to illustrate internal components of the clamshell crimper 800. As illustrated, the top shell 804 includes the first housing 810 and a second housing (removed in this illustration). The base shell 806 includes the first housing 812 and a second housing (removed in this illustration). The top shell 804 and the base shell 806 include a plurality of crimper elements 814. As further illustrated in FIG. 1C, which is an enlarged perspective view of the top shell 804 and the base shell 806, the crimper elements 814 of the top shell 804 form a top crimper channel 816. The crimper elements 814 of the base shell 806 for a bottom crimper channel 818. When the closed state, the top crimper channel 816 and the bottom crimper channel 818 form a crimper chamber 820, as illustrated in FIG. 7, which is a perspective view of the clamshell crimper 800 in the closed state.

In embodiments, the pivot connection 808 can be any type of mechanical joint or electro-mechanical joint that allows the top shell 804 and the base shell 806 to move relative to each other. For example, the pivot connection 808 can include one or more of a hinge, a tab, a rivet, a pivot pin, a pivot joint, an axle, a living hinge, etc. In an embodiment, the pivot connection 808 can include a movement assistance device to provide a force that assists in the movement of the top shell 804 and the base shell 806 relative to each other. For example, the pivot connection 808 can include a spring, a motor, etc.

Figure 2A:
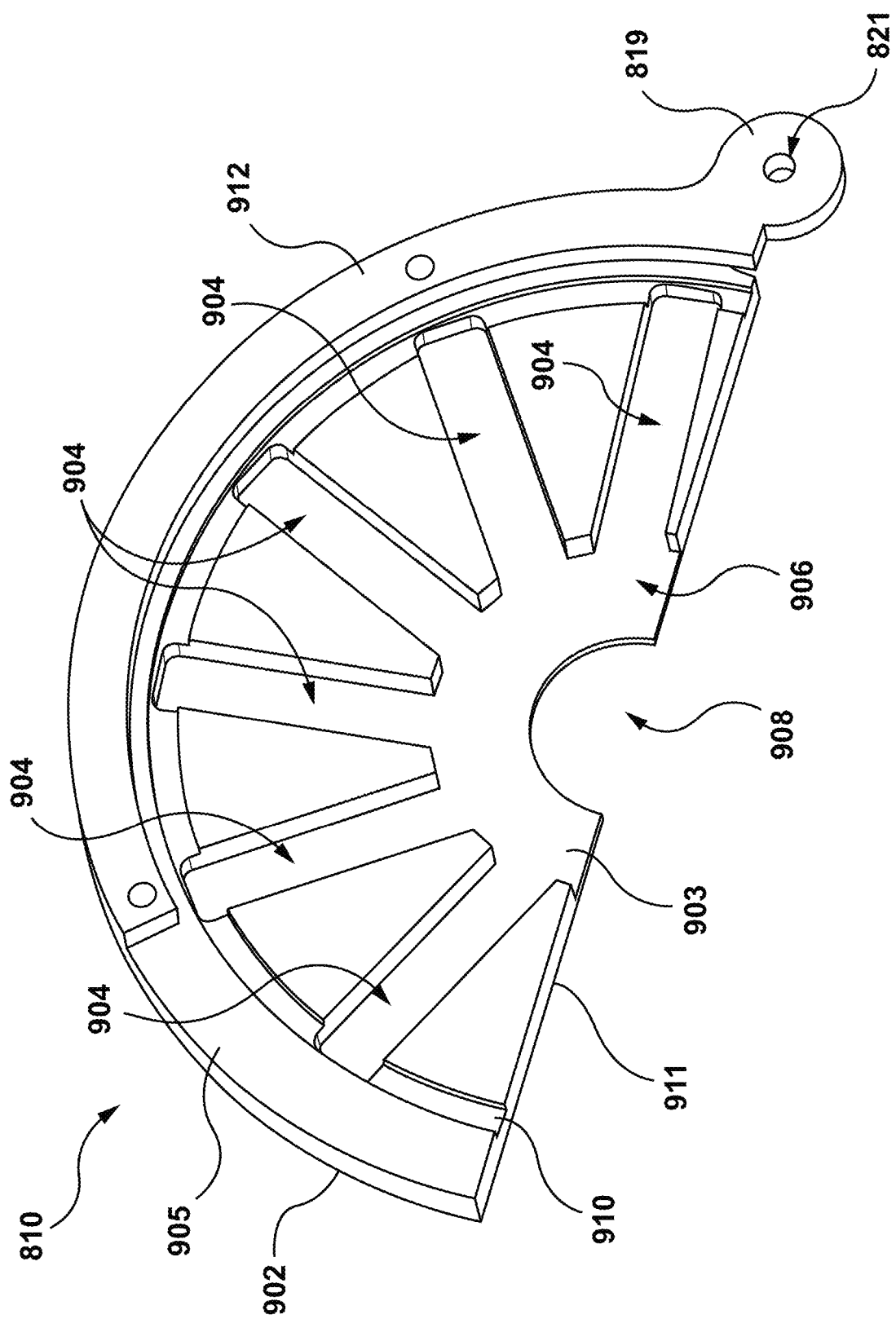
FIG. 2A depicts a perspective illustration of a side of a top shell of the crimper of FIGS. 1A-1E, according to an embodiment hereof.
Figure 2B:
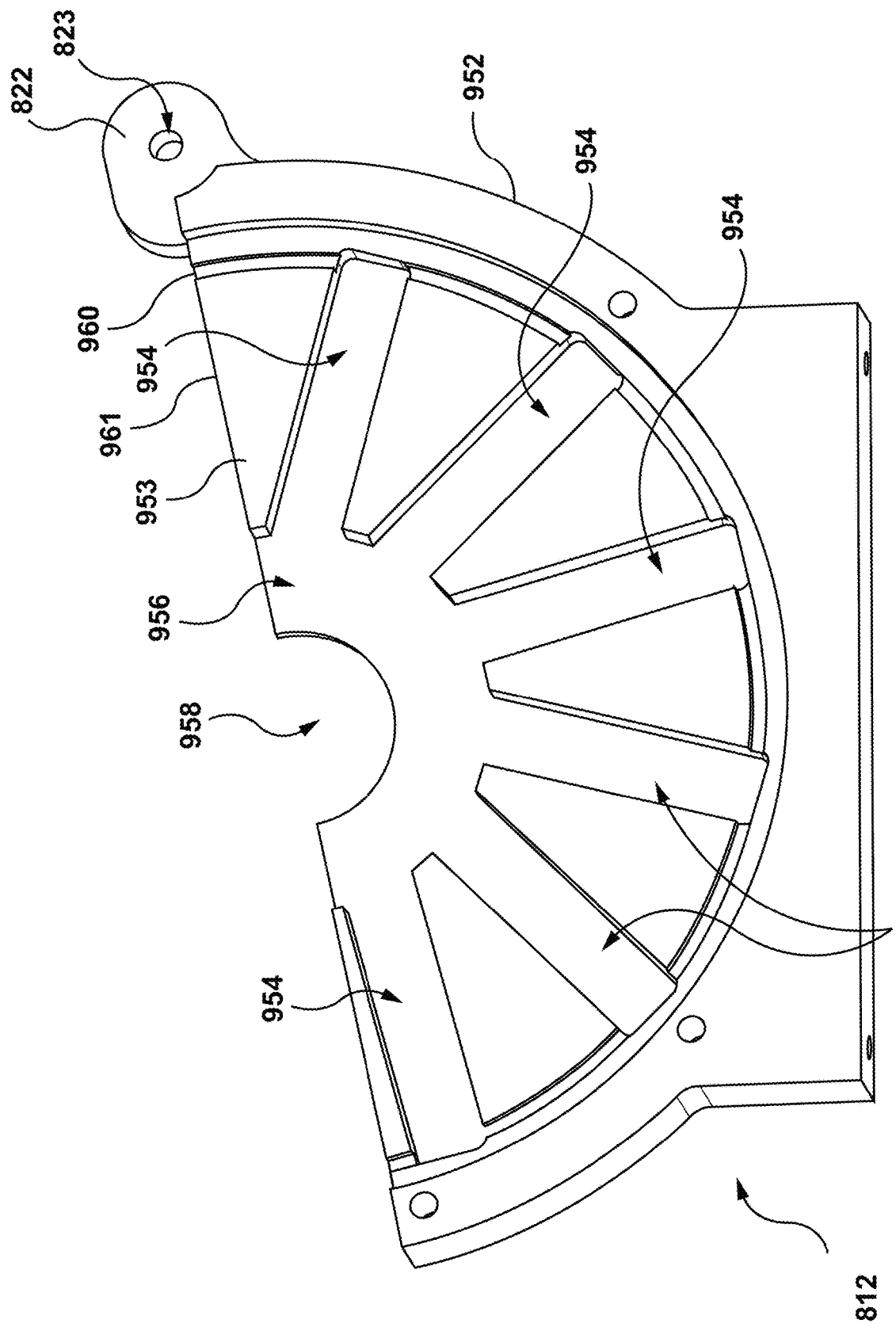
FIG. 2B depicts a perspective illustration of a side of a base shell of the crimper of FIGS. 1A-1E, according to an embodiment hereof.

In some embodiments, as illustrated in FIG. 1C, the first housing 810 of the top shell 804 can include a tab 819 that extends from a rear portion of the first housing 810. The tab 819 includes a pivot connection hole 821 (as illustrated in FIG. 2A discussed below). The first housing 812 of the base shell 806 can include a tab 822 that extends from rear portion of the first housing 812. The tab 822 includes a pivot connection hole 823 (as illustrated in FIG. 2B discussed below). When the tab 819 and the tab 822 (and tabs of the second housing of the top shell 804 and the base shell 806) are mated, the pivot connection hole 821 and the pivot connection hole 823 can form a concentric hole that operates as the pivot connection 808 when a pin, rivet, bolt, screw or other connecting mechanism is inserted in the concentric hole. For example, as described in further detail below, the pivot connection 808 can include a pin that is positioned in the corresponding concentric hole formed by the pivot connection hole 821 of the first housing 810, the pivot connection hole 823 in the first housing 812, and the pivot connections of the second housing of the top shell 804 and the base shell 806. For example, the pin can be a dowel pin, a bolt, and the like. The pin can be formed to a diameter to maintain the corresponding circular openings and cause the pin to operate as a fulcrum.

In an embodiment, the top shell 804 and the base shell 806 can be separate components that can be removably attached at the pivot connection 808 to form the clamshell crimper 800. In another embodiment, the top shell 804 and the base shell 806 can be part of a single component that fold towards each other, for instance, via a living hinge therebetween, to form an integrated clamshell crimper 800. The top shell 804 and the base shell 806 can be formed of any suitable material such as, but not limited to aluminum, stainless steel, or a polymeric material. While the clamshell crimper 800 is described as pivoting at the pivot connection 808, one skilled in the art will realize that top shell 804 and the base shell 806 can move relative to one another using other type of processes and mechanically connections.

As illustrated in FIG. 1C, the crimper elements 814 are arranged to partially overlap between the top shell 804 and the base shell 806, respectively, in a first direction. In an embodiment, the crimper elements 814 of the top shell 804 are arranged to partially overlap to form the top crimper channel 816 at distal ends of the crimper (e.g., described below with reference to FIG. 3A-3D). The crimper elements 814 of the base shell 806 are arranged to partially overlap to form the bottom crimper channel 818 at distal ends of the crimper elements 814 (e.g., described below with reference to FIGS. 3A-3D). When the clamshell crimper 800 is in the closed state, the top crimper channel 816 and the bottom crimper channel 818 define the crimper chamber 820. That is, when in the closed state, the crimper elements 814 of the top shell 804 and the crimper elements 814 of the base shell 806 form a cylindrical surface of overlapping ends of the crimper elements 814 with a cylindrically-shaped cavity passing through the center, defining the crimper chamber 820.

In an embodiment, the crimper elements 814 can be removable from the top shell 804 and/or base shell 806. As such, the crimper elements 814 may be interchangeable with other types of crimper elements configured to accommodate different dimensions and/or configurations of implantable medical devices and/or delivery devices. The crimper elements 814 may be formed of any suitable material such as, but not limited to aluminum, stainless steel, or a polymeric material.

Figure 1D:
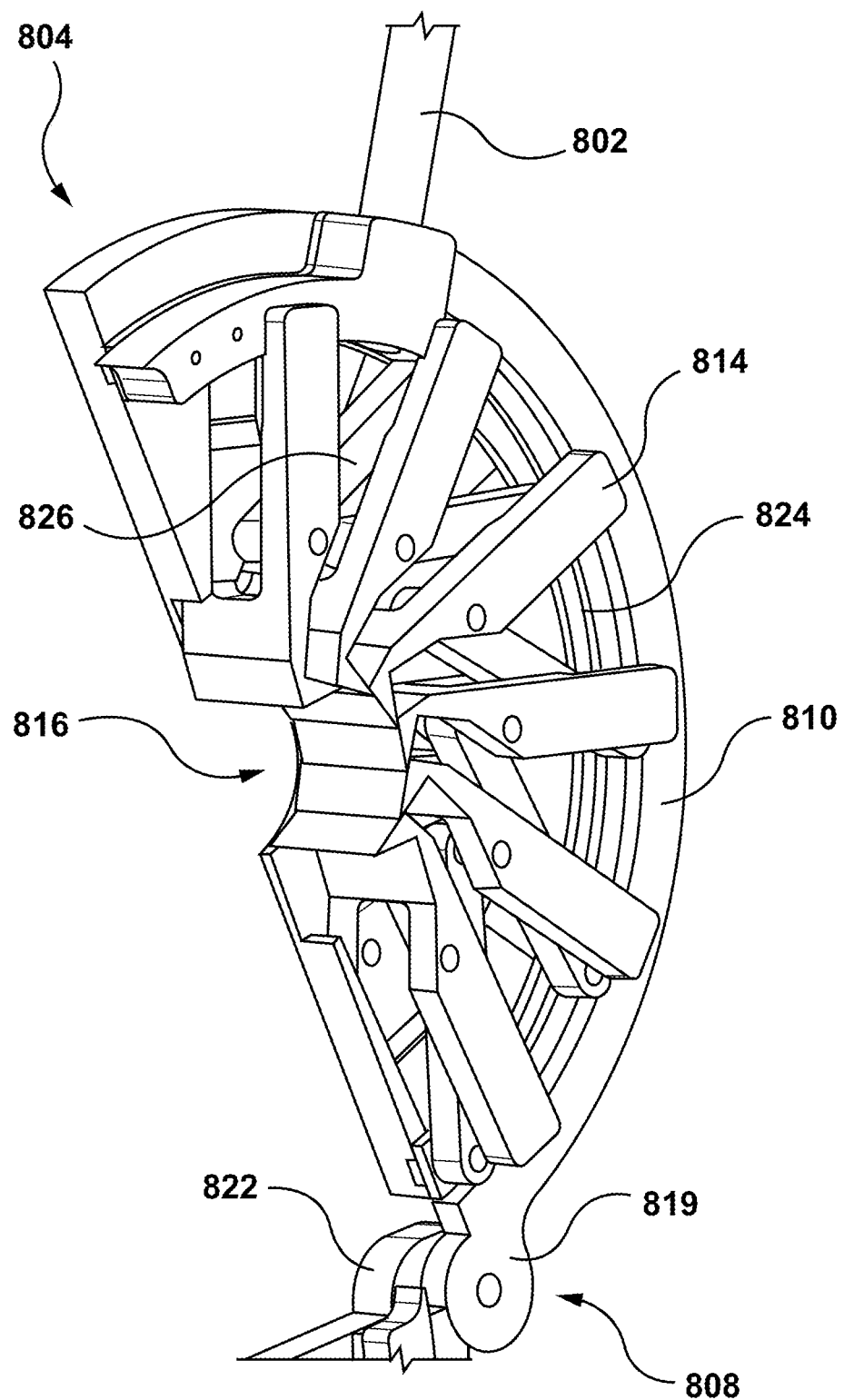

As illustrated in FIG. 1D, which is an enlarged perspective view of the top shell 804, the first housing 810 of the top shell 804 includes a top cam 824. The handle 802 is coupled the top cam 824 as further described below with reference to FIGS. 5A and 6A-6C. The top cam 824 is also coupled to the crimper elements 814 by rods 826. Each of the rods 826 extends from the top cam 824 to a middle region of one of the crimper elements 814, as described below with reference to FIGS. 3A-3D and 4. The top cam 824 operates to translate the rotational movement of the handle 802 to the crimper elements 814 via the rods 826.

Figure 1E:
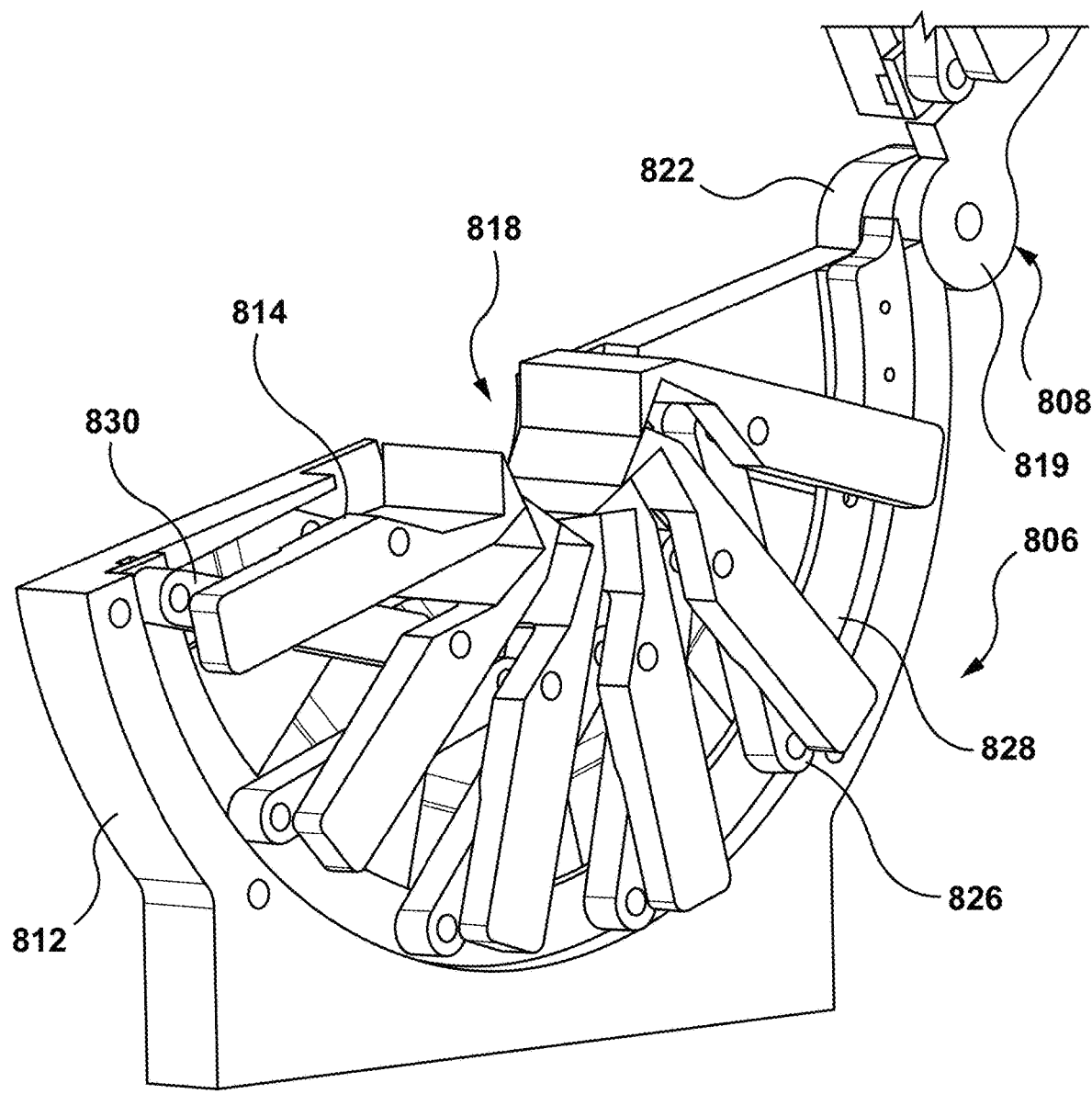

As illustrated in FIG. 1E, which is an enlarged perspective view of the base shell 806, the first housing 812 of the base shell 806 includes a bottom cam 828. The bottom cam 828 is also coupled to the crimper elements 814 by the rods 826. Each of the rods 826 extends from the bottom cam 828 to a middle region of one of the crimper elements 814, as described below with reference to FIGS. 3A-3D and 4. The bottom cam 828 operates to translate the movement of the handle 802 (through movement of the top cam 824) to the crimper elements 814 via the rods 826. When in the closed state, the bottom cam 828 is coupled to the top cam 824 such that the top cam 824 and the base cam 828 rotate together and function as a single cam. That is, when coupled, the top cam 824 and the bottom cam 828 from a cylindrical ring within the interior of the clamshell crimper 800. Examples of the top cam 824 and bottom cam 828 are described in further detail below with reference to FIGS. 5A and 5B.

When in the closed state, the crimper elements 814 are displaced by the movement of the handle 802. That is, as the handle 802 is moved, the top cam 824 and the bottom cam 828 rotate and function to translate the rotational motion of the handle 802 into linear motion of the crimper elements 814 via the rods 826, as described below in further detail. As such, the crimper elements 814 of the top shell 804 and the base shell 806 function as an iris to decrease or increase the volume of the crimper chamber 820 through the movement of the handle 802. As illustrated in FIG. 7, when in a closed state, the crimper chamber 820 can define a volume that approximates a cylinder. While the crimper chamber 820 is described above as defining a cylindrically shaped volume, one skilled in the art will realize that the shape and dimension of the crimper elements 814 can be changed to create a differently shaped volume as required by the implantable medical device being compressed and positioned.

In embodiments, the clamshell crimper 800 operates to convert an implantable medical device from its uncompressed state to its compressed state. Likewise, the clamshell crimper 800 operates to crimp or load the implantable medical device onto a delivery device. In operation, the implantable medical device is loaded into the bottom crimper channel 818 and positioned in a direction that is parallel to the axis of rotation, R, of the top shell 804 and the base shell 806. The delivery device can also be positioned and aligned relative to the implantable medical device. That is, the implantable medical device can be disposed around the delivery device. The clamshell crimper 800 is then moved from the open state to the closed state, and the handle 802 is actuated to convert the implantable medical device from its uncompressed state to its compressed state and load the implantable medical device onto the delivery device.

To operate the clamshell crimper 800, a force can be applied to the handle 802 in the direction of the base shell 806. When the force is applied, the top cam 824 and the bottom cam 828 rotate in the direction that the force is applied to the handle 802. The rotation of the top cam 824 and the bottom cam 828 cause the rods 826 to displace inward. The inward motion of the rods 826 cause the crimper elements 814 of the top shell 804 and the base shell 806 to displace inward thereby generating the iris effect. That is, the inward motion of the rods 826 is translated to the crimper elements 814 thereby causing the crimper elements to displace inward, as described in further detail below. As such, the volume of the crimper chamber 820 decreases and the crimper elements 814 apply a compression force to external surfaces of the implantable medical device to crimp the expandable medical device from its uncompressed state to its compressed state. For example, if the implantable medical device is round or cylindrical in shape, the crimper elements 814 apply a force on the surface of the implantable medical device from various directions as force is applied to the handle 802 thereby compressing the implantable medical device.

The clamshell crimper 800 can be utilized on any type of implantable medical device that requires a conversion from an uncompressed state to a compressed state. In an embodiment, the crimper can be applied to any implantable medical device that requires onsite crimping of the implanted medical device onto a catheter, e.g., organic tissue containing valve repair devices. In an embodiment, the crimper 800 can be used with balloon-expandable medical devices and/or mechanically expandable medical devices. For example, the clamshell crimper 800 can be utilized on implantable medical devices that are to be delivered transluminally, e.g., via a catheter, and need to be loaded onto or into a catheter. In this example, the implantable medical device can include a heart valve prosthesis, which includes a stent or frame, and a prosthetic valve attached to the interior of the frame. The stent/frame may be crimped to have a low profile such that the prosthesis can be delivered through the vessels to a target location in a compressed state, and then expanded at the target location, by a balloon of the delivery device, for instance, to replace the native heart valve.

By having the clamshell crimper 800 open at an angle large enough to view the bottom crimper channel 818, a user can properly locate and position such a heart valve prosthesis with respect to the catheter. For example, when a balloon catheter with a non-crimped stent/frame of a heart valve prosthesis is placed within the clamshell crimper 800, a user can visually ensure that the prosthesis is properly located over the balloon of the catheter before proceeding with the crimping operation. The open, top loading design of the clamshell crimper 800 provides increased visibility in loading and aligning the implantable medical device and the delivery device as well as rapid fine adjustments. That is, because the clamshell crimper 800 can be opened to provide easy access to the implantable medical device and the delivery device, the relative alignment of the implantable medical device and the delivery device can be monitored and adjusted without removing the implantable medical device and the delivery device from the clamshell crimper 800. For example, a heart valve prosthesis is typically loaded onto a delivery device or catheter at the time of the implantation procedure, e.g., at the hospital by hospital staff. The prosthesis needs to be properly aligned and loaded onto the delivery catheter because, if there is an error, the improperly aligned prosthesis may need to be discarded, which is wasteful and costly. The clamshell crimper 800 provides a straightforward and accurate procedure to crimp such a heart valve prosthesis onto a balloon catheter at the hospital. Moreover, the clamshell crimper 800 eliminates complex geometry and machining that normally defines iris crimpers.

Returning to FIGS. 1C and 1D, the handle 802 can be formed as a separate component that is attached to the top cam 824. In other embodiments, the handle 802 can be integrated with the top cam 824 to form a single component. In embodiments, the handle 802 can be shaped, sized, designed, and/or configured to accommodate different crimping operations. For example, the handle 802 can be extended and include a pivot point to add more leverage during crimping operations. Likewise, the handle 802 can include a foot pedal that assists in pulling down the handle 802. The handle 802 can be formed of any suitable material such as, but not limited to aluminum, stainless steel, or a polymeric material.

In embodiments, the top shell 804 can include a handle lock mechanism that locks the handle 802 into at a position where the crimper chamber 820 in an open position, e.g., the crimper chamber 820 being open to a maximum diameter. The top shell 804 and/or the base shell 806 can include a shell locking mechanism that locks the top shell 804 and the base shell 806 together in a closed state, e.g., the top shell 804 and base shell 806 being together. When the handle 802 is locked by the handle lock mechanism, the clamshell crimper 800 can be moved into an open state, e.g., the top crimper channel 816 and the bottom crimper channel 818 being separated, by pivoting the top shell 804 away from the base shell 806. During crimping operations, the top shell 804 can be closed, for example, using the handle 802, and the top shell 804 and the base shell 806 can be locked into the closed state, e.g., the top shell 804 and base shell 806 being together. The handle 802 can then be unlocked by disengaging the handle lock mechanism to perform crimping operations. The dual locking can prevent either the top crimper channel 816 the top shell 804 or bottom crimper channel 818 of the base shell 806 from moving to the closed position while the other half is in the open position.

In embodiments, the clamshell crimper 800 can also include one or more stops that operate to physically stop the crimper handle 802 at one or more predetermined positions that correspond to one or more predetermine diameters to which the implantable medical device may be crimped or compressed. In some embodiments, the clamshell crimper 800 can include a first stop and a second stop, such as a first stop 1950 and a second stop 1952 as illustrated in FIG. 12B and discussed in detail below. The first stop and the second stop provide a surface that stop the movement of the handle 802 in the downward direction. The first stop and the second stop provide a stop position of the handle 802 that corresponding to a predetermined diameter of the crimper chamber 820. That is, the first stop and the second stop operate a physically stops to allow an implantable medical device to be compressed to a predetermined diameter or compression. For example, the first stop can operate to allow an implantable medical device to be partially compressed. Likewise, for example, the second stop can operate to allow an implantable medical device to be fully compressed. The first stop and the second stop can be removably coupled to the top shell 804 and/or base shell 806. As such, the first top and/or the second stop can be added and/or removed to allow an implantable medical device to be compressed to predetermined diameters While the components of the clamshell crimper 800 are described above with relative terms "first," "second," "proximal," and "distal," one skilled in the art will realize that the use of these terms is intended only to identify components of the clamshell crimper 800 and do not define any preferred or ordinal arrangement of the components of the crimper 800. Likewise, for example, while the implantable medical device is described as being positioned in the bottom crimper channel 818 during operation, in an embodiment, the implantable medical device can be positioned in the top crimper channel 816.

FIG. 2A illustrates a detailed view of components of the first housing 810 of the top shell 804. One skilled in the art will realize that FIG. 2A illustrates one example of a housing of the top shell 804 and that existing components illustrated in FIG. 2A may be removed and/or additional components may be added to the first housing 810. Additionally, while the first housing 810 is only discussed below, one skilled in the art will realize that top shell 804 includes a second housing that may include the same components as illustrated in FIG. 2A. For example, the second housing may be formed as a "mirror" of the first housing 810 and can be coupled to the first housing 810 to form the top shell 804.

As illustrated in FIG. 2A, the first housing 810 includes a side plate 902 with an interior surface 903 and an exterior surface (not shown) opposite the interior surface. In an embodiment, the side plate 902 can be constructed as a semi-cylindrical plate with a semi-cylindrical opening 908. The semi-cylindrical opening 908 allows access to the top crimper channel 816 formed by the crimper elements 814.

Crimper element channels 904 are formed in the interior surface 903 of the side plate 902. The crimper element channels 904 can each be formed as a rectangular groove or channel that extends inward from an outer radius of the side plate 902 towards the semi-cylindrical opening 908. The crimper element channels 904 can be positioned in an arc, at equal distances, along the interior surface 903 of the side plate 902. The crimper element channels 904 are coupled to a center cavity 906 formed in the interior surface 903 of the side plate 902. The center cavity 906 can be formed as a semi-circular cavity having the approximately same depth as the crimper element channels 904.

The side plate 902 also includes a cam channel 910 formed within the interior surface 903 of the side plate 902. The cam channel 910 can extend in a semi-circular arc from a bottom surface 911 of the side plate 902. The cam channel 910 can be configured to receive and retain the top cam 824 and configured to allow the top cam 824 to move (e.g., rotate) within the top shell 804. The cam channel 910 can be formed to a depth that is less than the crimper element channel 904. The cam channel 910 can be formed to a width that accommodates the top cam 824.

The side plate 902 also include a handle stop 912 that extends from the interior surface 901 of the side plate 902. The handle stop 912 can extend in an arc partially around the circumference of the side plate 902 from the tab 819 to a stop position, thereby defining a handling opening 905. The handle stop 912 can operate as a stop from the handle 802 when the handle 802 is moved. The side plate 902 also includes the tab 819 that extends from a side surface of the side plate 902. While FIG. 2A illustrates the tab 819 being formed as a unitary component with the side plate 902, one skilled in the art will realize that the tab 819 can be a separate component that is coupled to the side plate 902.

FIG. 2B illustrates a detailed view of components of the first housing 812 of the base shell 806. One skilled in the art will realize that FIG. 2B illustrates one example of a housing of the base shell 806 and that existing components illustrated in FIG. 2B may be removed and/or additional components may be added to the first housing 812. Additionally, while the first housing 812 is only discussed below, one skilled in the art will realize that base shell 806 includes a second housing that may include the same components as illustrated in FIG. 2B. For example, the second housing may be formed as a "mirror" of the first housing 812 and can be coupled to the first housing 812 to form the base shell 806.

As illustrated in FIG. 2B, the first housing 812 includes a side plate 952 with an interior surface 953 and an exterior surface (not shown). In an embodiment, the side plate 952 can be constructed as a semi-cylindrical plate with a semi-cylindrical opening 958. The semi-cylindrical opening 958 allows access to the bottom crimper channel 818 formed by the crimper elements 814. Crimper element channels 954 are formed in the interior surface 953 of the side plate 952. Each of the crimper element channels 954 can be formed as a rectangular groove or channel that extends inward from an outer radius of the side plate 952 towards the semi-cylindrical opening 958. The crimper element channels 954 can be positioned in an arc, at equal distances, along the interior surface 953 of the side plate 952. The crimper element channels 954 are coupled to a center cavity 956 formed in the interior surface 953 of the side plate 952. The center cavity 956 can be formed as a semi-circular cavity having approximately the same depth as the crimper element channels 954.

The side plate 952 also includes a cam channel 960 formed within the interior surface 953 of the side plate 952. The cam channel 960 can extend in a semi-circular arc from a top surface 961 of the side plate 952. The cam channel 960 can be configured to receive and retain the bottom cam 828 and configured to allow the bottom cam 828 to move (e.g., rotate) within the base shell 806. The cam channel 960 can be formed to a depth that is less than the crimper element channels 954. The cam channel 960 can be formed to a width that accommodates the bottom cam 828. The side plate 952 also includes the tab 822 that extends from a side surface of the side plate 952. While FIG. 2B illustrates the tab 822 being formed as a unitary component with the side plate 952, one skilled in the art will realize that the tab 822 can be a separate component that is coupled to the side plate 952.

Figure 2C:
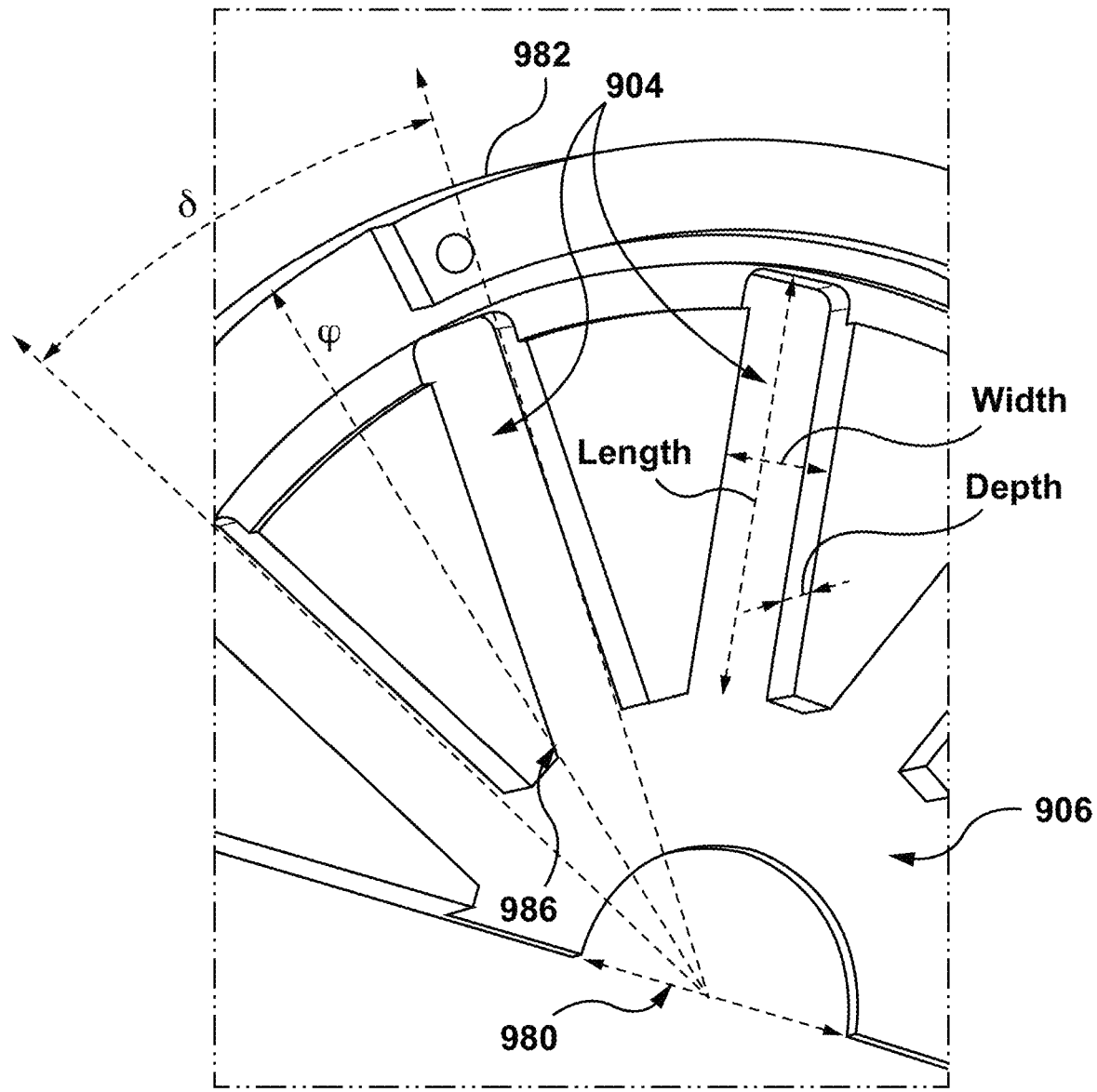
FIG. 2C depicts an enlarged portion of the perspective illustration of a side of a top shell of the crimper of FIG. 2A, according to an embodiment hereof.

The crimper element channels 904 and the center cavity 906 can be configured to moveably secure the crimper elements 814 within the top shell 904. Likewise, the crimper element channels 954 and the center cavity 956 can be configured to moveably secure the crimper elements 814 within the base shell 906. FIG. 2C illustrates an enlarged perspective view of the crimper element channels 904 and a portion of the center cavity 906, according to an embodiment hereof. While the configuration and dimensions of the side plate 902 of the top shell 802 are described with reference to FIG. 2C, one skilled in the art will realize that the configuration described in FIG. 2C can also be applied to the configuration of the side plate 952 of the base shell 806

As illustrated in FIG. 2C, the side plate 902 is formed having a radius that extends from a center point 980 of the semi-cylindrical opening 908 to a side surface 982 of the side plate 902. In embodiments, the radius can be formed to a length that accommodates the crimper elements 814 and allows for movement of the crimper elements within the top shell 804. For example, the radius can be formed to a length of approximately 112.5 mm. In embodiments, the crimper element channels 904 of the side plate 902 are formed to a width and depth to accommodate the crimper elements 814 when the side plate 902 of the first housing 810 is mated with a side plate of the second housing of the top shell 804. Likewise, the crimper element channels 804 of the side plate 902 are formed to a length and the center cavity 906 is formed to a radius that allows the crimper elements 814 move and perform the crimping operations of the clamshell crimper 800. For example, the crimper element channels 904 can be formed to a width of approximately 15.0 mm. The crimper element channels 904 can be formed to a depth of approximately 8.5 mm, from the interior surface 903 of the side plate 902. The crimper element channels 904 can be formed to a length of approximately 60.5 mm. The center cavity can be formed having a radius of approximately 40.0 mm from the center point 980 to the distal end of the crimper element channel 904.

As noted above, the crimper element channels 904 are formed in an arc around the side plate 902. In embodiments, each of the crimper element channels 904 are spaced in the arc at an angle, $\delta$, from an adjacent crimper element channel 904. For example, each of the crimper element channels 904 are spaced at an angle, $\delta$, of approximately 30 degrees. In embodiments, each of the crimper element channels 904 can be aligned to be offset relative to the Radius of the side plate 902 by an angle, $\varphi$. For example, as illustrated in FIG. 2C, the angle, $\varphi$, can be defined as an angle between the Radius and a sidewall 984 of a crimper element channel 904, when measured at an intersection 986 of the Radius and the sidewall 984. The offset can cause the crimper elements 814 to move in a direction that is offset from the center point 980.

For example, the crimper element channels 906 can be offset by an angle, φ, that is approximately 15 degrees.

FIGS. 3A-3D illustrate detailed views of a crimper element 814, according to an embodiment hereof. One skilled in the art will realize that FIGS. 3A-3D illustrate one example of a crimper element and that existing components illustrated in FIGS. 3A-3D may be removed and/or additional components may be added to the crimper element 814. While only one crimper element 814 is discussed, one skilled in the art will realize that the crimper elements 814 of the top shell 804 and the base shell 806 may have the same configuration and include the same components as the crimper element 814 described in FIGS. 3A-3D.

Figure 3A:
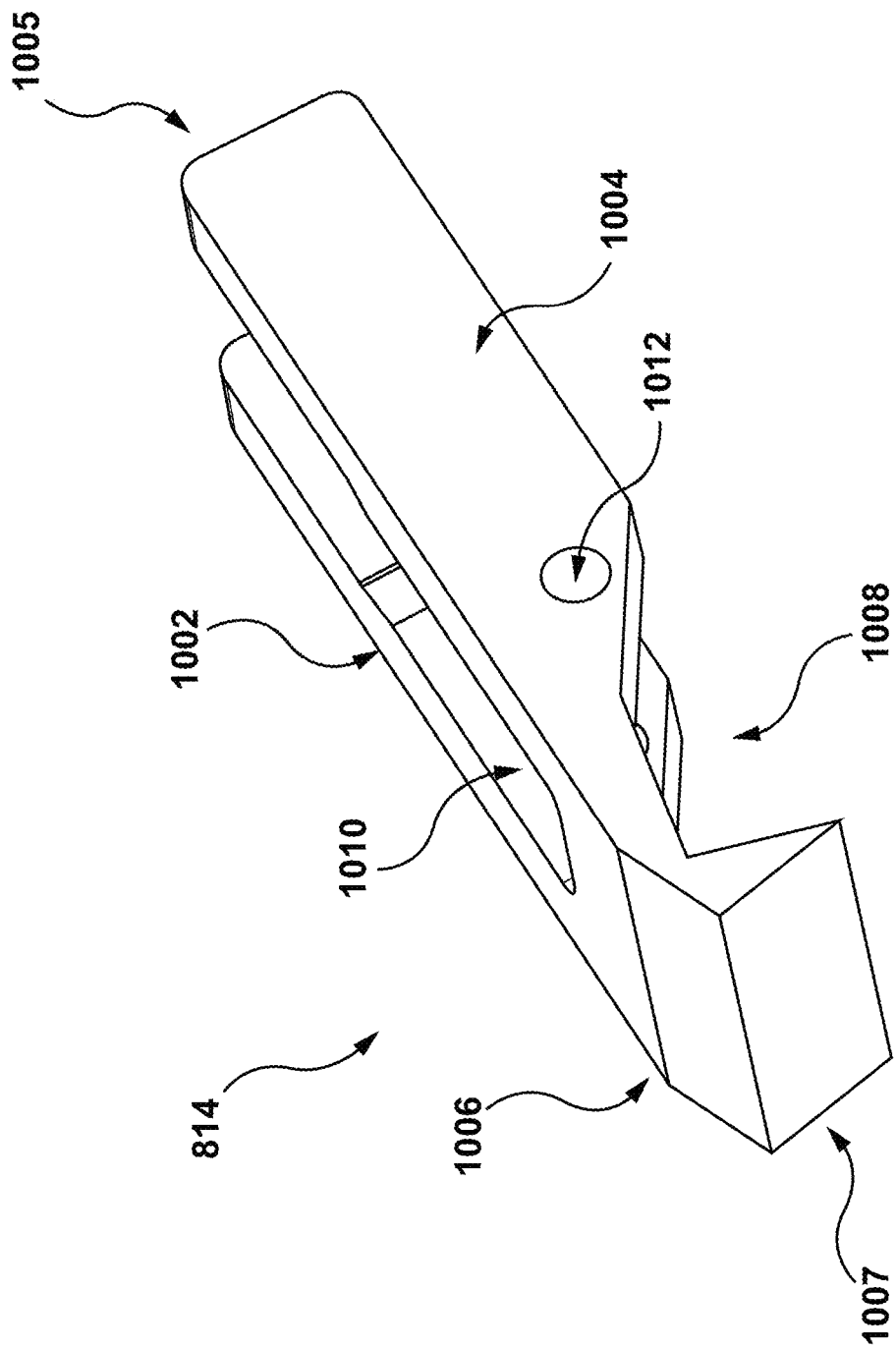
FIG. 3A-3H depict several views of a crimper element of FIGS. 1A-1E, according to an embodiment hereof.

As illustrated in FIG. 3A, which is a perspective view, the crimper element 814 has a first leg 1002, a second leg 1004, and a crimper lobe 1006 coupled to the first leg 1002 and the second leg 1004. The first leg 1002 and the second leg 1004 extend, parallel to a long axis of the crimper element 814, from a proximal end 1005 of the crimper element 814 to the crimper lobe 1006. The first leg 1002 and the second leg 1004 are spaced apart and define a rod channel 1010. The crimper lobe 1006 extends from the first leg 1002 and the second leg 1004 to a distal end 1007 of the crimper element 814. The crimper lobe 1006 is configured to define a crimper space 1008. The crimper space 1008 is configured to accommodate an adjacent crimper element 814.

Figure 3B:
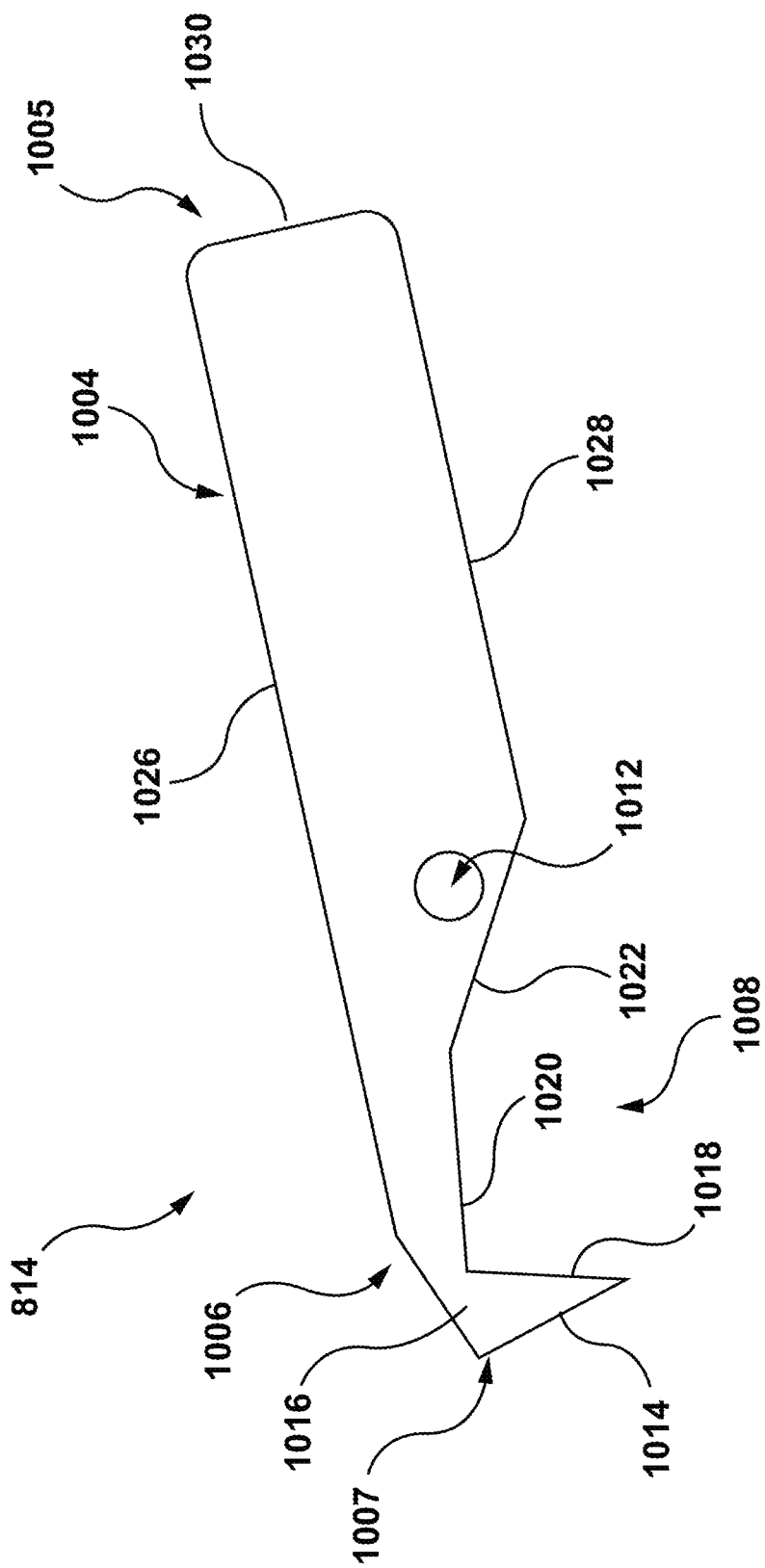

As illustrated in FIG. 3B, which is a side view, the crimper element 814 includes a top surface 1026, a bottom surface 1028, and a distal surface 1030 formed at the ends of the first leg 1002 and the second leg 1004. The crimper lobe 1006 includes a first exterior ramp 1014 and a second exterior ramp 1016. The crimper lobe 1006 also includes a first interior ramp 1018 and a second interior ramp 1020. The intersection of the first leg 1002 and the crimper lobe 1006 and the intersection of the second leg 1004 and the crimper lobe 1006 form a sloped edge 1022. As in FIG. 3B, which is a bottom view, the first interior ramp 1018, the second interior ramp 1020, and the sloped edge 1022 define the crimper space 1008.

Figure 3C:
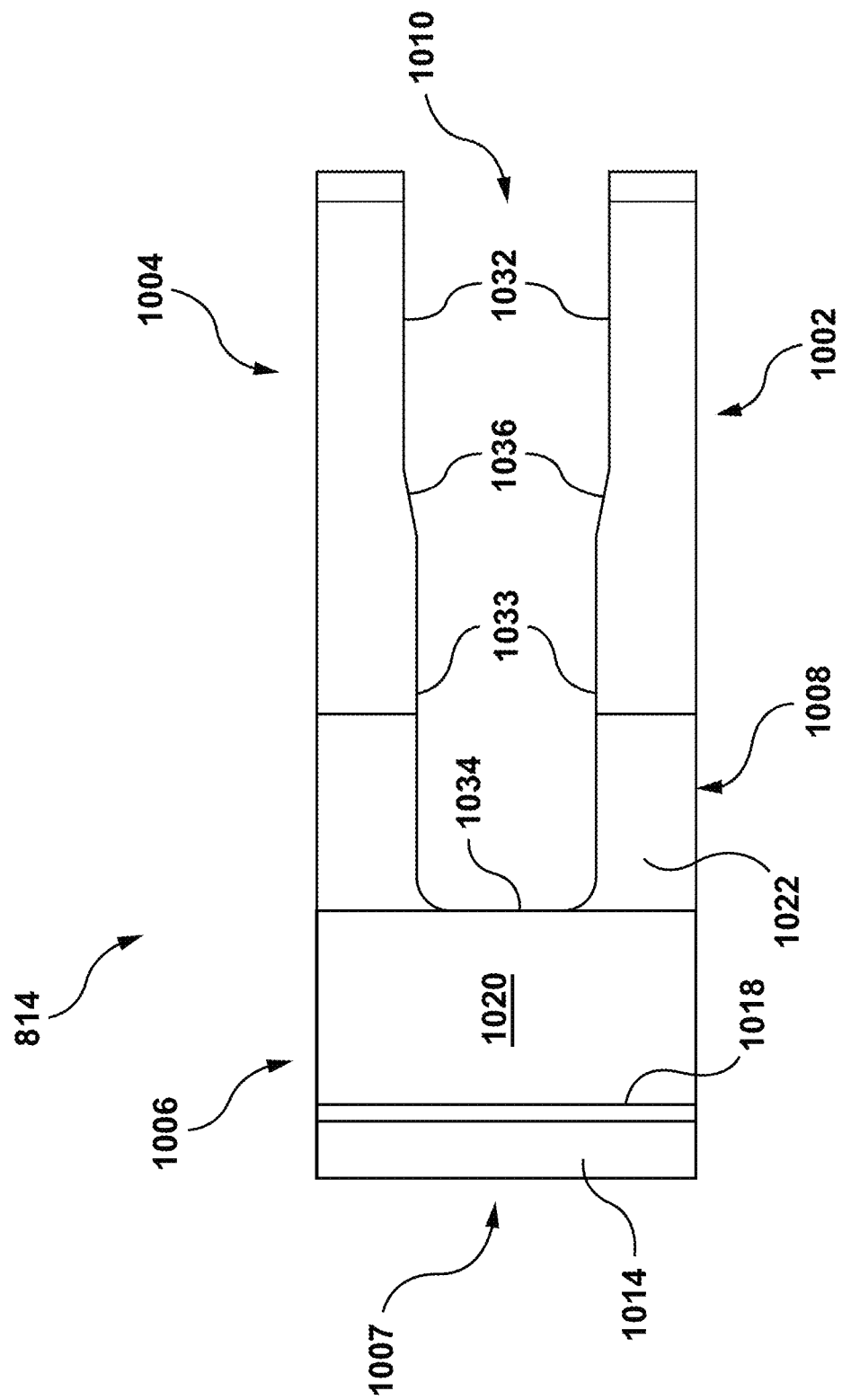
Figure 3D:
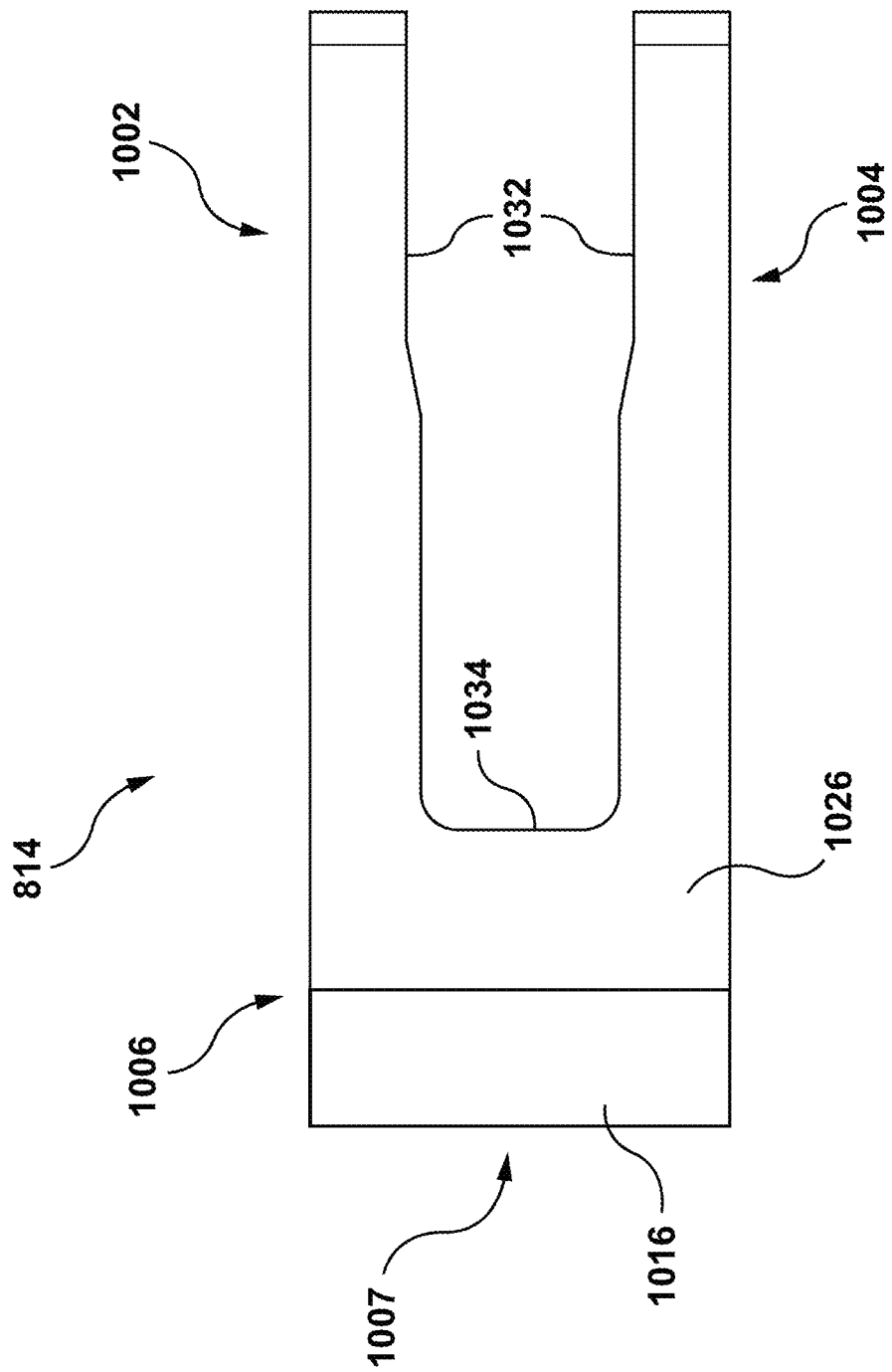

As illustrated in FIG. 3D, which is a top view, the first exterior ramp 1014 and the second exterior ramp 1016 form a surface between the top surface 1026 and the distal end 1007 and the bottom surface 1028. The first exterior ramp 1014 and the second exterior ramp 1016 can be formed at angles relative to the top surface 1026 and the bottom surface 1028. Likewise, the first interior ramp 1018 and the second interior ramp 1020 can be formed at angles relative to the top surface 1026 and the bottom surface 1028. The intersection of the first leg 1002 and the crimper lobe 1006 and the intersection of the second leg 1004 and the crimper lobe 1006 form a sloped edge 1022.

In embodiments, the first leg 1002 and second leg 1004 include interior surfaces 1032 and 1033 and a sloped edge 1036 between the interior surface 1032, 1033. A rod channel 1010 is defined by the interior surfaces 1032 and 1033, the sloped edge 1036, and a proximal end 1034 of the crimper lobe 1006. The rod channel 1010 is configured to accommodate one of the rods 826. The crimper elements 814 also includes connection holes 1012. The connection holes 1012 are formed in the first leg 1002 and the second leg 1004. In an embodiment, the crimper elements 814 can include two connection holes 1012 that are positioned at opposing locations on the first leg 1002 and the second leg 1004. In embodiments, the connection holes 1012 can be configured to receive a pin that passes through the two connection holes and a connection hole of the rod 826. For example, the pin can be a dowel pin, a bolt, and the like. The pin can be formed to a diameter to maintain the corresponding circular openings and cause the pin to operate as a fulcrum. The connection holes 1012 operate to moveably couple the crimper elements 814 to the rods 826. The rods 826 are coupled within the rod channel 1010. The rod channels 1010 allow the rods 826 to rotate relative to the crimper elements 814 during operation of the clamshell crimper 800.

Figure 3E:
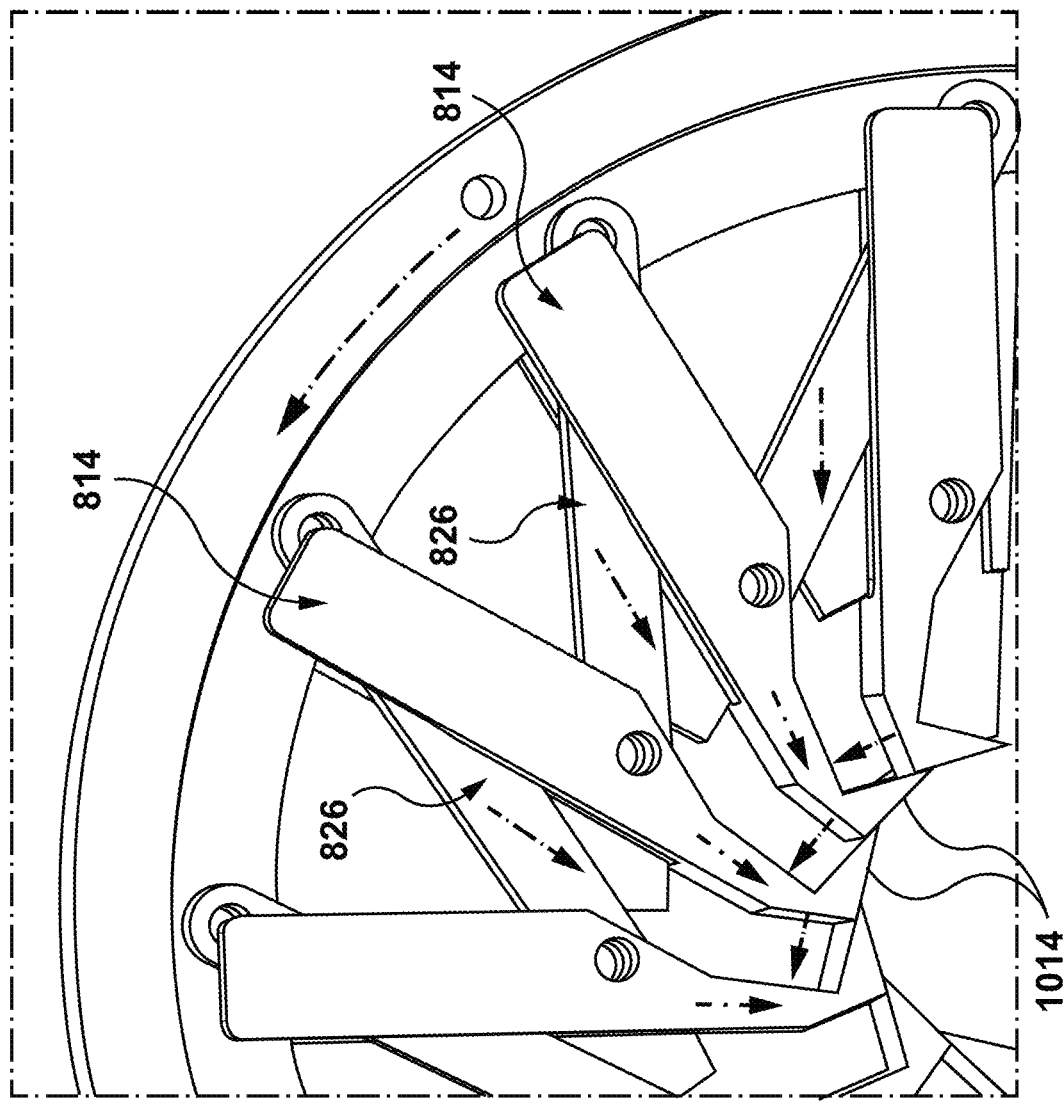

In embodiments, the crimper element 814 are configured to work in combination to produce the iris effect of the clamshell crimper 800. FIG. 3E is an enlarged side view of several crimper element 814 in which the crimper elements 814 are positioned in a fully open position. As illustrated, a first exterior ramp 1014 of a first crimper element 814 rests against a first interior ramp 1018 of a second crimper element 814, forming an overlap. The overlap of the crimper elements 814 defines the crimper chamber 820. During operation, for example, the handle 802 is actuated in a downward motion (counter-clockwise direction as illustrated in FIG. 3E) thereby causing the cam (the top cam 824 illustrated in FIG. 3E) to rotate. The rotation of the top cam 824 forces the rods 826 inward. The motion of the rods 826 forces the crimper elements 814 inward. In particular, the crimper elements 814 move inward generally towards the center of the crimper chamber 820. As the crimper elements 814 move inward, the space available for the crimper elements 814 to occupy is reduced. As such, the space between the crimper elements 814 is reduced. As such, the first exterior ramp 1014 of the first crimper element 814 slides against the first interior ramp 1018 of the second crimper element 814. In response, the area of the crimper chamber 820 is reduced.

In an embodiment, the width of each crimper element 814 can range from approximately 25 mm to approximately 50 mm and the length of each crimper element 514 can range from approximately 1 mm to approximately 40 mm. The slope of the first exterior ramp 1014 and the second exterior ramp 1016 (angle relative to the top surface 1026 and the bottom surface 1028) can depend on the number of crimper elements included in the clamshell crimper 800. Likewise, the slope of the first interior ramp 1018, the second interior ramp 1020, and the sloped edge 1022 (angle relative to the top surface 1026 and the bottom surface 1028) can depend on the number of crimper elements included in the clamshell crimper 800. In an embodiment, the slope can be determined by dividing 360 degrees by the number of crimper elements 814 in the clamshell crimper 800. In an embodiment, the number of crimper elements can range from 10 to 12. The first interior ramp 1018, the second interior ramp 1020, and the sloped edge 1022 are configured to contact a neighboring crimper element and generate the iris effect when the crimper elements are displaced.

Figure 3F:
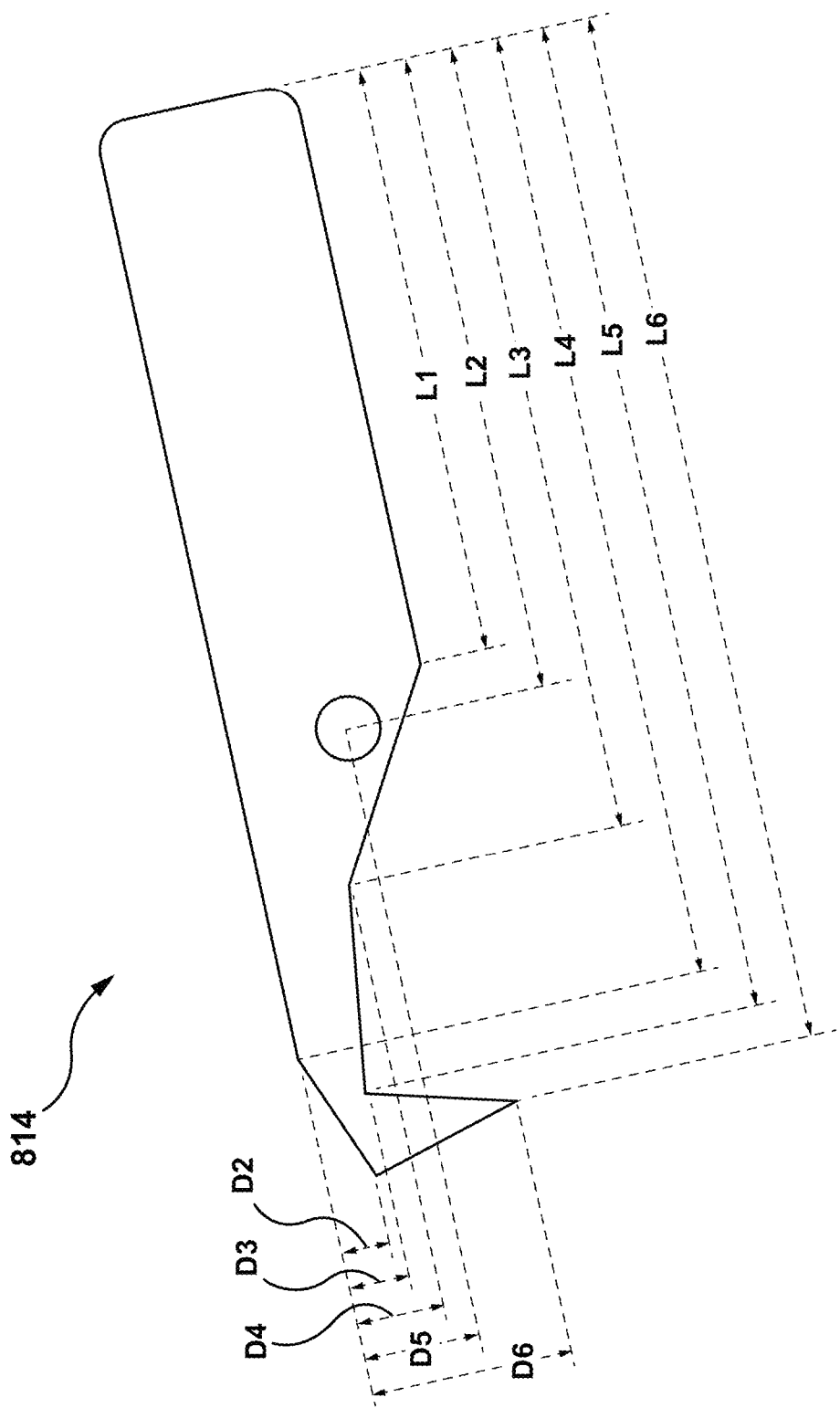
Figure 3G:
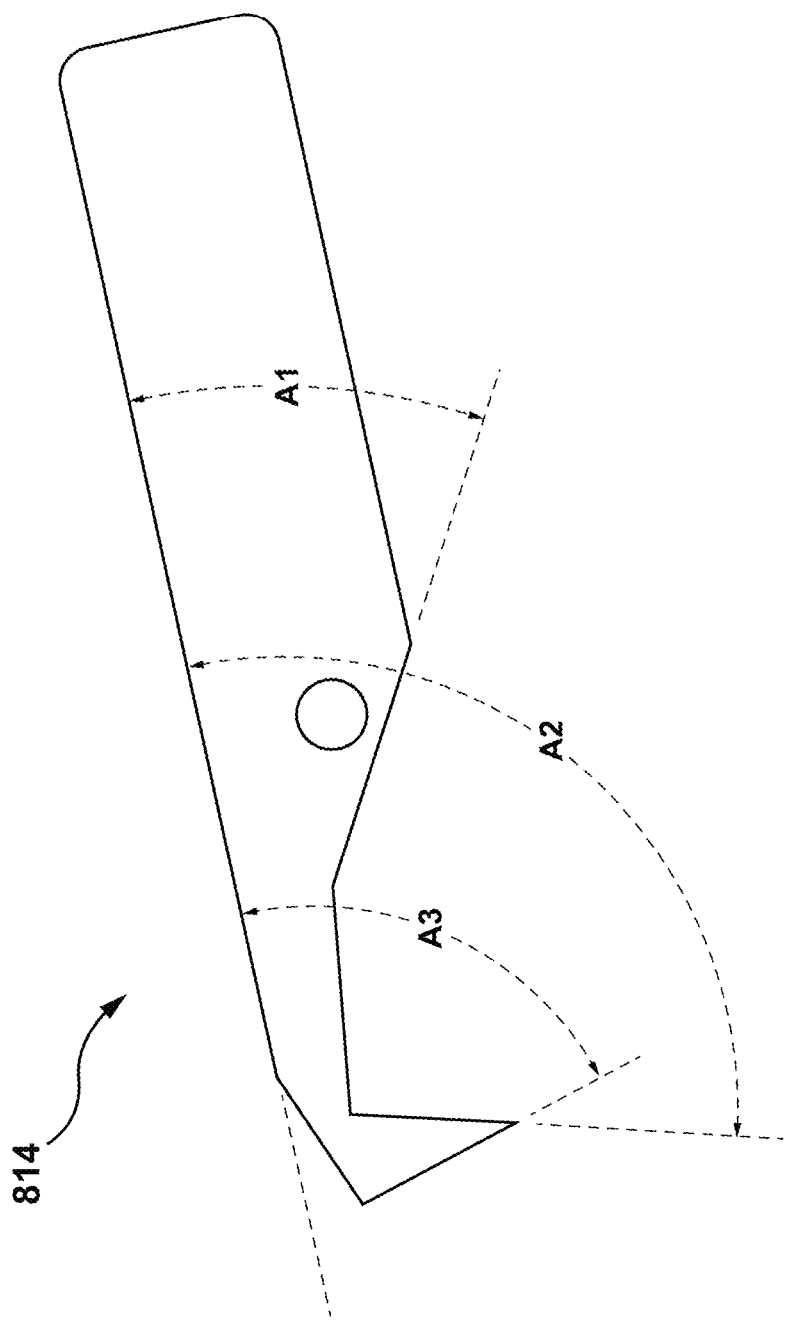
Figure 3H:
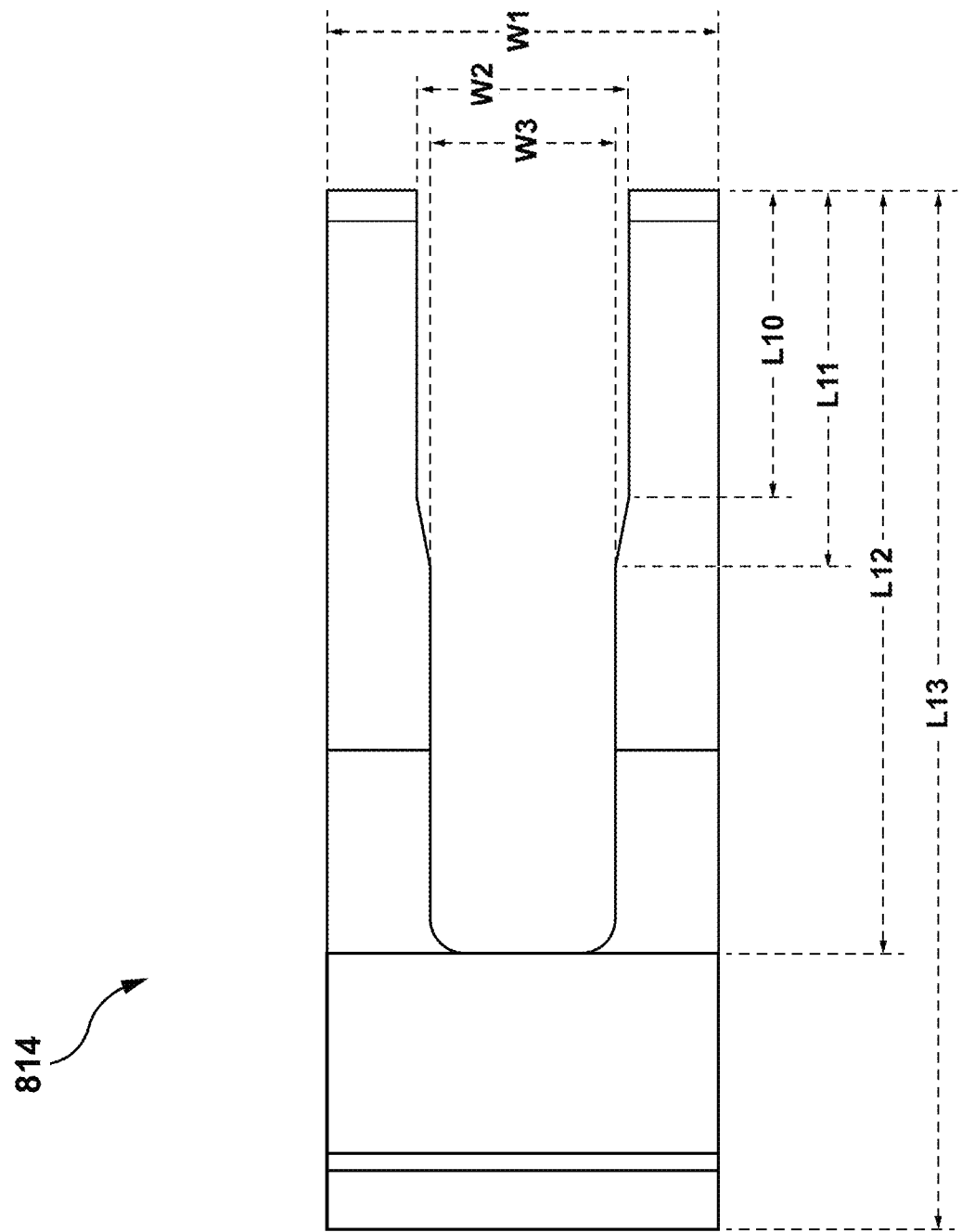

FIGS. 3F-3H illustrates examples of dimensions for a crimper element 814 having a 30 mm configuration, according to an embodiment hereof. For clarity in illustrating the dimension, reference numbers for the crimper element 814 have been omitted and can be found in FIGS. 3A-3D. Table 1 below describes the dimension illustrated in FIGS. 3F-3H and provides example values for the dimensions. One skilled in the art will realize that the values for the dimension are one example, and the crimper element 814 can have different values for the dimension based on the particular configuration of the clamshell crimper 800 and the crimping application.

TABLE 1

| Dimension | Description | ~Value |
|---|---|---|
| L1 | Proximal End 1005 to beginning of Sloped Edge 1022 | 44.0 mm |
| L2 | Proximal End 1005 to midpoint of Connection Hole 1012 | 47.50 mm |
| L3 | Proximal End 1005 to end of Sloped Edge 1022 | 58.7 mm |
| L4 | Proximal End 1005 to beginning of Exterior ramp 1016 | 70.5 mm |
| L5 | Proximal End 1005 to end of Interior Ramp 1020 | 74.1 mm |
| L6 | Proximal End 1005 to end of Interior Ramp 1018 | 77.04 mm |
| L10 | Proximal End 1005 to beginning of Sloped Edge 1036 | 23.8 mm |
| L11 | Proximal End 1005 to end of Sloped Edge 1036 | 29.4 mm |
| L12 | Proximal End 1005 to Proximal End 1034 of Crimper Lobe 1006 | 58.7 mm |
| L13 | Proximal End 1005 to Distal End 1007 | 80.04 mm |
| D1 | Top Surface 1026 to Bottom Surface 1028 | 14.85 mm |
| D2 | Top Surface 1026 to end of Exterior Ramp 1016 | 3.69 mm |
| D3 | Top Surface 1026 to end of Interior Ramp 1020 | 4.0 mm |
| D4 | Top Surface 1026 to beginning of Interior Ramp 1020 | 6.3 mm |
| D5 | Top Surface 1026 to midpoint of Connection Hole 1012 | 8.63 mm |
| D6 | Top Surface 1026 to beginning of Exterior Ramp 1014 | 14.90 mm |
| W1 | Exterior Surface 1036 of Legs | 30.0 mm |
| W2 | Width of Rod Channel 1010 between Interior Surfaces 1032 | 16.0 mm |
| W3 | Width of Rod Channel 1010 between Interior Surfaces 1033 | 14.0 mm |
| A1 | Angle between Top Surface 1026 and Sloped Edge 1022 | 30 degrees |
| A2 | Angle between Top Surface 1026 and Interior Ramp 1018 | 105 degrees |
| A3 | Angle between Top Surface 1026 and Exterior Ramp 1014 | 75 degrees |

Figure 4:
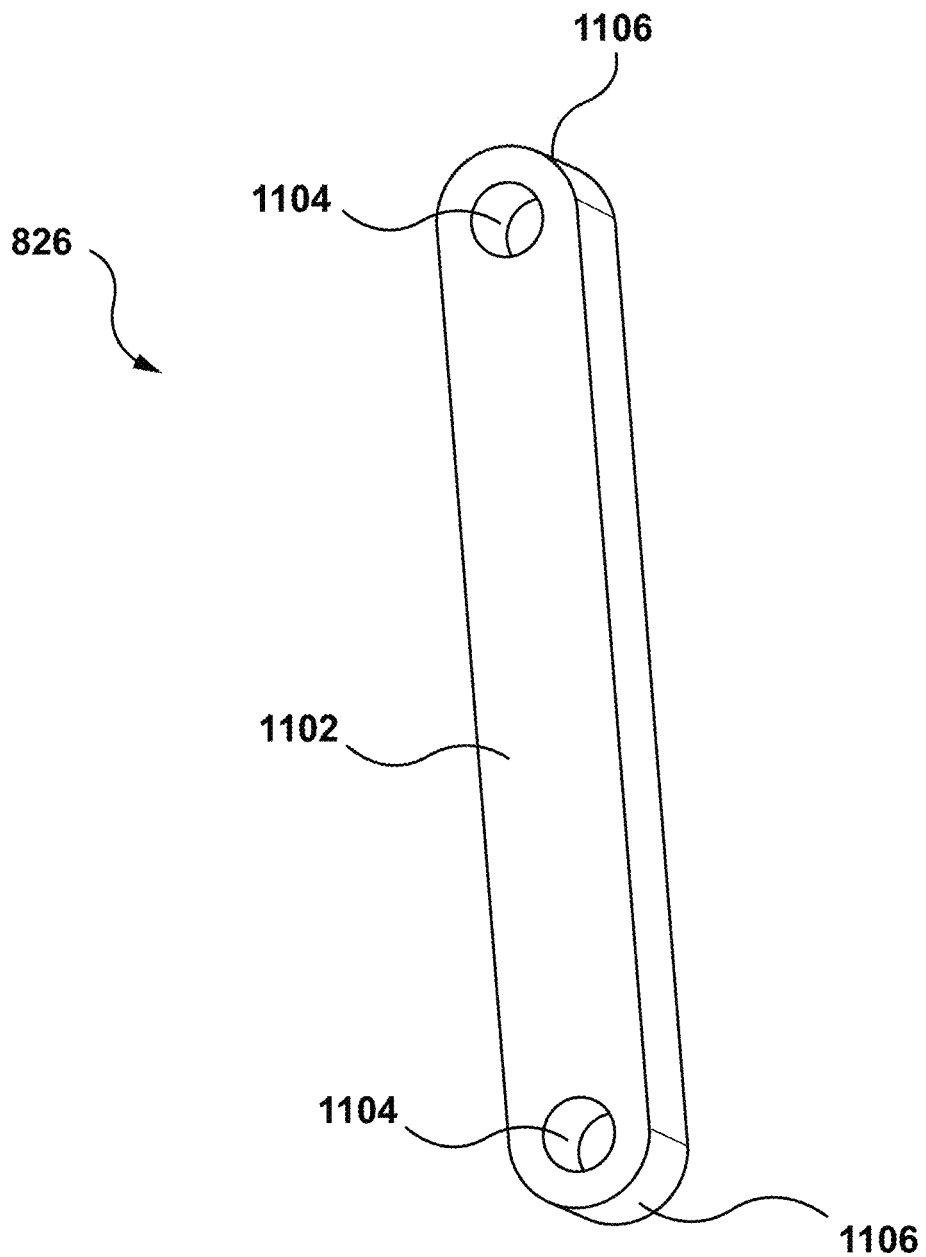
FIG. 4 depicts a perspective illustration of a rod of FIGS. 1A-1E, according to embodiment hereof.

FIG. 4 illustrates an example of the rod 826. As illustrated, the rod 826 is formed as a rectangular bar 1102 with connection holes 1104. The rectangular bar 1102 can include rounded ends 1106 that are formed in a semi-cylindrical shape. One of the connection holes 1104 operates to moveably couple the crimper elements 814 to the rod 826. In embodiments, a first of the connection holes 1104 align with the connection holes 1012 of the crimper element 814. As described above, the first of the connection holes 1104 can be configured to receive a pin that passes through the two connection holes 1012 of the crimper element 814. For example, the pin can be a dowel pin, a bolt, and the like. The pin can be formed to a diameter to maintain the corresponding circular openings and cause the pin to operate as a fulcrum.

In embodiments, a second of the connection holes 1104 aligns with a connection hole of the top cam 824 or bottom cam 828, described below. The second of the connection holes 1104 can be configured to receive a pin that passes through the connection holes of the top cam 824 or bottom cam 828. For example, the pin can be a dowel pin, a bolt, and the like. The pin can be formed to a diameter to maintain the corresponding circular openings and cause the pin to operate as a fulcrum. When the top cam 824 or bottom cam 828 rotate clockwise or counter-clockwise, the combination of the pin and the connection hole 1104 allow the rod 826 to rotate about the pin.

Figure 5A:
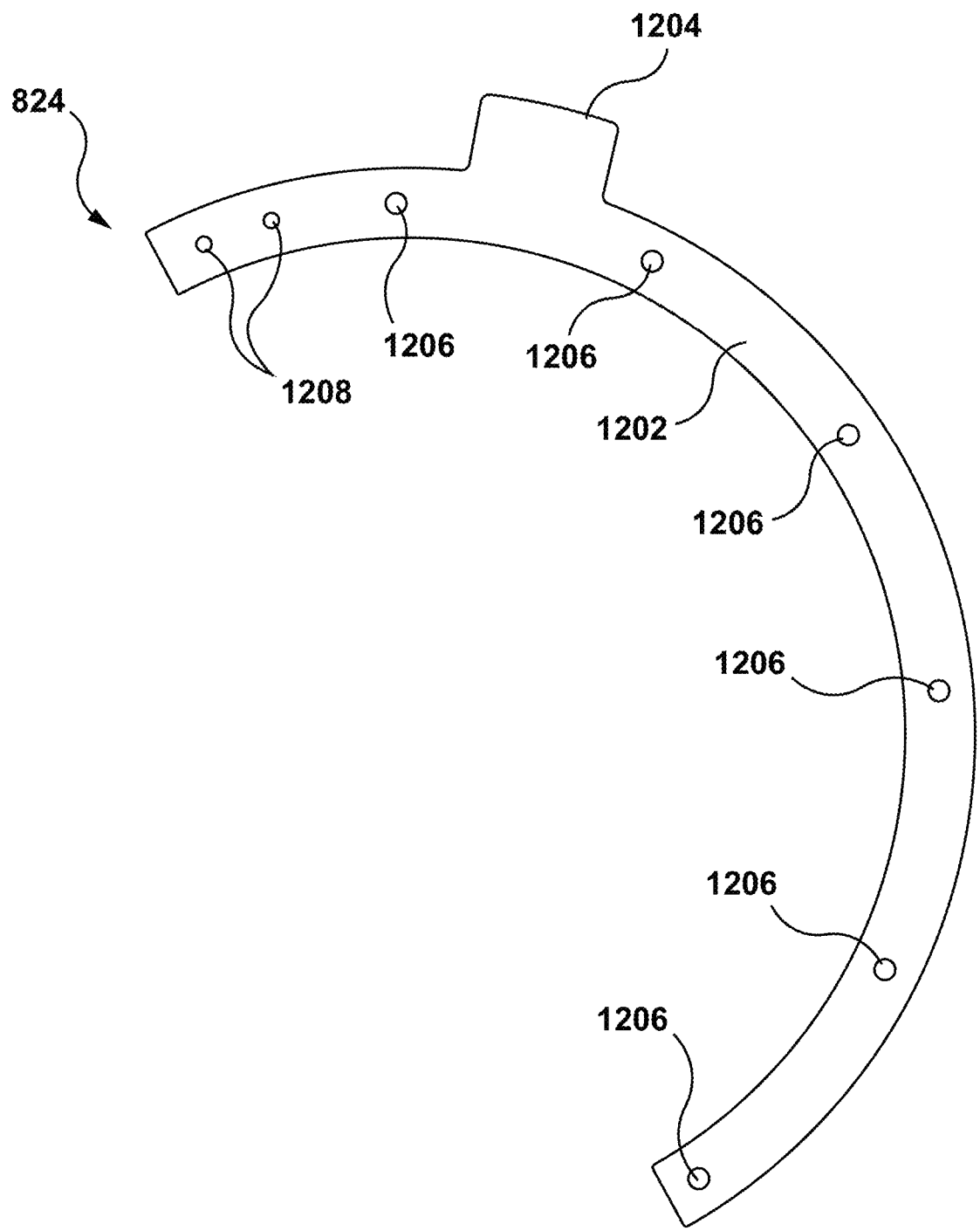
FIG. 5A depicts a perspective illustration of a top cam of the crimper of FIGS. 1A-1E, according to an embodiment hereof.

FIG. 5A illustrates a side view of the top cam 824, according to an embodiment hereof. One skilled in the art will realize that FIG. 5A illustrates one example of a cam and that existing components illustrated in FIG. 5A may be removed and/or additional components may be added to the top cam 824.

As illustrated, the top cam 824 includes a semi-circular ring 1202. The semi-circular ring 1202 includes a handle support 1204, rod connection holes 1206, and handle connection holes 1208. As discussed above, a second of the connection holes 1104 of a rod 826 aligns with a connection hole 1206 of the top cam 824 or bottom cam 828, described below. The second of the connection holes 1104 can be configured to receive a pin that passes through the connection holes 1206 of the top cam 824 or bottom cam 828, whether directly or through a connection member of the handle 802. For example, the pin can be a dowel pin, a bolt, and the like. The semi-circular ring 1202 is formed to a width that is slightly smaller than the cam channel 910. This allows the top cam 824 to move within the cam channel 910 when a force is applied to the handle 802, thereby translating the force to the semi-circular ring 1202 and causing the top cam 824 to rotate clockwise or counter-clockwise (depending on the direction of the force applied to the handle 802).

Figure 5B:
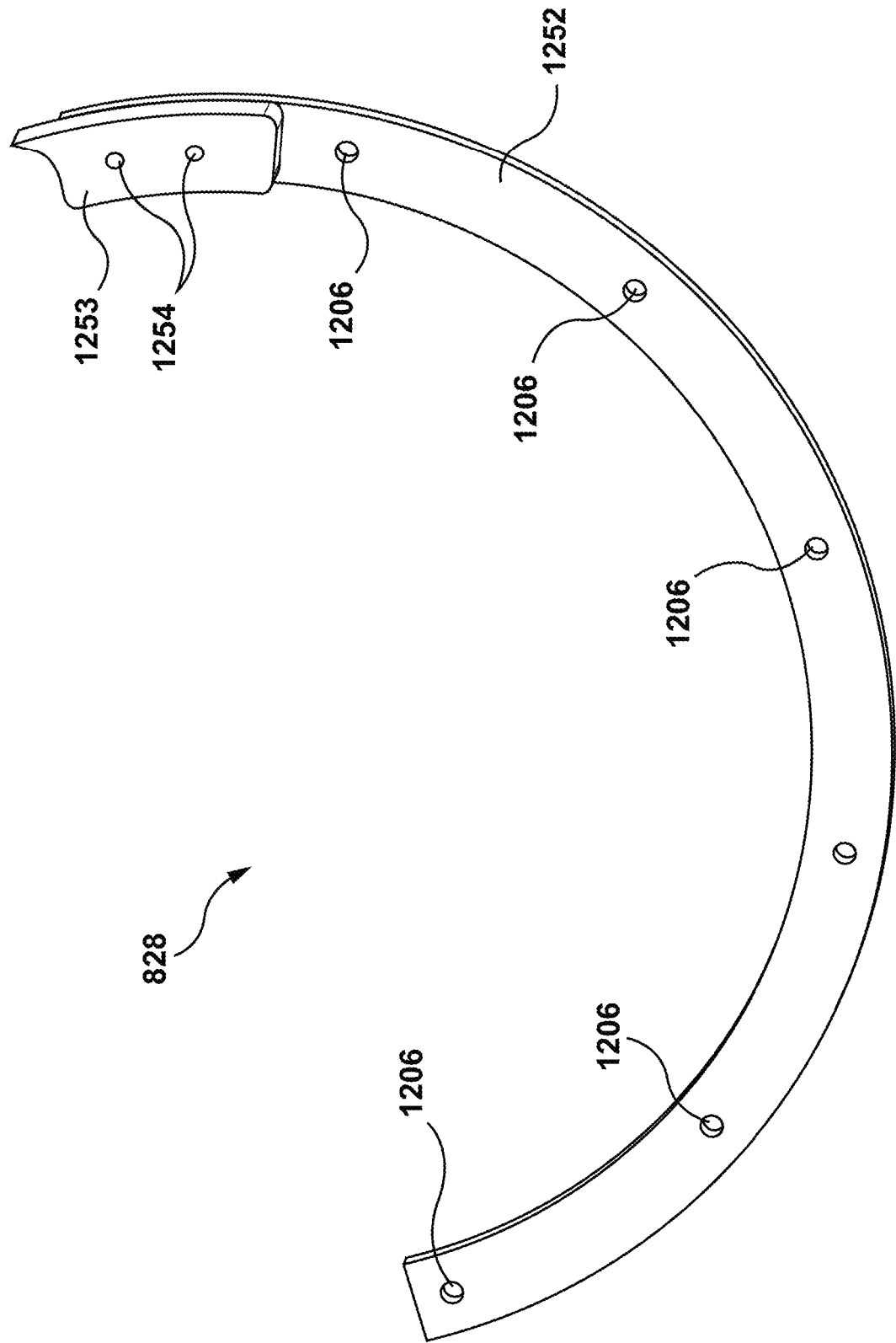
FIG. 5B depicts a perspective illustration of a bottom cam of the crimper of FIGS. 1A-1E, according to an embodiment hereof.

FIG. 5B illustrates a side view of the bottom cam 828, according to an embodiment hereof. One skilled in the art will realize that FIG. 5B illustrates one example of a cam and that existing components illustrated in FIG. 5B may be removed and/or additional components may be added to the bottom cam 828.

As illustrated, the bottom cam 828 includes a semi-circular ring 1252. The semi-circular ring 1252 includes rod connection holes 1206 and a cam connection member 1253 with connection holes 1254. As described above, the rod connection holes 1206 can be configured to receive a pin that passes through a second of the connection holes 1104 of a rod 826. The semi-circular ring 1252 is formed to a width that is slightly smaller than the cam channel 960. This allows the bottom cam 828 to move within the cam channel 960 when a force is applied to the handle 802 and thereby translated to the semi-circular ring 1252 via the top cam 824.

The cam connection member 1253 operates to couple the bottom cam 828 to the top cam 824. The connection holes 1254 are configured to receive a connection device to couple the cam connection member 1252 to the bottom cam 828. The connection device can be any type of device to couple the cam connection member 1253 to the bottom cam 828 such as a bolt, screw, pin, etc. In some embodiments, the cam connection member 1253 can be integrated with the bottom cam 828 as a single component.

Figure 6A:
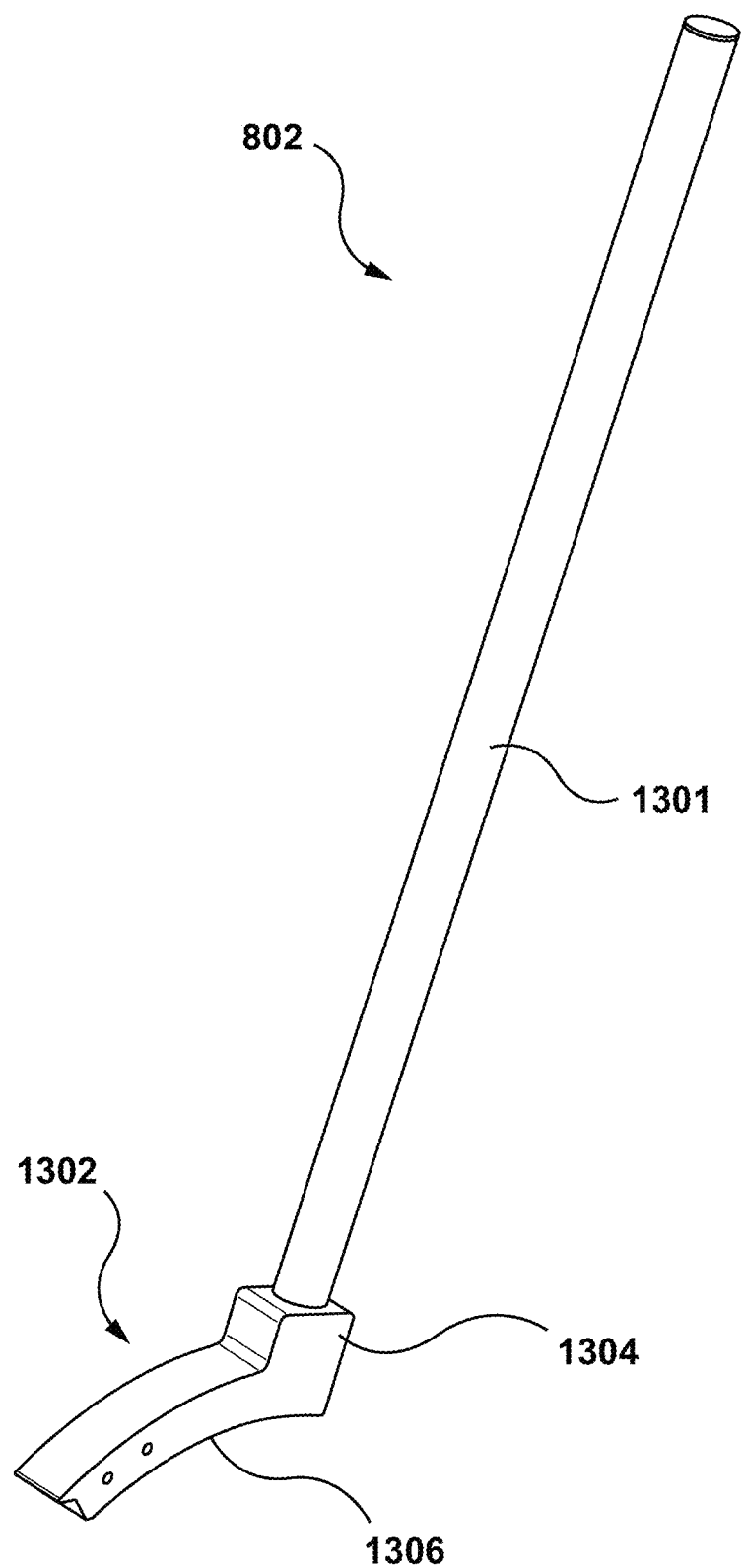
FIG. 6A-6C depict several views of a handle of the crimper of FIGS. 1A-1E, according to an embodiment hereof.
Figure 6B:
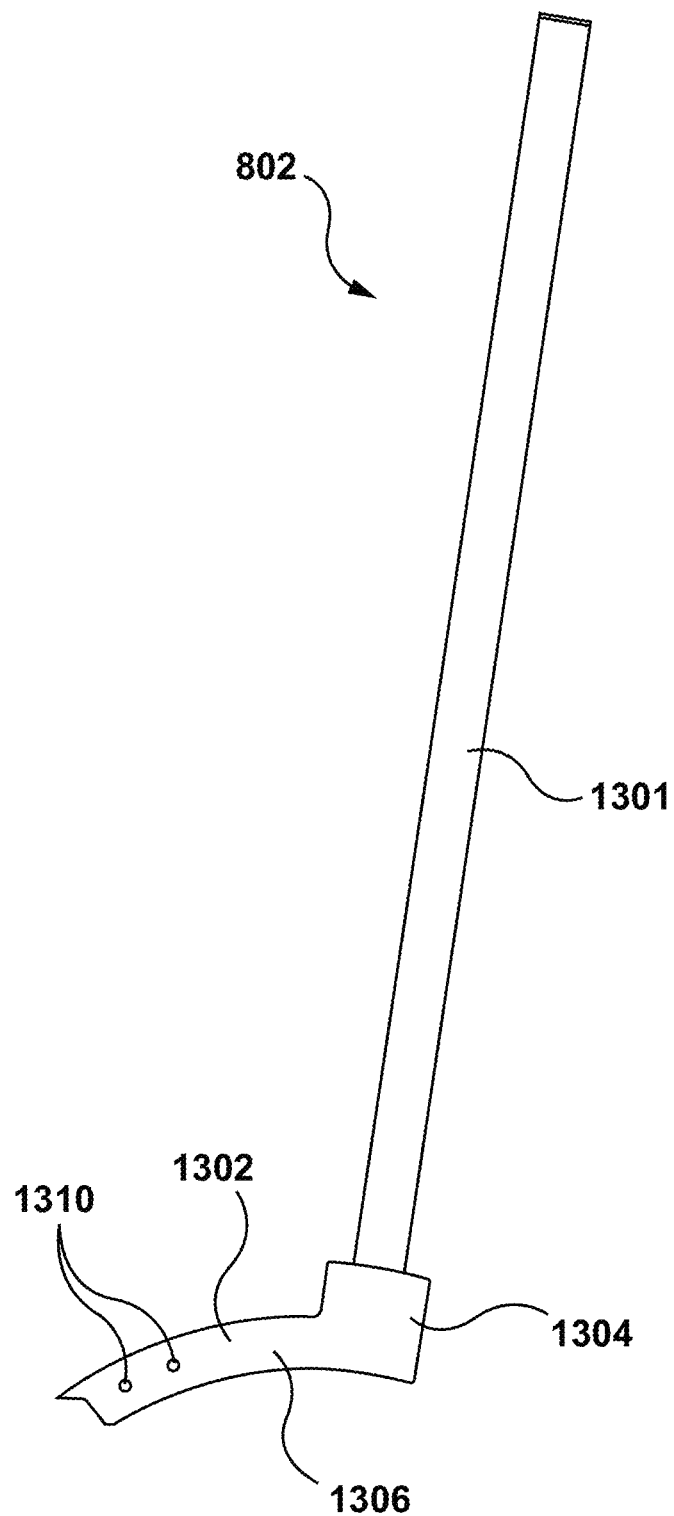
Figure 6C:
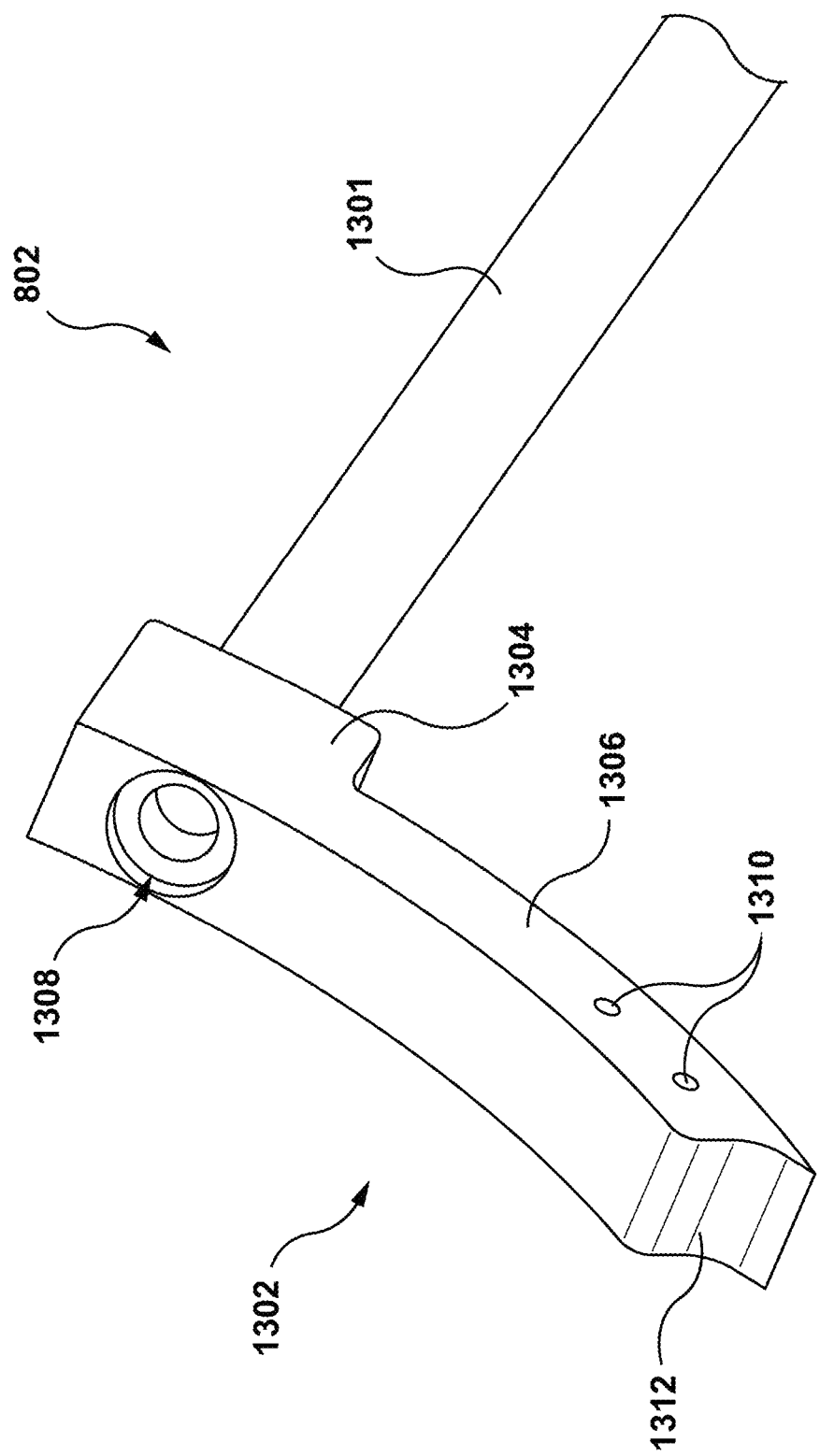

FIGS. 6A-6C illustrate detailed views of the handle 802, according to an embodiment hereof. One skilled in the art will realize that FIGS. 6A-6C illustrate one example of a handle and that existing components illustrated in FIGS. 6A-6C may be removed and/or additional components may be added to the handle 802.

As illustrated FIGS. 6A and 6B, which are a perspective view and a side view respectively, the handle 802 includes a handle bar 1301 and a handle base 1302. The handle base 1302 includes a handle bar connection member 1304 and atop cam connection member 1306. As illustrated in FIG. 3C, which is another perspective view of the handle 802, the handle bar connection member 1304 include a connection hole for receiving a portion of the handle bar 1301.

The top cam connection member 1306 includes connection holes 1310 for coupling the handle base 1302 to the top cam 824. The connection holes 1310 are configured to receive a connection device to couple the top cam connection member 1306 to the top cam 824. The connection device can be any type of device to couple the top cam connection member 1306 to the top cam 824 such as a bolt, screw, pin, etc.

FIGS. 8A-8F illustrate an example of a crimper 1500 in accordance with an embodiment hereof. One skilled in the art will realize that FIGS. 8A-8F illustrate one example of a crimper and that existing components illustrated in FIGS. 8A-8F may be removed and/or additional components may be added to the crimper 1500.

Figure 8B:
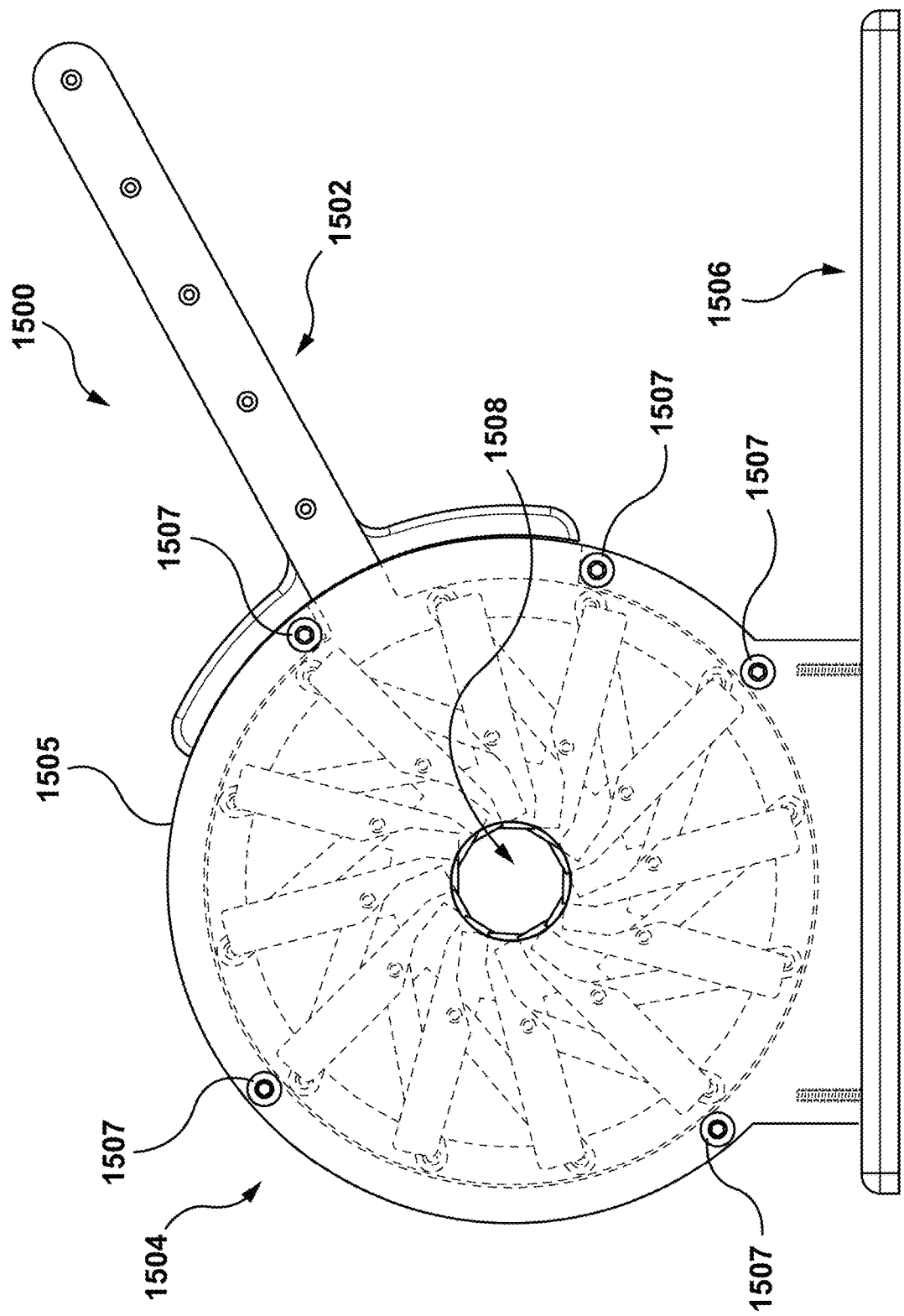

FIG. 8A is a first side view of a first side of the crimper 1500. As illustrated in FIG. 8A, the crimper 1500 includes a handle 1502, a crimper housing 1504, and a base 1506. The crimper housing 1504 includes a first side 1503 as illustrated in FIG. 8A and a second side 1505 positioned opposite the first side 1503 as illustrated in FIG. 8B, which is a second side view of the crimper 1500. The first side 1503 of the crimper housing 1504 can be coupled to the second side 1505 of the crimper housing 1504 by one or more connectors 1507. The connectors 1507 can be any type of device to couple the first side 1503 of the crimper housing 1504 to the second side 1505 of the crimper housing 1504 such as a bolt, screw, pin, etc.

The crimper housing 1504 includes an opening 1508 from a first side 1503 of the crimper housing 1504 to a second side 1505 of the crimper housing 1504. The opening 1508 can be formed in an approximate circular cross-sectional shape. The opening 1508 can allow access to a crimper chamber 1516 of the crimper 1500 as described in further detail below.

Figure 8C:
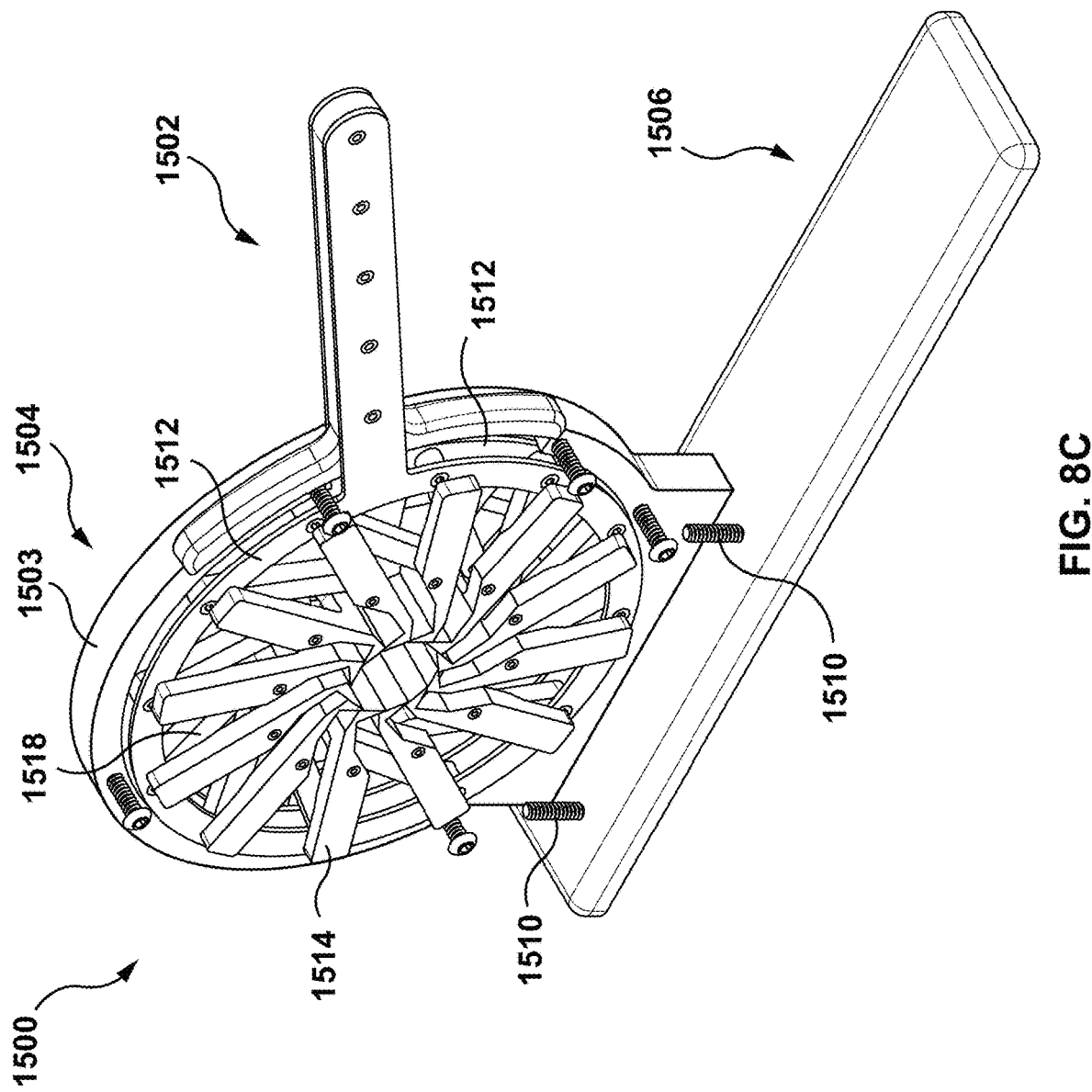
Figure 8D:
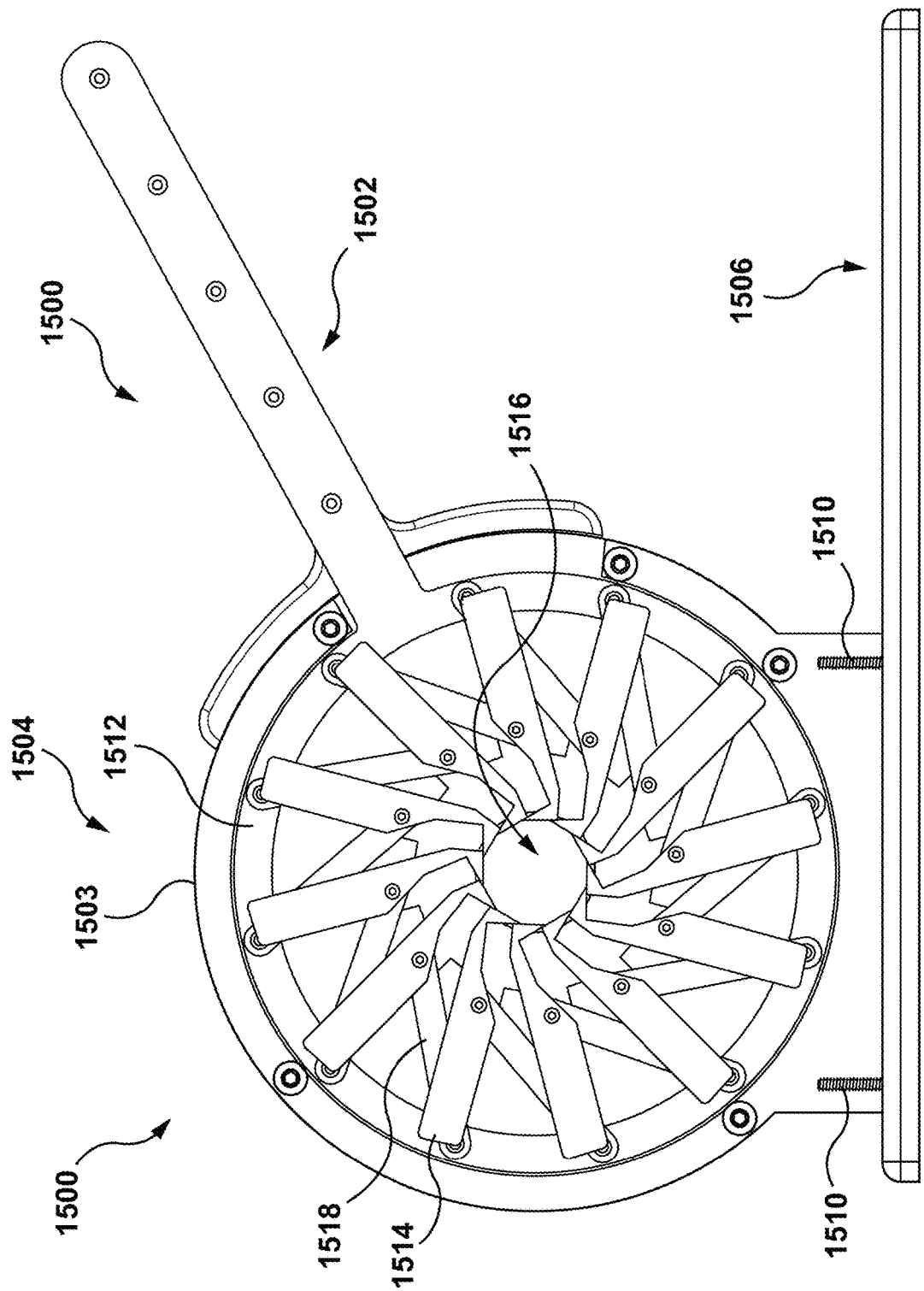

FIG. 8C and FIG. 8D illustrate a perspective view and a side view of the crimper 1500, respectively, in which the second side 1505 of the crimper housing 1504 has been removed to illustrate internal components of the crimper 1500. As illustrated, the handle 1502 extends into the crimper housing 1504 and includes two cams 1512. The cams 1512 are coupled to a plurality of crimper elements 1514 by rods 1518. The crimper elements 1514 form the crimper chamber 1516.

Figure 10A:
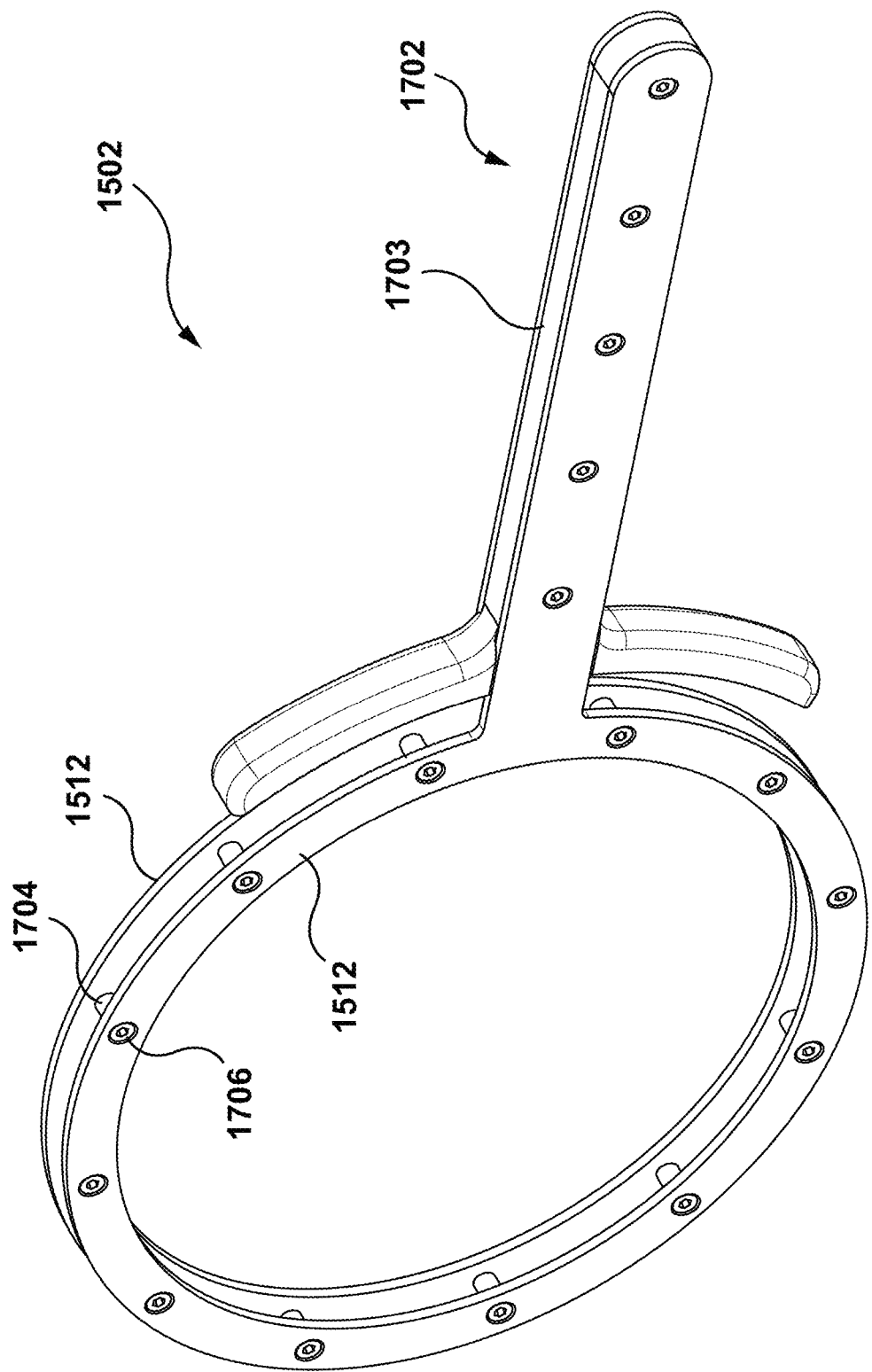
FIGS. 10A and 10B depict several views of a handle of the crimper of FIGS. 8A-8F, according to an embodiment hereof.
Figure 10B:
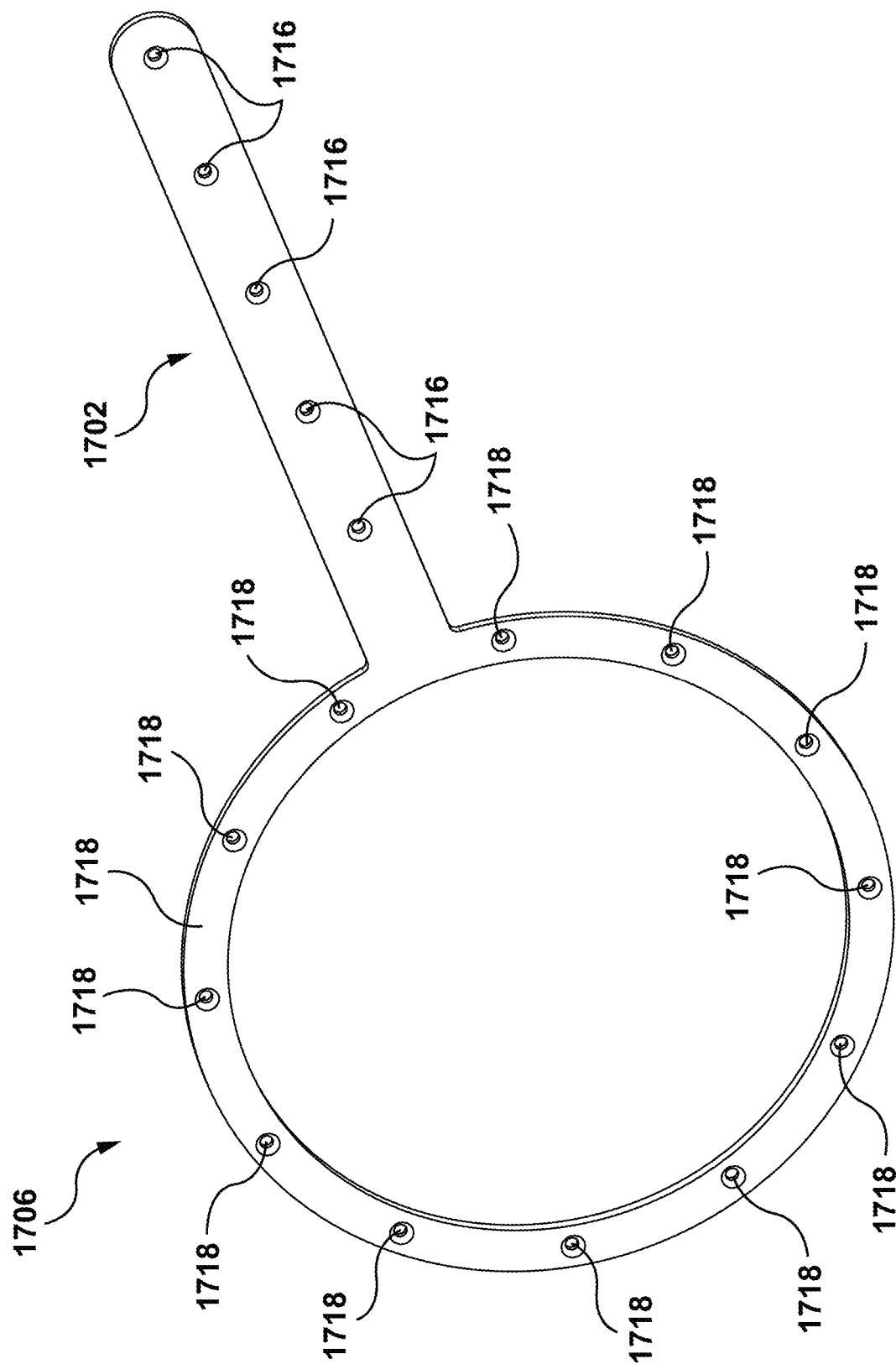

Each of the rods 1518 extends from the two cams 1512 to a middle region of one of the crimper elements 1514, as explained in further details with reference to FIGS. 10A and 10B. Each of the cams 1512 can be formed as a circular ring in which the rods 1518 are movably coupled between the two cams 1512. That is, when the two cams 1512 rotate in response to movement of the handle 1512, the rods 1518 are allowed to rotate relative to the two cams 1512. Likewise, the rods 1518 are rotatably coupled to the crimper elements 1514. That is, when the rods 1518 move in response to the rotation of the two cams 1512, the motion of the rods 1518 are translated to the crimper elements 1514, thereby causes linear motion of the crimper elements 1514. In embodiments, the crimper element 1514 can be configured and include components similar to those described above in FIGS. 3A-3D. Likewise, in embodiments, the rods 1518 can be configured and can include components similar to those described above in FIG. 4.

The two cams 1512 operate to translate the rotational movement of the handle 1502 to the crimper elements 1514 via the rods 1518. In operation, the crimper elements 1514 are displaced by the movement of the handle 1502. That is, as the handle 1502 is moved, the two cams 1512 rotate and the rods 1518 function to translate the rotational motion of the two cams 1512 into linear motion of the crimper elements 1514. As such, the crimper elements 1514 of the crimper housing 1504 function as an iris to decrease or increase the volume of the crimper chamber 1516 through the movement of the handle 1502, as described below in further detail. As illustrated in FIG. 8C, the crimper chamber 1516 can define a volume that approximates a cylinder. While the crimper chamber 1516 is described above as defining a cylindrically shaped volume, one skilled in the art will realize that the shape and dimension of the lobes can be changed to create a differently shaped volume as required by the implantable medical device being compressed and positioned.

As illustrated in any of FIGS. 8A-8D, the base 1506 of the crimper 1500 can be formed as a rectangular plate. The base 1506 can be formed to a width and length that extends beyond the length and width of the crimper housing 1504 and the handle 1502. The base 1506 provides a stable platform for operating the crimper 1500 during crimping procedures. As illustrated in FIGS. 8C and 8D, the crimper housing 1504 is coupled to the base 1506 by one or more connectors 1510. The connectors 1510 can be any type of device to couple the crimper housing 1504 to the base 1506 such as a bolt, screw, pin, etc.

In embodiments, the crimper 1500 operates to convert an implantable medical device from its uncompressed state to its compressed state. In operation, the implantable medical device is loaded into the crimper chamber 1516 and positioned in a direction that is parallel to the long axis of the base 1506. The delivery device can also be positioned and aligned relative to the implantable medical device. That is, the implantable medical device can be disposed around the delivery device. The handle 1502 is actuated to convert the implantable medical device from its uncompressed state to its compressed state and load the implantable medical device onto the delivery device.

Figure 8E:
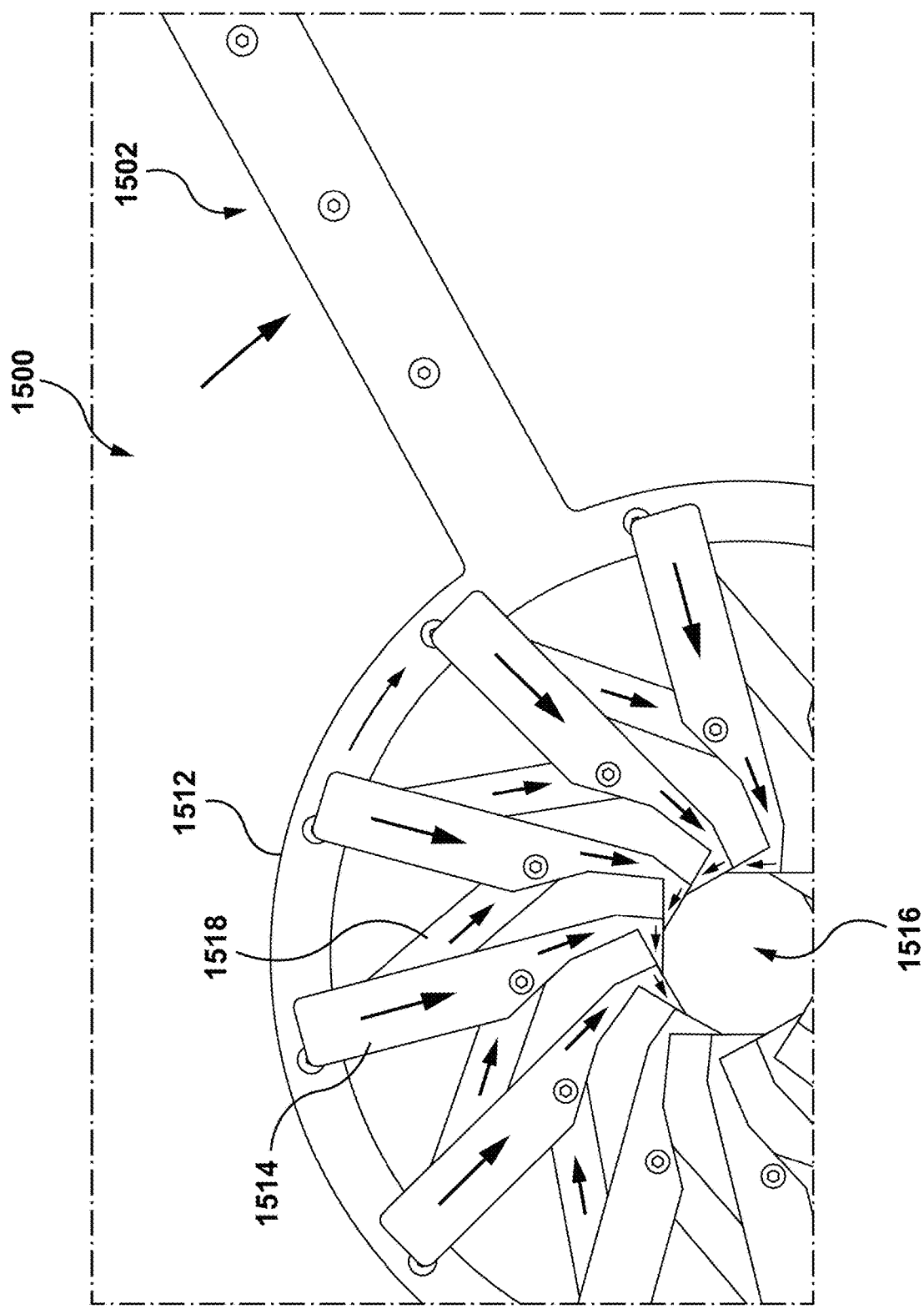
Figure 8F:
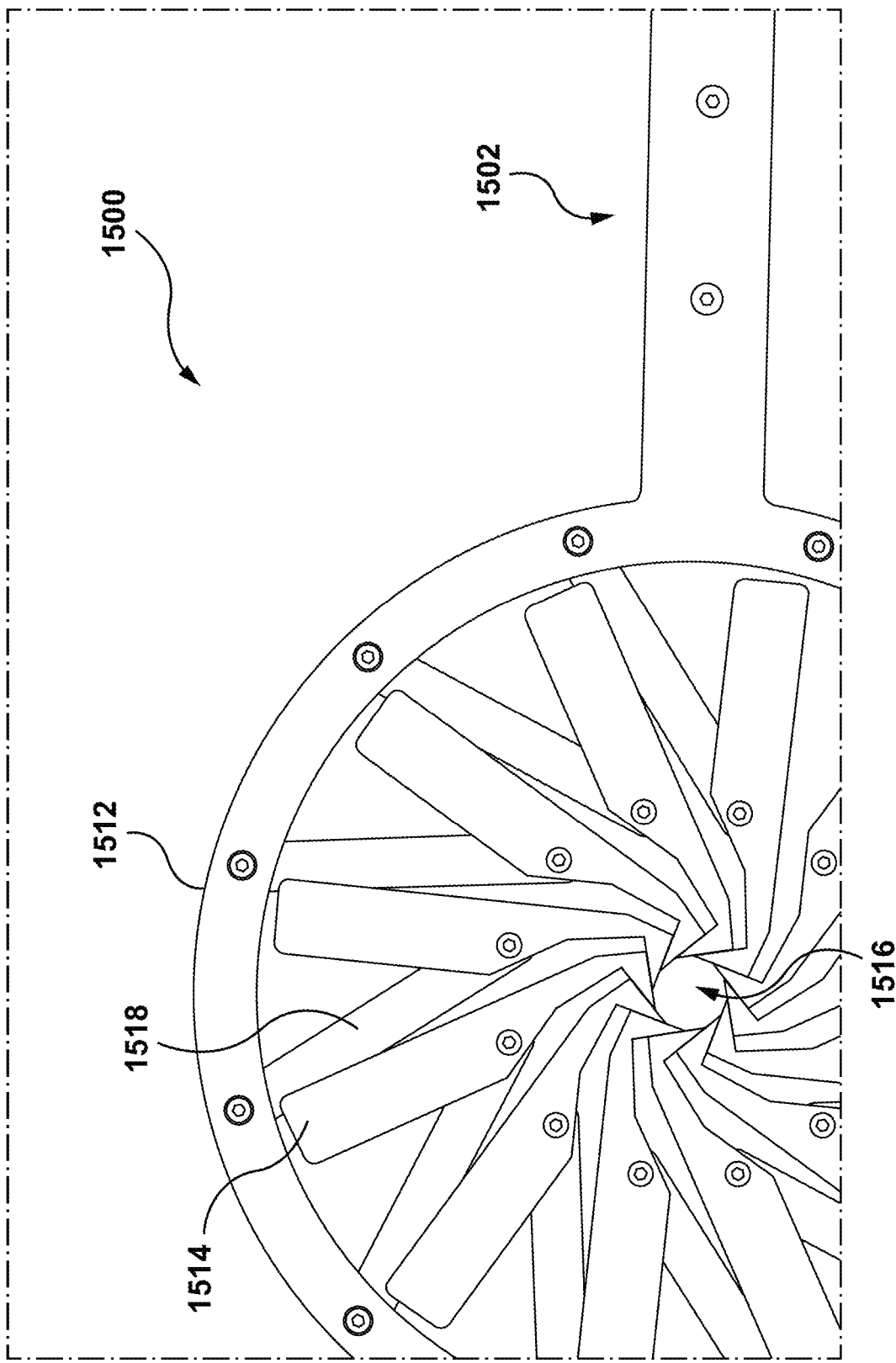

To operate the crimper 1500, a force can be applied to the handle 1502 in the direction of the base 1506. As illustrated in FIG. 8E (an enlarged view of the crimper 1500 with the crimper housing 1504 removed), when the force is applied, the two cams 1512 rotate in the direction that the force is applied to the handle 1502. Once the two cams 1512 rotate, the rotational movement of the two cams 1512 is translated to approximate linear motion by the rods 1518 and transferred to the crimper elements 1514. As illustrated in FIG. 8E, the overlap of the crimper elements 1514 define the crimper chamber 1516. During operation, for example, the handle 1502 being actuated in a downward motion (clockwise direction as illustrated in FIG. 8E) thereby causing the cams 1512 to rotate in a clockwise direction. Because each rod 1518 is fixed at one end to the cams 1512 and at the opposite end to one of the crimper elements 1514 (rotation is allowed), when the cams 1512 are rotated, the distance between the connection of the rod 1518 to the cams 1512 and the connection of the rod 1518 to the crimper element 1514 must remain the same. However, as the cams 1512 are rotated, that distance can only remain the same if the crimper element 1514 is pushed radially inward by the rods 1518, as shown by comparing FIG. 8E to FIG. 8F. Thus, rotation of cams 1512 forces the crimper elements 1514 inward via the rods 1518 inward. In particular, the crimper elements 1514 move inward generally towards the center of the crimper chamber 1516. As the crimper elements 1514 move inward, the space available for the crimper elements 1514 to occupy is reduced. As such, the space between the crimper elements 1514 is reduced, as described in further detail above with reference to FIG. 3E.

The crimper elements 1514 are displaced inward generating the iris effect. As such, the volume of the crimper chamber 1516 decreases and the crimper elements 1514 apply a compression force to external surfaces of the implantable medical device to crimp the expandable medical device from its uncompressed state to its compressed state. For example, if the implantable medical device is round or cylindrical in shape, the crimper elements apply a force on the surface of the implantable medical device from various directions as force is applied to the handle 1502 thereby compressing the implantable medical device.

The crimper 1500 can be utilized on any type of implantable medical device that requires a conversion from an uncompressed state to a compressed state. In an embodiment, the crimper can be applied to any implantable medical device that requires onsite crimping of the implanted medical device onto a catheter, e.g., organic tissue containing valve repair devices. In an embodiment, the crimper 1500 can be used with balloon-expandable medical devices and/or mechanically expandable medical devices.

For example, the crimper 1500 can be utilized on implantable medical devices that are to be delivered transluminally, e.g., via a catheter, and need to be loaded onto or into a catheter. In this example, the implantable medical device can include a heart valve prosthesis, which includes a stent or frame, and a prosthetic valve attached to the interior of the frame. The stent/frame may be crimped to have a low profile such that the prosthesis can be delivered through the vessels to a target location in a compressed state, and then expanded at the target location, by a balloon of the delivery device, for instance, to replace the native heart valve. For example, a heart valve prosthesis is typically loaded onto a delivery device or catheter at the time of the implantation procedure, e.g., at the hospital by hospital staff.

While the components of the crimper 1500 are described above with relative terms "first," "second," "proximal," and "distal," one skilled in the art will realize that the use of these terms is intended only to identify components of the crimper 1500 and do not define any preferred or ordinal arrangement of the components of the crimper 1500.

Figure 9A:
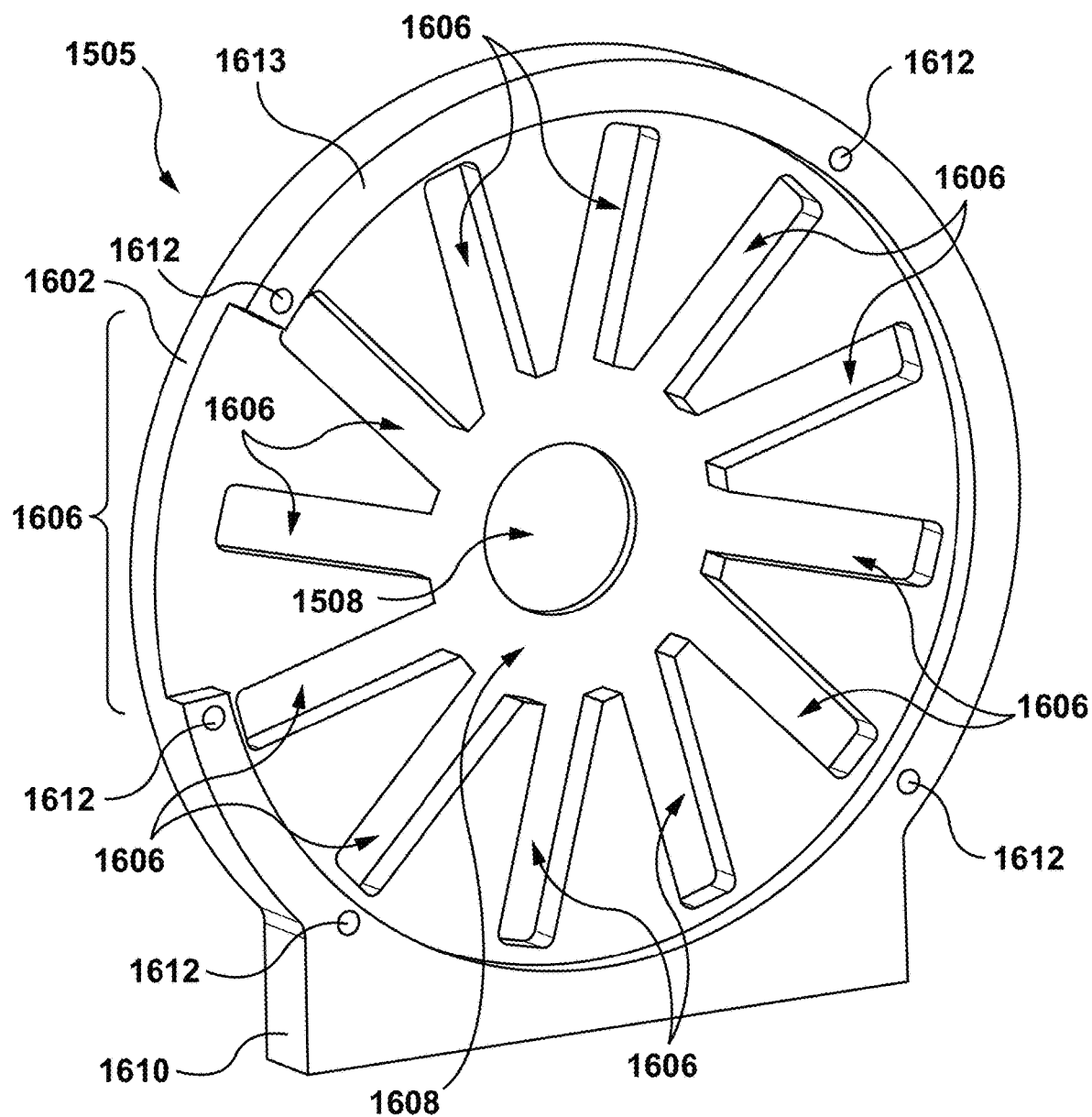
FIG. 9A depicts a perspective illustration of a side of a housing of the crimper of FIGS. 8A-8F, according to an embodiment hereof.
Figure 9B:
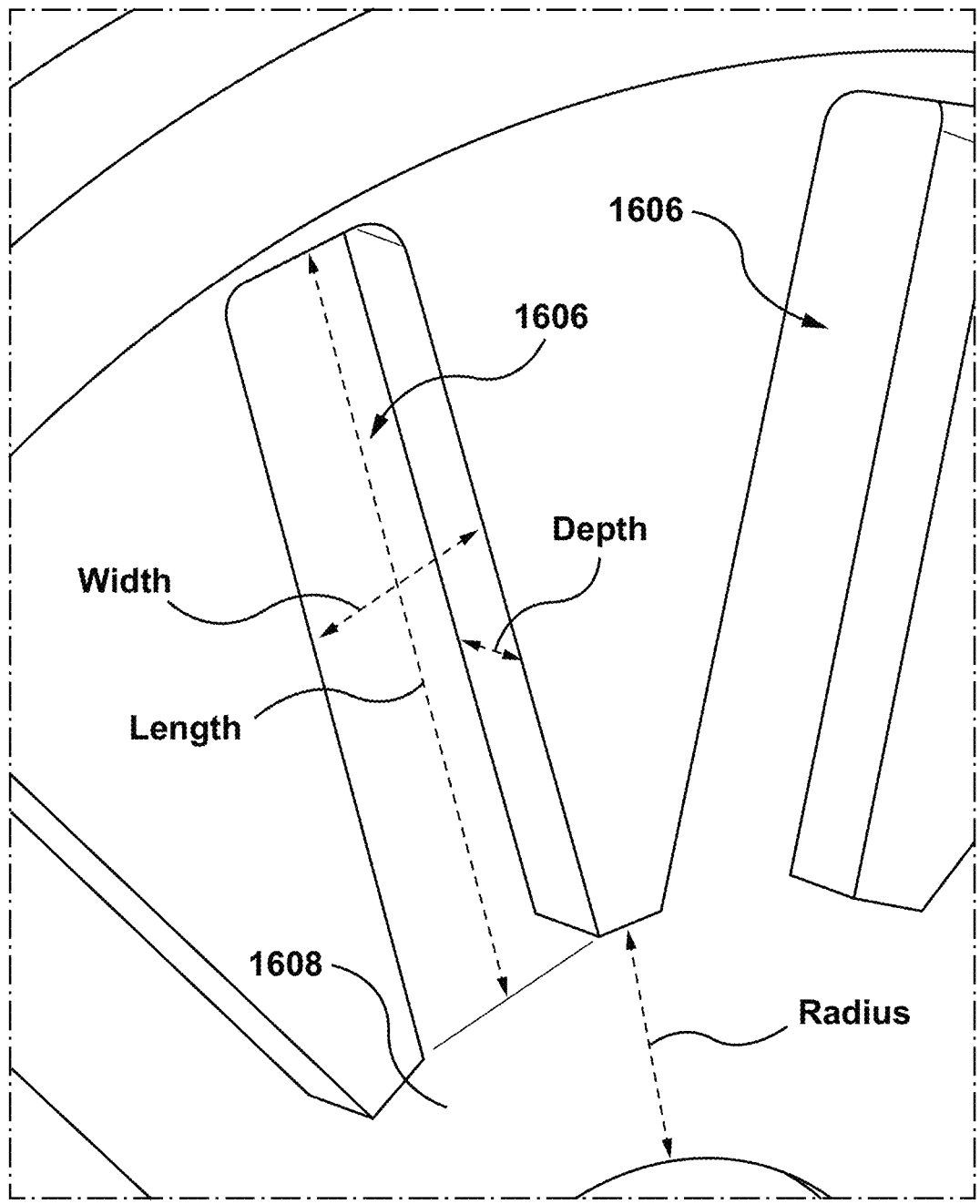
FIG. 9B depicts an enlarged portion of the perspective illustration of the side of the housing FIG. 9A, according to an embodiment hereof.

FIGS. 9A and 9B illustrate detailed views of components of the second side 1505 of the crimper housing 1504. One skilled in the art will realize that FIGS. 9A and 9B illustrate one example of a side of the crimper housing 1504 and that existing components illustrated in FIGS. 9A and 9B may be removed and/or additional components may be added to the second side 1505. Additionally, while the second side 1505 of the crimper housing 1504 is only discussed below, one skilled in the art will realize that crimper housing 1504 includes a first side that may include the same components as illustrated in FIGS. 9A and 9B. For example, the first side 1503 of the crimper housing 1504 may be formed as a "mirror" of the second side 1505 of the crimper housing 1504 and can be coupled to the second side 1505 to form the crimper housing 1504.

As illustrated in FIG. 9A, which is a perspective view, the second side 1505 of the crimper housing 1504 includes an interior surface 1602 and an exterior surface (not shown). In an embodiment, the second side 1505 can be constructed as a cylindrical plate with a base portion 1610 that is formed in an approximate partial rectangle shape. The second side 1505 can include the opening 1508. The cylindrical opening 1508 allows access to the crimper chamber 1516 formed by the crimper elements 1514. The second side 1505 also includes a handle opening 1604 that is formed by a handle stop 1613 that extends from the interior surface 1602 of the second side 1505. The handle stop 1613 can extend in an arc partially around the circumference of the interior surface 1602 of the second side 1505 thereby forming the handle opening 1604. The handle stop 1613 can operate as a stop in both the clockwise and counter-clockwise direction for the handle 1502 when the handle 1502 is moved.

Crimper element channels 1606 are formed in the interior surface 1602 of the second side 1505. The crimper element channels 1606 can be formed as a rectangular groove or channel that extends from inward from an outer radius of the second side 1505 towards the opening 1508. The crimper element channels 1606 can be positioned in an arc, at equal distances, along the interior surface 1602 of the second side 1505. The crimper element channels 1606 are coupled to a center cavity 1608 formed in the interior surface 1602 of the second side 1505. The center cavity 1608 can be formed as a circular cavity having approximately the same depth as the crimper element channels 1606.

The crimper element channels 1606 and the center cavity 1608 can be configured to moveably secure the crimper elements 1514 within the crimper housing 1504. As illustrated in FIG. 9B, which is an enlarged perspective view of the crimper element channels 1606 and a portion of the center cavity 1608, the crimper element channels 1606 of the second side 1505 are formed to a width and depth to accommodate the crimper elements 1514 when the second side 1505 of the crimper housing 1504 is mated with the first side 1503 of the crimper housing 1504. In embodiments, the second side 1505 of the crimper housing 1504 can be formed to a configuration and dimensions as described above with reference to FIGS. 2A-2C.

FIGS. 10A and 10B illustrate detailed views of the handle 1502, according to an embodiment hereof. One skilled in the art will realize that FIGS. 10A and 10B illustrate one example of a handle and that existing components illustrated in FIGS. 10A and 10B may be removed and/or additional components may be added to the handle 1502.

As illustrated in FIG. 10A, which is a perspective view of the handle 1502, the handle 1502 includes a handle bar 1702 that is coupled to the two cams 1512. In embodiment, the handle bar 1702 can be formed as an integrated extension of the cams 1512. The handle bar 1702 can include a spacer member 1703 that is coupled between the sides of the handle bar 1702. Likewise, the two cams 1512 can be coupled by spacers 1704 and pins 1706. The spacers 1704 and pins 1706 serve as a connection point for the rods 1518. For example, the spacers 1704 and pins 1706 can pass through a second of the connection holes 1104 of a rod 1518, as similarly described above with reference to a rod 826. In some embodiments, a pin 1706 can be a dowel pin, a bolt, and the like. In some embodiments, a spacer 1704 can be a hollow cylindrical tube and the like.

As illustrated in FIG. 10B, which is a side view of one of the cams 1512 and handle bar 1702, the handle bar 1702 can include connection holes 1716. The connection holes 1716 can be configured to receive pins that couple the spacer member 1703 between the sides of the handle bar 1702. The cam 1512 can also include connection holes 1718 for receiving the pins 1706. Additionally, while one of the cams 1512 is discussed below with reference to FIG. 10B, one skilled in the art will realize that both cams 1512 may include the same components as illustrated in FIG. 10.

FIGS. 11A-11D illustrate an example of the operation of the crimper 1500 in accordance with an embodiment hereof. One skilled in the art will realize that FIGS. 11A-11D illustrate one example of the operation of the crimper 1500 and that existing components illustrated in FIGS. 11A-11D may be removed and/or additional components may be added to the crimper 1500 without departing from the scope of the present invention. Additionally, one skilled in the art will realize that FIGS. 11A-11D illustrate only a few operating states in order to illustrate the operation of the crimper 1500, and will realize that the crimper 1500 can assume other operational states without departing from the scope of the present invention.

Figure 11B:
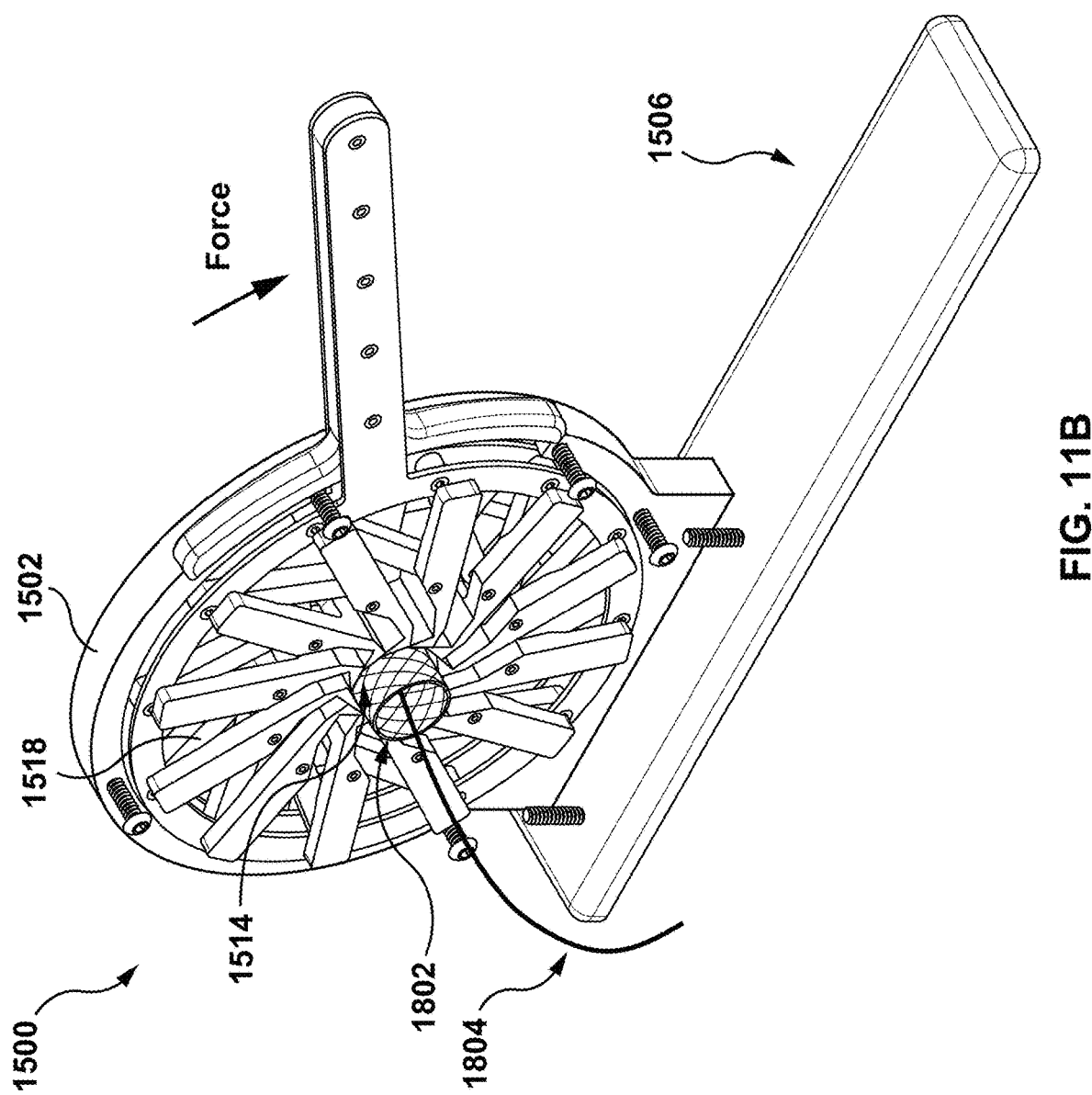

As illustrated in FIG. 11A, which is a side view, and FIG. 11B, which is a perspective view with the second side 1505 removed, an implantable medical device 1802 and a delivery device 1804 can be loaded into the crimper chamber 1516 of the crimper housing 1504. For example, an implantable medical device 1802 can be placed in crimper chamber 1516 of the crimper housing 1504. Likewise, the delivery device 1804 can be positioned relative to the implantable medical device 1802.

Figure 11C:
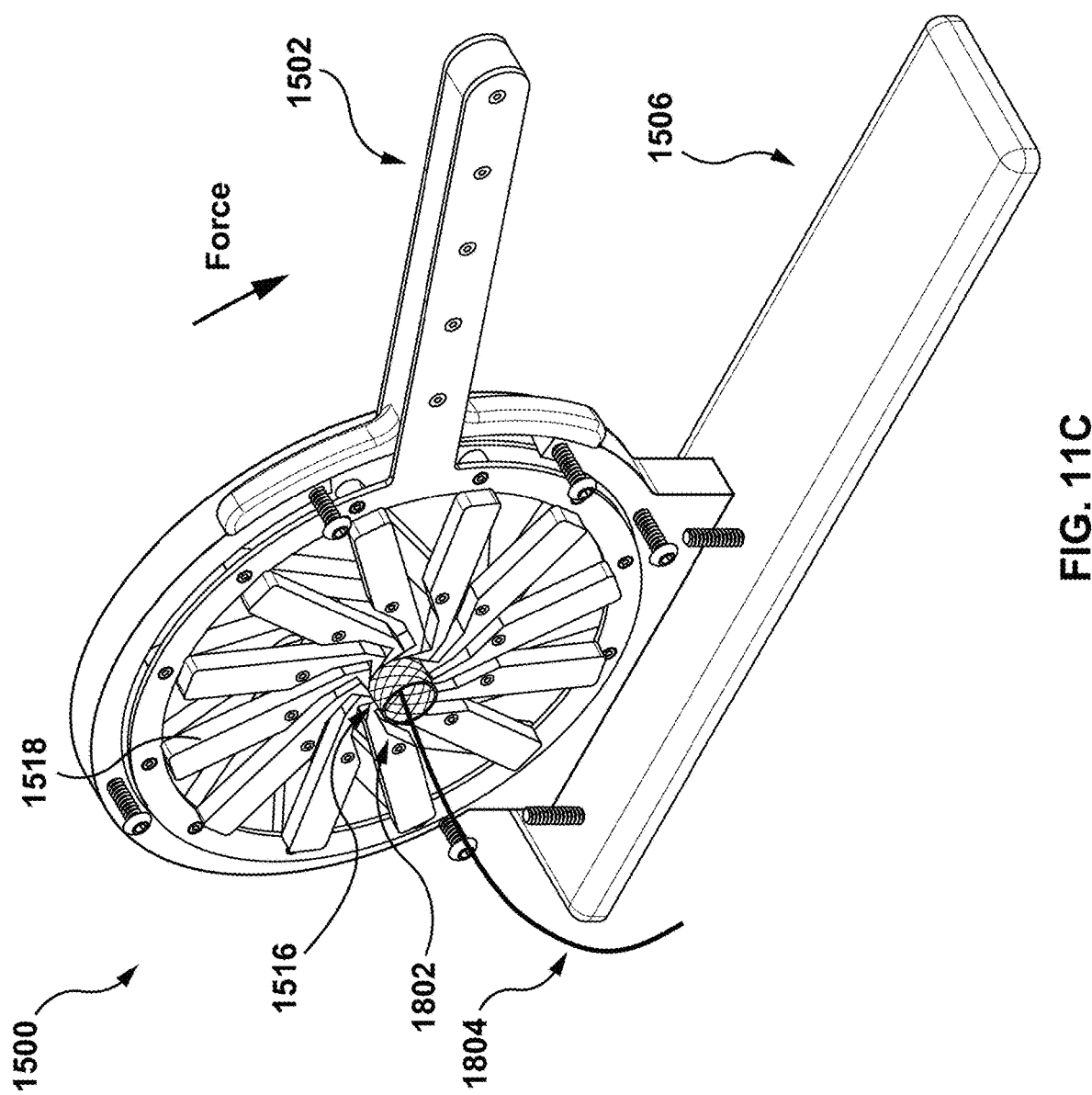

As illustrated in FIG. 11B, the crimper elements 1514 form the crimper chamber 1516. As illustrated in FIGS. 11C and 11D, to compress the medical device 1802, a force is applied to the handle 1102 in the direction of the base 1106. In response, the two cams 1512 rotate in a clockwise direction. As the cam 1512 rotates, force is applied to the crimper elements 1514 through the rods 1518. Due to the shape of the connection channels, the crimper elements 1514 displace inward, e.g., each crimper element 1514 slides along the interior ramps of a neighboring crimper element 1514. As such, the displacement of the crimper elements 1514 inward creates an iris effect thereby decreasing the volume of the crimper chamber 1516. As the volume of the crimper chamber 1516 decreases, the crimper elements 1514 apply a compression force to external surfaces of the medical device 1802 to crimp alter the medical device 1802 from its uncompressed state to its compressed state.

Figure 12A:
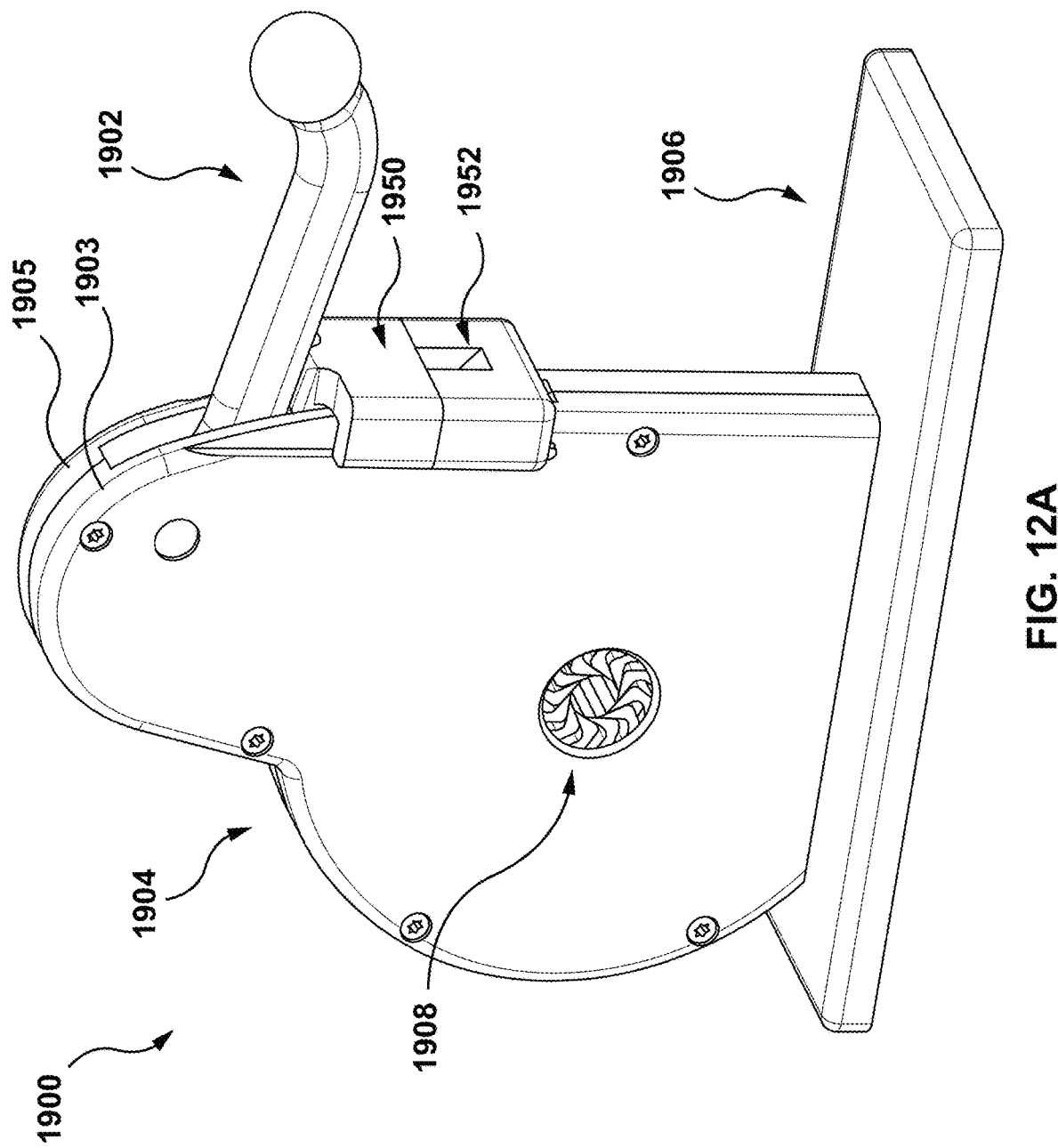
FIGS. 12A and 12B depict different views of another example of a crimper for use with a medical device, according to an embodiment hereof.
Figure 12B:
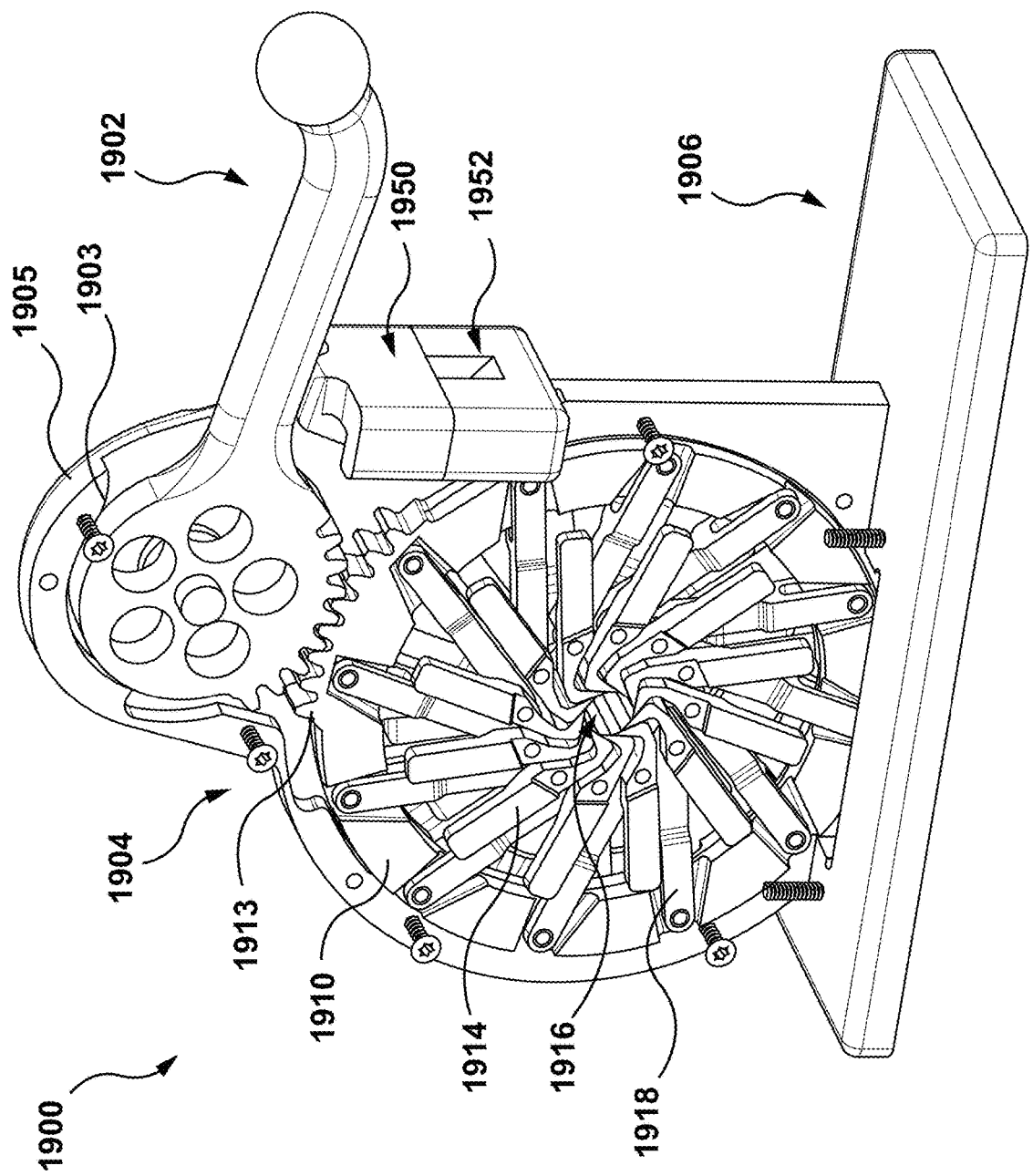

FIGS. 12A and 12B illustrate another example of a crimper 1900 in accordance with an embodiment hereof. One skilled in the art will realize that FIGS. 12A and 12B illustrate one example of a crimper and that existing components illustrated in FIGS. 12A and 12B may be removed and/or additional components may be added to the crimper 1900.

FIG. 12A is a perspective view of the crimper 1900. As illustrated in FIG. 12A, the crimper 1900 includes a handle 1902, a crimper housing 1904, and a base 1906. The crimper housing 1904 includes a first side 1903 and a second side 1905 positioned opposite the first side 1903. The first side 1903 of the crimper housing 1904 can be coupled to the second side 1905 of the crimper housing 1904 by one or more connectors 1907. The connectors 1907 can be any type of device to couple the first side 1903 of the crimper housing 1904 to the second side 1905 of the crimper housing 1904 such as a bolt, screw, pin, etc.

The crimper housing 1904 includes an opening 1908 from a first side 1903 of the crimper housing 1904 to a second side 1905 of the crimper housing 1904. The opening 1908 can be formed in an approximate circular cross-sectional shape. The opening 1908 can allow access to a crimper chamber 1916 of the crimper 1900 as described in further detail below.

FIG. 12B illustrates a perspective view of the crimper 1900 in which the first side 1903 of the crimper housing 1904 has been removed to illustrate internal components of the crimper 1900. As illustrated, the crimper 1500 includes a cam 1910. The handle 1902 extends into the crimper housing 1904 and includes a gear 1912. The gear 1912 is coupled to the cam 1910 at a gear portion 1913 of the cam 1910. In other words, the gear 1912 of the handle 1902 includes teeth that mate with teeth of the gear portion 1013 of the cam 1910. The crimper housing 1904 also includes a plurality of crimper elements 1914. The cam 1910 is coupled to a plurality of crimper element 1914 by rods 1918. The crimper elements 1914 form the crimper chamber 1916.

Each of the rods 1918 extends from the cam 1910 to a middle region of one of the crimper elements 1914, as explained in further detail with reference to FIGS. 15A, 15B, and 16A-16D. The cam 1910 can be formed as a circular ring to which the rods 1918 are rotatably coupled. That is, when the cam 1910 rotates in response to movement of the handle 1912, the rods 1918 are allowed to rotate relative to the cam 1910. Likewise, the rods 1918 are rotatably coupled to the crimper elements 1914. That is, when the rods 1918 move in response to the rotation of the cam 1910, the crimper elements 1914 are allowed to rotate relative to the rods 1918. In some embodiments, the crimper elements 1914 can be configured and can include components similar to those described above in FIGS. 3A-3D. In some embodiments, the rods 1918 can be configured and can include components similar to those described above in FIG. 4. In some embodiments, the crimper elements 1914 can be configured and can include components as described below in FIGS. 16A-16D. Likewise, in some embodiments, the rods 1918 can be configured and can include components as described below in FIGS. 15A and 15B.

The cam 1910 operates to translate the rotational movement of the handle 1902 to the crimper elements 1914 via the rods 1918. In operation, the crimper elements 1914 are displaced by the movement of the handle 1902. That is, as the handle 1902 is moved, the cam 1910 rotates and functions to translate the rotational motion of the handle 1902 into linear motion of the crimper elements 1914 via the rods 1918. As such, the crimper elements 1914 of the crimper housing 1904 function as an iris to decrease or increase the volume of the crimper chamber 1916 through the movement of the handle 1902, as described below in further detail. As illustrated in FIG. 12B, the crimper chamber 1916 can define a volume that approximates a cylinder. While the crimper chamber 1916 is described above as defining a cylindrical shaped volume, one skilled in the art will realize that the shape and dimension of the lobes can be changed to create a differently shaped volume as required by the implantable medical device being compressed and positioned.

As illustrated in FIGS. 12A and 12B, the base 1906 of the crimper 1900 can be formed as a rectangular plate. The base 1906 can be formed to a width and length that extends beyond the length and width of the crimper housing 1904 and the handle 1902. The base 1906 provides a stable platform for operating the crimper 1500 during crimping procedures. The crimper housing 1904 is coupled to the base 1906 by one or more connection devices 1920. The connection devices 1920 can be any type of device to couple the crimper housing 1904 to the base 1906 such as a bolt, screw, pin, etc.

In embodiments, the crimper 1900 operates to convert an implantable medical device from its uncompressed state to its compressed state. In operation, the implantable medical device is loaded into the crimper chamber 1916 and positioned in a direction that is parallel to the long axis of the base 1906. The delivery device can also be positioned and aligned relative to the implantable medical device. The crimper 1900 is then moved from the open state to the closed state, and the handle 1902 is actuated to convert the implantable medical device from its uncompressed state to its compressed state and load the implantable medical device onto the delivery device. To operate the crimper 1900, a force can be applied to the handle 1902 in the direction of the base 1906. When the force is applied, the cam 1910 rotate in the direction that is opposite to the force is applied to the handle 1902. For example, the handle 1902 can be actuated in a downward motion thereby causing the cam 1912 to rotate in a clockwise direction. In response, causing the cam 1910 to rotate in a clockwise direction. Because each rod 1918 is fixed at one end to the cam 1910 and at the opposite end to one of the crimper elements 1914 (rotation is allowed), when the cam 1910 is rotated, the distance between the connection of the rod 1918 to the cam 1910 and the connection of the rod 1918 to the crimper element 1914 must remain the same. However, as the cam 1910 is rotated, that distance can only remain the same if the crimper element 1914 is pushed radially inward by the rods 1918. Thus, rotation of the cam 1910 forces the crimper elements 1914 inward via the rods 1918 inward. In particular, the crimper elements 1914 move inward generally towards the center of the crimper chamber 1516.

As the crimper elements 1914 move inward, the space available for the crimper elements 1914 to occupy is reduced. As such, the space between the crimper elements 1914 is reduced. As such, the volume of the crimper chamber 1916 decreases and the crimper elements 1914 apply a compression force to external surfaces of the implantable medical device to crimp the expandable medical device from its uncompressed state to its compressed state. For example, if the implantable medical device is round or cylindrical in shape, the crimper elements apply a force on the surface of the implantable medical device from various directions as force is applied to the handle 1902 thereby compressing the implantable medical device. The operation of the crimper 1900 is explained in further detail below with reference to FIGS. 17A-17D.

The crimper 1900 can be utilized on any type of implantable medical device that requires a conversion from an uncompressed state to a compressed state. In an embodiment, the crimper can be applied to any implantable medical device that requires onsite crimping of the implanted medical device onto a catheter, e.g., organic tissue containing valve repair devices. In an embodiment, the crimper 1900 can be used with balloon-expandable medical devices and/or mechanically expandable medical devices. For example, the clamshell crimper 1900 can be utilized on implantable medical devices that are to be delivered transluminally, e.g., via a catheter, and need to be loaded onto or into a catheter. In this example, the implantable medical device can include a heart valve prosthesis, which includes a stent or frame, and a prosthetic valve attached to the interior of the frame. The stent/frame may be crimped to have a low profile such that the prosthesis can be delivery through the vessels to a target location in a compressed state, and then expanded at the target location, by a balloon of the delivery device, for instance, to replace the native heart valve.

As illustrated in FIG. 12B, the crimper 1900 also include a first stop 1950 and a second stop 1952. The first stop 1950 and the second stop 1952 provide a surface that stop the movement of the handle 1902 in the downward direction. The first stop 1950 and the second stop 1952 provide a stop position of the handle 1902 that corresponding to a predetermined diameter of the crimper chamber 1916. That is, the first stop 1950 and the second stop 1952 operate a physically stops to allow an implantable medical device to be compressed to a predetermined diameter or compression. For example, the first stop 1950 can operate to allow an implantable medical device to be partially compressed. Likewise, for example, the second stop 1952 can operate to allow an implantable medical device to be fully compressed. The first stop 1950 and the second stop 1952 can be removably coupled to the crimper housing 1904. As such, the first top 1950 and/or the second stop 1952 can be added and/or removed to allow an implantable medical device to be compressed to predetermined diameters.

While the components of the crimper 1900 are described above with relative terms "first," "second," "proximal," and "distal," one skilled in the art will realize that the use of these terms is intended only to identify components of the crimper 1900 and do not define any preferred or ordinal arrangement of the components of crimper 1900.

FIGS. 13A-13D illustrate a detailed view of components of the second side 1905 of the crimper housing 1904. One skilled in the art will realize that 13A-13D illustrate one example of a side of the crimper housing 1904 and that existing components illustrated in FIGS. 13A-13D may be removed and/or additional components may be added to the second side 1905. Additionally, while the second side 1905 of the crimper housing 1904 is only discussed below, one skilled in the art will realize that crimper housing 1904 includes a first side that may include the same components as illustrated in FIGS. 13A-13D. For example, the first side 1903 of the crimper housing 1904 may be formed as a "mirror" of the second side 1905 of the crimper housing 1904 and can be coupled to the second side 1905 to from the crimper housing 1904.

Figure 13A:
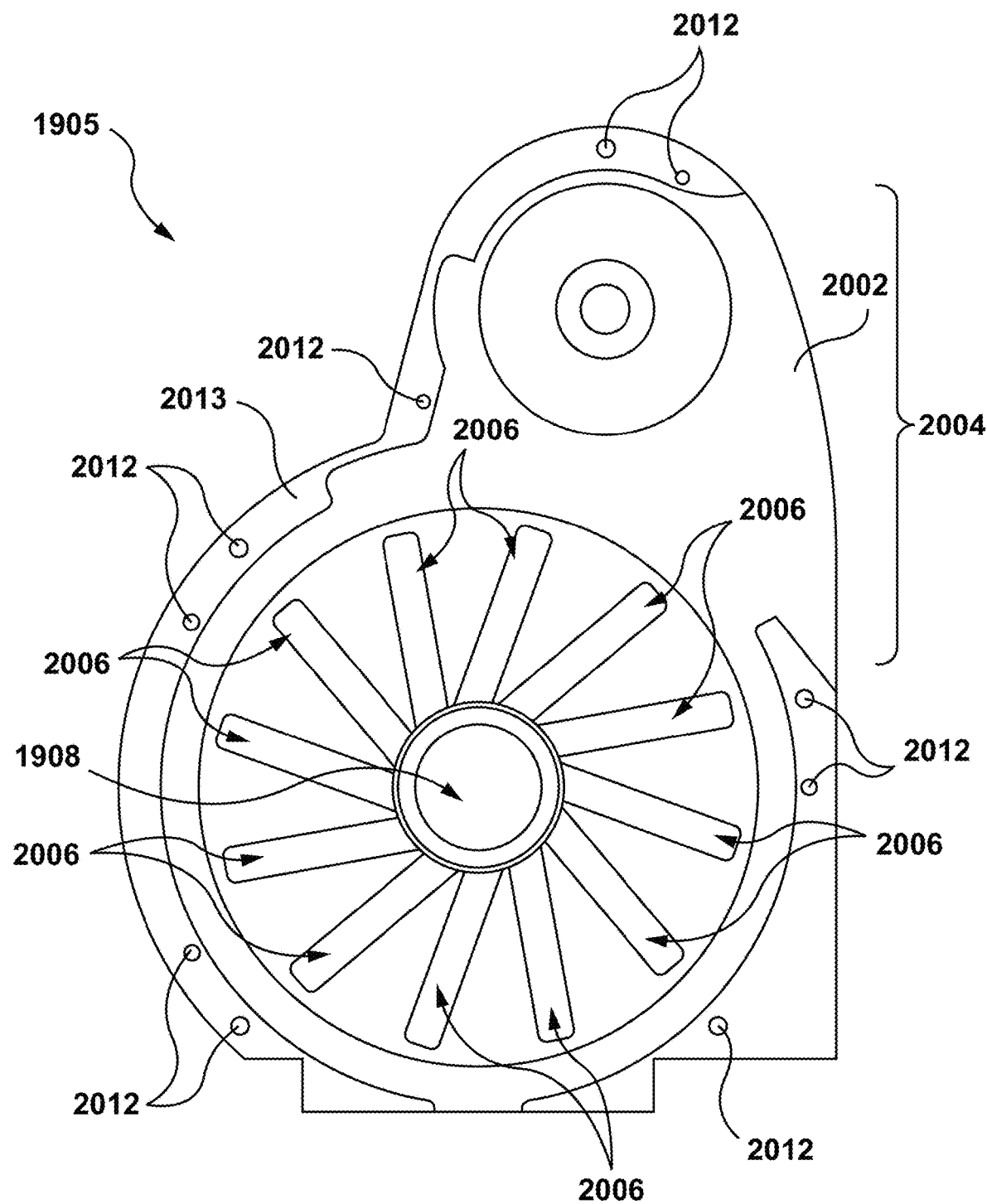
FIGS. 13A and 13B depict perspective illustrations of a side of a housing of the crimper of FIGS. 12A and 12B, according to an embodiment hereof.
Figure 13B:
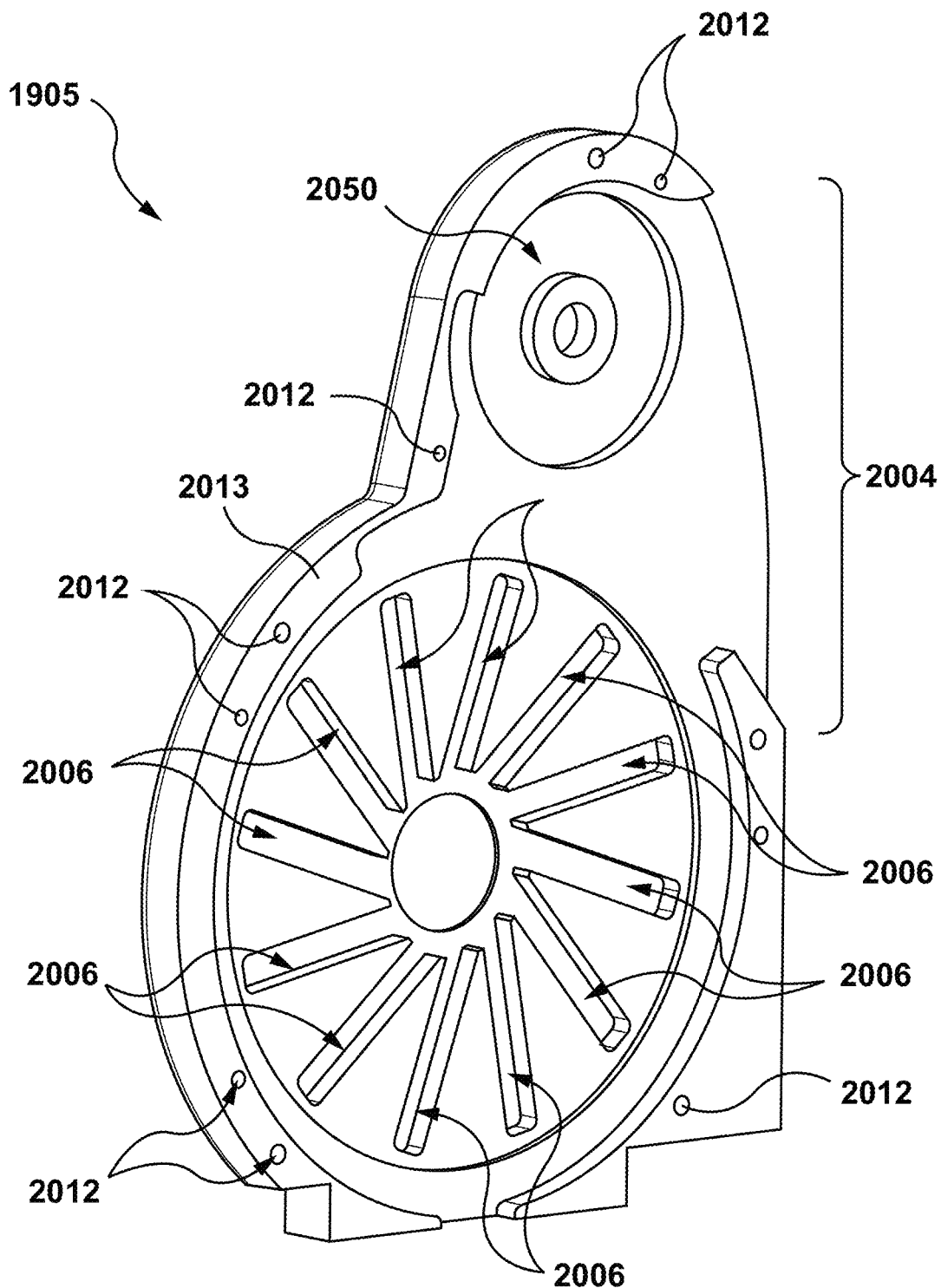

As illustrated in FIG. 13A, which is a cross-sectional side view, and FIG. 13B, which is a perspective view, the second side 1905 of the crimper housing 1904 includes an interior surface 2002 and an exterior surface (not shown). In an embodiment, the second side 1905 can be constructed as a cylindrical plate with a base portion 2010 that is formed in an approximate square shape. The second side 1905 can include the opening 1908. The cylindrical opening 1908 allows access to the crimper chamber 1916 formed by the crimper elements 1914. The second side 1905 also includes a handle opening 2004 that is formed by a handle stop 2013 that extends from the interior surface 2002 of the second side 1905. The handle stop 2013 can extend partially around the perimeter of the interior surface 2002 of the second side 1905 thereby forming the handle opening 2004. The handle stop 2013 can operate as a stop in both the clockwise and counter-clockwise direction for the handle 1902 when the handle 1902 is moved. The handle opening 2004 is also configured to receive the first stop 1950 and the second stop 1952.

Crimper element channels 2006 are formed in the interior surface 2002 of the second side 1905. The crimper element channels 2006 can be formed as a rectangular groove or channel that extends from inward from an outer radius of the second side 1905 towards the opening 1908. The crimper element channels 2006 can be positioned in an arc, at equal distances, along the interior surface 2002 of the second side 1905. The crimper element channels 2006 are coupled to a center cavity 2008 formed in the interior surface 2002 of the second side 1905. The center cavity 2008 can be formed as a circular cavity having the approximately same depth as the crimper element channel 2006.

Figure 13C:
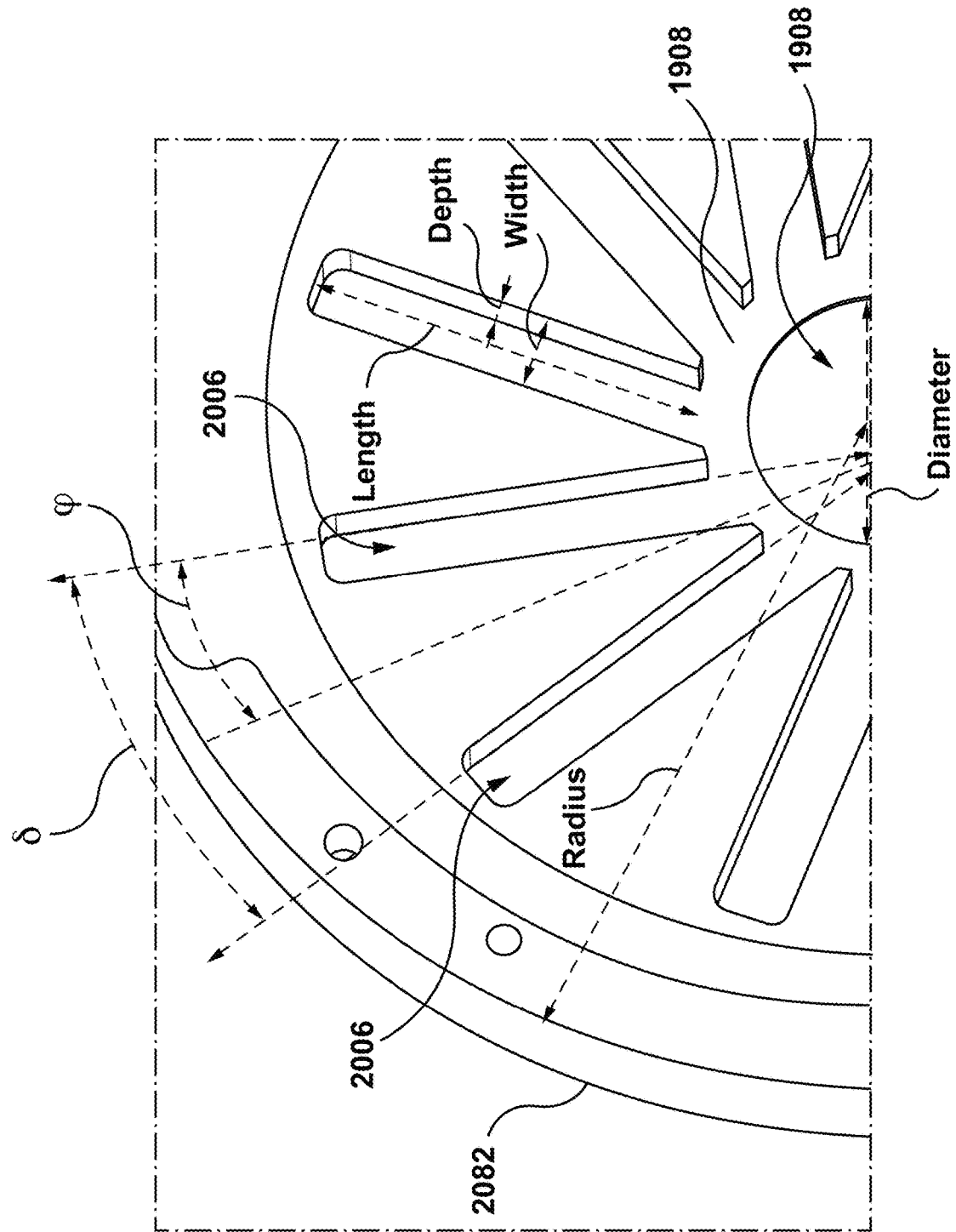
FIGS. 13C and 13D depict enlarged portions of the perspective illustration of the side of the housing FIGS. 13A and 13B, according to an embodiment hereof.
Figure 13D:
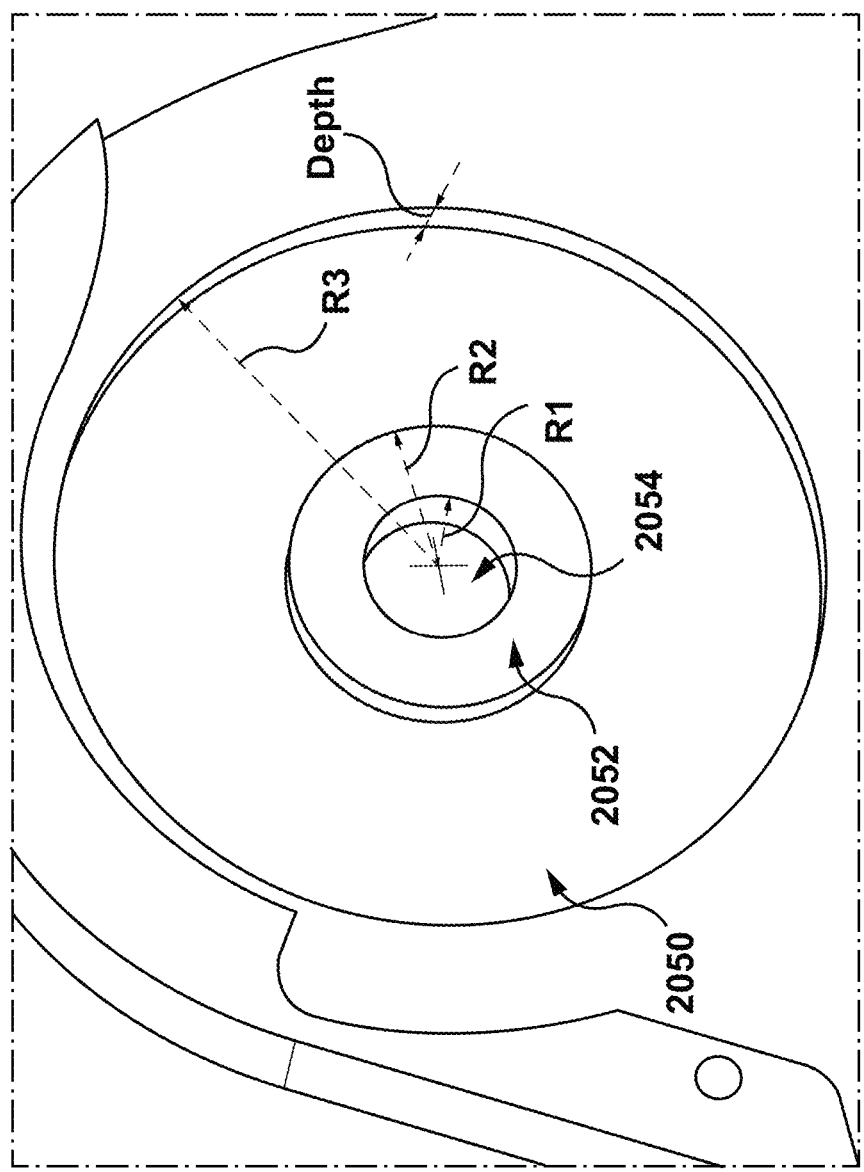

The crimper element channels 2006 and the center cavity 2008 can be configured to moveably secure the crimper elements 1914 within the crimper housing 1904. As illustrated in FIG. 13C, which is an enlarged perspective view of the crimper element channels 2006 and a portion of the center cavity 2008, the crimper element channels 2006 of the second side 1905 are formed to a width and depth to accommodate the crimper elements 1914 when the second side 1905 of the crimper housing 1904 is mated with the first side 1903 of the crimper housing 1904. As illustrated in FIG. 13C, the side plate 1902 is formed having a radius that extends from a center point 2080 of the opening 1908 to a side surface 2082 of the second side 1905.

In embodiments, the radius can be formed to a length that accommodates the crimper elements 1914 and allows for movement of the crimper elements 1914 within the crimper housing 1904. In embodiments, the crimper element channels 2006 of the second side 1905 are formed to a width and depth to accommodate the crimper elements 1914 when the second side 1905 of the crimper housing 1904 is mated with the first side of the crimper housing 1904. Likewise, the crimper element channels 2006 of the second side 1905 are formed to a length and the center cavity 2008 is formed to a radius that allows the crimper elements 1914 to move and perform the crimping operations of the crimper 1900.

As noted above, the crimper element channels 2006 are formed in an arc around the second side 1905. In embodiments, each of the crimper element channels 2006 are spaced in the arc at an angle, δ, from an adjacent crimper element channel 2006. In embodiments, each of the crimper element channels 2006 can be aligned to be offset relative to the radius of the second side 1905 by an angle, φ. The offset can cause the crimper elements 1914 to move in a direction that is offset from the center point 2080. In some embodiments, the angle, φ, can range between approximately 0 degrees and 30 degrees.

Figure 14A:
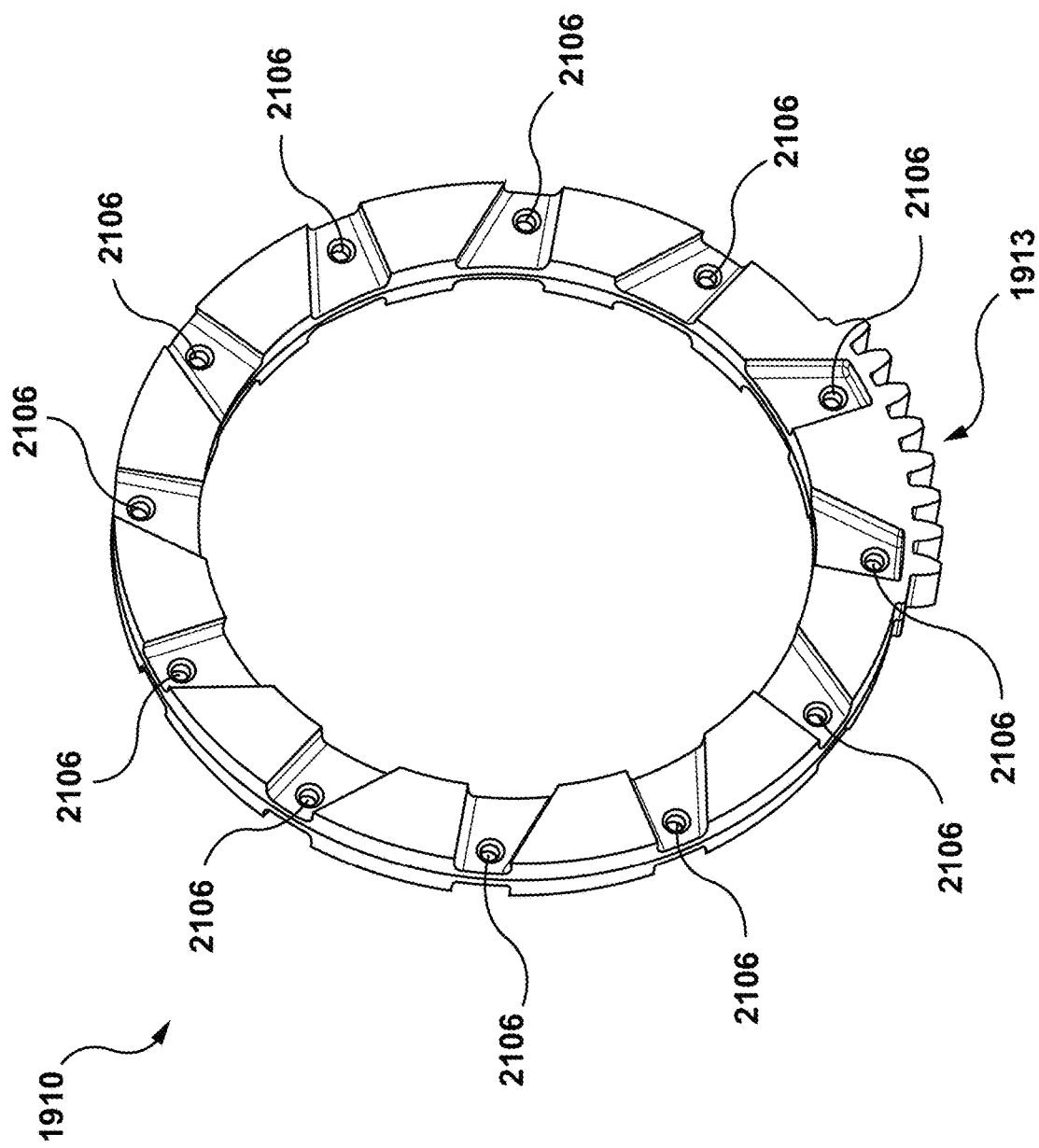
FIGS. 14A and 14B depict several views of a cam of the crimper of FIGS. 12A and 12B, according to an embodiment hereof.
Figure 14B:
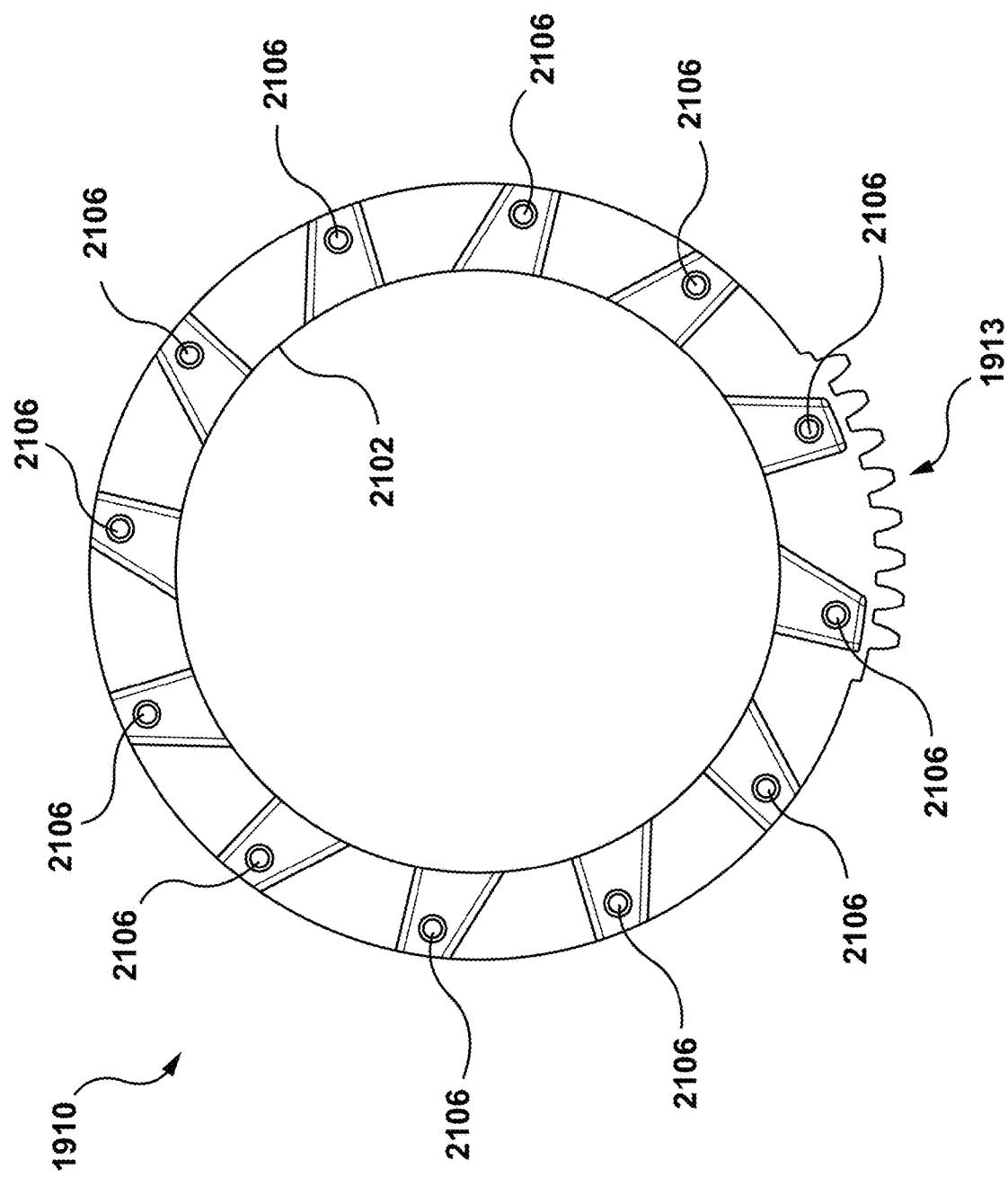

FIGS. 14A and 14B illustrate a detailed view of the cam 1910, according to an embodiment hereof. One skilled in the art will realize that FIGS. 14A and 14B illustrate one example of a cam and that existing components illustrated in FIGS. 14A and 14B may be removed and/or additional components may be added to the cam 1910.

As illustrated in FIG. 14A, which is a perspective view, and FIG. 14B, which is a side view, the cam 1910 include one or more rod channels 2102. Each of the rod channels 2102 include a connection hole 2106. The connection hole 2106 is configured to receive a pin that couples the cam 1910 to connections holes of a rod 1918. The connection hole 2106 can be configured to receive a pin that passes through the connection holes of the rod 1918. For example, the pin can be a dowel pin, a bolt, and the like. The rod channel 2102 can also be configured to limit rotational movement of the rods 1918. The cam 1910 also include the gear 1913 that is configured to engage with the gear 1912 of the handle 1902.

Figure 15A:
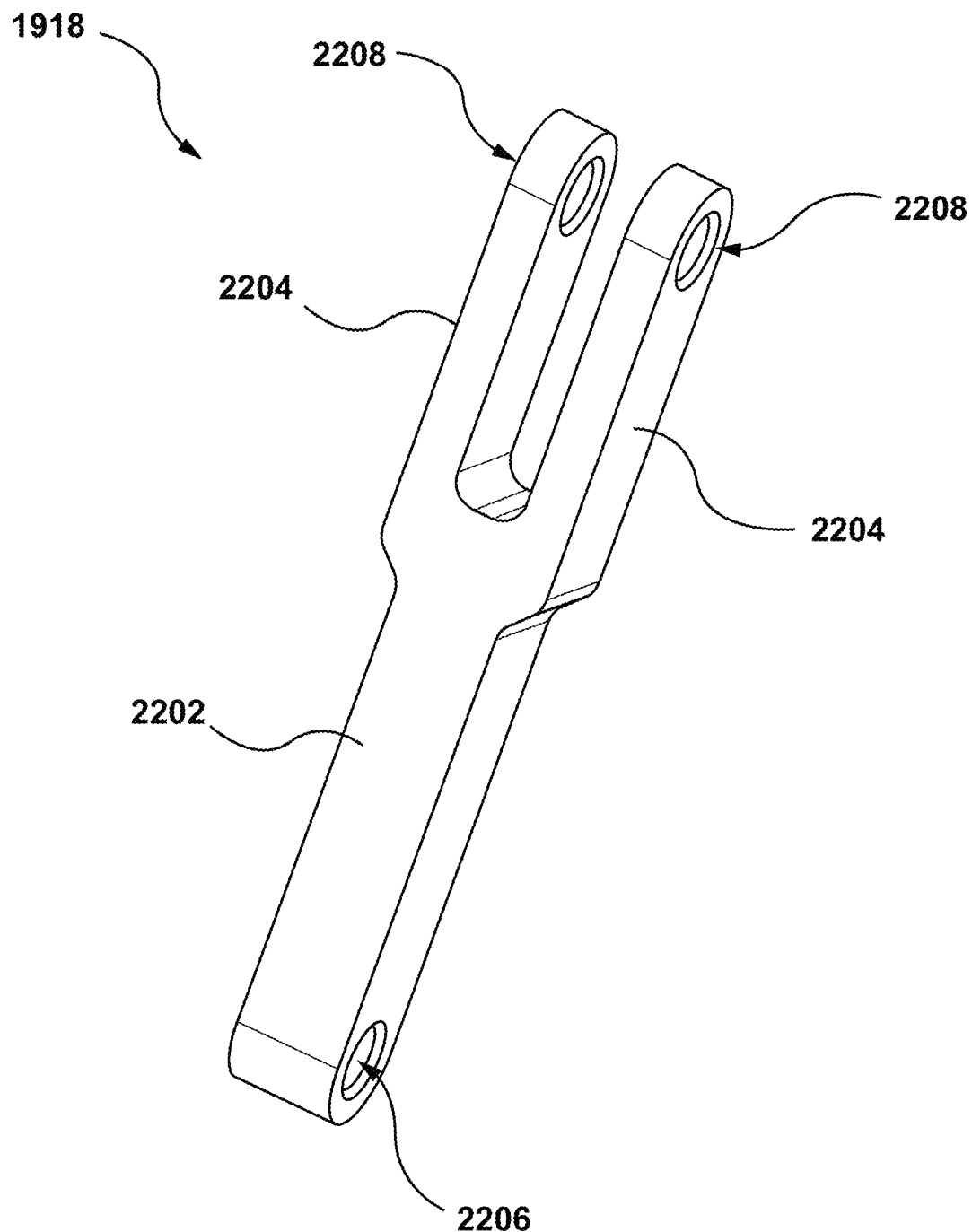
FIGS. 15A and 15B depicts a several views of a rod of FIGS. 12A and 12B, according to embodiment hereof.
Figure 15B:
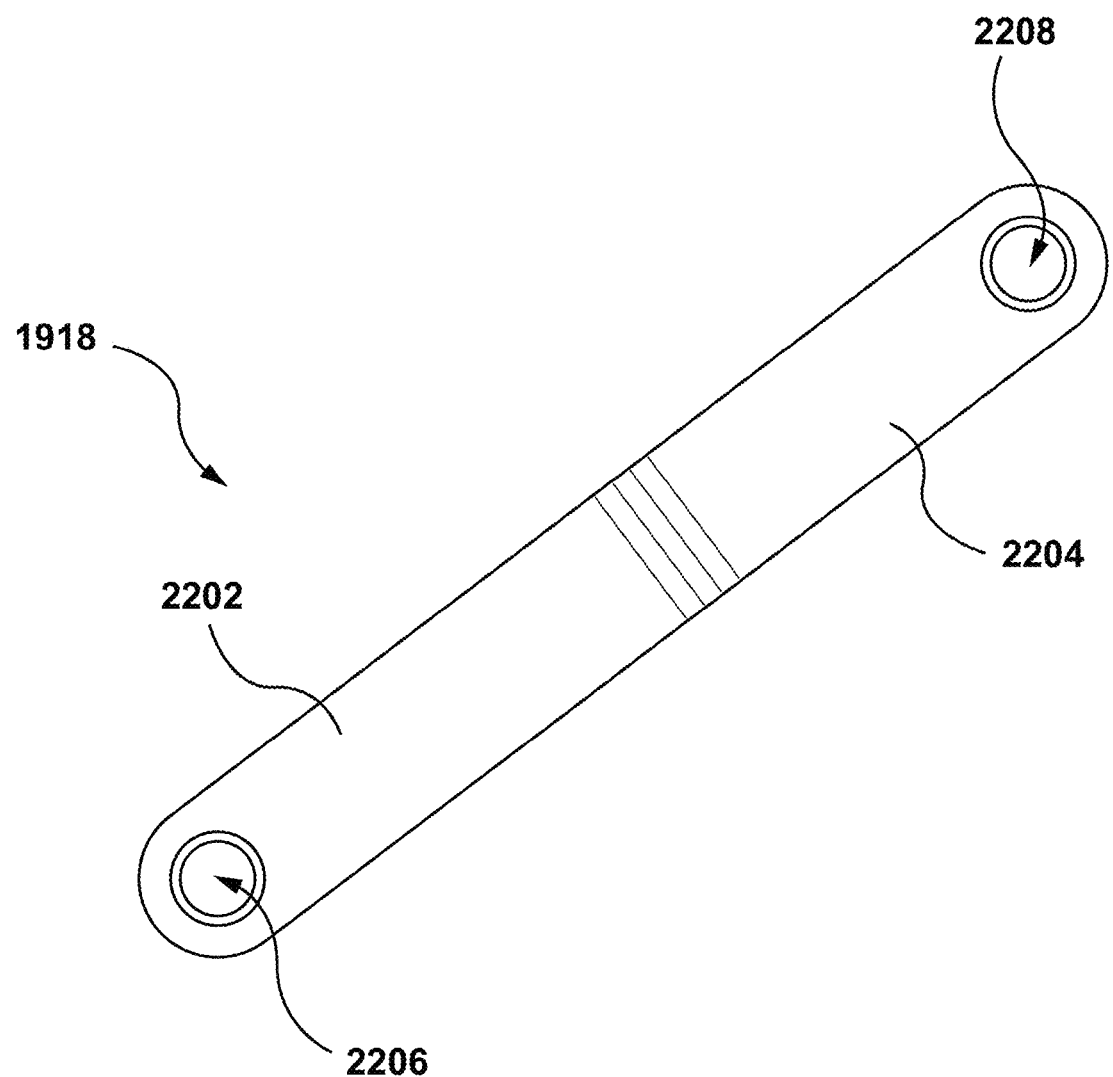

FIGS. 15A and 15B illustrates an example of a rod 1918. As illustrated, the rod 1918 is formed as a rectangular bar 2202 that is coupled to two parallel legs 2204. The rectangular bar 2202 include a connection hole 2206. The rectangular bar 2202 can include rounded ends 1106 that are formed in a semi-cylindrical shape. The connection hole 2206 operates to moveably couple the crimper elements 1914 to the rod 1918. In embodiments, the connection hole 2206 aligns with the connection holes of the crimper element 1914. The connection hole 2206 can be configured to receive a pin that passes through two connection holes of the crimper element 1914. For example, the pin can be a dowel pin, a bolt, and the like. The pin can be formed to a diameter to maintain the corresponding circular openings and cause the pin to operate as a fulcrum.

In embodiments, the legs 2204 can each include a connection hole 2208. The connection holes 2208 align with a connection hole 2106 of the cam 1910, described above. The connection holes 2208 can be configured to receive a pin that passes through the connection hole 2106 of the cam 1910. For example, the pin can be a dowel pin, a bolt, and the like. The pin can be formed to a diameter to maintain the corresponding circular openings and cause the pin to operate as a fulcrum. When cam 1910 rotates clockwise or counterclockwise, the combination of the pin and the connection holes 2208 allow the rod 1918 to rotate about the pin, as limited by the rod channel 2102.

FIGS. 16A-16D illustrate a detailed view of a crimper element 1914, according to an embodiment hereof. One skilled in the art will realize that FIGS. 16A-16D illustrate one example of a crimper element and that existing components illustrated in FIGS. 16A-16D may be removed and/or additional components may be added to the crimper element 1914. While only one crimper element 1914 is discussed, one skilled in the art will realize that the any of the crimper elements 1914 of the crimper 1900 may have the same configuration and include the same components as the crimper element 1914 described in FIGS. 16A-16D.

Figure 16A:
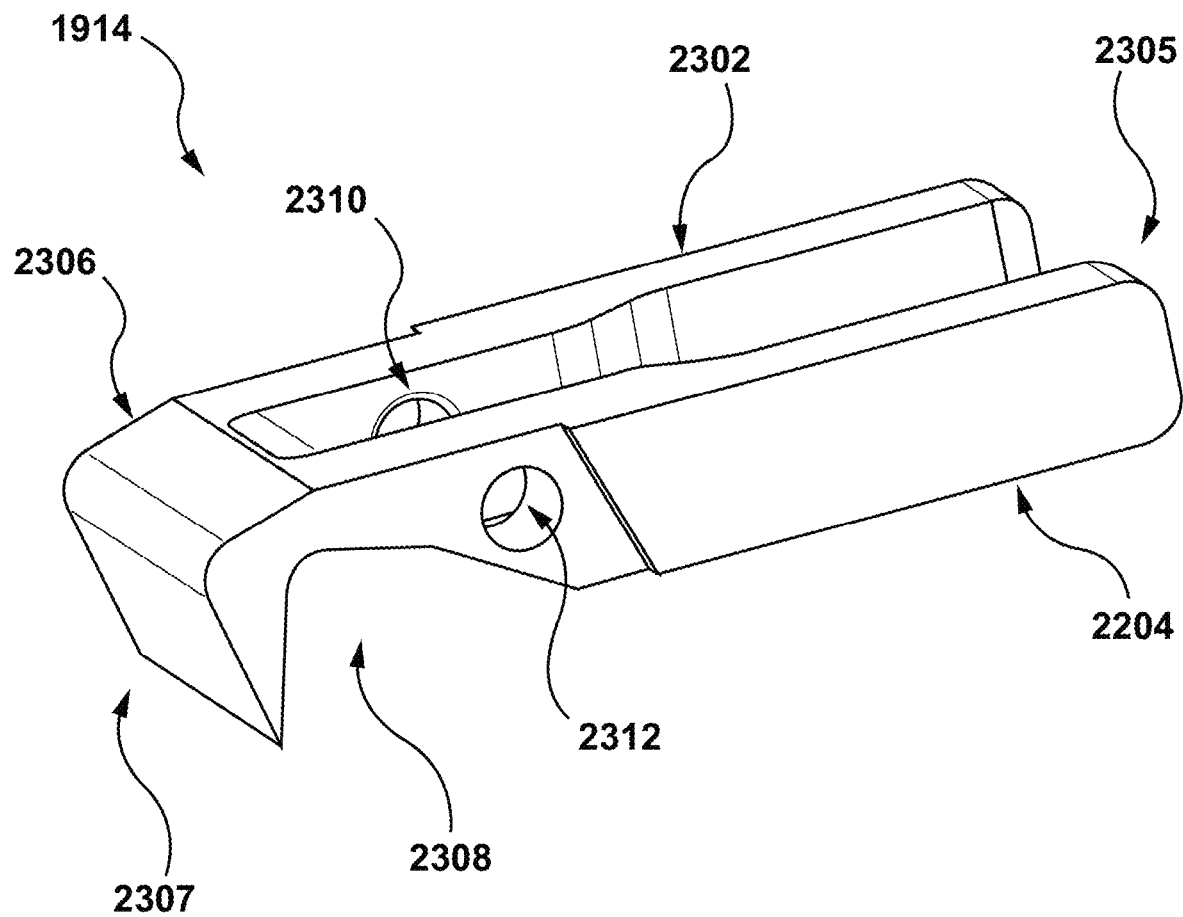
FIG. 16A-16D depict several views of a crimper element of FIGS. 12A and 12B, according to an embodiment hereof.

As illustrated in FIG. 16A, which is a perspective view, the crimper element 1914 has a first leg 2302, a second leg 2304, and a crimper lobe 2306 coupled to the first leg 2302 and the second leg 2304. The first leg 2302 and the second leg 2304 extend, parallel to a long axis of the crimper element 2314, from a proximal end 2305 of the crimper element 1914 to the crimper lobe 2306. The first leg 2302 and the second leg 2304 are spaced apart and define a rod channel 2310. The crimper lobe 2306 extends from the first leg 2302 and the second leg 2304 to a distal end 2307 of the crimper element 1914. The crimper lobe 2306 is configured to define a crimper space 2308. The crimper space 2308 is configured to accommodate an adjacent crimper element 1914.

Figure 16B:
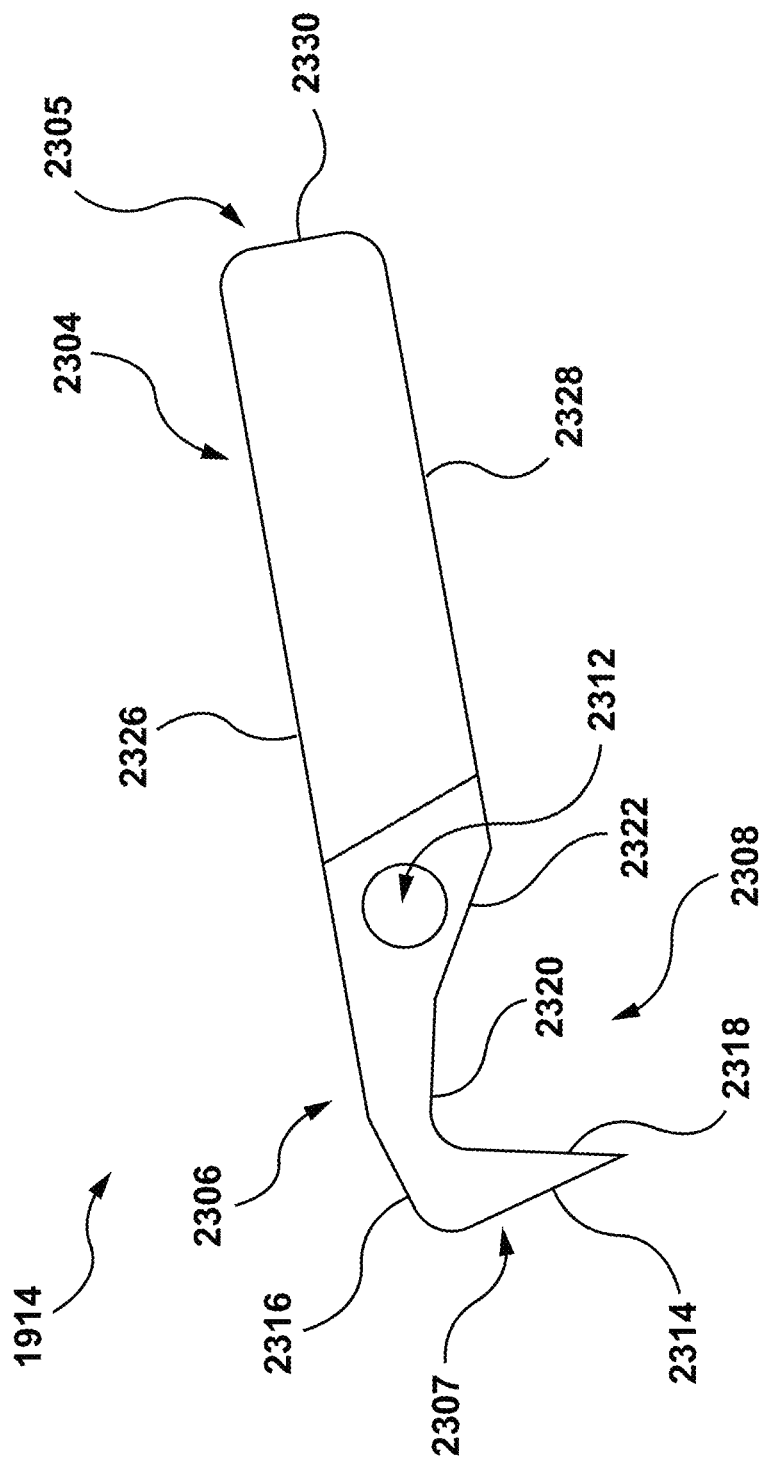
Figure 16C:
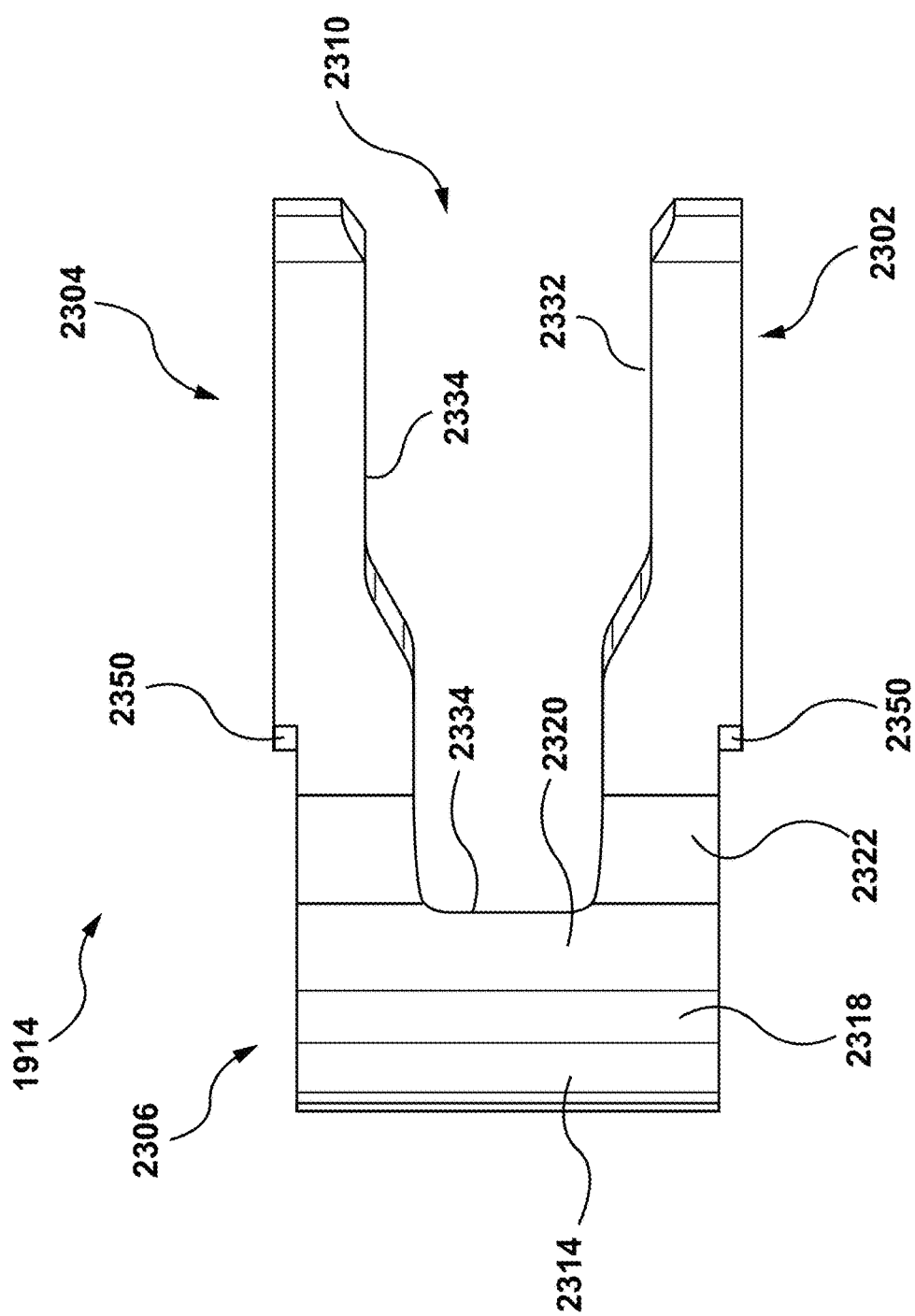

As illustrated in FIG. 16B, which is a side view, the crimper element 1914 includes a top surface 2326, a bottom surface 2328, and a distal surface 2330 formed at the ends of the first leg 2302 and the second leg 2304. The crimper lobe 2306 includes a first exterior ramp 2314 and a second exterior ramp 2316. The crimper lobe 2306 also include a first interior ramp 2318 and a second interior ramp 2320. The intersection of the first leg 2302 and the crimper lobe 2306 and the intersection of the second leg 2304 and the crimper lobe 2306 form a sloped edge 2322. As in FIGS. 16B and 16C, which is a bottom view, the first interior ramp 2318, the second interior ramp 2320, and the sloped edge 2322 define the crimper space 2308.

Figure 16D:
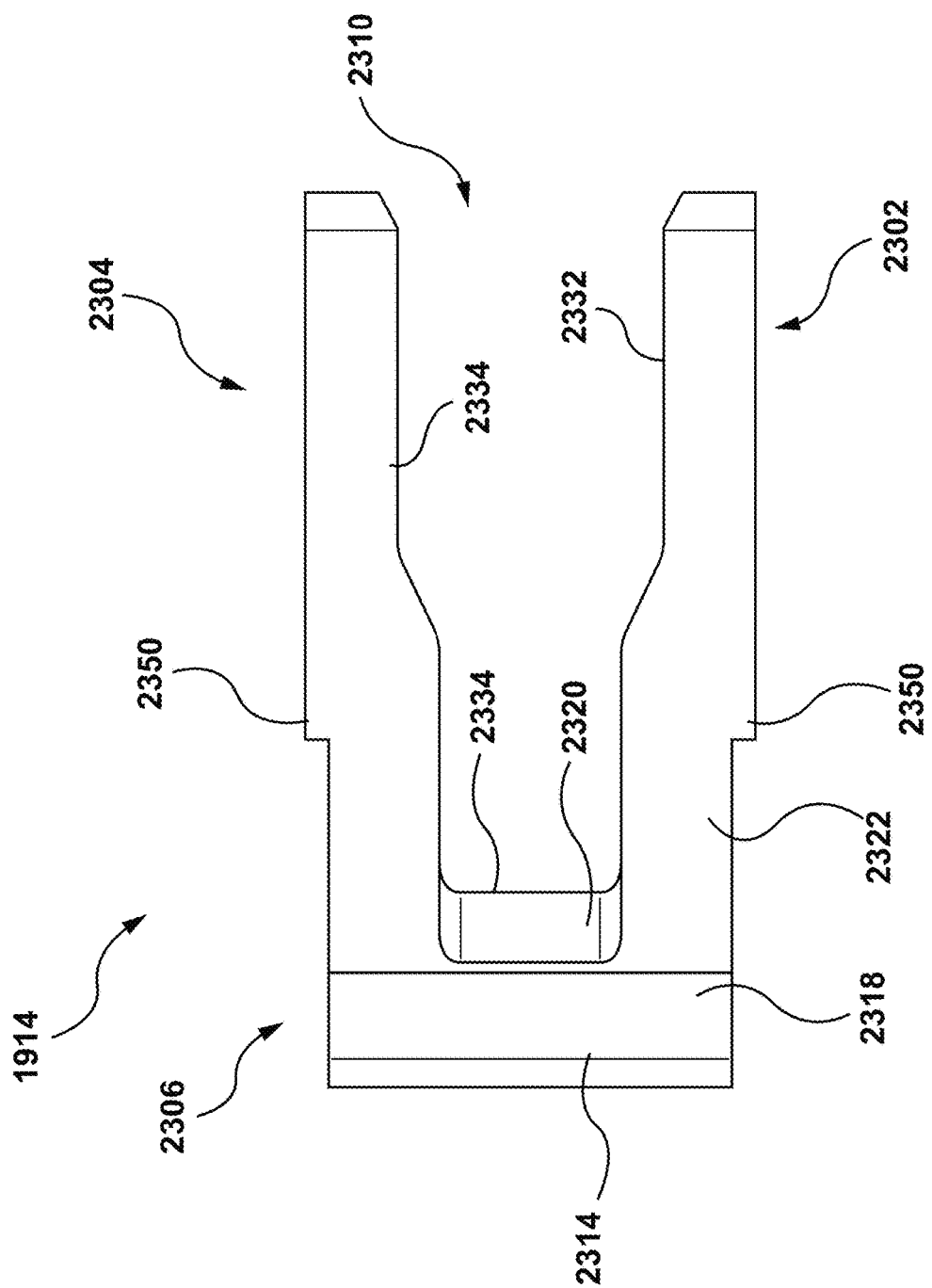

As illustrated in FIG. 16D, which is a top view, the first exterior ramp 2314 and the second exterior ramp 2316 from a plane between the top surface 2326 and the distal end 2307 and the bottom surface 2328. The first exterior ramp 2314 and the second exterior ramp 2316 can be formed at angles relative to the top surface 2326 and the bottom surface 2328. Likewise, the first interior ramp 2318 and the second interior ramp 2320 can be formed at angles relative to the top surface 2326 and the bottom surface 2328. The intersection of the first leg 2302 and the crimper lobe 2306 and the intersection of the second leg 2304 and the crimper lobe 2306 form a sloped edge 2322.

The dimensions of the crimper element 1914 can be governed by a size of the object being crimped. In an embodiment, the width of the crimper element 1914 can range from approximately 25 mm to approximately 50 mm and the length of the crimper element 1914 can range from approximately 1 mm to approximately 40 mm. The slope of the first exterior ramp 2314 and the second exterior ramp 2316 (angle relative to the top surface 2326 and the bottom surface 2328) can depend on the crimper elements included in the clamshell crimper 1900. Likewise, the slope of the first interior ramp 2318, the second interior ramp 2320, and the sloped edge 2322 (angle relative to the top surface 2326 and the bottom surface 2328) can depend on the crimper elements included in the clamshell crimper 1900. In an embodiment, the slope can be determined by dividing 360 degrees by the number of crimper elements 1914 in the clamshell crimper 1900. In an embodiment, the number of crimper elements can range from 10 to 12. The first interior ramp 2318, the second interior ramp 2320, and the sloped edge 2322 are configured to contact a neighboring crimper element and generate the iris effect when the crimper elements are displaced.

The crimper elements 1914 also includes connection holes 2312. The connection holes 2312 are formed in the first leg 2302 and the second leg 2304. In an embodiment, the crimper elements 1914 can include two connection holes 12312 that are positioned at opposing location on the first leg 2302 and the second leg 2304. In embodiments, the connection holes 1912 can be configured to receive a pin that passes through the two connection holes and a connection hole of the rod 1926. For example, the pin can be a dowel pin, a bolt, and the like. The pin can be formed to a diameter to maintain the corresponding circular openings and cause the pin to operate as a fulcrum. The connection holes 2312 operate to moveably couple the crimper elements 1914 to the rod 1918. The rods 1918 are coupled within the rod channel 2310. The rod channel 2310 allows the rods 1918 to rotate relative to the crimper elements 1914 during operation of the clamshell crimper 1900.

In embodiment, the crimper element 1914 can include two sloped shoulders 2350 formed on an exterior surface of the first leg 2302 and the second leg 2304, respectively. The sloped shoulders 2350 can operate to maintain the first leg 2302 and the second leg 2304 in one of the channels 2006. That is, the sloped shoulders 2350 extend from the first leg 2302 and the second leg 2304 to extend a width of the crimper element 1914 thereby engaging one or the channel 2006. In an embodiment, a width of the exterior ramp 2314 can be specific to a size of the implantable medical device being crimped. As such, the exterior shoulder 2350 may vary in size based on a size of the implantable medical device being crimped.

In embodiment, the crimper element 1914 having a 30 mm configuration can be defined by dimensions similar to the dimensions described above with reference to FIGS. 3F-3H. Table 2 below describes the dimensions, as defined by FIGS. 3F-3H, and provides example values for the dimensions for a crimper element 1914. One skilled in the art will realize that the values for the dimension are one example, and the crimper element 1914 can have different values for the dimension based on the particular configuration of the crimper 1900 and the crimping application.

TABLE 2

| Dimension | Description | ~Value |
| --- | --- | --- |
| L1 | Proximal End 2305 to beginning of Sloped Edge 2322 | 37.5 mm |
| L2 | Proximal End 2305 to midpoint of Connection Hole 2312 | 39.88 mm |
| L3 | Proximal End 2305 to end of Sloped Edge 2322 | 45.6 mm |
| L4 | Proximal End 2305 to beginning of Exterior ramp 2316 | 52.0 mm |
| L5 | Proximal End 2305 to end of Interior Ramp 2320 | 53.0 mm |
| L6 | Proximal End 2305 to end of Interior Ramp 2318 | 56.79 mm |
| L10 | Proximal End 2305 to beginning of Sloped Edge 2336 | 22.2 mm |
| L11 | Proximal End 2305 to end of Sloped Edge 2336 | 31.2 mm |
| L12 | Proximal End 2305 to Proximal End 2334 of Crimper Lobe 2306 | 46.4 mm |

TABLE 2-continued

| Dimension | Description | ~Value |
| --- | --- | --- |
| L13 | Proximal End 2305 to Distal End 2307 | 59.7 mm |
| D1 | Top Surface 2326 to Bottom Surface 2328 | 9.85 mm |
| D3 | Top Surface 2326 to end of Interior Ramp 2320 | 3.5 mm |
| D4 | Top Surface 2326 to beginning of Interior Ramp 2320 | 5.0 mm |
| D5 | Top Surface 2326 to midpoint of Connection Hole 2312 | 4.35 mm |
| D6 | Top Surface 2326 to beginning of Exterior Ramp 2314 | 14.42 mm |
| W1 | Exterior Surface 2336 of Legs | 30.0 mm |
| W2 | Width of Rod Channel 2310 between Interior Surfaces 2332 | 18.0 mm |
| W3 | Width of Rod Channel 2310 between Interior Surfaces 2333 | 9.3 mm |
| A1 | Angle between Top Surface 2326 and Sloped Edge 2322 | 30 degrees |
| A2 | Angle between Top Surface 2326 and Interior Ramp 2318 | 105 degrees |
| A3 | Angle between Top Surface 2326 and Exterior Ramp 2314 | 75 degrees |

FIGS. 17A-17E illustrate detailed views of the handle 1902, according to an embodiment hereof. One skilled in the art will realize that FIGS. 17A-17E illustrate one example of a handle and that existing components illustrated in FIGS. 17A-17E may be removed and/or additional components may be added to the handle 1902.

Figure 17A:
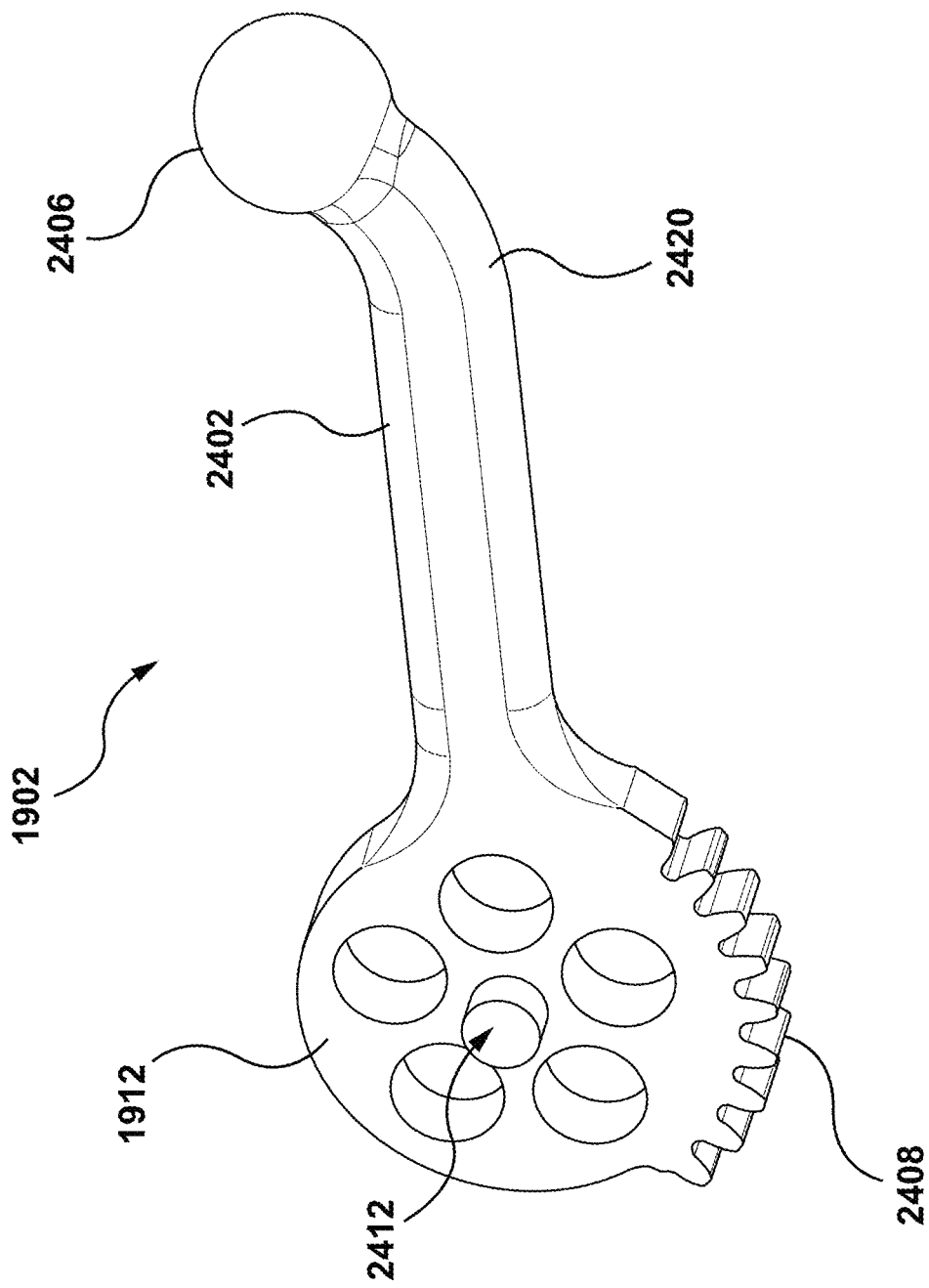
FIG. 17A-17D depict several views of a handle of the crimper of FIGS. 12A and 12B, according to an embodiment hereof.
Figure 17B:
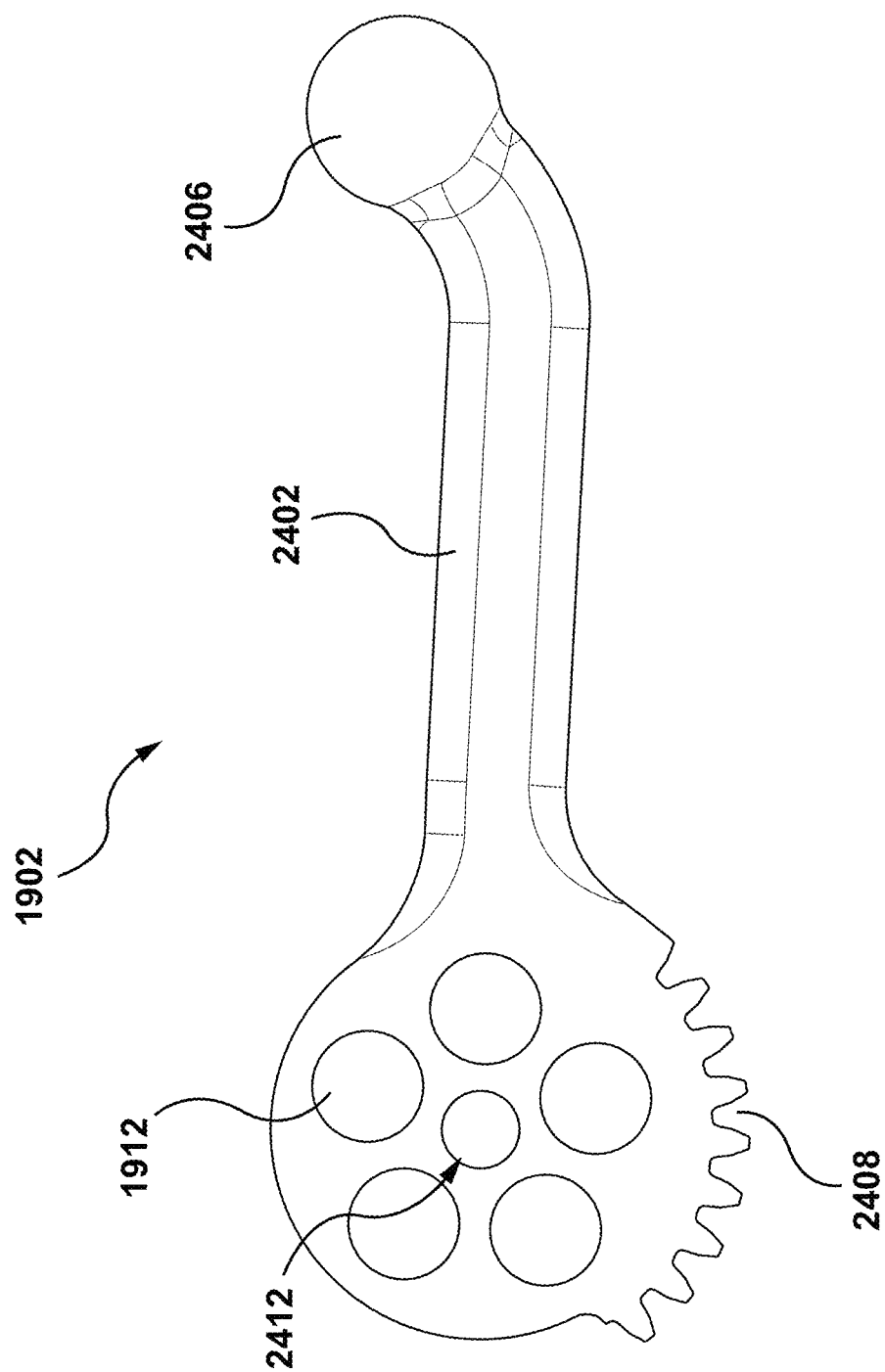

As illustrated FIGS. 17A and 17B, which are a perspective view and a side view respectively, the handle 1902 includes a handle bar 2402 and the cam 1912. The handle bar 2402 includes a handle bar end 2406. The can 1912 can include teeth 2408 and a connection member 2412. The connection member 2412 can be formed as a tab that is configured to engage connection channel 2054 formed by the circular ridge 2052 in the cam channel 2050 of the crimper housing 1904. The teeth 2408 are configured to engage teeth of the cam 1910.

Figure 17C:
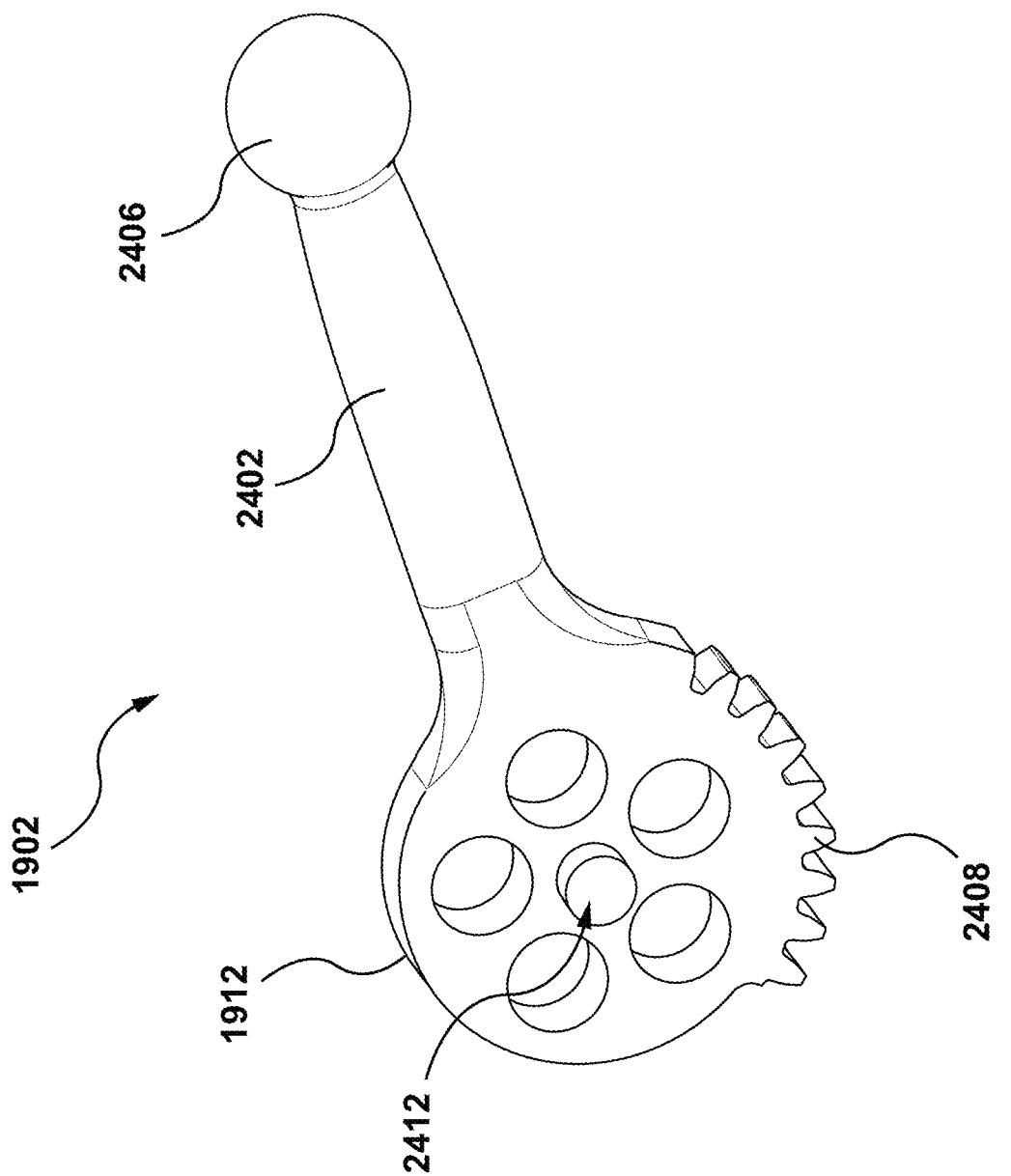
Figure 17D:
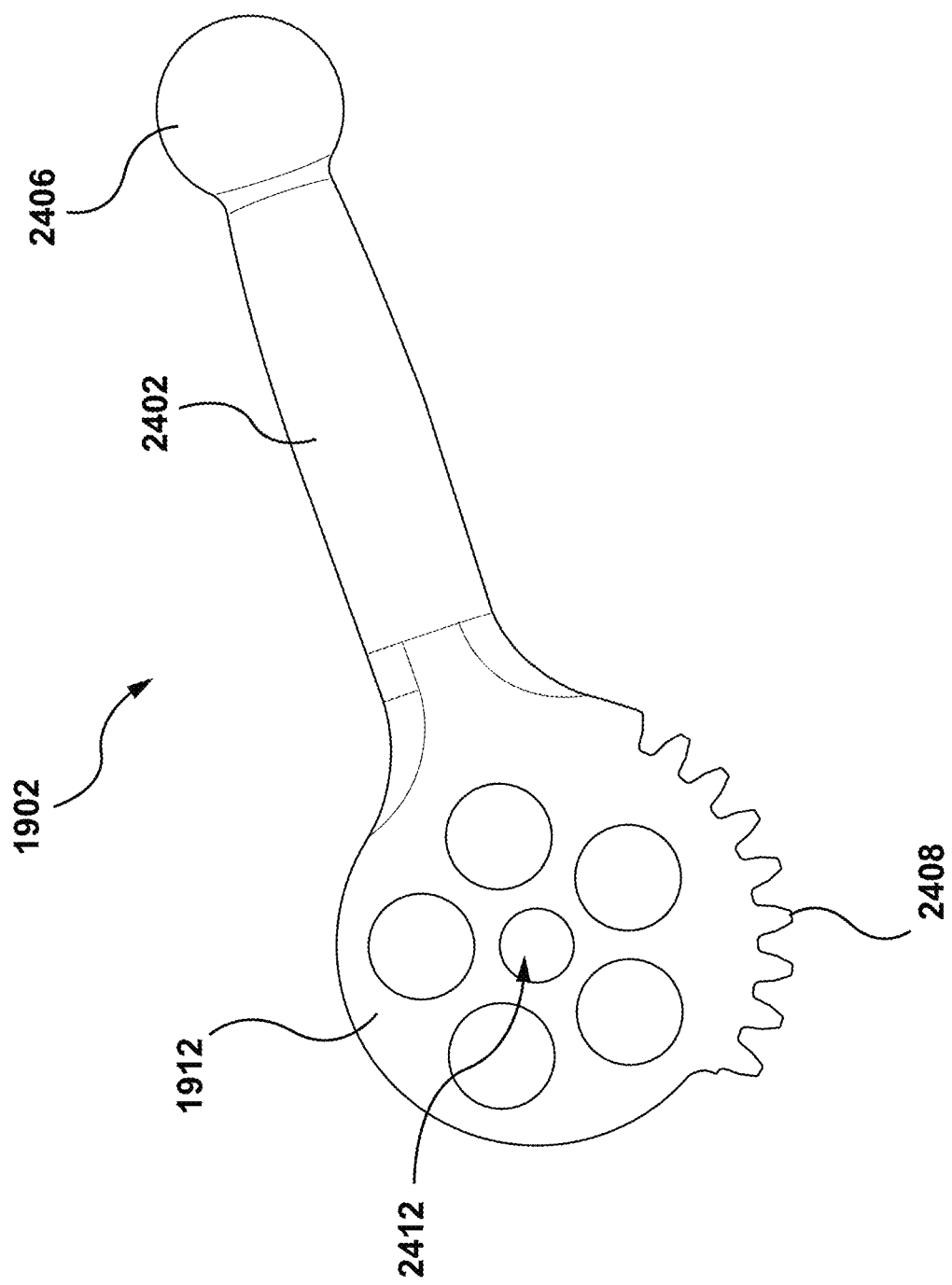

As illustrated in FIGS. 17A and 17B, the handle bar 2402 can include a curve or bend 2420. The curve or bend 2420 provide leverage when a user operates the handle 1902. As illustrated in FIGS. 17C and 17D, the curve or bend 2420 may be removed from the handle bar 2402.

FIGS. 18A-18D illustrate an example of the operation of the crimper 1900 in accordance with an embodiment hereof. One skilled in the art will realize that FIGS. 18A-18D illustrate one example of the operation of the crimper 1900 and that existing components illustrated in FIGS. 18A-18D may be removed and/or additional components may be added to the crimper 1900 without departing from the scope of the present invention. Additionally, one skilled in the art will realize that FIGS. 18A-18D illustrate only a few operating states in order to illustrate the operation of the crimper 1900, and will realize that the crimper 1900 can assume other operational states without departing from the scope of the present invention.

Figure 18A:
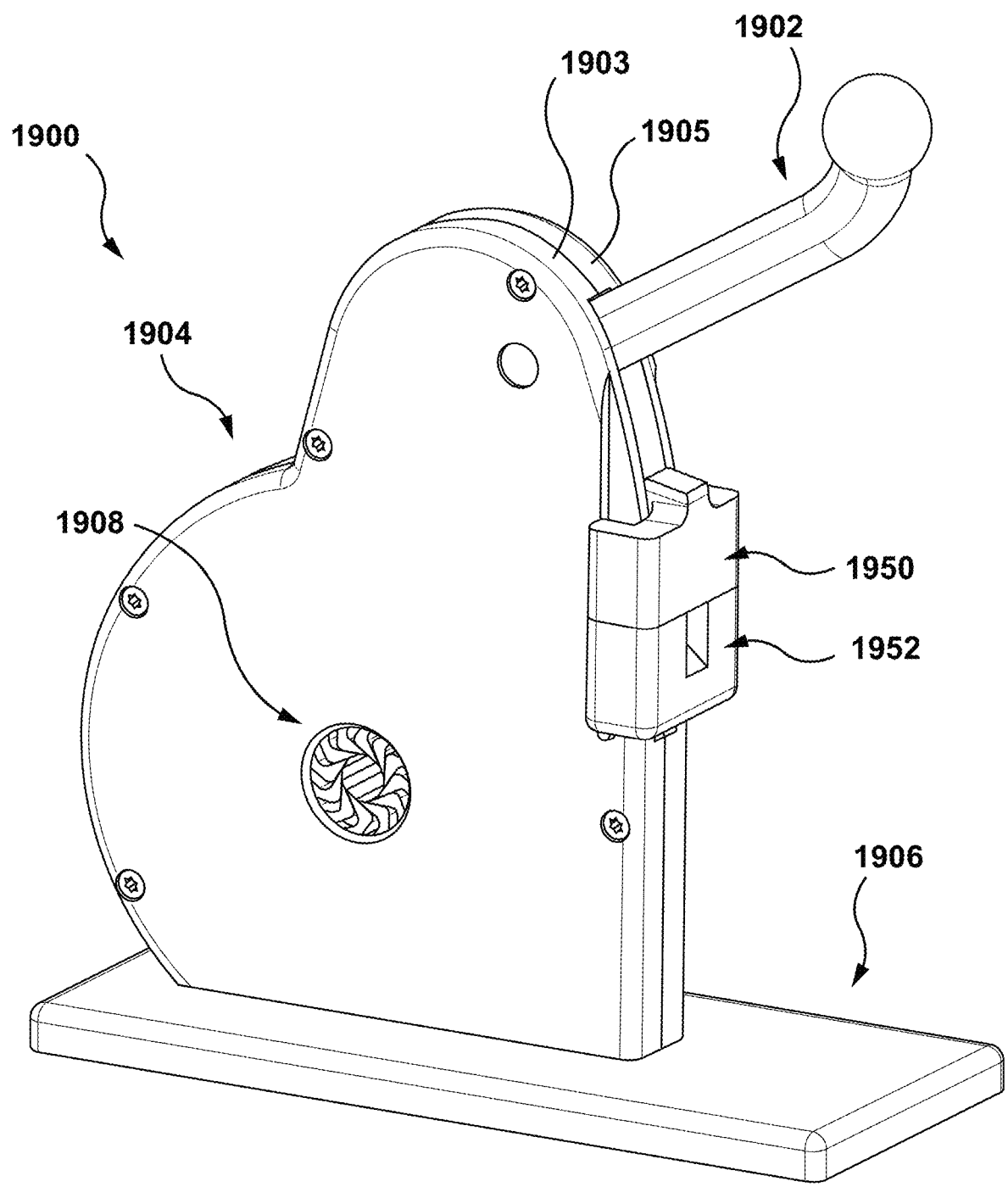
Figure 18B:
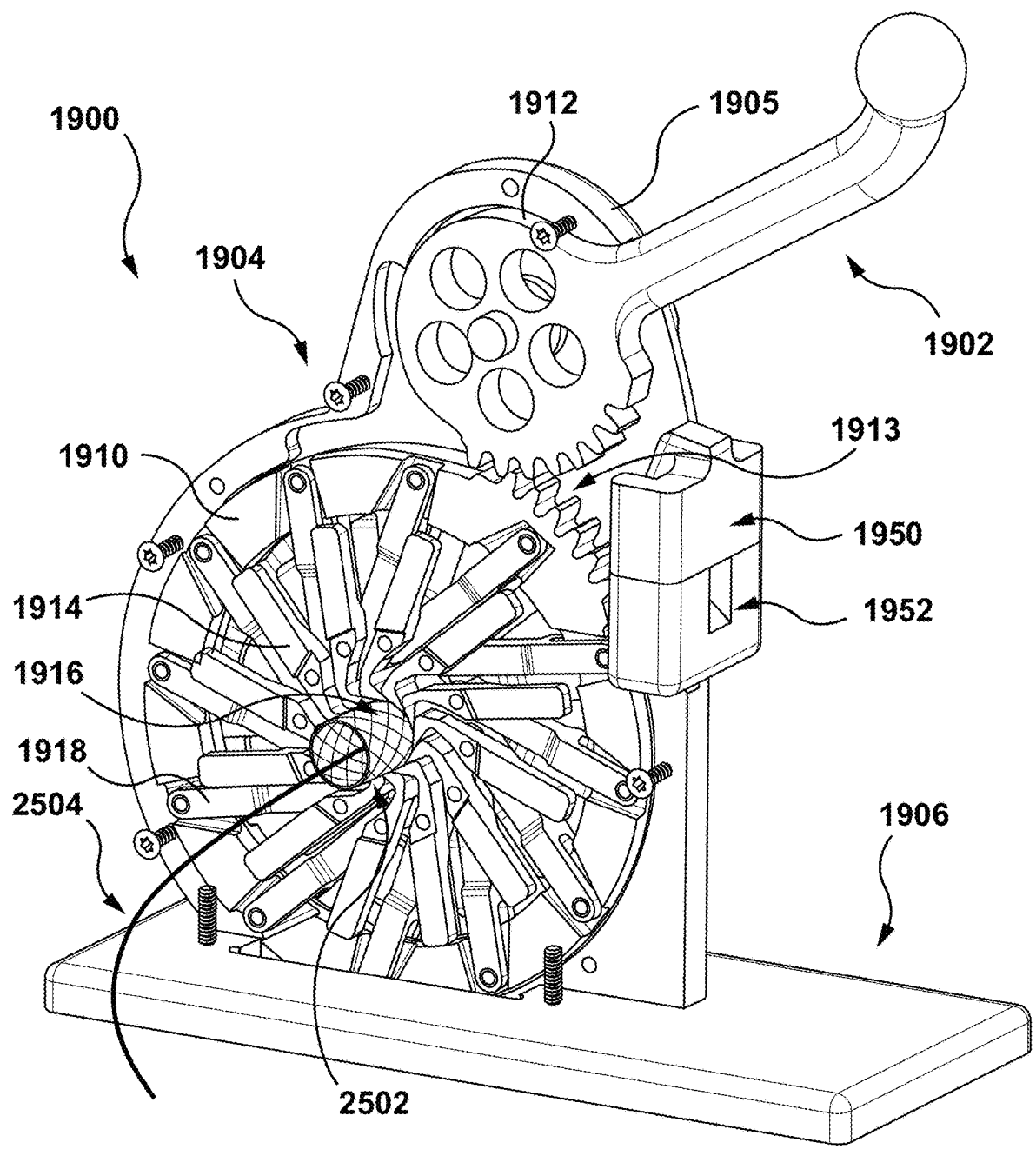

As illustrated in FIG. 18A, which is a side view, and FIG. 18B, which is a perspective view with the first side 1903 removed, an implantable medical device 2502 and a delivery device 2504 can be loaded into the crimper chamber 1916 of the crimper housing 1904. For example, an implantable medical device 2502 can be placed in the crimper chamber 1916 of the crimper housing 1904. Likewise, the delivery device 2504 can be positioned relative to the implantable medical device 2502.

Figure 18C:
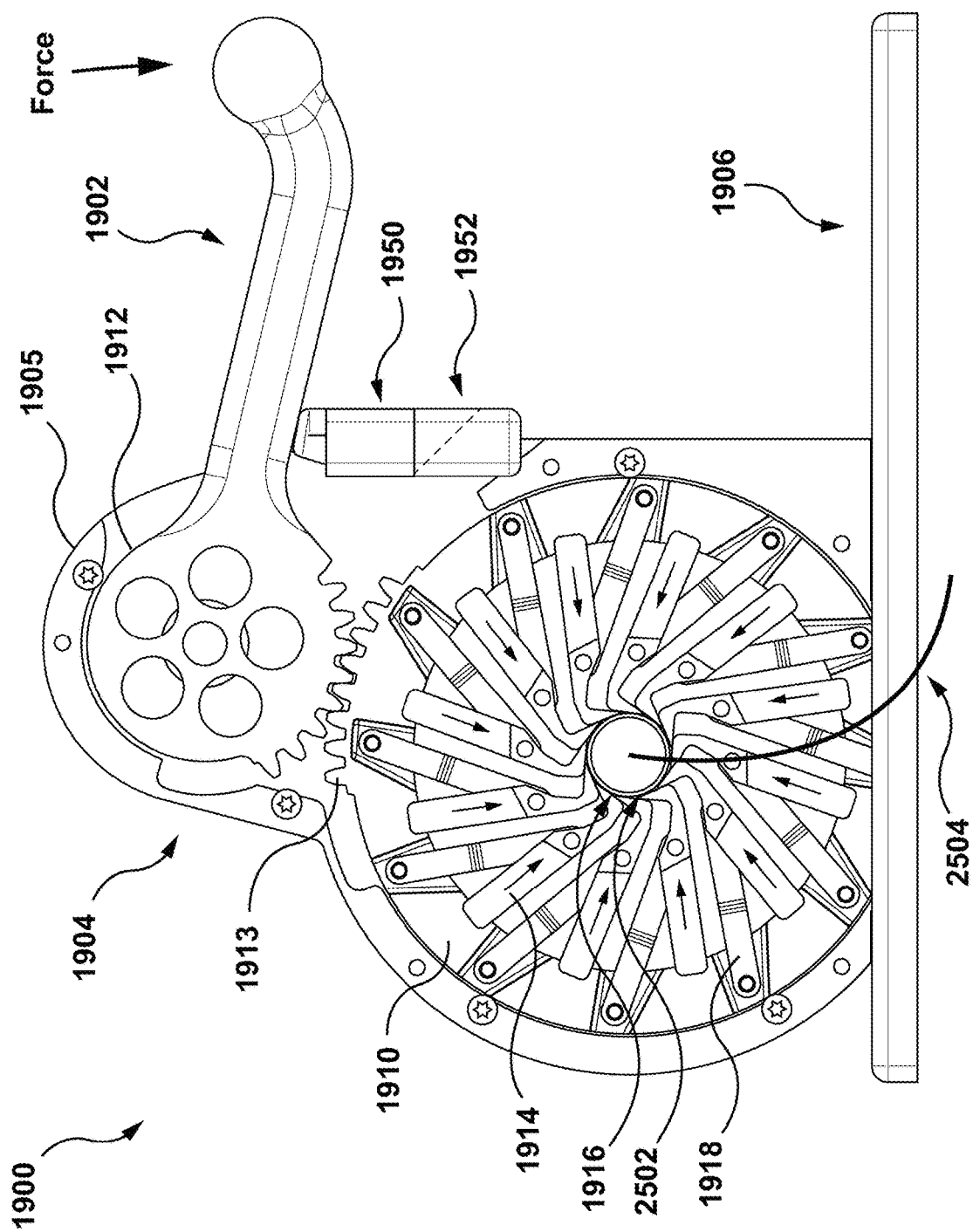

As illustrated in FIG. 18B, the crimper elements 1914 form the crimper chamber 1916. As illustrated in FIG. 18C-18E, to compress the medical device 2502, To operate the crimper 1900, a force can be applied to the handle 1902 in the direction of the base 1906. When the force is applied, the cam 1910 rotate in the direction that is opposite to the force is applied to the handle 1902. For example, the handle 1902 can be actuated in a downward motion thereby causing the cam 1912 to rotate in a clockwise direction. In response, causing the cam 1910 to rotate in a clockwise direction. Because each rod 1918 is fixed at one end to the cam 1910 and at the opposite end to one of the crimper elements 1914 (rotation is allowed), when the cam 1910 is rotated, the distance between the connection of the rod 1918 to the cam 1910 and the connection of the rod 1918 to the crimper element 1914 must remain the same. However, as the cam 1910 is rotated, that distance can only remain the same if the crimper element 1914 is pushed radially inward by the rods 1918. Thus, rotation of the cam 1910 forces the crimper elements 1914 inward via the rods 1918 inward. In particular, the crimper elements 1914 move inward generally towards the center of the crimper chamber 1516.

As the crimper elements 1914 move inward, the space available for the crimper elements 1914 to occupy is reduced. As such, the space between the crimper elements 1914 is reduced. As such, the volume of the crimper chamber 1916 decreases and the crimper elements 1914 apply a compression force to external surfaces of the implantable medical device to crimp the expandable medical device from its uncompressed state to its compressed state. For example, if the implantable medical device is round or cylindrical in shape, the crimper elements apply a force on the surface of the implantable medical device from various directions as force is applied to the handle 1902 thereby compressing the implantable medical device.

As illustrated in FIG. 18C, the handle 1902 can be moved downward until the handle 1902 abuts the first stop 1950, thereby partially compressing the implantable medical device 2502 to a predetermined diameter. If the implantable medical device 2502 requires only a partial compression, the handle 1902 can be moved upward and the implantable medical device 2502 removed. As illustrated in FIGS. 18D and 18E, if the implantable medical device 2502, the stop 1950 can be removed, and the handle 1902 can be further moved downward until the handle 1902 abuts the second stop 1952. The further movement of the handle 1902 causes additional compression of the implantable medical device 2502.

FIGS. 19A-19G illustrate another example of a clamshell crimper 2600 in accordance with an embodiment hereof. One skilled in the art will realize that FIGS. 19A-19G illustrate one example of a crimper and that existing components illustrated in FIGS. 19A-19G may be removed and/or additional components may be added to the clamshell crimper 2600.

Figure 19A:
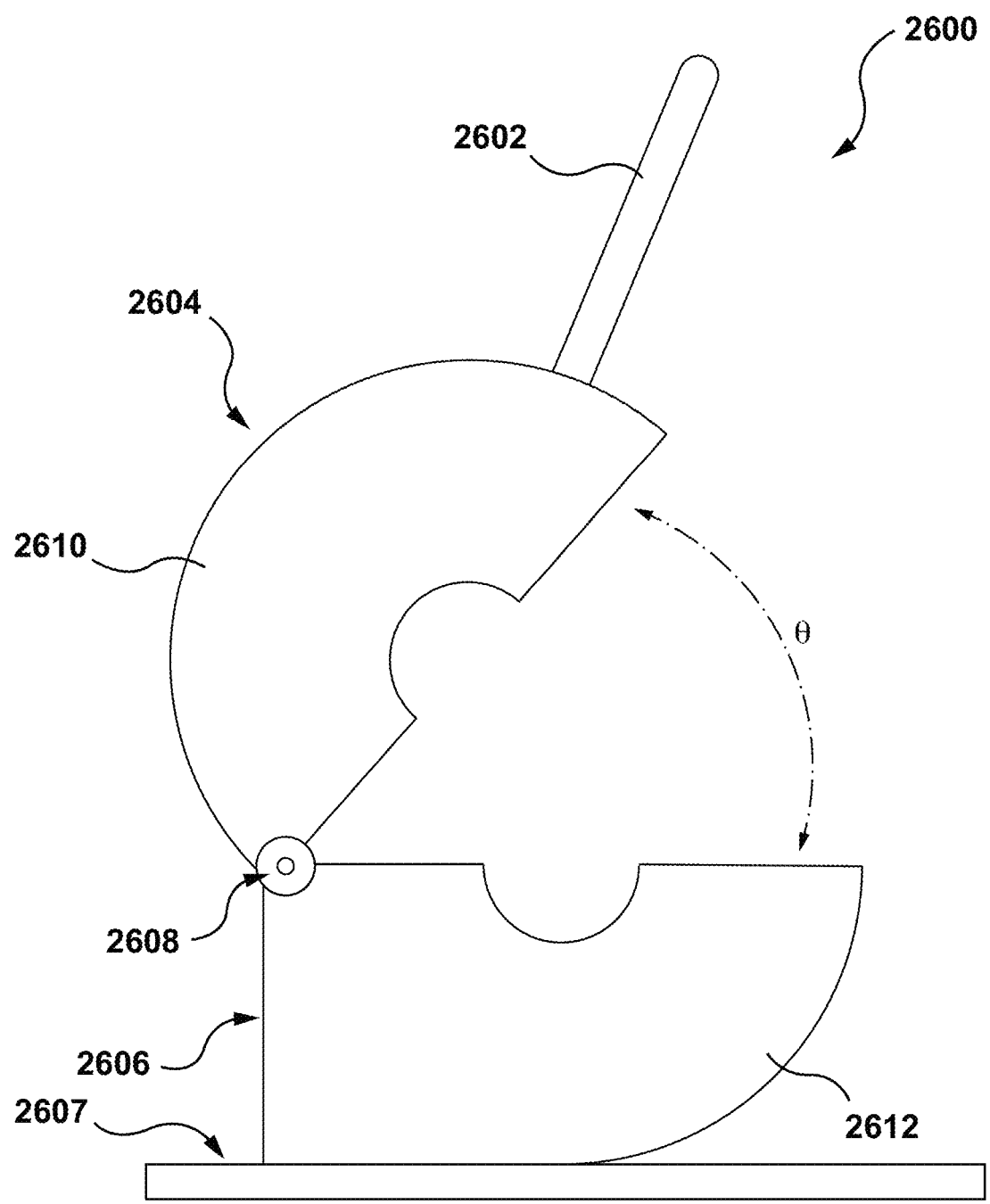
FIGS. 19A-19G depict different views of another example of a clamshell crimper for use with a medical device, according to an embodiment hereof.
Figure 19B:
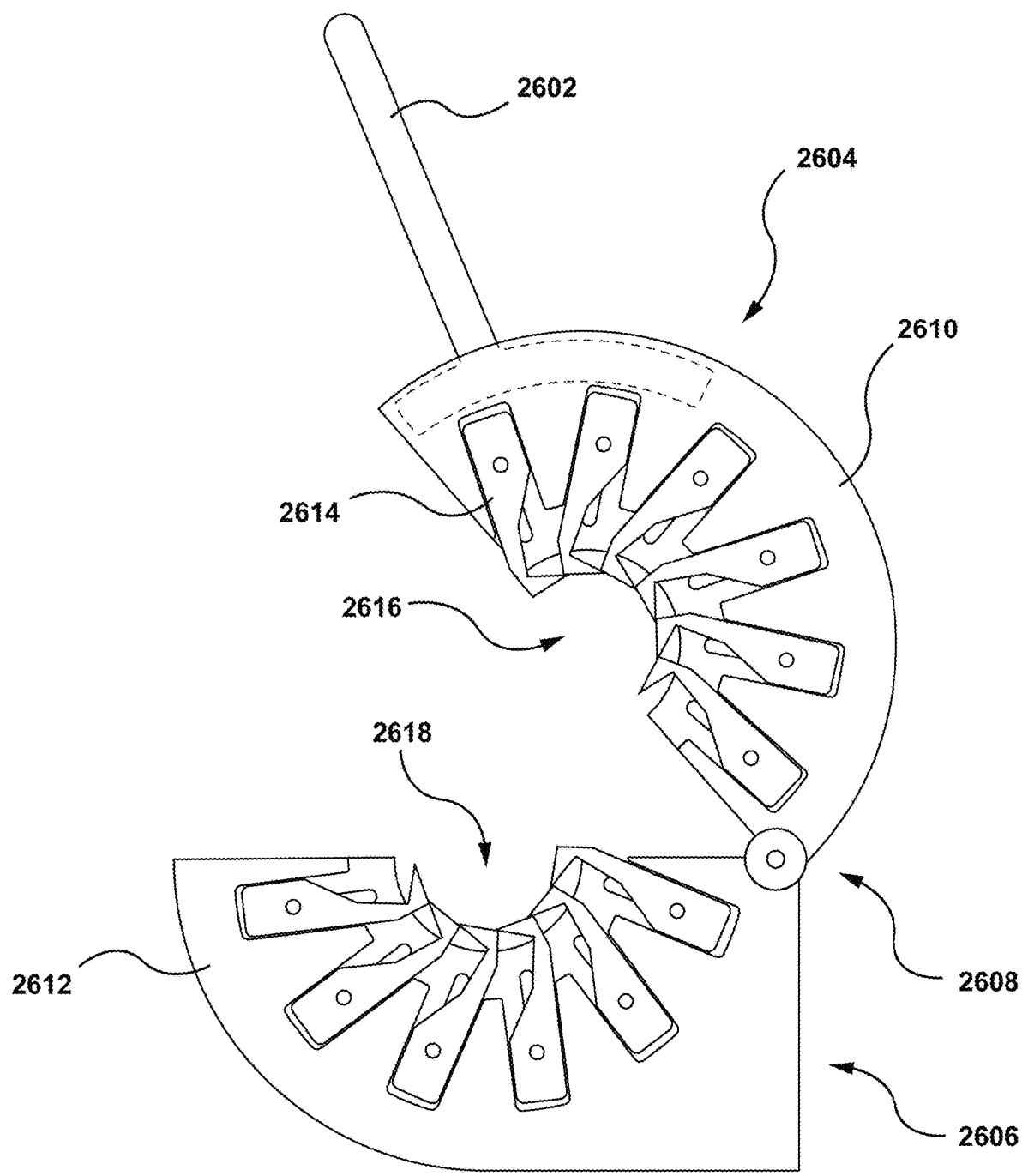
Figure 19C:
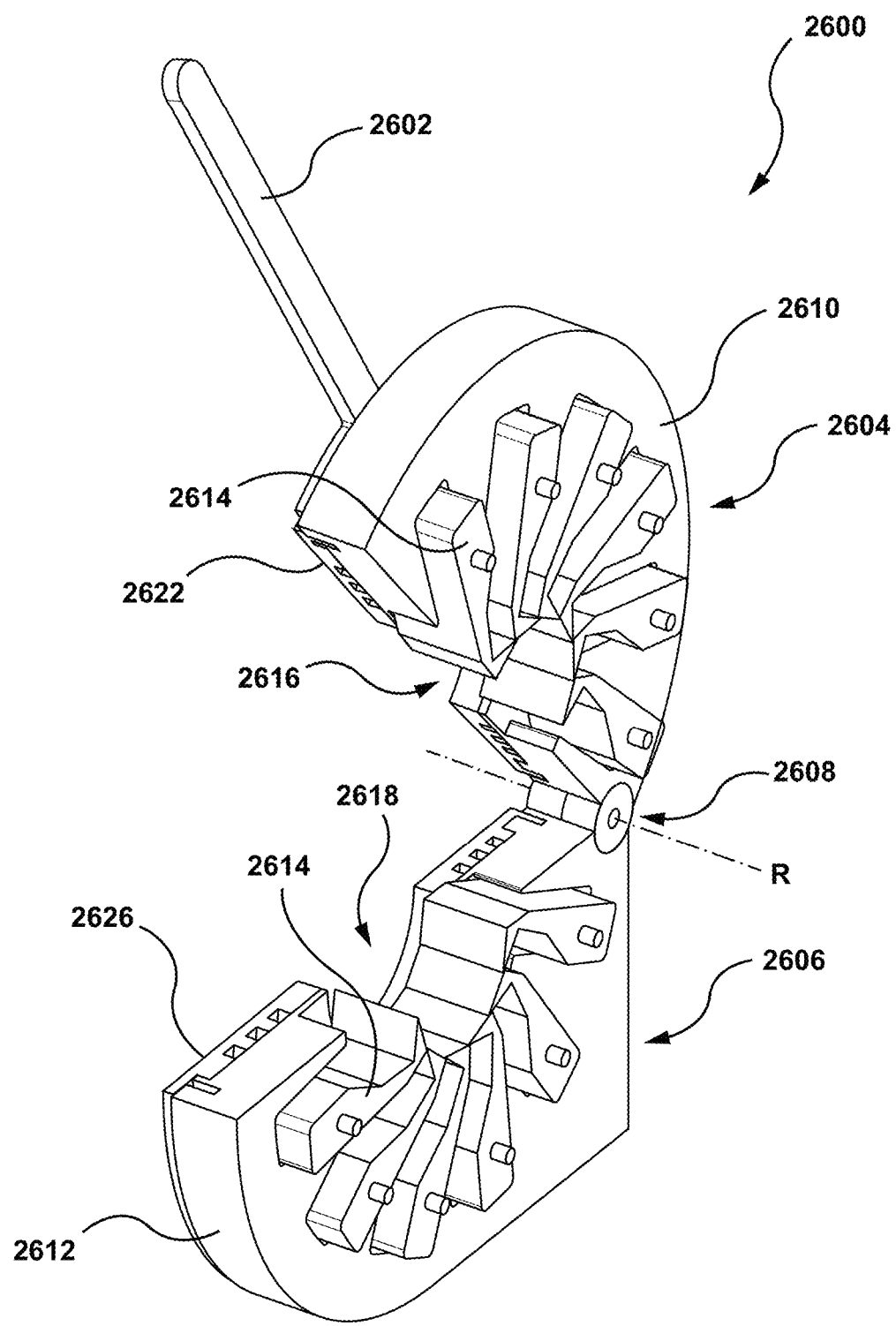

FIG. 19A is a side view of a first side 2601 of the clamshell crimper 2600. As illustrated in FIG. 19A, the clamshell crimper 2600 includes a handle 2602, a top shell 2604 (or top iris shell), and a base shell 2606 (or base iris shell). The top shell 2604 includes a first exterior housing 2610, and the base shell 2606 includes a first exterior housing 2612. The top shell 2604 and the base shell 2606 are coupled at a pivot connection 2608. The pivot connection 2608 allows an angle, θ, between the top shell 2604 and the base shell 2606 to be increased or decreased by rotating the top shell 2604 away from the base shell about an axis of rotation, R, (illustrated in FIG. 19C) located at the pivot connection 2608. The pivot connection 2608 is configured to allow the top shell 2604 and the base shell 2606 to move relative to each other from an open state (as illustrated in FIGS. 19A-19C) to a closed state (as illustrated in FIG. 19F). As illustrated in FIG. 19G, which is a perspective view, the clamshell crimper 2600 can include the first side 2601 and a second side 2603 coupled to the first side 2601. In embodiments, the second side 2603 can include the components of the first side 2601, as disclosed below in further detail. The clamshell crimper 2600 can be coupled to a base 2607 or other structure to provide support to the clamshell crimper 2600.

As discussed above, an open state for the clamshell crimper 2600 defines any angle, θ, between the top shell 2604 and the base shell 2606 that allows a user to insert an implantable medical device and/or delivery device in the clamshell crimper 2600 and that allows a user to view the insertion to properly align the implantable medical device and the delivery device. Likewise, as noted above, the closed state defines any angle, θ, between the top shell 2604 and the base shell 2606 in which the clamshell crimper 2600 is operating to compress the implantable medical device and to crimp or load the implantable medical device onto a delivery device. For example, in an embodiment, the angle, θ, between the top shell 2604 and the base shell 2606, when in the open state, can range from approximately 45 degrees to approximately 180 degrees. Likewise, for example, in an embodiment, the angle, θ, between the top shell 2604 and the base shell 2606, when in closed state, can be approximately 0 degrees.

FIG. 19B illustrates different view of the first side 2601 of the clamshell crimper 2600 that is opposite the first side. In the view of FIG. 19B, housings of the second side 2603 of the clamshell crimper 2600 are removed to illustrate internal components of the clamshell crimper 2600. As illustrated, the top shell 2604 includes the first exterior housing 2610 and a second exterior housing (removed in this illustration). The base shell 2606 includes the first housing 2612 and a second exterior housing (removed in this illustration). The top shell 2604 and the base shell 2606 include a plurality of crimper elements 2614. As further illustrated in FIG. 19C, which is an enlarged perspective view of the top shell 2604 and the base shell 2606, the crimper elements 2614 of the top shell 2604 form a top crimper channel 2616. The crimper elements 2614 of the base shell 2606 for a bottom crimper channel 2618. When the closed state, the top crimper channel 2616 and the bottom crimper channel 2618 form a crimper chamber 2619, as illustrated in FIG. 19F, which is a perspective view of the clamshell crimper 2600 in the closed state.

In embodiments, the pivot connection 2608 can be any type of mechanical joint or electro-mechanical joint that allows the top shell 2604 and the base shell 2606 to move relative to each other. For example, the pivot connection 2608 can include one or more of a hinge, a tab, a rivet, a pivot pin, a pivot joint, an axle, a living hinge, etc. In an embodiment, the pivot connection 2608 can include a movement assistance device to provide a force that assists in the movement of the top shell 2604 and the base shell 2606 relative to each other. For example, the pivot connection 2608 can include a spring, a motor, etc.

Figure 19D:
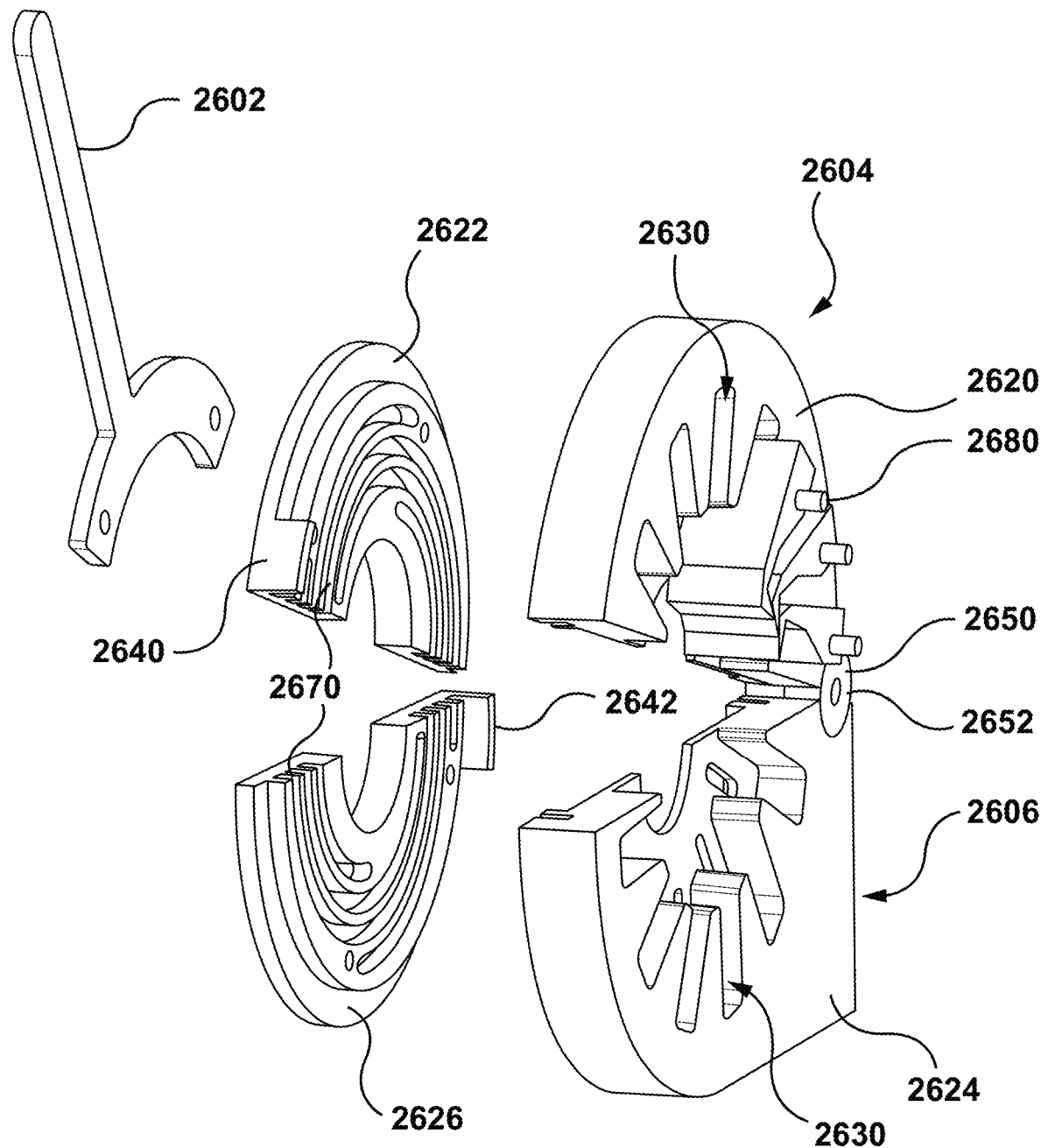
Figure 19E:
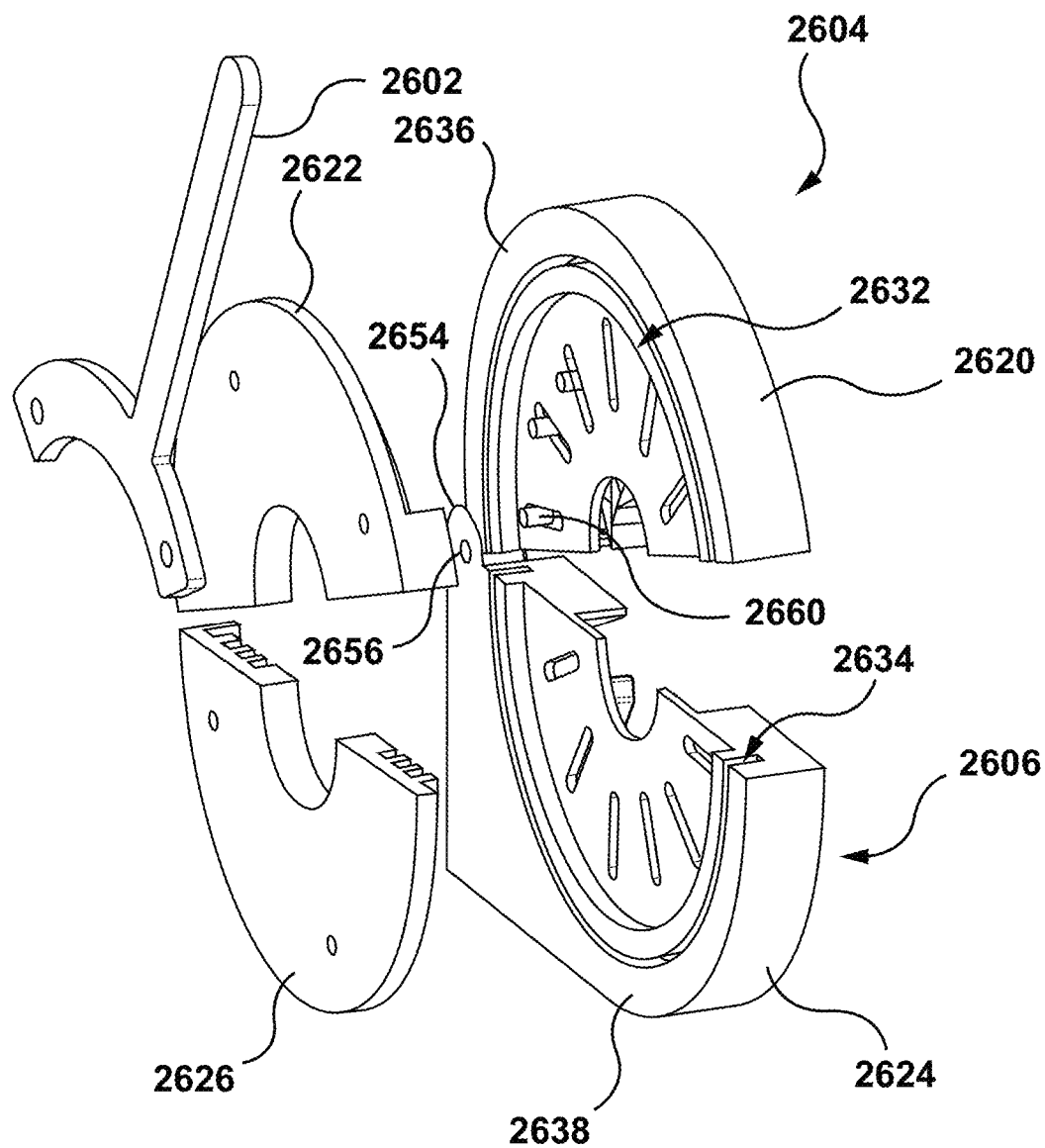
Figure 19F:
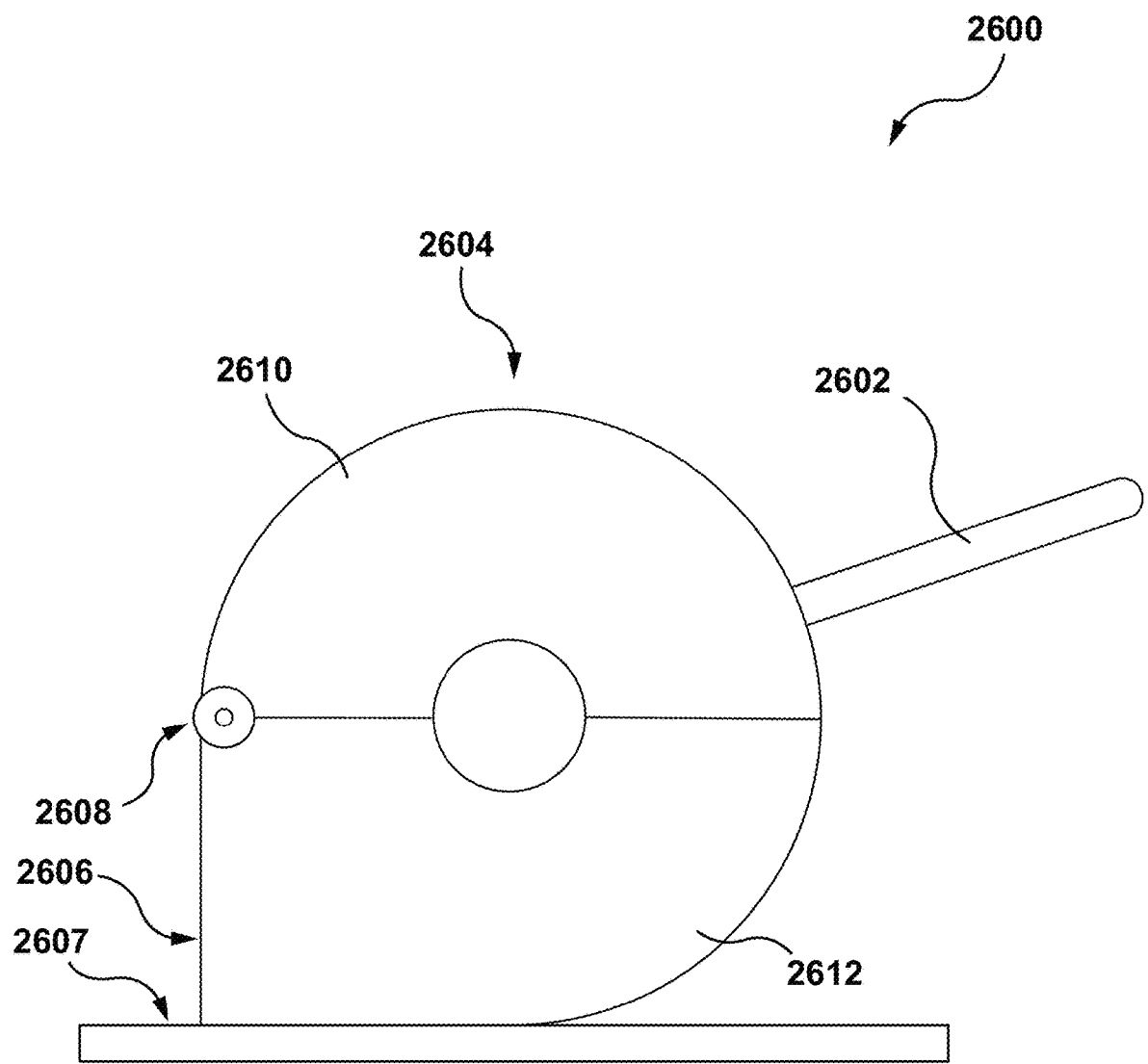
Figure 19G:
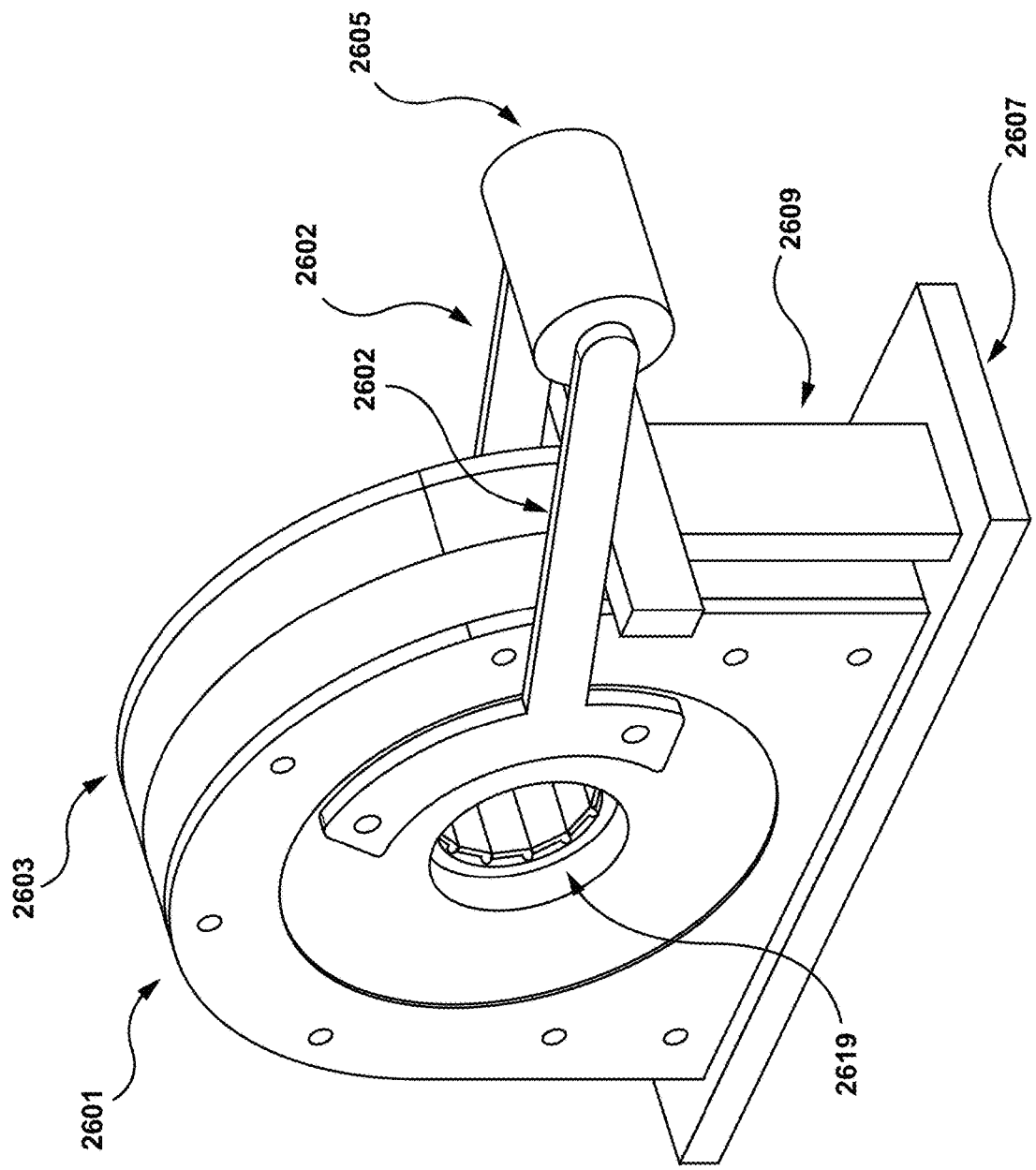

As illustrated in FIGS. 19D and 19E, which are exploded views of the internal components of the crimper 2600, the first exterior housing 2610 of the top shell 2604 (which has been removed) can include a top crimper element housing 2620 and a top cam 2622. The handle 2602 is coupled the top cam 2622 as further described below with reference to FIG. 19E. The first exterior housing 2610 of the base shell 2606 can include a base crimper element housing 2624 and a base cam 2626. The top crimper element housing 2620 and the base crimper element housing 2624 can be configured to moveably hold the crimper element 2614 within crimper element channels 2630 of the top crimper element housing 2620 and the base crimper element housing 2624, as discussed below in further detail with reference to FIGS. 20A and 20B. In embodiments, the second side 2603 can include a top cam, bottom cam and handle, which is coupled to the handle 2602 by a handle bar 2605 as illustrated in FIG. 19G.

In embodiments, each of the crimper elements 2614 can include pins 2680. As shown in FIGS. 19D and 19E, each of the crimper elements 2614 can include two pins 2680 that are formed on opposing sides of each of the crimper elements 2614. The top cam 2622 and the base cam 2626 can be coupled to the crimper elements 2614 by pins 2680. That is, the top cam 2622 and the base cam 2626 includes a number of pin channels 2670, as illustrated in FIG. 19D. Likewise, the top cam and bottom cam of the second side 2603 can be coupled to the crimper elements 2614 by pins 2608 positioned on an opposite surface of the crimper elements 2614. Each of the pins 2680 extends from a middle region of one of the crimper elements 2614 to one of the pin channels 2670 of the top cam 2622 or the base cam 2626, as described below with reference to FIGS. 21A-21G. The top cam 2624 operates to translate the rotational movement of the handle 2602 to the crimper elements 2614 via one of the pins 2680 that is moveably coupled to the top cam 2624. The base cam 2626 operates to translate the movement of the handle 2602 (through movement of the top cam 2622) to the crimper elements 2614 via one of the pins 2680 that is coupled to the base cam 2626. When in the closed state, the base cam 2626 is coupled to the top cam 2622 such that the top cam 2622 and the base cam 2626 rotate together and function as a single cam. That is, when coupled, the top cam 2622 and the base cam 2626 from a cylindrical ring within the interior of the clamshell crimper 2600. An example of the top cam 2622 and base cam 2626 is described in further detail below with reference to FIGS. 22A and 22B.

As illustrated in FIG. 19E, the top cam 2622 is configured to be moveably held within a top cam channel 2632 formed in the top crimper element housing 2620. Likewise, the base cam 2626 is configured to be moveably held within a base cam channel 2634 formed in the base crimper element housing 2624. The top cam channel 2632 can be a semi-circular channel formed around an exterior surface 2636 of the top crimper element housing 2620. The base cam channel 2634 can be a semi-circular channel formed around an exterior surface 2638 of the base crimper element housing 2624. When the clamshell crimper 2600 is in a closed state, the top cam channel 2632 and the base cam channel 2634 can form a circular channel that receives a top cam tab 2640 of the top cam 2622 and a base cam tab 2642 of the base cam 2624. The top cam tab 2640 and the base cam tab 2642 can be configured to move within the top cam channel 2632 and the base cam channel 2634 to allow the top cam 2622 and the base cam 2626 to rotate relative to the top crimper element housing 2620 and the base crimper element housing 2624, as described below in further detail.

In some embodiments, as illustrated in FIG. 19D, the top crimper element housing 2620 of the top shell 2604 can include a tab 2650 that extends from a rear portion of the top crimper element housing 2620. The tab 2650 includes a pivot connection hole 2652. As illustrated in FIG. 19E, the base crimper element housing 2624 of the base shell 2606 can include a tab 2654 that extends from rear portion of the base crimper element housing 2624. The tab 2654 includes a pivot connection hole 2626. When the tab 2650 and the tab 2654 are mated, the pivot connection hole 2652 and the pivot connection hole 2656 can form a concentric hole that operates as the pivot connection 2608 when a pin, rivet, bolt, screw or other connecting mechanism is inserted in the concentric hole. For example, the pivot connection 2608 can include a pin that is positioned corresponding concentric hole formed by the pivot connection hole 2652 of the top crimper element housing 2656 and the pivot connection hole 2656 in the base crimper element housing 2624. For example, the pin can be a dowel pin, a bolt, and the like. The pin can be formed to a diameter to maintain the corresponding circular openings and cause the pin to operate as a fulcrum.

In an embodiment, the top shell 2604 and the base shell 2606 can be separate components that can be removably attached at the pivot connection 2608 to form the clamshell crimper 2600. In another embodiment, the top shell 2604 and the base shell 2606 can be a single component that fold towards each other, for instance, via a living hinge therebetween, to form an integrated clamshell crimper 2600. The top shell 2604 and the base shell 2606 can be formed of any suitable material such as, but not limited to aluminum, stainless steel, or a polymeric material. While the clamshell crimper 2600 is described as pivoting at the pivot connection 2608, one skilled in the art will realize that top shell 2604 and the base shell 2606 can move relative to one another using other type of processes and mechanically connections.

As illustrated in FIGS. 19C and 19D, the crimper elements 2614 are arranged to partially overlap between the top shell 2604 and the base shell 2606, respectively, in a first direction. In an embodiment, the crimper elements 2614 of the top shell 2604 are arranged to partially overlap to form the top crimper channel 2616 at distal ends of the crimper (e.g., described below with reference to FIGS. 21A-21G). The crimper elements 2614 of the base shell 2606 are arranged to partially overlap to form the bottom crimper channel 2618 at distal ends of the crimper elements 2616. When the clamshell crimper 2600 is in the closed state, the top crimper channel 2616 and the bottom crimper channel 2618 define the crimper chamber 2619. That is, when in the closed state, the crimper elements 2614 of the top shell 2604 and the crimper elements 2614 of the base shell 2606 form a cylinder of overlapping ends of the crimper elements 2614 with a cylindrical-shaped cavity passing through the center, defining the crimper chamber 2619.

In embodiments, the clamshell crimper 2600 can operate similar to the clamshell crimper 800, as discussed above. That is, when in the closed state, the crimper elements 2614 are displaced by the movement of the handle 2602. When the force is applied, the top cam 2622 and the base cam 2626 rotate in the direction that the force is applied to the handle 2602. In embodiments, the pin channels 2670 are formed in a spiral pattern on the top cam 2622 and the base cam 2626. That is, each of the pin channels 2670 is formed as an arc where a distance from each of the pin channels 2670 to the crimper chamber 2619 decreases in a first direction. During rotation of the handle 2602, the crimper elements 2614 are moveably held within the crimper element channels 2630 of the top crimper element housing 2620 and the base crimper element housing 2624. The crimper element channels 2630 allow the crimper elements 2614 to move inward towards the crimper chamber 2619.

When the handle 2602 is moved, the rotation of the top cam 2622 and the base cam 2626 apply a force to the pins 2680 thereby causing the pins 2680 to displace inward as the pins 2680 travel within the pin channels 2670 that have a decreasing distance from the crimper chamber 2619. The inward motion of the pins 2680 cause the crimper elements 2614 of the top shell 2604 and the base shell 2606 to displace inward within the crimper element channels 2630 thereby generating the iris effect. That is, the inward motion of the pins 2680 is translated to the crimper elements 2614 thereby causing the crimper elements 2614 to displace inward, as described in further detail below. As such, the volume of the crimper chamber 2619 decreases and the crimper elements 2614 apply a compression force to external surfaces of the implantable medical device to crimp the expandable medical device from its uncompressed state to its compressed state.

For example, if the implantable medical device is round or cylindrical in shape, the crimper elements 2614 apply a force on the surface of the implantable medical device from various directions as force is applied to the handle 2602 thereby compressing the implantable medical device. That is, when in the closed state, the crimper elements 2614 are displaced by the movement of the handle 2602. As the handle 2602 is moved, the top cam 2622 and the base cam 2626 rotate and function to translate the rotational motion of the handle 2602 into linear motion of the crimper elements 2614 via the pins 2680. As such, the crimper elements 2614 of the top shell 2604 and the base shell 2606 function as an iris to decrease or increase the volume of the crimper chamber 2619 through the movement of the handle 2602. In operation, the implantable medical device is loaded into the bottom crimper channel 2618 and positioned in a direction that is parallel to the axis of rotation, R, of the top shell 2604 and the base shell 2606. The delivery device can also be positioned and aligned relative to the implantable medical device. That is, the implantable medical device can be disposed around the delivery device. As such, the volume of the crimper chamber 2619 decreases and the crimper elements 2614 apply a compression force to external surfaces of the implantable medical device to crimp the expandable medical device from its uncompressed state to its compressed state. For example, if the implantable medical device is round or cylindrical in shape, the crimper elements 2614 apply a force on the surface of the implantable medical device from various directions as force is applied to the handle 2602 thereby compressing the implantable medical device.

As illustrated in FIG. 19F, when in a closed state, the crimper chamber 2619 can define a volume that approximates a cylinder. While the crimper chamber 2619 is described above as defining a cylindrical shaped volume, one skilled in the art will realize that the shape and dimension of the crimper elements 2614 can be changed to create a differently shaped volume as required by the implantable medical device being compressed and positioned. The clamshell crimper 2600 is configured to receive an implantable medical device and alter the implantable medical device from an uncompressed state to a compressed state by the crimper elements 2614, which causes the decrease of the volume of the crimper chamber 2619. Additionally, the clamshell crimper 2600 is configured to crimp or load the implantable medical device onto a delivery device. In an embodiment, the crimper elements 2614 can be removable from the top shell 2604 and/or base shell 2606. As such, the crimper elements 2614 may be interchangeable with other types of crimper elements configured to accommodate different dimensions and/or configurations of implantable medical devices and/or delivery devices. The crimper elements 2614 may be formed of any suitable material such as, but not limited to aluminum, stainless steel, or a polymeric material.

The clamshell crimper 2600 can be utilized on any type of implantable medical device that requires a conversion from an uncompressed state to a compressed state. In an embodiment, the crimper can be applied to any implantable medical device that requires onsite crimping of the implanted medical device onto a catheter, e.g., organic tissue containing valve repair devices. In an embodiment, the crimper 2600 can be used with balloon-expandable medical devices and/or mechanically expandable medical devices. For example, the clamshell crimper 2600 can be utilized on implantable medical devices that are to be delivered transluminally, e.g., via a catheter, and need to be loaded onto or into a catheter. In this example, the implantable medical device can include a heart valve prosthesis, which includes a stent or frame, and a prosthetic valve attached to the interior of the frame. The stent/frame may be crimped to have a low profile such that the prosthesis can be delivered through the vessels to a target location in a compressed state, and then expanded at the target location, by a balloon of the delivery device, for instance, to replace the native heart valve.

By having the clamshell crimper 2600 open at an angle large enough to view the bottom crimper channel 2618, a user can properly locate and position such a heart valve prosthesis with respect to the catheter. For example, when a balloon catheter with a non-crimped stent/frame of a heart valve prosthesis is placed within the clamshell crimper 2600, a user can visually ensure that the prosthesis is properly located over the balloon of the catheter before proceeding with the crimping operation. The open, top loading design of the clamshell crimper 2600 provides increased visibility in loading and aligning the implantable medical device and the delivery device as well as rapid fine adjustments. That is, because the clamshell crimper 2600 can be opened to provide easy access to the implantable medical device and the delivery device, the relative alignment of the implantable medical device and the delivery device can be monitored and adjusted without removing the implantable medical device and the delivery device from the clamshell crimper 2600. For example, a heart valve prosthesis is typically loaded onto a delivery device or catheter at the time of the implantation procedure, e.g., at the hospital by hospital staff. The prosthesis needs to be properly aligned and loaded onto the delivery catheter because, if there is an error, the improperly aligned prosthesis may need to be discarded, which is wasteful and costly. The clamshell crimper 2600 provides a straightforward and accurate procedure to crimp such a heart valve prosthesis onto a balloon catheter at the hospital. Moreover, the clamshell crimper 2600 eliminates complex geometry and machining that normally defines iris crimpers.

Returning to FIGS. 19D and 19E, the handle 2602 can be formed as a separate component that is attached to the top cam 2622. In other embodiments, the handle 2602 can be integrated as a one piece handle with the top cam 2622. In embodiments, the handle 2602 can be shape, size, design, and/or configuration to accommodate different crimping operations. For example, the handle 2602 can be extended and include a pivot point to add more leverage during crimping operations. Likewise, the handle 2602 can include one or more attachments that assists in pulling down the handle 2602, for example, a handle extension that can be operated by a user's foot. The handle 2602 can be formed of any suitable material such as, but not limited to aluminum, stainless steel, or a polymeric material.

In embodiments, the top shell 2604 can include a handle lock mechanism that locks the handle 2602 into at a position where the crimper chamber 2619 in an open position, e.g., the crimper chamber 2619 being open to a maximum diameter. The top shell 2604 and/or the base shell 2606 can include a shell locking mechanism that locks the top shell 2604 and the base shell 2606 together in a closed state, e.g., the top shell 2604 and base shell 2606 being together. When the handle 2602 is locked by the handle lock mechanism, the clamshell crimper 2600 can be moved into an open state, e.g., the top crimper channel 816 and the bottom crimper channel 2618 being separated, by pivoting the top shell 2604 away from the base shell 2606. During crimping operations, the top shell 2604 can be closed, for example, using the handle 2602, and the top shell 2604 and the base shell 2606 can be locked into the closed state, e.g., the top shell 2604 and base shell 2606 being together. The handle 802 can then be unlocked by disengaging the handle lock mechanism to perform crimping operations. The dual locking can prevent either the top crimper channel 2616 the top shell 2604 or bottom crimper channel 2618 of the base shell 2606 from moving to the closed position while the other half is in the open position.

In embodiments, the clamshell crimper 2600 can also include one or more stops, for example, stop 2609 that operate to physically stop the crimper handle 2602 (and crimper handle of the second side 2603) at one or more predetermined positions that correspond to one or more predetermine diameters to which the implantable medical device may be crimped or compressed. While not illustrated, in some embodiments, the clamshell crimper 2600 can include a first stop and a second stop. The first stop and the second stop provide a surface that stop the movement of the handle 2602 in the downward direction. The first stop and the second stop provide a stop position of the handle 2602 that corresponding to a predetermined diameter of the crimper chamber 2619. That is, the first stop and the second stop operate a physically stops to allow an implantable medical device to be compressed to a predetermined diameter or compression. For example, the first stop can operate to allow an implantable medical device to be partially compressed. Likewise, for example, the second stop can operate to allow an implantable medical device to be fully compressed. The first stop and the second stop can be removably coupled to the top shell 2604, base shell 2606, and/or a base of the clamshell crimper 2600. As such, the first top and/or the second stop can be added and/or removed to allow an implantable medical device to be compressed to predetermined diameters.

While the components of the clamshell crimper 2600 are described above with relative terms "first," "second," "proximal," and "distal," one skilled in the art will realize that the use of these terms is intended only to identify components of the clamshell crimper 2600 and do not define any preferred or ordinal arrangement of the components of the crimper 2600. Likewise, for example, while the implantable medical device is described as being positioned in the bottom crimper channel 2618 during operation, in an embodiment, the implantable medical device can be positioned in the top crimper channel 2616.

Figure 20A:
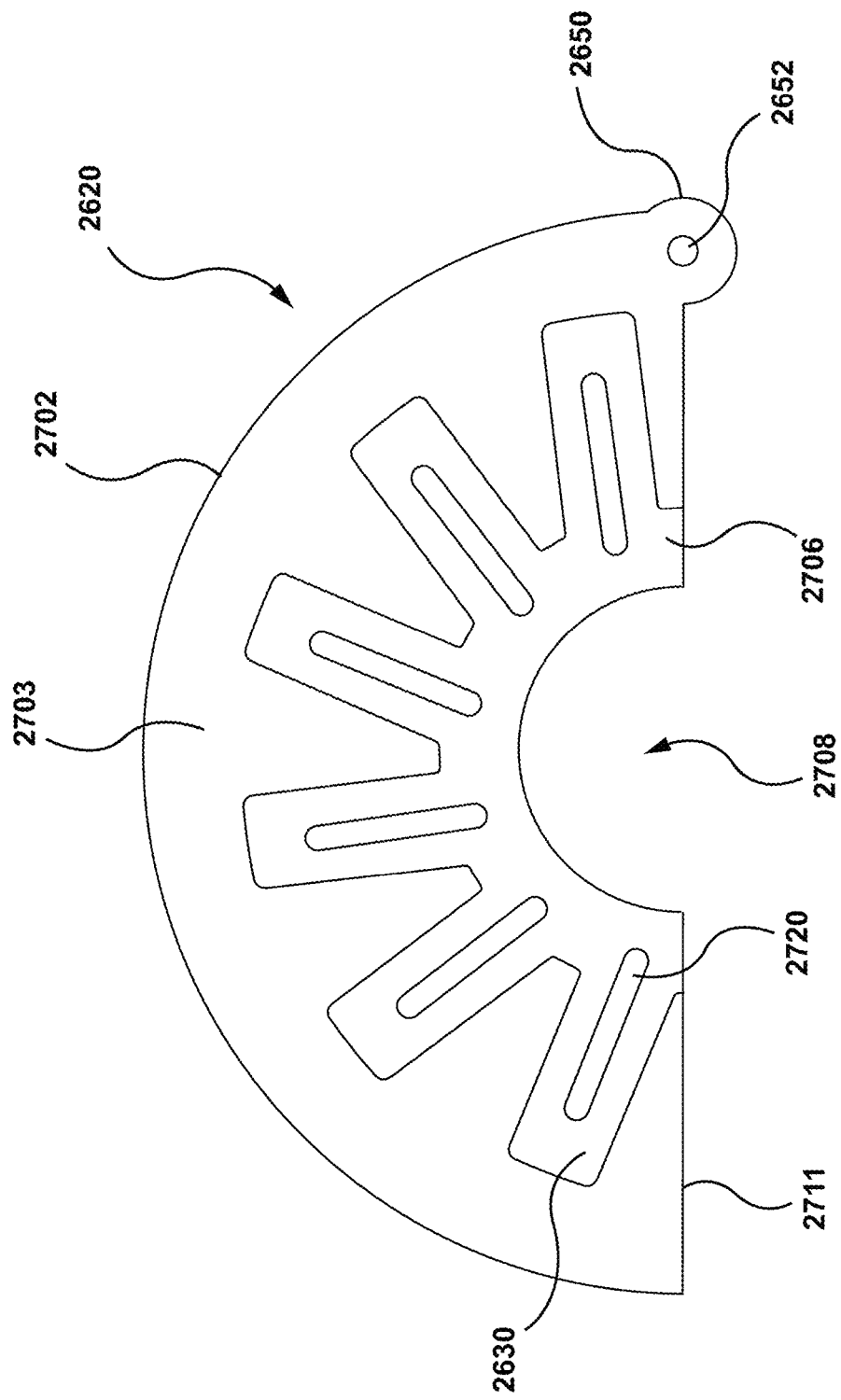
FIG. 20A depicts a perspective illustration of a side of a top shell of the crimper of FIGS. 19A-19G, according to an embodiment hereof.

FIG. 20A illustrates a detailed view of components of the top crimper element housing 2620 of the top shell 2604. One skilled in the art will realize that FIG. 20A illustrates one example of an element housing of the top shell 2604 and that existing components illustrated in FIG. 20A may be removed and/or additional components may be added to the top crimper element housing 2620. Additionally, while the top crimper element housing 2620 is only discussed below, one skilled in the art will realize that, in some embodiments, the top shell 2604 includes a second housing that may include the same components as illustrated in FIG. 20A. For example, the second housing may be formed as a "mirror" of the top crimper element housing 2620 and can be coupled to the top crimper element housing 2620 to form the top shell 2604. Alternatively, in some embodiments, the second side of the top shell 2604 may include pin channels that mirror the pin channels 2670 of the top cam 2622.

As illustrated in FIG. 20A, the top crimper element housing 2620 includes a side plate 2702 with an interior surface 2703 and an exterior surface (not shown) opposite the interior surface. In an embodiment, the side plate 2702 can be constructed as a semi-cylindrical plate with a semi-cylindrical opening 2708. The semi-cylindrical opening 2708 allows access to the top crimper channel 2616 formed by the crimper elements 2614. The crimper element channels 2630 are formed in the interior surface 2703 of the side plate 2702. The crimper element channels 2630 can be formed as a rectangular groove or channel that extends inward from an outer radius of the side plate 2702 towards the semi-cylindrical opening 2708. The crimper element channels 2630 can be positioned in an arc, at equal distances, along the interior surface 2703 of the side plate 2702. The crimper element channels 2654 are coupled to a center cavity 2706 formed in the interior surface 2703 of the side plate 2702. The center cavity 2706 can be formed as a semi-circular cavity having the approximately same depth as the crimper element channels 2630.

Each of the crimper element channels 2630 includes a pin slot 2720. The pin slot 2720 is configured to allow a pin 2680 of a crimper element 2614 to pass through the side plate 2702 and engage with the top cam 2622. The side plate 2702 also includes the cam channel 2632 formed within the exterior surface of the side plate 2702. The cam channel 2632 can extend in a semi-circular arc from a bottom surface 2711 of the side plate 2702. The cam channel 2632 can be configured to receive and retain the top cam 2622 via the tab 2640 and configured to allow the top cam 2622 to move (e.g., rotate) within the top shell 2604.

Figure 20B:
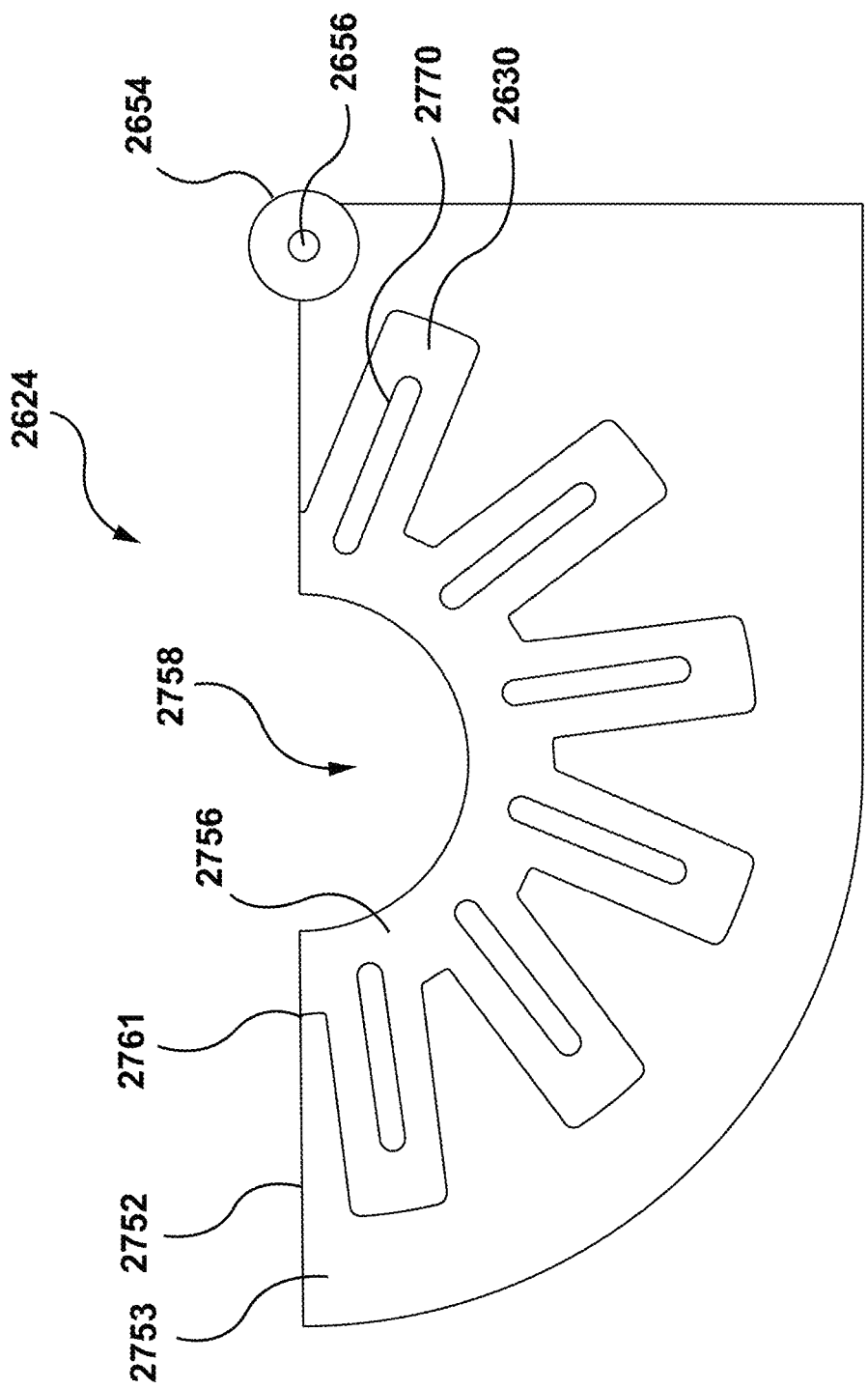
FIG. 20B depicts a perspective illustration of a side of a base shell of the crimper of FIGS. 19A-19G, according to an embodiment hereof.

FIG. 20B illustrates a detailed view of components of the base crimper element housing 2624 of the base shell 2606. One skilled in the art will realize that FIG. 20B illustrates one example of a housing of the base shell 2606 and that existing components illustrated in FIG. 20B may be removed and/or additional components may be added to the base crimper element housing 2624. Additionally, while the base crimper element housing 2624 is only discussed below, one skilled in the art will realize that the base shell 2506 includes a second housing that may include the same components as illustrated in FIG. 20B. For example, the second housing may be formed as a "mirror" of the base crimper element housing 2624 and can be coupled to the base crimper element housing 2624 to form the base shell 2606. Alternatively, in some embodiments, the second side of the base shell 2506 may include pin channels that mirror the pin channels 2670 of the top cam 2626.

As illustrated in FIG. 20B, the base crimper element housing 2624 includes a side plate 2752 with an interior surface 2753 and an exterior surface (not shown). In an embodiment, the side plate 2752 can be constructed as a semi-cylindrical plate with a semi-cylindrical opening 2758. The semi-cylindrical opening 2758 allows access to the bottom crimper channel 2618 formed by the crimper elements 2614. The crimper element channels 2630 are formed in the interior surface 2753 of the side plate 2752. The crimper element channels 2630 can be formed as a rectangular groove or channel that extends inward from an outer radius of the side plate 2752 towards the semi-cylindrical opening 2758. The crimper element channels 2630 can be positioned in an arc, at equal distances, along the interior surface 2753 of the side plate 2752. The crimper element channels 2654 are coupled to a center cavity 2756 formed in the interior surface 2753 of the side plate 2752. The center cavity 2756 can be formed as a semi-circular cavity having the approximately same depth as the crimper element channels 2630.

Each of the crimper element channels 2630 includes a pin slot 2770. The pin slot 2770 is configured to allow a pin 2680 of a crimper element 2614 to pass through the side plate 2752 and engage with the base cam 2626. The side plate 2752 also includes the cam channel 2632 formed within the exterior surface of the side plate 2752. The cam channel 2638 can extend in a semi-circular arc from a top surface 2761 of the side plate 2752. The cam channel 2632 can be configured to receive and retain the base cam 2626 via the tab 2642 and configured to allow the base cam 2626 to move (e.g., rotate) within the base shell 2606.

Figure 20C:
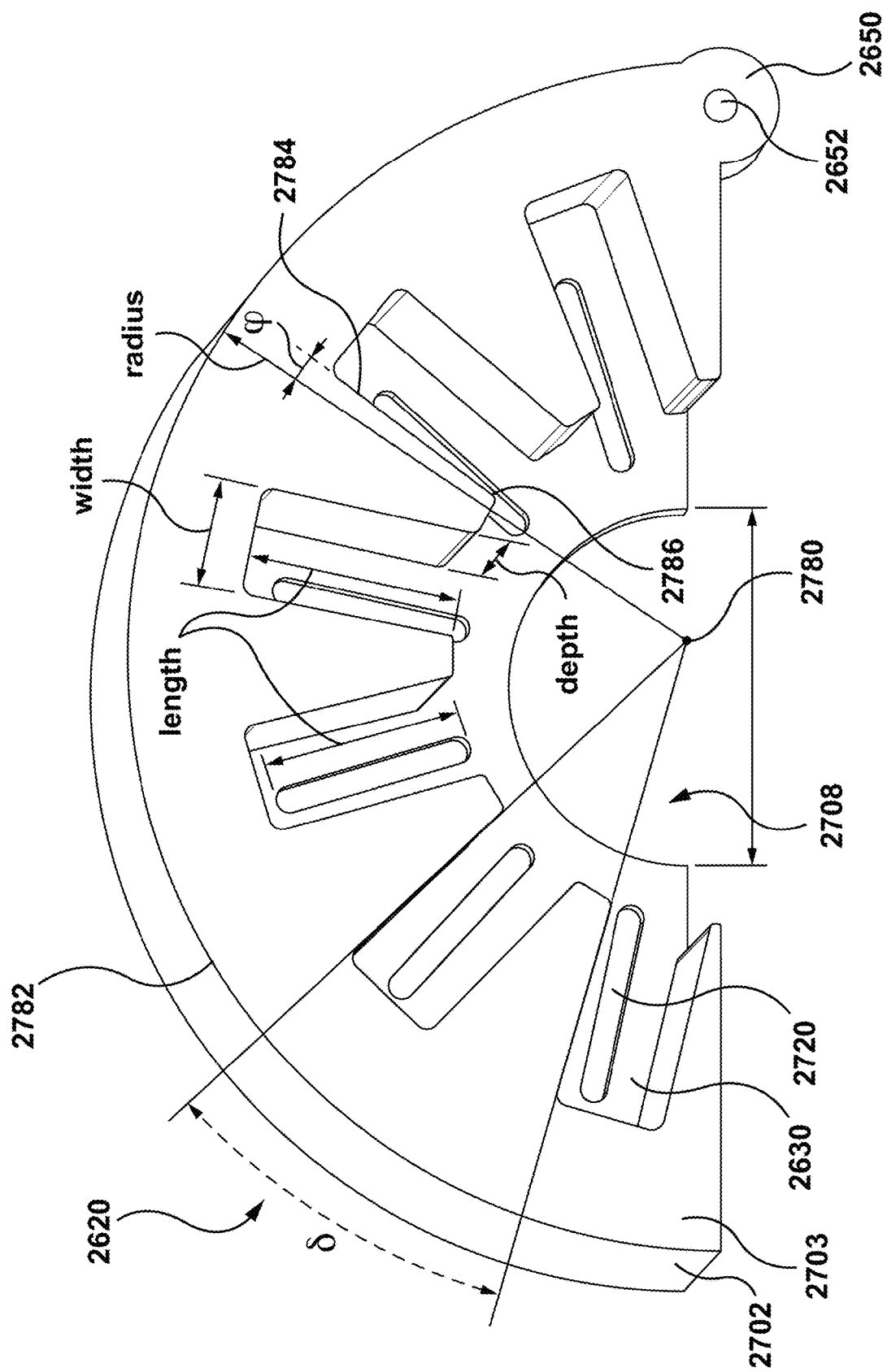
FIG. 20C depicts a perspective view of the top shell of FIG. 20A.

The crimper element channels 2630 and the center cavity 2706 can be configured to moveably secure the crimper elements 2614 within the top shell 2604. Likewise, the crimper element channels 2630 and the center cavity 2756 can be configured to moveably secure the crimper element 2614 within the base shell 2606. FIG. 20C illustrates enlarged perspective view of the crimper element channels 2630 and a portion of the center cavity 2706, according to an embodiment hereof. While the configuration and dimensions of the side plate 2702 of the top shell 2604 are described with reference to FIG. 20C, one skilled in the art will realize that the configuration described in FIG. 20C can also be applied to the configuration of the side plate 2752 of the base shell 2606.

As illustrated in FIG. 20C, the side plate 2702 is formed having a radius that extends from a center point 2780 of the semi-cylindrical opening 2708 to a side surface 2782 of the side plate 2702. In embodiments, the radius can be formed to a length that accommodates the crimper elements 2614 and allows for movement of the crimper elements within the top shell 2604. In embodiments, the crimper element channels 2630 of the side plate 2702 are formed to a width and depth to accommodate the crimper elements 2614 when the side plate 2602. Likewise, the crimper element channels 2630 of the side plate 2702 are formed to a length and the center cavity 2706 is formed to a radius that allows the crimper elements 2614 move and perform the crimping operations of the clamshell crimper 2600. The pin slots 2720 can have a slot length.

As noted above, the crimper element channels 2630 are formed in an arc around the side plate 2702. In embodiments, each of the crimper element channels 2630 are spaced in the arc at an angle, $\delta$, from an adjacent crimper element channel 2630. For example, each of the crimper element channels 2630 can be spaced at an angle, $\delta$, of approximately 30 degrees. In embodiments, each of the crimper element channels 2630 can be aligned to be offset relative to the Radius of the side plate 2702 by an angle, $\varphi$. For example, as illustrated in FIG. 20C, the angle, $\varphi$, can be defined as an angle between the Radius and a sidewall 2784 of a crimper element channel 2630, when measured at an intersection 2786 of the radius and the sidewall 2784. The offset can cause the crimper elements 2614 to move in a direction that is offset from the center point 2780. For example, the crimper element channels 2630 can be offset by an angle, $\varphi$, that is approximately 15 degrees.

FIGS. 21A-21H illustrate a detailed view of a crimper element 2614, according to an embodiment hereof. One skilled in the art will realize that FIGS. 21A-21H illustrate one example of a crimper element and that existing components illustrated in FIGS. 21A-21H may be removed and/or additional components may be added to the crimper element 2614. While only one crimper element 2614 is discussed, one skilled in the art will realize that the crimper elements 2614 of the top shell 2604 and the base shell 2606 may have the same configuration and include the same components as the crimper element 2614 described in FIGS. 21A-21H.

Figure 21A:
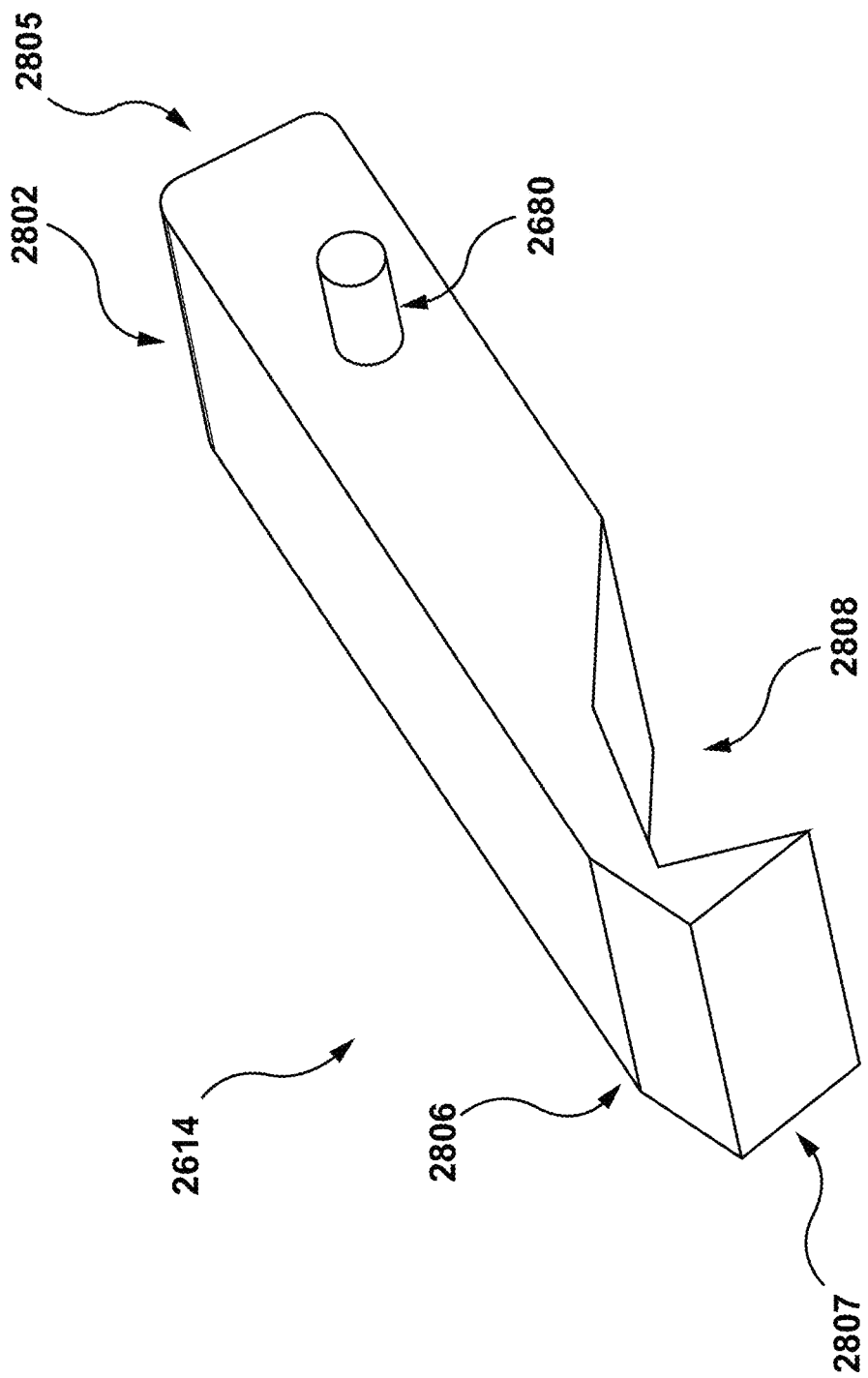
FIGS. 21A-21H depict several views of a crimper element of FIGS. 19A-19G, according to an embodiment hereof.

As illustrated in FIG. 21A, which is a perspective view, the crimper element 2614 has a body 2802 and a crimper lobe 2806 coupled to the body 2802. The body 2802 extends parallel to a long axis of the crimper element 2614, from a proximal end 2805 of the crimper element 2614 to the crimper lobe 2806. The crimper lobe 2806 extends from the body 2802 to a distal end 2807 of the crimper element 2614.

Figure 21B:
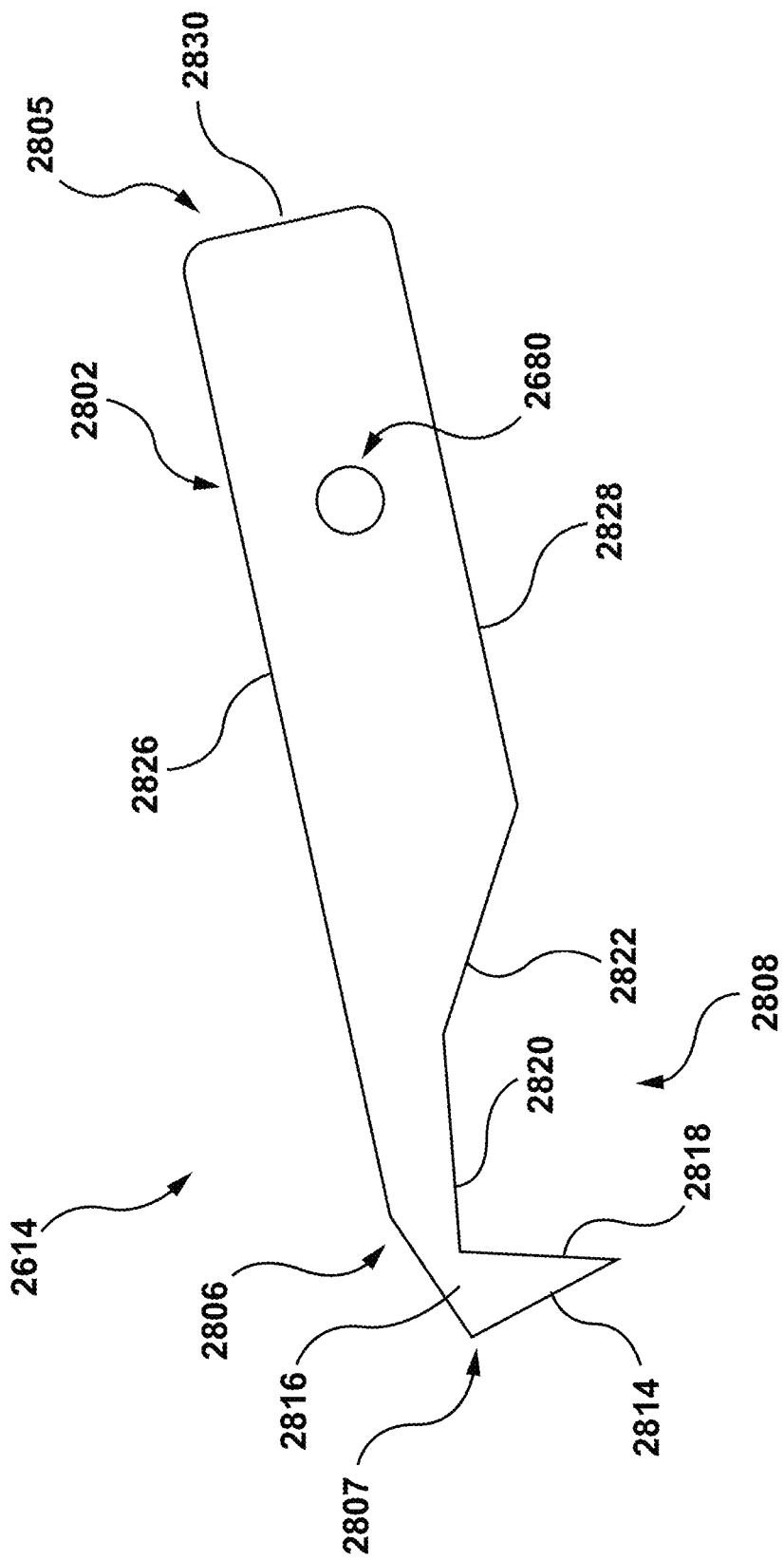
Figure 21C:
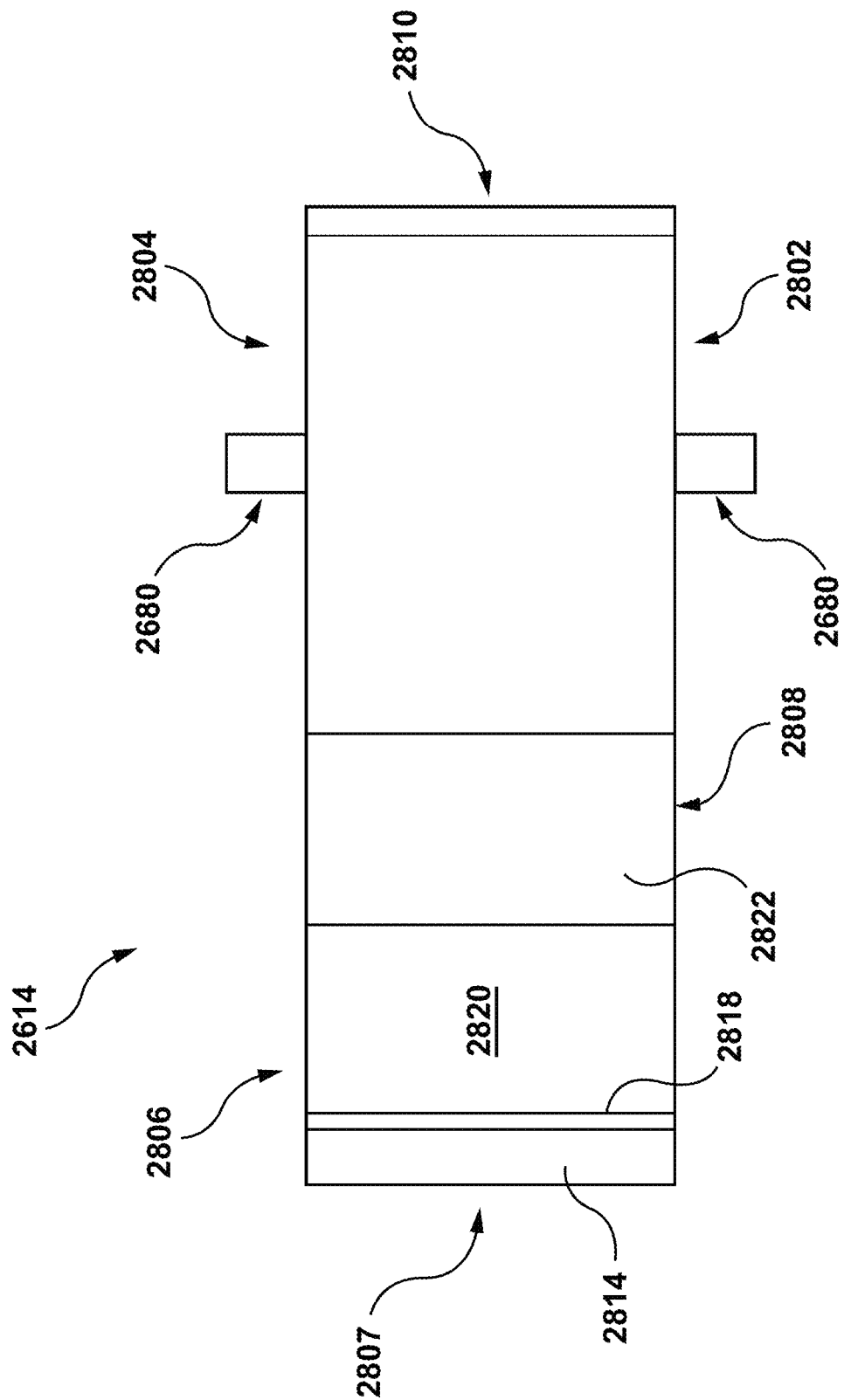

As illustrated in FIG. 21B, which is a side view, the crimper element 2614 includes a top surface 2826, a bottom surface 2828, and a distal surface 2830 formed at the end of the body 2802. The crimper lobe 2806 includes a first exterior ramp 2814 and a second exterior ramp 2816. The crimper lobe 2806 also include a first interior ramp 2818 and a second interior ramp 2820. The intersection of the body 2802 and the crimper lobe 2806 form a sloped edge 2822. As in FIGS. 21B and 21C, which is a bottom view, the first interior ramp 2818, the second interior ramp 2820, and the sloped edge 2822 define the crimper space 2808.

Figure 21D:
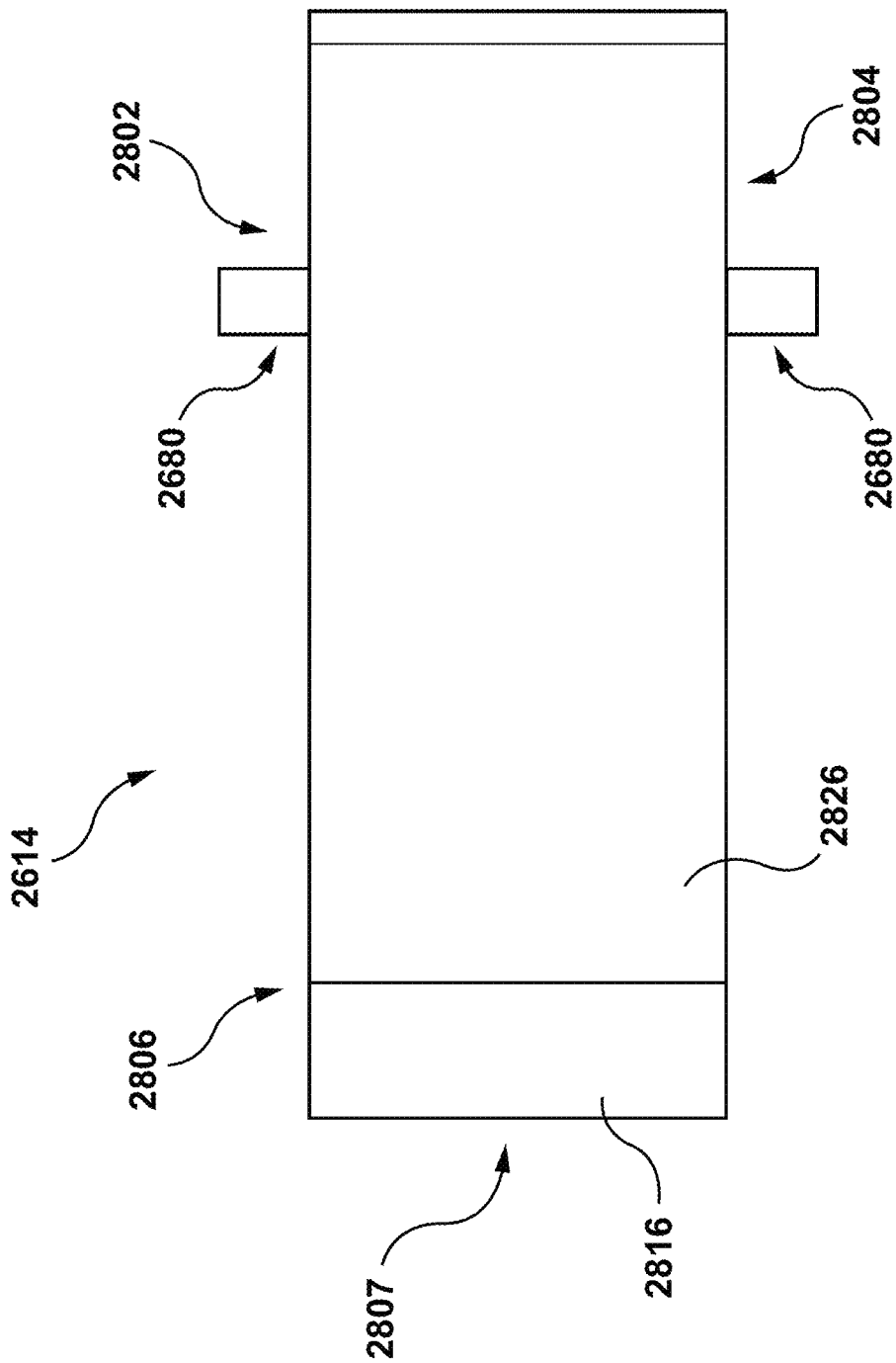

As illustrated in FIG. 21D, which is a top view, the first exterior ramp 2814 and the second exterior ramp 2816 from a plane between the top surface 2826 and the distal end 2807 and the bottom surface 2828. The first exterior ramp 2814 and the second exterior ramp 2816 can be formed at angles relative to the top surface 2826 and the bottom surface 2828. Likewise, the first interior ramp 2818 and the second interior ramp 2820 can be formed at angles relative to the top surface 2826 and the bottom surface 2828. The intersection of the body 2802 and the crimper lobe 2806 form a sloped edge 2822.

The crimper element 2614 also includes pins 2680. The pins 2680 are formed in the first side and the second side of the body 2802. In an embodiment, the crimper elements 2614 can include two pins 2680 that are positioned at opposing location on the first side and the second side of the body 2802. In embodiments, the pins 2680 can be configured to moveably coupled to the top cam 2622 and the base cam 2626. For example, the pins 2680 can be a dowel pin, a bolt, and the like. The pin can be formed to a diameter to maintain the corresponding pin channels 2670 and cause the pin to move within the pin channels. The pins 2680 operate to moveably couple the top cam 2622 and the base cam 2626 to the crimper elements 2614. The pins 2680 allow the crimper elements 2614 to move relative to the rotation of the top cam 2622 and the base cam 2626 during operation of the clamshell crimper 2600.

In an embodiment, the width of the crimper element 2614 can range from approximately 25 mm to approximately 50 mm and the length of the crimper element 2614 can range from approximately 1 mm to approximately 40 mm. The slope of the first exterior ramp 2814 and the second exterior ramp 2816 (angle relative to the top surface 2826 and the bottom surface 2828) can depend on the crimper elements included in the clamshell crimper 2600. Likewise, the slope of the first interior ramp 2818, the second interior ramp 2820, and the sloped edge 2822 (angle relative to the top surface 2826 and the bottom surface 2728) can depend on the crimper elements included in the clamshell crimper 2600. In an embodiment, the slope can be determined by dividing 360 degrees by the number of crimper elements 2614 in the clamshell crimper 2600. In an embodiment, the number of crimper elements can range from 10 to 12. The first interior ramp 2818, the second interior ramp 2820, and the sloped edge 2822 are configured to contact a neighboring crimper element and generate the iris effect when the crimper elements are displaced.

Figure 21E:
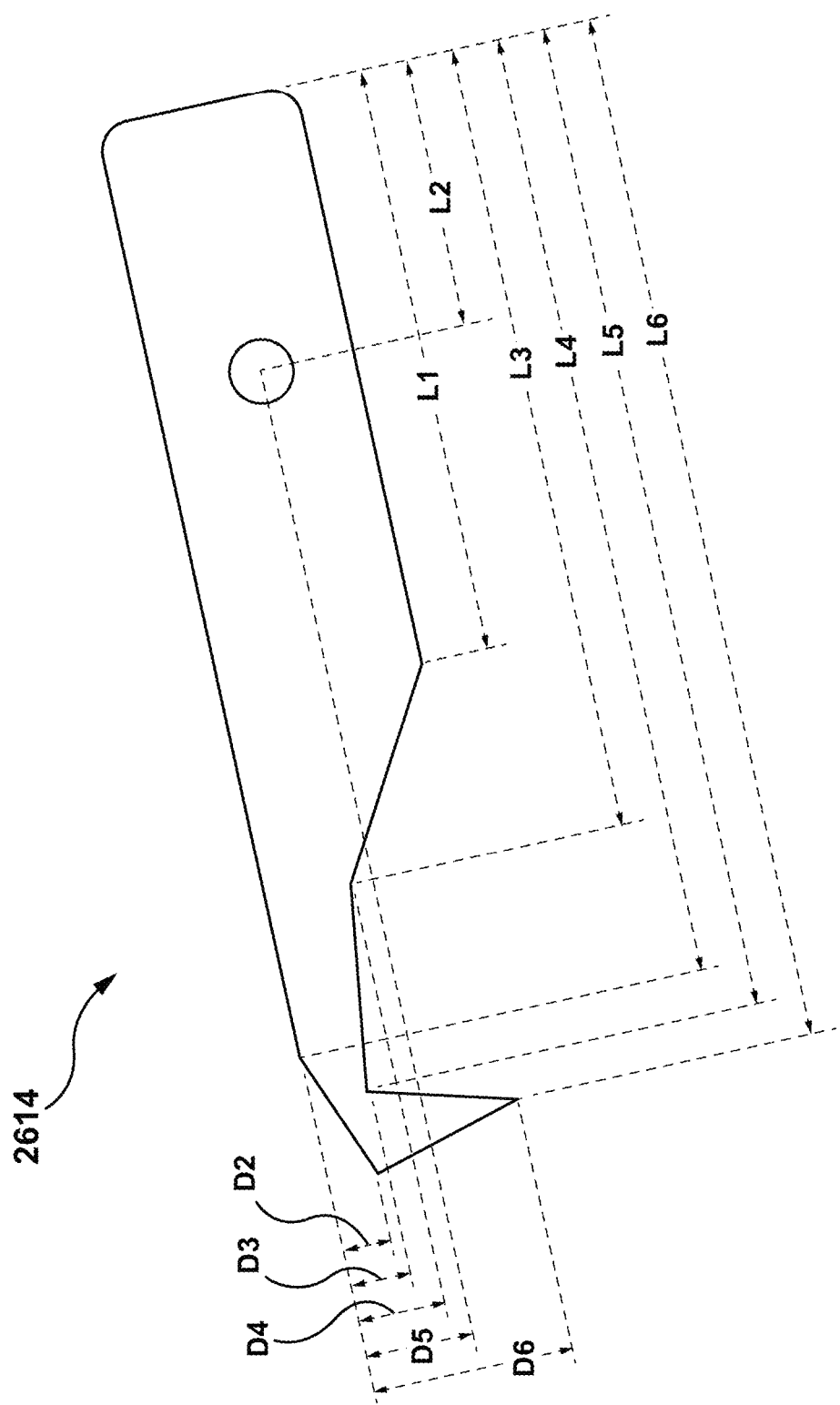
Figure 21F:
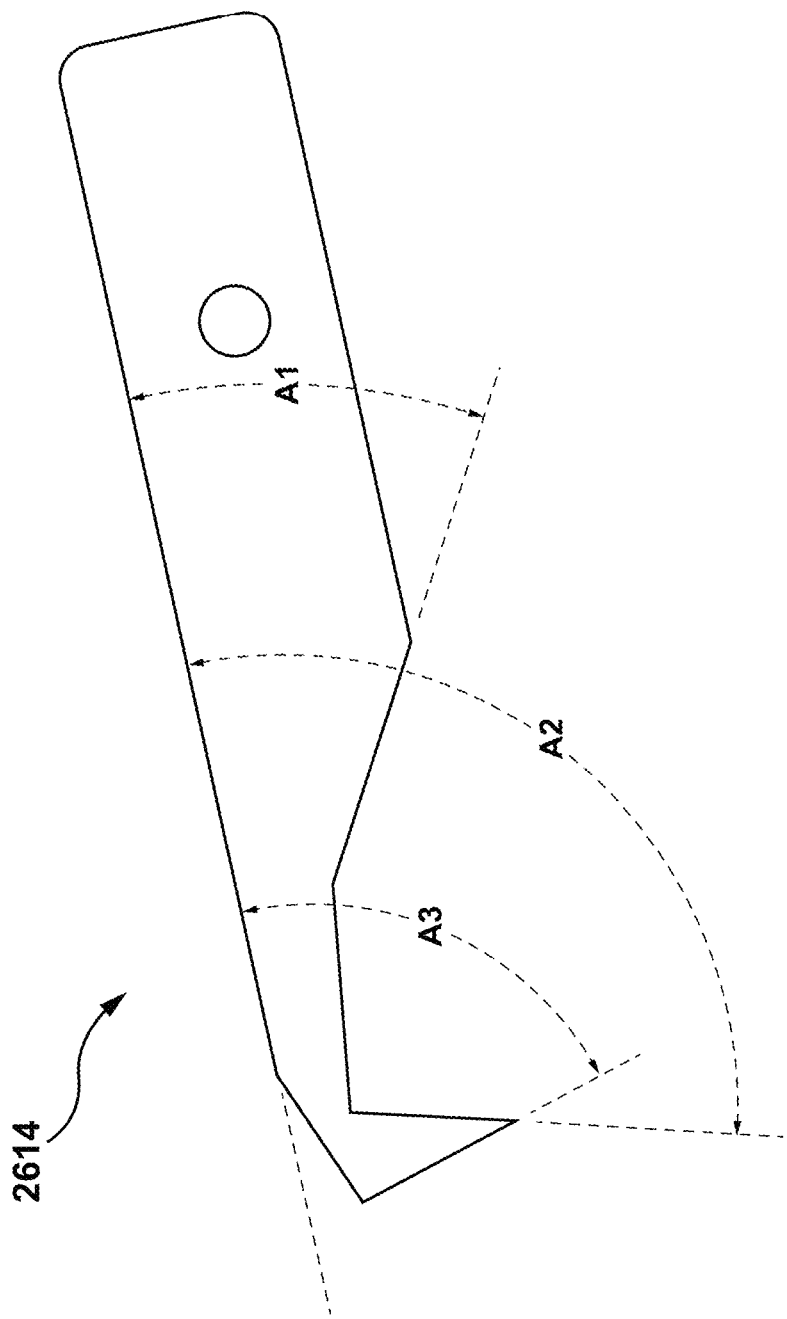
Figure 21G:
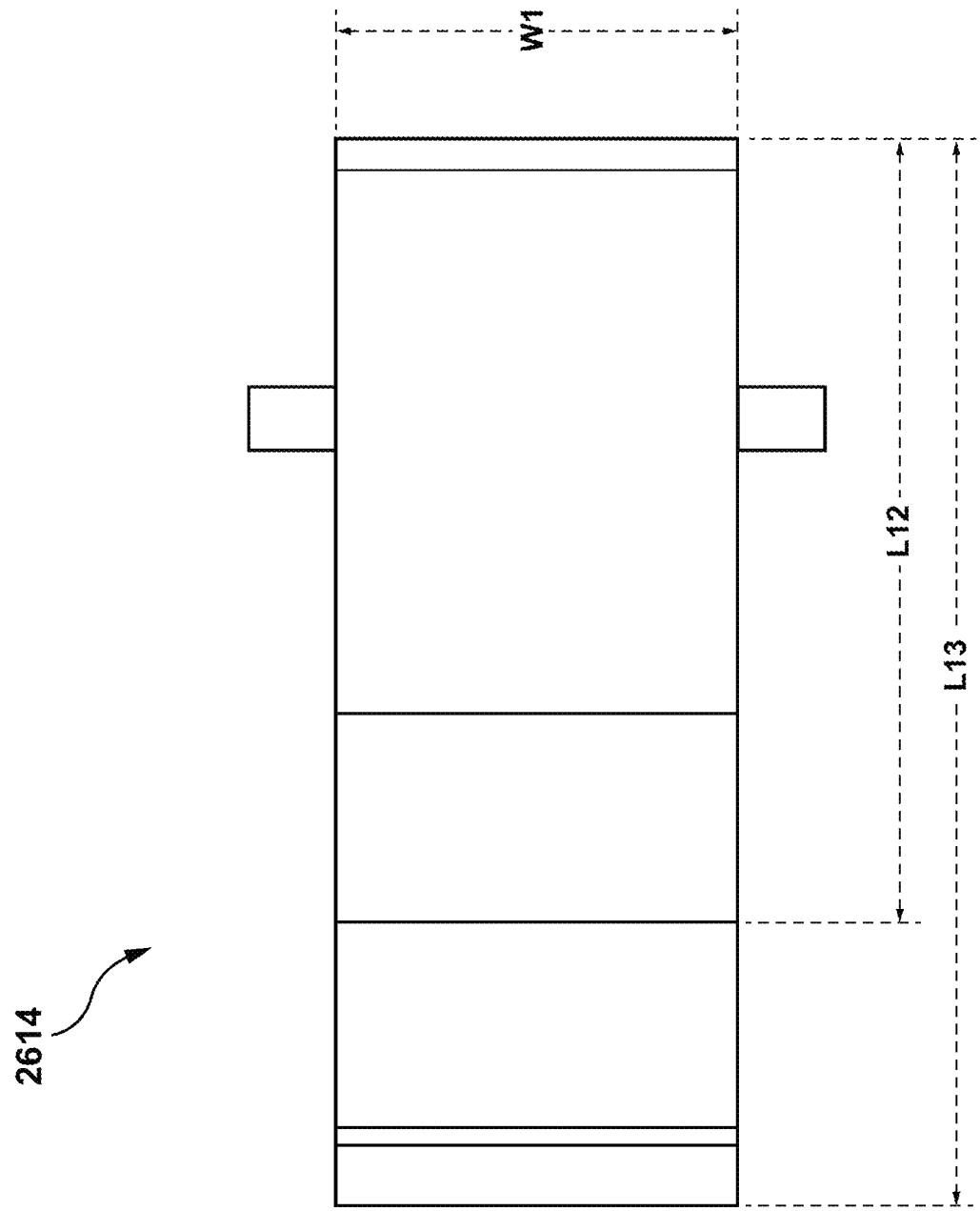

FIGS. 21E-21G illustrates examples of dimensions for a crimper element 2614 having a 30 mm configuration, according to an embodiment hereof. For clarity in illustrating the dimension, reference numbers for the crimper element 2614 have been omitted and can be found in FIGS. 21A-21D. Table 1 below describes the dimension illustrated in FIGS. 21E-21G and provides example values for the dimensions. One skilled in the art will realize that the values for the dimension are one example, and the crimper element 2614 can have different values for the dimension based on the particular configuration of the clamshell crimper 2600 and the crimping application. One skilled in the art will realize that any examples of dimensions describe herein are approximate values and can vary by, for example, +/−5.0%, based on manufacturing tolerances, operating conditions, and/or other factors.

TABLE 1

| Dimension | Description | ~Value |
|---|---|---|
| L1 | Proximal End 2705 to beginning of Sloped Edge 2722 | 44 mm |
| L2 | Proximal End 2705 to midpoint of a Pin 2528 | 20-40 mm |
| L3 | Proximal End 2705 to end of Sloped Edge 2722 | 59 mm |
| L4 | Proximal End 2705 to beginning of Exterior ramp 2716 | 70.5 mm |
| L5 | Proximal End 2705 to end of Interior Ramp 2720 | 74 mm |
| L6 | Proximal End 2705 to end of Interior Ramp 2718 | 77 mm |
| L10 | Proximal End 2705 to beginning of Sloped Edge 2736 | 23.8 mm |
| L11 | Proximal End 2705 to end of Sloped Edge 2736 | 29.4 mm |
| L12 | Proximal End 2705 to Proximal End 2734 of Crimper Lobe 2806 | 58.8 mm |
| L13 | Proximal End 2705 to Distal End 2707 | 80 mm |
| D1 | Top Surface 2726 to Bottom Surface 728 | 15 mm |
| D2 | Top Surface 2726 to end of Exterior Ramp 2716 | 3.7 mm |
| D3 | Top Surface 2726 to end of Interior Ramp 2720 | 4 mm |
| D4 | Top Surface 2726 to beginning of Interior Ramp 2720 | 6.4 mm |
| D5 | Top Surface 2726 to midpoint of Pins 2528 | 8.75 mm |
| D6 | Top Surface 2726 to beginning of Exterior Ramp 2714 | 15 mm |
| W1 | Exterior Surface 2736 of Body 2802 | 90 mm |
| A1 | Angle between Top Surface 2726 and Sloped Edge 2722 | 30 degrees |
| A2 | Angle between Top Surface 2726 and Interior Ramp 2718 | 105 degrees |
| A3 | Angle between Top Surface 2726 and Exterior Ramp 2714 | 75 degrees |

Figure 21H:
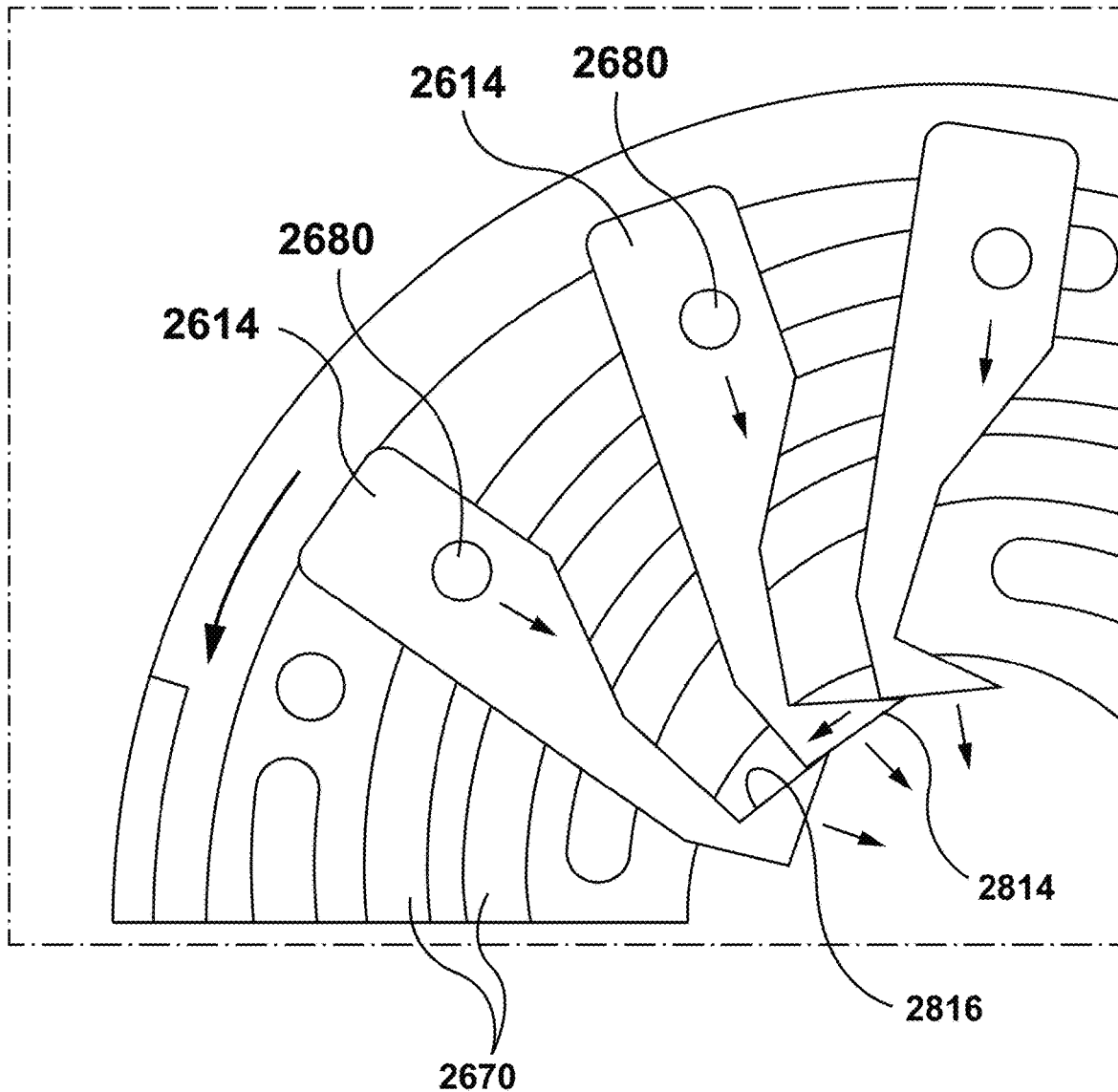

In embodiments, the crimper elements 2614 are configured to work in combination to produce the iris effect of the clamshell crimper 2600. FIG. 21H is an enlarged side view of several crimper elements 2614 in which the crimper elements 2614 are positioned in a fully open position. As illustrated, a first exterior ramp 2814 of a first crimper element 2814 rest against a first interior ramp 2816 of a second crimper element 2614, forming an overlap. The overlap of the crimper elements 2614 define the crimper chamber 2619. During operation, for example, the handle 2602 is actuated in a downward motion (counter-clockwise direction as illustrated in FIG. 21H) thereby causing the cam (the top cam 2622 illustrated in FIG. 21H) to rotate. The rotation of the top cam 2522 forces the pins 2680 inward. The motion of the pins 2680 forces the crimper elements 2614 inward. In particular, the crimper elements 2614 move inward generally towards the center of the crimper chamber 2619. As the crimper elements 2614 move inward, the space available for the crimper elements 2614 to occupy is reduced. As such, the space between the crimper elements 2614 is reduced. As such, the first exterior ramp 2814 of the first crimper element 2814 slides against the first interior ramp 2816 of the second crimper element 2614. In response, the area of the crimper chamber 2619 is reduced.

Figure 22:
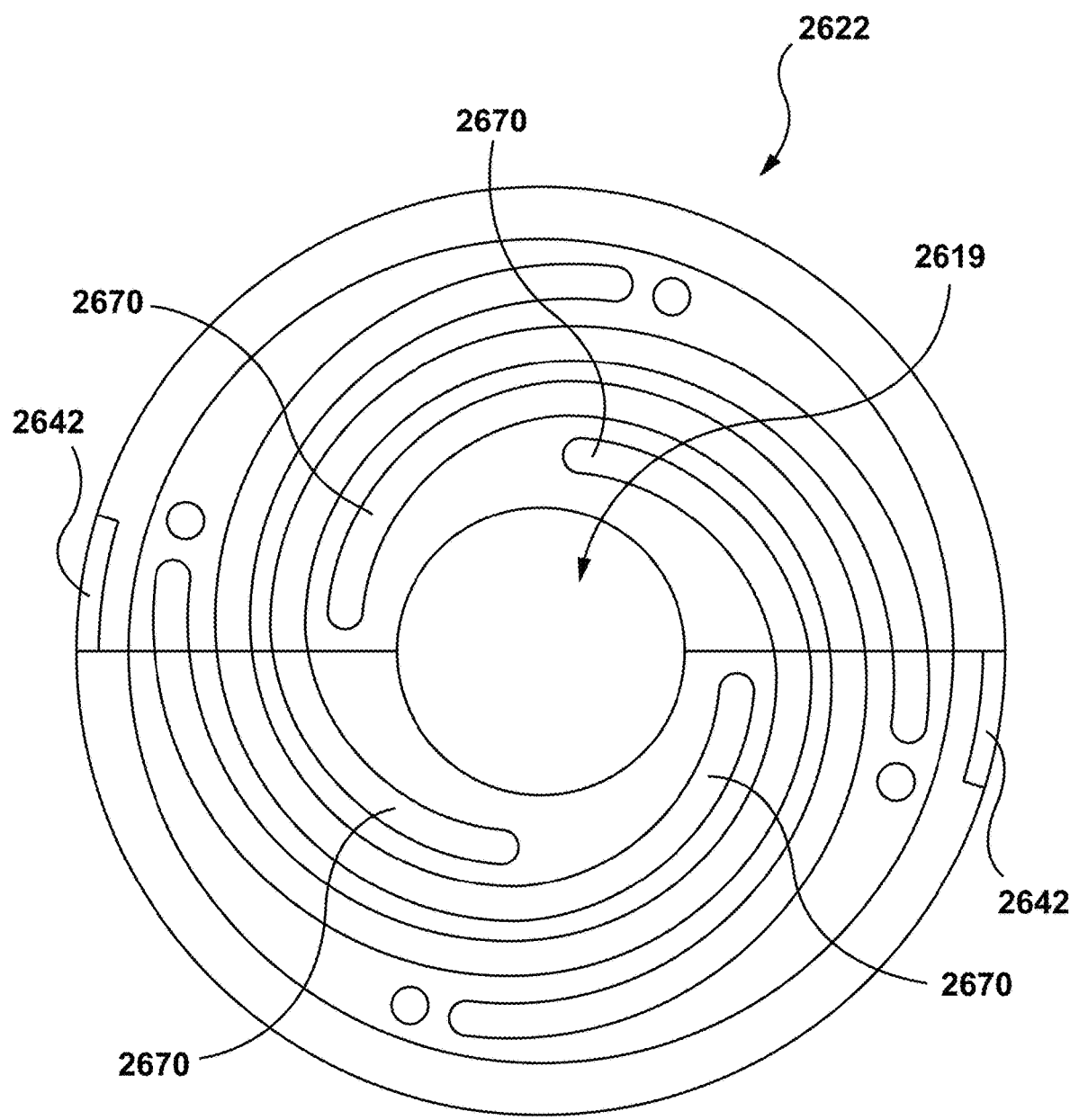
FIG. 22 depicts a side view a top cam and a base cam of the crimper of FIGS. 19A-19G, according to an embodiment hereof.

FIG. 22 illustrates a side view of the top cam 2622 and the base cam 2626 when in a closed state, according to an embodiment hereof. One skilled in the art will realize that FIG. 22 illustrates one example of a top cam/base cam and that existing components illustrated in FIG. 22 may be removed and/or additional components may be added to the top cam 2622 and the base cam 2626.

As illustrated, the top cam 2622 includes a semi-circular ring 2902. Likewise, the base cam 2626 includes a semi-circular ring 2952. The semi-circular ring 2902 includes a handle connection holes 2904 and the pin channels 2670. Likewise, the semi-circular ring 2952 includes the pin channels 2670. The top cam 2622 also includes the tab 2640, and the base cam 2626 includes the tab 2642. The tab 2640 is configured to engage with the cam channel 2632, and the tab 2642 is configured to engage with the cam channel 2634. This allows the top cam 2622 and the base cam 2626 to move relative to the top crimper element housing 2620 and the base crimper element housing 2624 when a force is applied to the handle 2602 and thereby translating the force to the semi-circular rings 2902/2952 and causing the top cam 2622 and the base cam 2626 to rotate clockwise or counter-clockwise (depending on the force applied to the handle 2602).

When the top cam 2622 and the base cam 2626 are in the closed state, the top cam 2622 and the base cam 2626 form the crimper chamber 2619. As illustrated, the pin channels 2670 are formed in a spiral pattern on the top cam 2622 and the base cam 2626. The pin channels 2670 are formed having a decreasing distance from the crimper chamber 2619. As such, as the pins 2680 move within the pin channels 2670, the pins 2680 move either inward or outward relative to the crimper chamber 2619. The inward motion of the pins 2680 cause the crimper elements 2614 of the top shell 2604 and the base shell 2606 to displace inward within the crimper element channels 2630 thereby generating the iris effect. That is, the inward motion of the pins 2680 is translated to the crimper elements 2614 thereby causing the crimper elements 2614 to displace inward.

Figure 23:
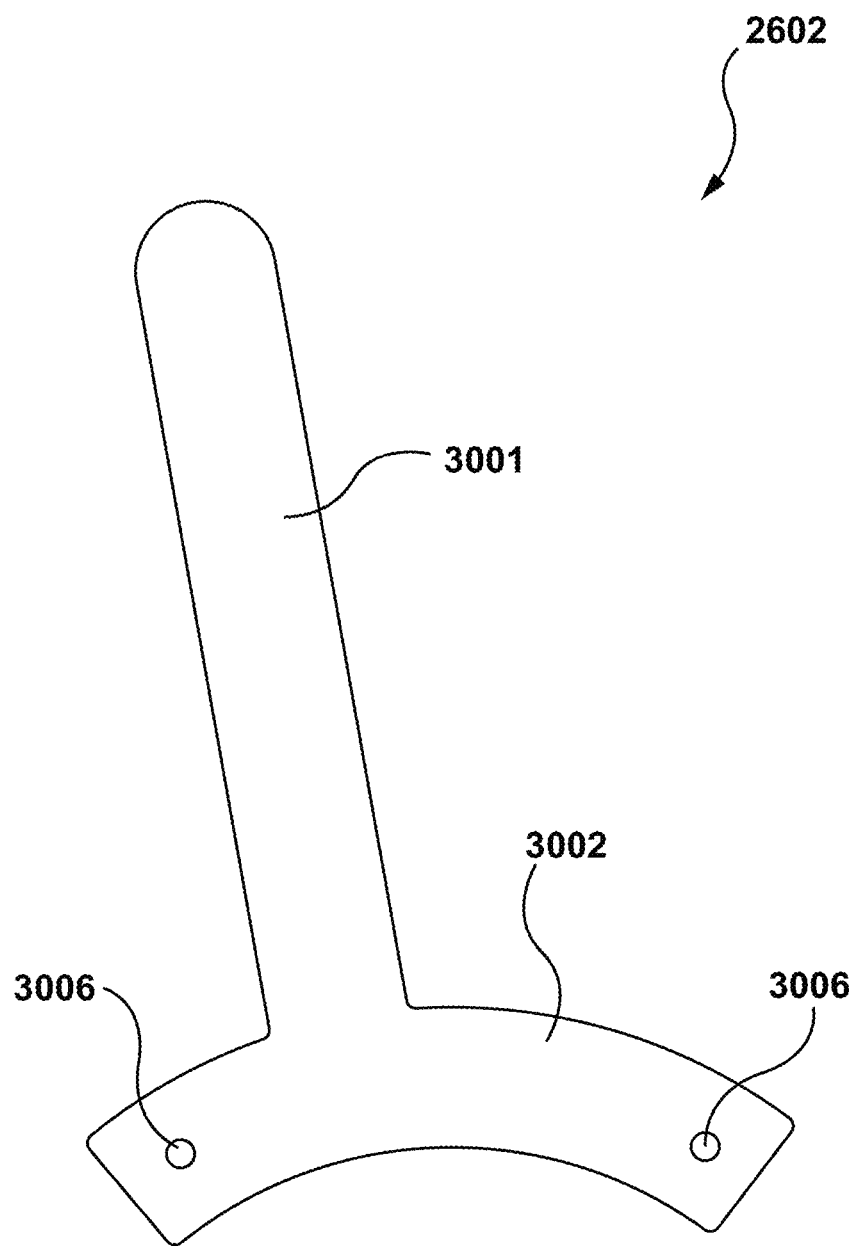
FIG. 23 depicts of a handle of the crimper of FIGS. 19A-19G, according to an embodiment hereof.

FIG. 23 illustrates a detailed view of the handle 2602, according to an embodiment hereof. One skilled in the art will realize that FIG. 23 illustrate one example of a handle and that existing components illustrated in FIG. 23 may be removed and/or additional components may be added to the handle 2602.

As illustrated FIG. 23, which is a side view respectively, the handle 2602 includes a handle bar 3001 and a handle base 3002. The handle base 3002 includes a top cam connection holes 3006. The top cam connection holes 3006 are configured to couple the handle base 3002 to the top cam 2622. The top cam connection holes 3006 are configured to receive a connection device to couple handle base 3002 to the top cam 2622. The connection device can be any type of device to couple the handle base 3002 to the top cam 2622 such as a bolt, screw, pin, etc.

Figure 24A:
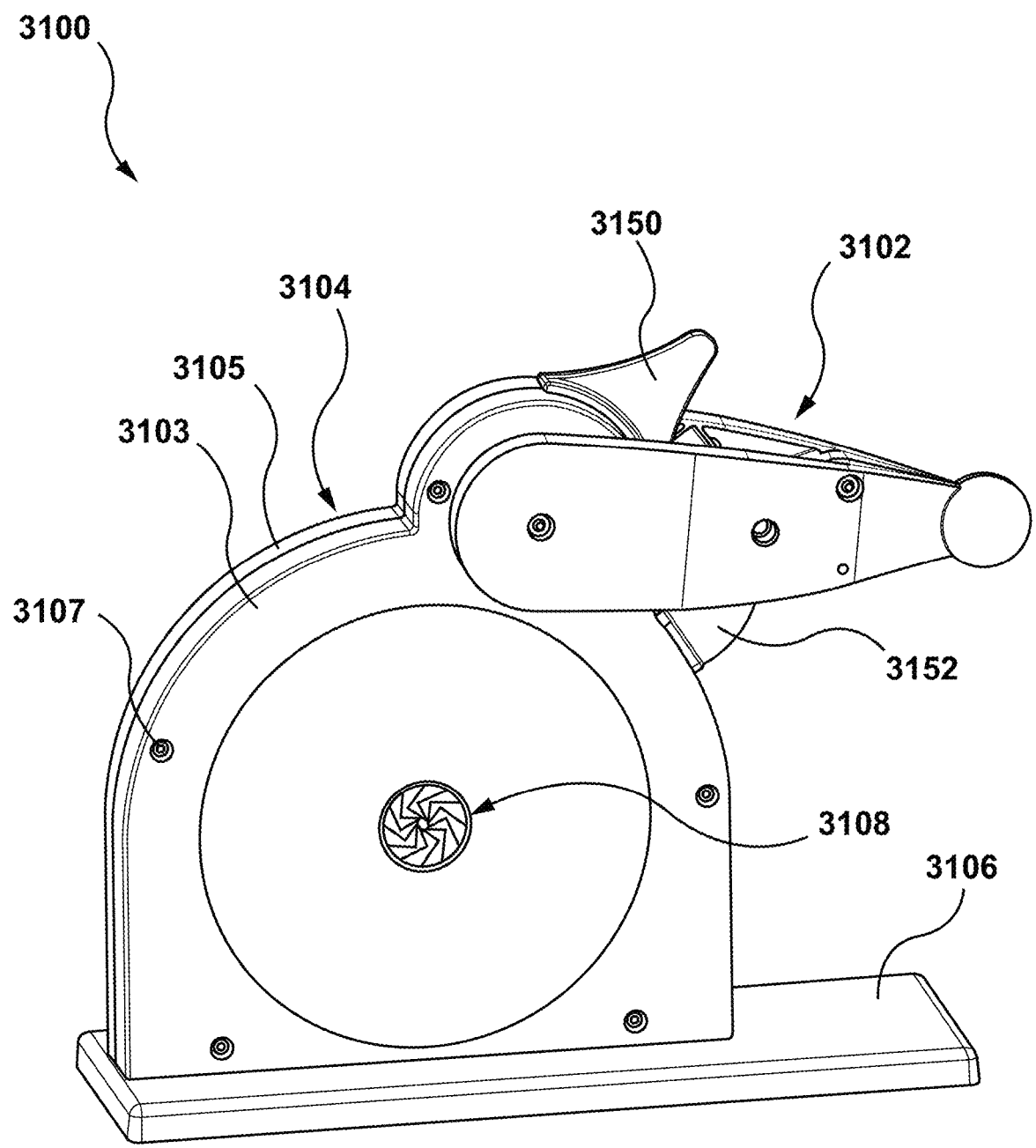
FIGS. 24A and 24B depict different views of another example of a crimper for use with a medical device, according to an embodiment hereof.
Figure 24B:
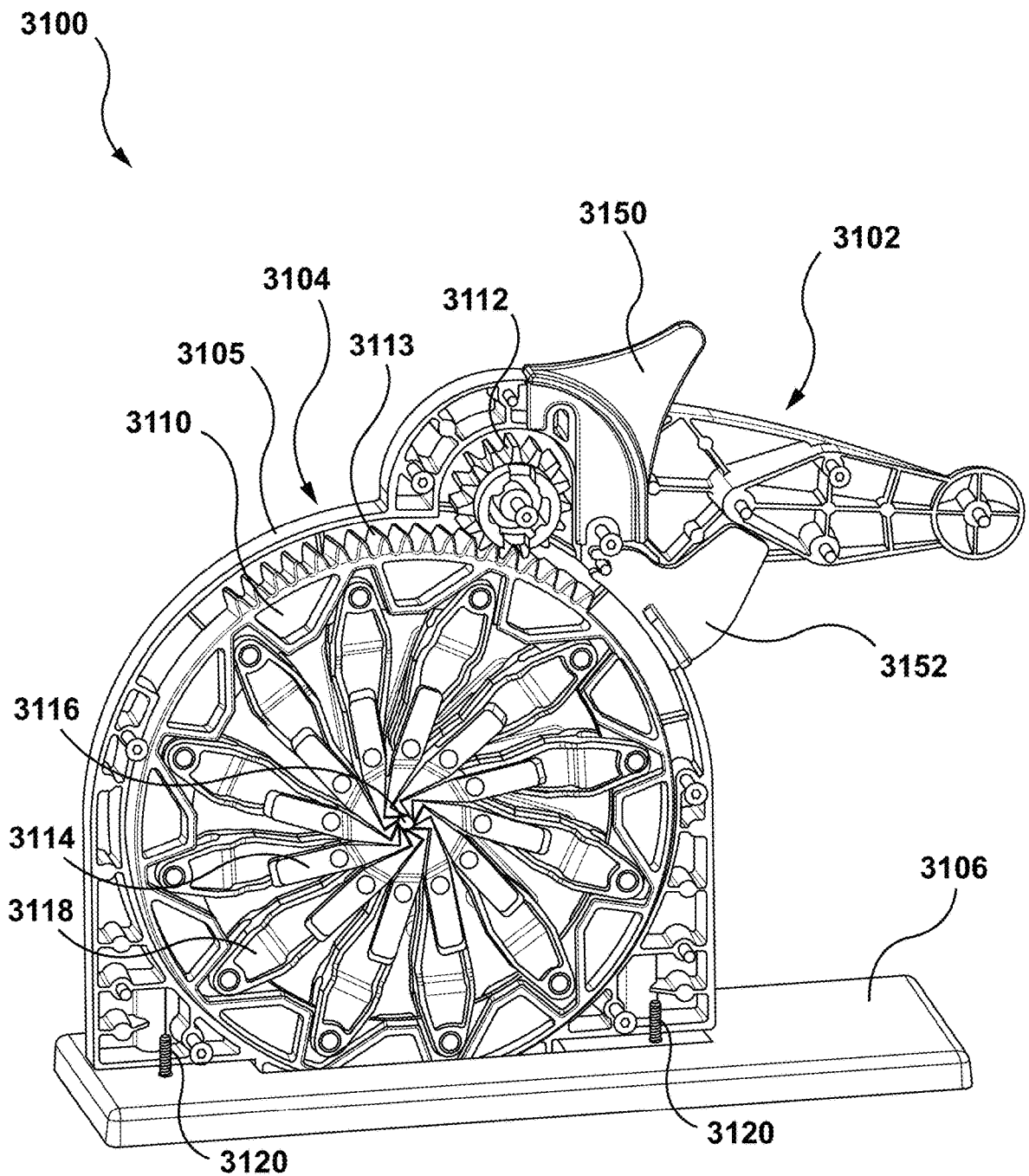

FIGS. 24A and 24B illustrate an example of a crimper 3100 in accordance with an embodiment hereof. One skilled in the art will realize that FIGS. 24A and 24B illustrate one example of a crimper and that existing components illustrated in FIGS. 24A and 24B may be removed and/or additional components may be added to the crimper 3100. In the embodiment of FIGS. 24A and 24B, as will be described in more detail herein, the crimper 3100 includes a plurality of crimper elements that are configured to apply non-uniform radial compression along a length of an implantable medical device. As used herein, the plurality of crimper elements are configured to apply non-uniform radial compression due to the non-uniform shape thereof. More particularly, the force applied by the crimper 3100 is essentially uniform across the length of the crimper chamber 3116 but the non-uniform radial shape created by the assembled crimper elements results in an application of force to the implantable medical device that is variable along the length of the crimper chamber 3116 because the point of contact to the implantable medical device varies. For example, the larger diameter of the crimper chamber 3116 applies a lower force than the smaller diameter of the crimper chamber 3116 because the larger diameter of the crimper chamber 3116 does not apply a force until it contacts the implantable medical device whereas the smaller diameter of the crimper chamber 3116 is already compressing the implant. Thus, the non-uniform radial compression or force that is applied to the implantable medical device varies and is not constant along a length of an implantable medical device to which the force is applied.

There are instances when non-uniform radial compression along the length of the implantable medical device is desirable and beneficial. One instance is to preferably crimp the ends of the implantable medical device to increase the retention of the implantable medical device on the delivery system. Another instance may be to lessen the radial compression in certain portions of the implantable medical device to reduce possible damage from over-crimping a sensitive feature of the implantable medical device. In this instance, the non-uniform radial compression results in a substantially uniform profile in the compressed state of the implantable medical device due to more force being applied over the denser portions of the implantable medical device, i.e., portions of the implantable medical device that have a greater density relative to other portions of the implantable medical device. As used herein, "substantially uniform profile" includes an implantable medical device having the same diameter in the compressed state along the length of the implantable medical device after being crimped, including normal tolerances permitted during manufacturing processes. Thus, a non-uniform radial compression can improve implant retention to the delivery system and decrease damage to an implantable medical device caused by excessive crimping of sensitive regions while minimizing the profile.

While the components of the crimper 3100 are described herein with relative terms "first," "second," "proximal," and "distal," one skilled in the art will realize that the use of these terms is intended only to identify components of the crimper 3100 and do not define any preferred or ordinal arrangement of the components of crimper 3100.

In addition, it will be apparent to one of ordinary skill in the art that the crimper 3100 may be modified to have a clamshell configuration as described in previous embodiments hereof in which the crimper includes a top iris shell and a base iris shell. The top iris shell can be rotated away from the base iris shell to expose a channel for loading and positioning the implantable medical device and the delivery device. When closed, the channel of the base iris shell and a corresponding channel in the top iris shell form a crimper chamber around the implantable medical device. The clamshell crimper can then be actuated to decrease the volume of the crimper chamber though the process of iris-style displacement of crimper elements.

FIG. 24A is a perspective view of the crimper 3100. As illustrated in FIG. 24A, the crimper 3100 includes a handle 3102, a crimper housing 3104, and a base 3106. The crimper housing 3104 includes a first side 3103 and a second side 3105 positioned opposite the first side 3103. The first side 3103 of the crimper housing 3104 is coupled to the second side 3105 of the crimper housing 3104 by one or more connectors 3107. The connectors 3107 can be any type of device to couple the first side 3103 of the crimper housing 3104 to the second side 3105 of the crimper housing 3104 such as a bolt, screw, pin, snap-fit features, etc.

The crimper housing 3104 includes an opening 3108 that extends therethrough or from the first side 3103 of the crimper housing 3104 to the second side 3105 of the crimper housing 3104. In an embodiment, the opening 3108 is formed in an approximate circular cross-sectional shape. The opening 3108 allows access to a crimper chamber 3116 of the crimper 3100 as described in further detail below.

The base 3106 of the crimper 3100 is formed as a rectangular plate. The base 3106 can be formed to a width and length that extends beyond the length and width of the crimper housing 3104 and the handle 3102. The base 3106 provides a stable platform for operating the crimper 3100 during crimping procedures. The crimper housing 3104 is attached or fixed to the base 3106 by one or more connection devices 3120. The connection devices 3120 can be any type of device to couple the crimper housing 3104 to the base 3106 such as a bolt, screw, pin, snap-fit features, etc.

FIG. 24B illustrates a perspective view of the crimper 3100 in which the first side 3103 of the crimper housing 3104 has been removed to illustrate internal components of the crimper 3100. The crimper 3100 includes a cam 3110, a plurality of rods 3118, and a plurality of crimper elements 3114 that form the crimper chamber 3116. The handle 3102 is coupled to the cam 3110 via a gear 3112 as will be described in more detail herein. The cam 3110 is coupled to the plurality of crimper element 3114 by the plurality of rods 3118. To operate the crimper 3100, a force is applied by a user to the handle 3102 in the direction towards the base 3106. Via the gear 3112, the force applied to the handle 3102 causes the gear 3112 to rotate clockwise, which then causes the cam 3110 to rotate in an opposing counter-clockwise direction. Rotation of the cam 3110 causes the crimper elements 3112 to move radially inward, as will be described in more detail herein.

In embodiments, the crimper 3100 operates to convert an implantable medical device from its uncompressed state to its compressed state. In operation, the implantable medical device is loaded into the crimper chamber 3116. One skilled in the art will realize that the dimension of the lobes can be changed to create a different volume as required by the implantable medical device being compressed and positioned. The delivery device of the implantable medical device can also be positioned and aligned relative to the implantable medical device. The crimper 3100 is then moved from the open state to the closed state via actuation of the handle 3102 to convert the implantable medical device from its uncompressed state to its compressed state and load the implantable medical device onto the delivery device. As the crimper elements 3114 move radially inward, the space available for the crimper elements 3114 to occupy reduces and therefore the space between the crimper elements 3114 reduces. As such, the volume of the crimper chamber 3116 decreases and the crimper elements 3114 apply a compression force to external surfaces of the implantable medical device to crimp the implantable medical device from an uncompressed or radially expanded state to a radially compressed state. For example, if the implantable medical device is generally cylindrical in shape, the crimper elements 3114 apply a force on the surface of the implantable medical device from various directions as the handle 3102 is actuated, thereby compressing the implantable medical device. As will be described in more detail herein with reference to FIGS. 29A-29C, in this embodiment, the crimper elements 3114 are configured to apply non-uniform radial compression along a length of the implantable medical device. The operation of the crimper 3100 is explained in further detail below with reference to FIGS. 39A-39E.

The crimper 3100 also include a first stop 3150 and a second stop 3152. The first stop 3150 and the second stop 3152 provide a surface that stops the movement of the handle 3102 in the downward direction. The first stop 3150 and the second stop 3152 provide predetermined stop positions of the handle 3102 that correspond to or result in a predetermined diameter of the crimper chamber 3116. That is, the first stop 3150 and the second stop 3152 are physically stops to cause an implantable medical device to be compressed to a predetermined diameter or compression. For example, the first stop 3150 can operate to allow an implantable medical device to be partially compressed. Likewise, for example, the second stop 3152 can operate to allow an implantable medical device to be fully compressed. The first stop 3150 and the second stop 3152 can be removably coupled to the crimper housing 3104. As such, the first stop 3150 and/or the second stop 3152 can be added and/or removed to allow an implantable medical device to be compressed to predetermined diameters.

Figure 25A:
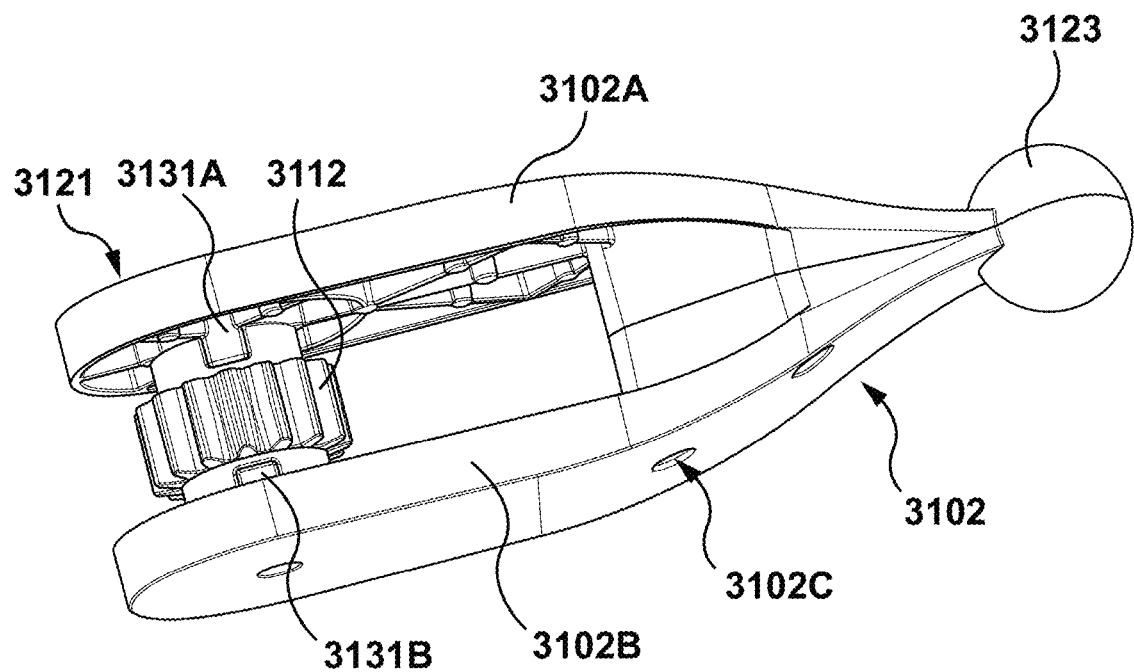
FIGS. 25A, 25B, and 25C depict perspective, side, and exploded views, respectively, of a handle and gear subassembly of the crimper of FIGS. 24A and 24B, according to an embodiment hereof.
Figure 25B:
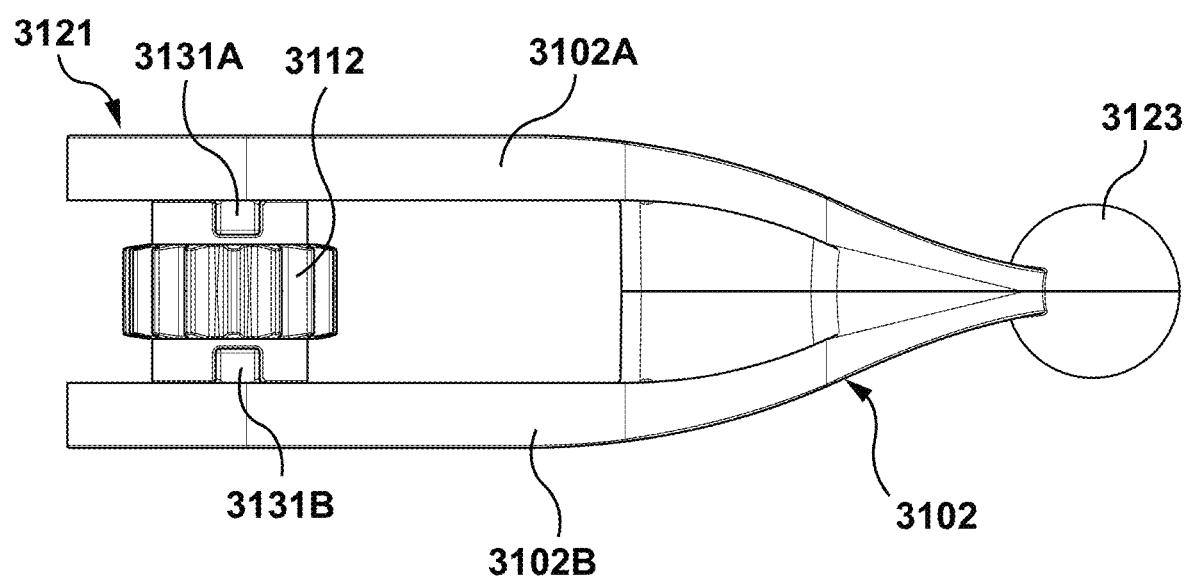
Figure 25C:
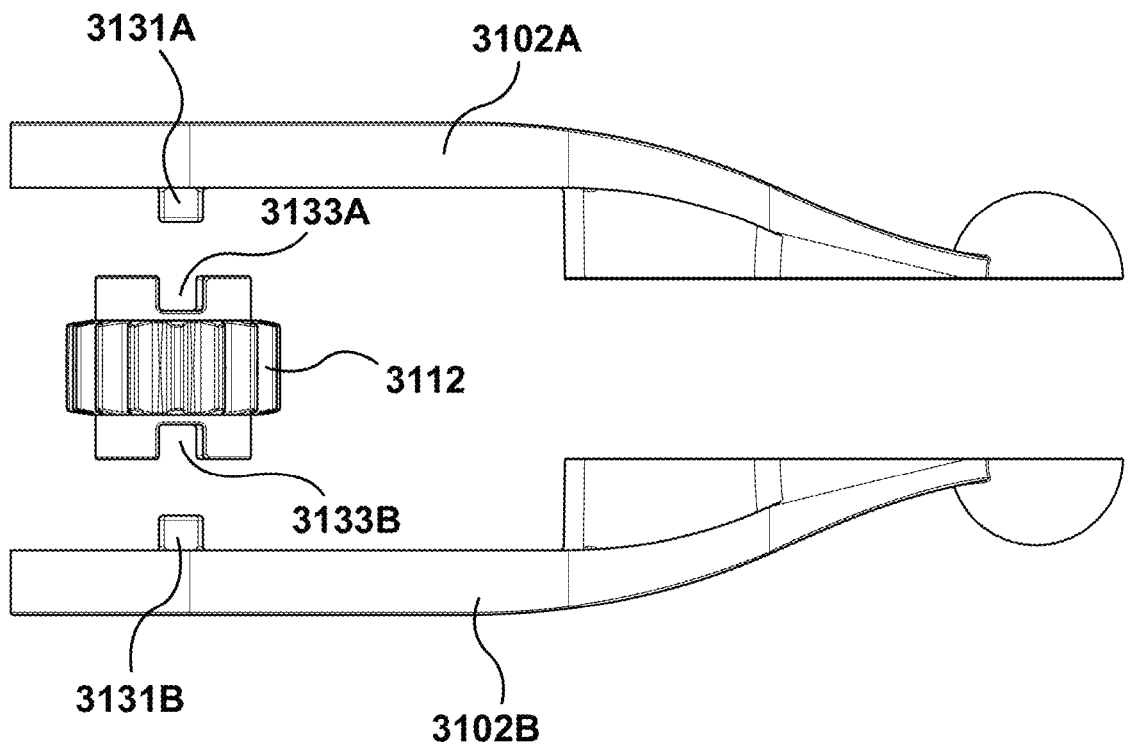

The internal components of the crimper 3100 and their operation thereof will now be described in more detail herein. FIGS. 25A, 25B, and 25C depict perspective, side, and exploded views, respectively, of a subassembly of the handle 3102 and the gear 3112 of the crimper 3100. One skilled in the art will realize that FIGS. 25A-25C illustrate one example of the handle-gear subassembly and that existing components illustrated in FIGS. 25A-25C may be removed and/or additional components may be added to the handle-gear subassembly.

The handle 3102 is accessible to the user and is coupled to the crimper housing 3104. The handle 3102 includes a first side 3102A and a second side 3102B positioned opposite the first side 3102A. The first side 3102A of the handle 3102 is formed as a "mirror" of the second side 3102B of the handle 3102 and is coupled to the second side 3102B to collectively form the handle 3102. The first side 3102A of the handle 3102 is coupled to the second side 3102B of the handle 3102 by one or more connectors 3102C. The connectors 3107 can be any type of device to couple the first side 3103 of the crimper housing 3104 to the second side 3105 of the crimper housing 3104 such as a bolt, screw, pin, etc. In addition, the first side 3102A of the handle 3102 is coupled to the second side 3102B of the handle 3102 by the gear 3112 as will be described in more detail with respect to FIG. 28C.

The handle 3102 includes a first end 3121 and a second or opposing end 3123. The first end 3121 of the handle 3102 is coupled to the crimper housing 3104, and the second end 3123 is free or unattached to the crimper housing 3104. At the first end 3121 thereof, the first side 3102A and the second side 3102B are coupled to the crimper housing 3104 and are coupled to the gear 3112, which is disposed within the crimper housing 3104. At the second end 3123 thereof, the first side 3102A and the second side 3102B collectively have a rounded ball configuration for easy handling by the user during manipulation of the handle 3102. When handle 3102 is rotated by the user for operation of the crimper 3100, the user generally grasps or holds the second end 3123 of the handle 3102.

At the first end 3121 thereof, the first side 3102A and the second side 3102B of the handle 3102 are spaced apart such that a gap is formed therebetween, with the gap being sized and configured to receive the gear 3112. On an interior surface of the first side 3102A, a tab or protrusion 3131A extends inward towards the second side 3102B. Similarly, on an interior surface of the second side 3102B, a tab or protrusion 3131B extends inward towards the first side 3102A. The tabs 3131A, 3131B are sized and configured to be received within a corresponding recess 3133A, 3133B, respectively, of the gear 3112 to couple the first and second sides 3102A, 3102B to the gear 3112. By forming the gear 3112 and the handle 3102 as separate components, the subassembly is stronger and is less prone to breakage. In addition, forming the gear 3112 and the handle 3102 as separate components simplifies the manufacturing thereof. The gear 3112 is a cylindrical component having a plurality of teeth formed on circumferentially around an outer surface thereof. As will be described in more detail below, the gear 3112 is configured to mate with a gear portion 3113 of the cam 3110. In other words, the gear 3112 includes a plurality of teeth on an outer surface thereof that are sized and shaped to mate or mesh with the plurality of teeth of the gear portion 3113 of the cam 3110.

Figure 26A:
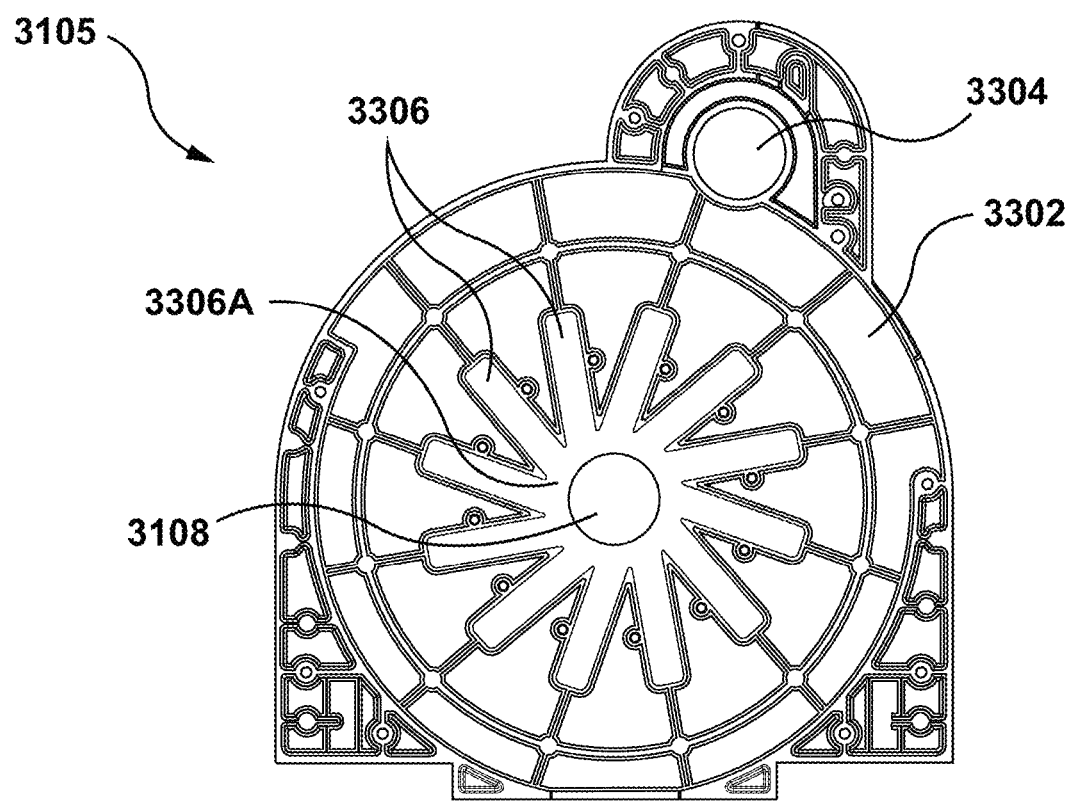
FIGS. 26A and 26B depict side and perspective views, respectively, of a side of a housing of the crimper of FIGS. 24A and 24B, according to an embodiment hereof.
Figure 26B:
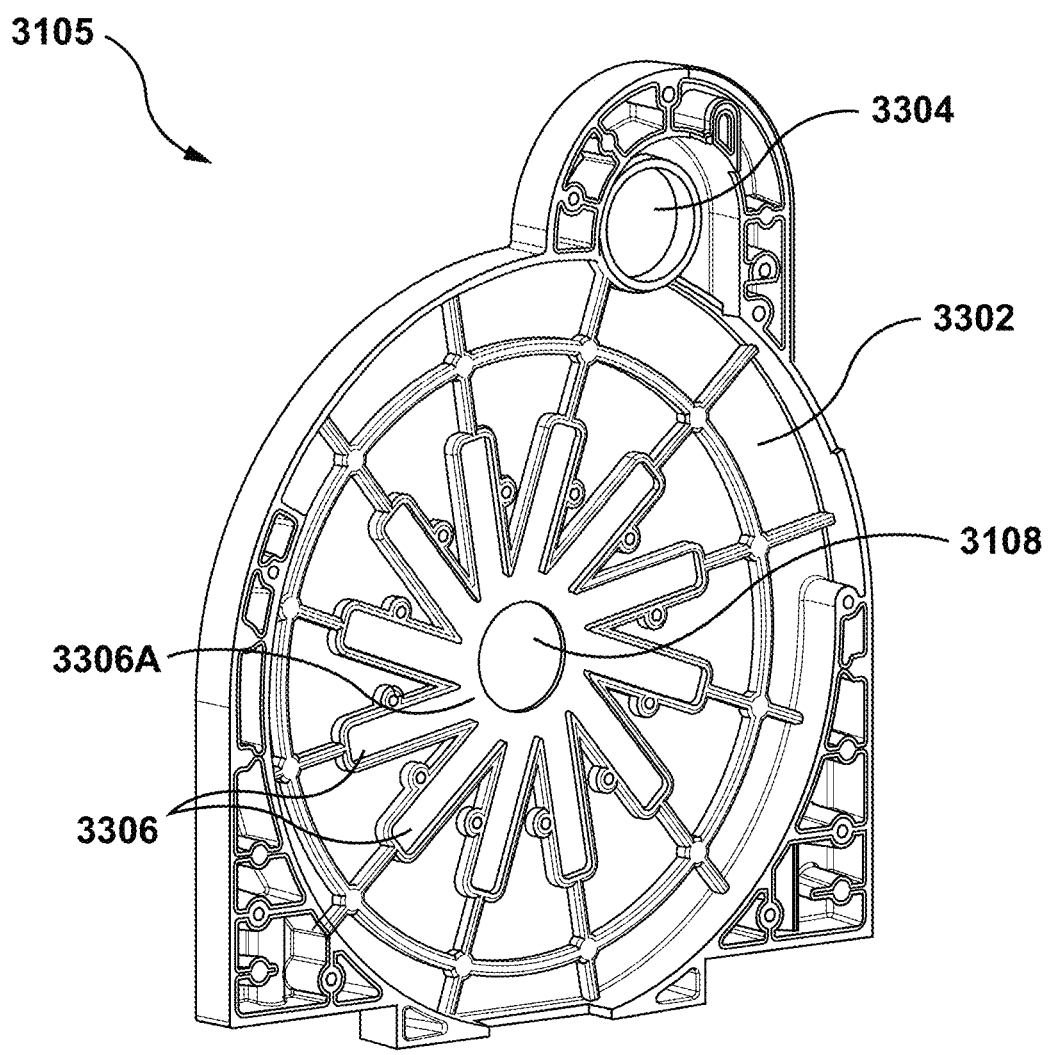

FIGS. 26A and 26B depict side and perspective views, respectively, of the second side 3105 of the crimper housing 3104. One skilled in the art will realize that FIGS. 26A and 26B illustrates one example of a side of the crimper housing 3104 and that existing components illustrated in FIGS. 26A and 26B may be removed and/or additional components may be added to the second side 3105. Additionally, while the second side 3105 of the crimper housing 3104 is only discussed below, one skilled in the art will realize that the first side 3103 of the crimper housing 3104 include the same components as illustrated in FIGS. 26A and 26B. For example, the first side 3103 of the crimper housing 3104 is formed as a "mirror" of the second side 3105 of the crimper housing 3104 and is coupled to the second side 3105 to collectively form the crimper housing 3104.

The second side 3105 of the crimper housing 3104 includes an interior surface 3302 and an opposing or exterior surface (not shown). The second side 3105 includes the opening 3108 which allows access to the crimper chamber 3116 formed by the crimper elements 3114. The second side 3105 also includes a handle opening 3304 that is formed therethrough and configured to receive the handle 3102 therein. The handle opening 3304 is also configured to receive the first stop 3150 and the second stop 3152. Crimper element channels 3306 are formed on the interior surface 3302 of the second side 3105. Each crimper element channels 3306 may be formed as a generally rectangular groove or channel that extends inward from a midportion of the second side 3105 towards the opening 3108 in a generally radial direction. The crimper element channels 3306 are formed in an arc around the second side 3105 and are disposed at equal, circumferentially spaced-apart increments around the opening 3108. A central annular cavity 3306A is a circular groove or channel formed in the interior surface 3302 of the second side 3105 that surrounds or encircles the opening 3108. The central annular cavity 3306A has the same depth as the crimper element channels 3306, and the crimper element channels 3306 extend into or terminate at the central annular cavity 3306A. Thus, the crimper element channels 3306 and the central annular cavity 3306A form a continuous groove or cavity formed in the interior surface 3302 of the second side 3105.

The crimper element channels 3306 and the central annular cavity 3306A are configured to moveably secure the crimper elements 3114 within the crimper housing 3104. As described above with respect to crimper element channels 2006 of FIG. 13C, the crimper element channels 3306 are formed with a width and depth to accommodate the crimper elements 3114 when the second side 3105 of the crimper housing 3104 is mated with the first side 3103 of the crimper housing 3104. As noted above, the crimper element channels 3306 are formed in an arc around the second side 3105. In embodiments, as described above with respect to crimper element channels 2006 of FIG. 13C, each of the crimper element channels 3306 are spaced in the arc at an angle, δ, from an adjacent crimper element channel 3306 and each of the crimper element channels 3306 can be aligned to be offset relative to the radius of the second side 3105 by an angle, φ. The offset can cause the crimper elements 3114 to move in a direction that is offset from the center point of the second side 3105. In some embodiments, the angle, φ, can range between approximately 0 degrees and 30 degrees.

The crimper element channels 3306 also function to limit the radially outward motion or travel of the crimper elements 3114 in order to ensure that the crimper chamber 3116 is not inadvertently over-opened. If the radially outward motion or travel of the crimper elements 3114 is not restricted in any way, the crimper chamber 3116 may be continually opened to a size or dimension in which portions of the crimper elements 3114 no longer overlap, thereby resulting in gaps that could pinch and damage the implantable medical device disposed within the crimper chamber 3116. Stated another way, the crimper element channels 3306 are configured to set or limit a maximum diameter of the crimper chamber 3116. In an embodiment, each crimper element channel 3306 may be sized to limit the travel of the crimper elements 3114 and thereby set or limit a maximum diameter of the crimper chamber 3116. In another embodiment, at least one crimper element channel 3306 is sized to limit travel of the crimper elements 3114 and thereby set or limit a maximum diameter of the crimper chamber 3116. In such an embodiment, the at least one crimper element channel is shorter than the remaining crimper element channels. In another embodiment, between two and six crimper element channels 3306 may be sized to limit the travel of the crimper elements 3114 and thereby set or limit a maximum diameter of the crimper chamber 3116. In such an embodiment, the between two and six crimper element channels are shorter than the remaining crimper element channels.

Figure 27A:
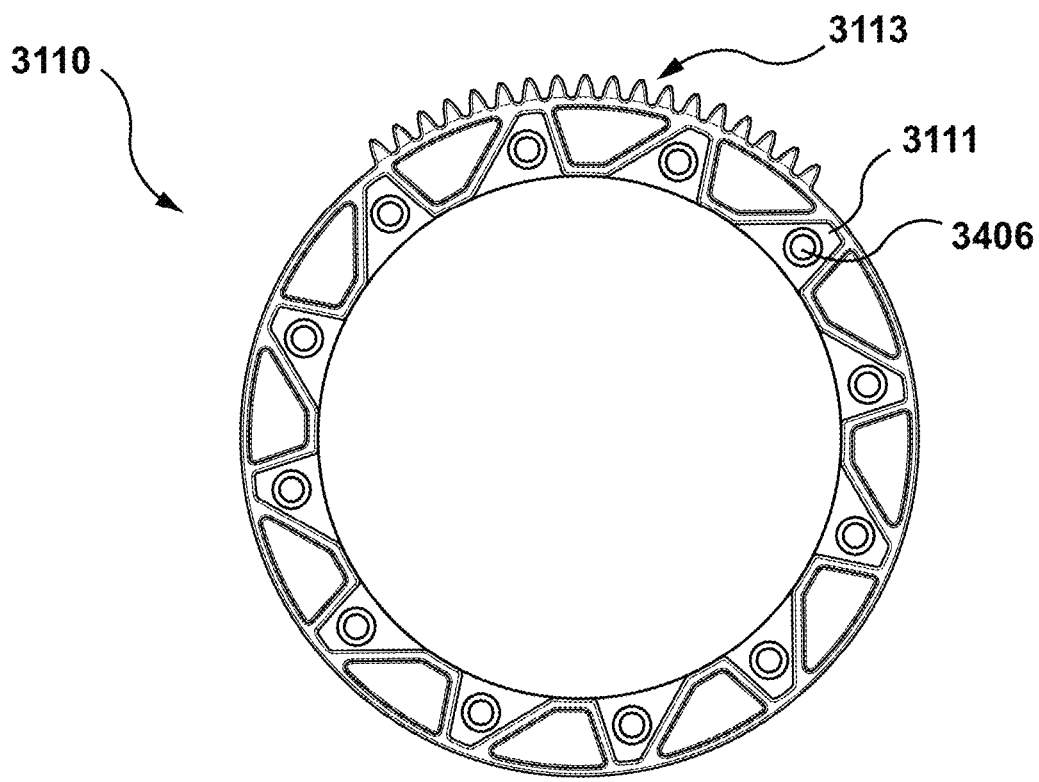
FIGS. 27A and 27B depict side and perspective views, respectively, of a cam of the crimper of FIGS. 24A and 24B, according to an embodiment hereof.
Figure 27B:
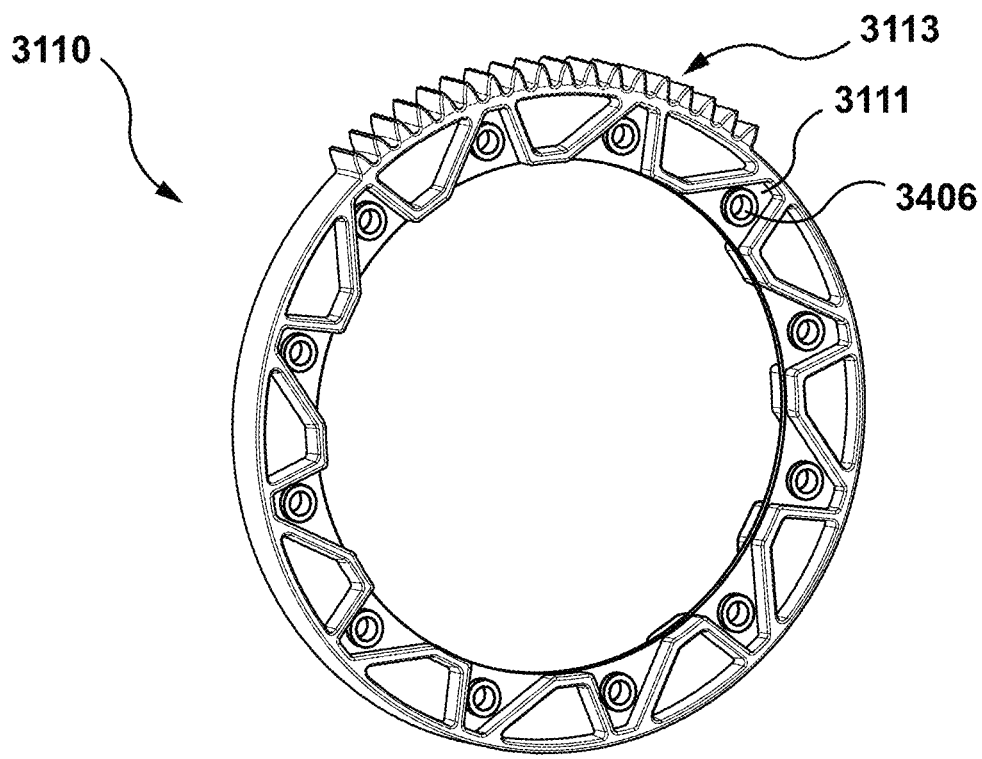

FIGS. 27A and 27B depict side and perspective views of the cam 3110, according to an embodiment hereof. One skilled in the art will realize that FIGS. 27A and 27B illustrate one example of a cam and that existing components illustrated in FIGS. 27A and 27B may be removed and/or additional components may be added to the cam 3110. The cam 3110 is an annular element or circular ring that is disposed within the crimper housing 3104.

The cam 3110 operates to translate the rotational movement of the handle 3102 to the crimper elements 3114 via the rods 3118. As the handle 3102 moves, the cam 3110 rotates and translates or transforms the rotational motion of the handle 3102 into linear motion of the crimper elements 3114 via the rods 3118. The cam 3110 includes an integrated plurality of teeth or gear portion 3113 formed on an outer surface thereon. The gear portion 3113 is configured to engage with the gear 3112. More particularly, the plurality of teeth of gear portion 3113 are sized and shaped to mesh or mate with the plurality of teeth of gear 3112 so that rotation of gear 3112 causes rotation of the cam 3110. The gear portion 3113 and the gear 3112 have opposing orientations such that rotation of the gear 3112 in a first direction causes rotation of the cam 3110 in a second or opposing direction. When disposed within the crimper housing 3104, the cam 3110 is oriented such that gear portion 3113 engages the gear 3112, near the handle opening 3304 of the crimper housing 3104.

As illustrated in FIGS. 27A and 27B, the cam 3110 includes a plurality of rod channels or grooves 3111. Each of the rod channels 3111 is configured to receive a rod 3118. A connection hole 3406 extends through the cam 3110 and is disposed within each rod channel 3111. Each connection hole 3406 is configured to receive a pin (not shown) that couples the cam 3110 to a rod 3118 that is disposed within the rod channel 3111. Stated another way, a plurality of pins are utilized to couple the cam 3110 to the rods 3118, with each pin passing through the connection hole 3406 and passing through similar connection holes formed through the rod 3118. For example, the pin can be a dowel pin, a bolt, and the like. The rod channel 3111 is also configured to limit rotational movement of the rods 3118, as described in more detail herein.

Figure 28A:
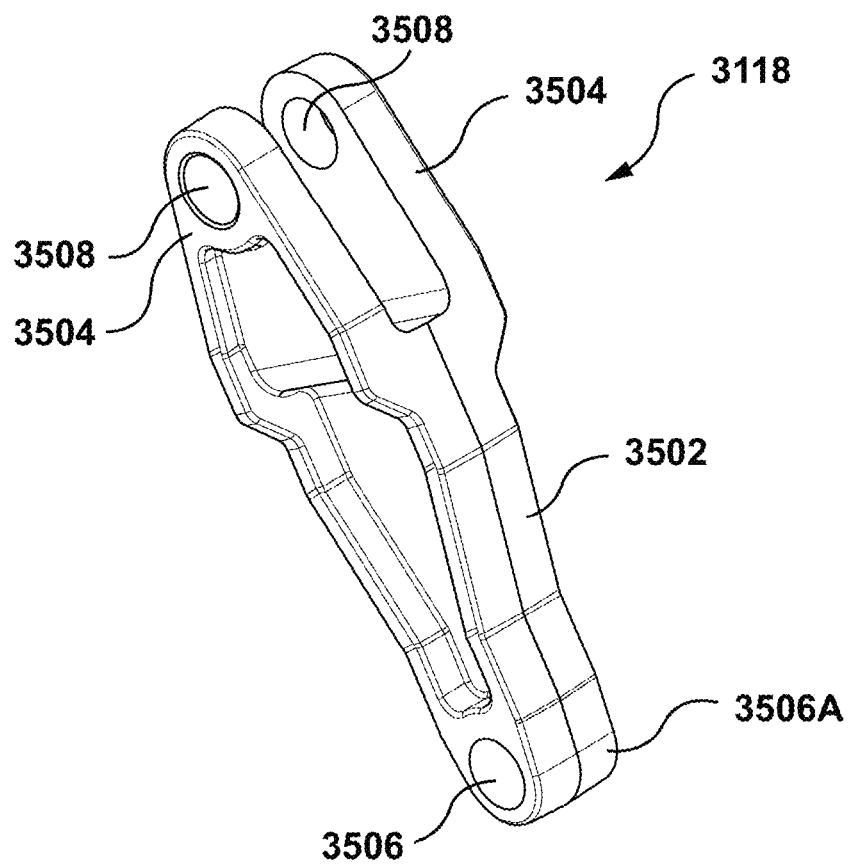
FIGS. 28A and 28B depict perspective and front views, respectively, of a rod of FIGS. 24A and 24B, according to embodiment hereof.
Figure 28B:
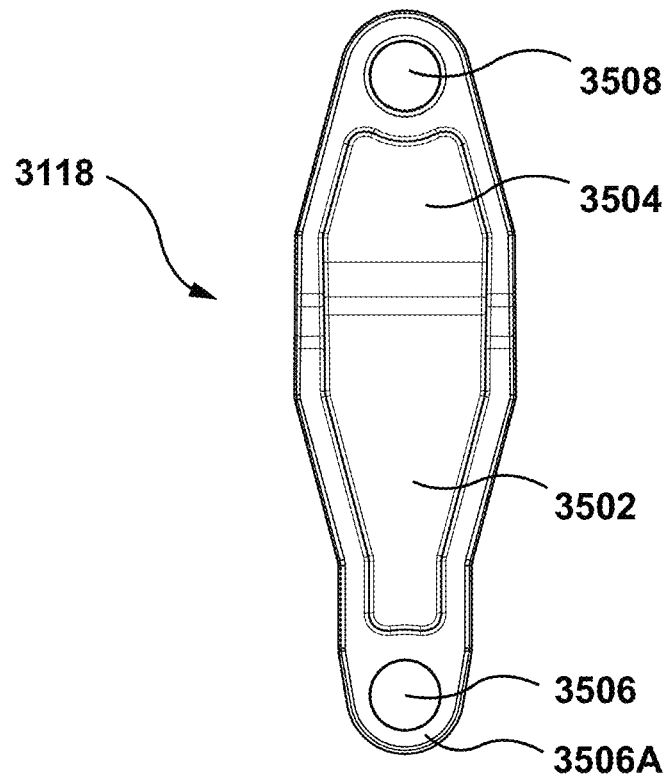

FIGS. 28A and 28B depict perspective and front views, respectively, of a rod 3118. One skilled in the art will realize that FIGS. 28A-28B illustrate one example of a rod and that existing components illustrated in FIGS. 28A-28B may be removed and/or additional components may be added to the rod 3118. While only one rod 3118 is discussed, one skilled in the art will realize that all of the rods 3118 of the crimper 3100 have the same configuration and include the same components as the rod 3118 described in FIGS. 28A-28B.

A rod 3118 is disposed within each rod channel 3111, and functions or operates to couple the cam 3110 to the plurality of crimper elements 3114. Each rod of the plurality of rods 3118 extends from the cam 3110 to a middle region of one of the crimper elements 3114. The rods 3118 are rotatably coupled to the cam 3110. That is, when the cam 3110 rotates in response to movement of the handle 3102, the rods 3118 are allowed to rotate relative to the cam 3110. Likewise, the rods 3118 are rotatably coupled to the crimper elements 3114. That is, when the rods 3118 move in response to the rotation of the cam 3110, the crimper elements 3114 are allowed to rotate relative to the rods 3118. In some embodiments, the rods 3118 can be configured and can include components similar to those described above in FIG. 4 or FIGS. 15A and 15B.

As illustrated, the rod 3118 includes a base 3502 and two parallel legs 3504 extending from the base 3502. The legs 3504 of the rod 3118 each include a connection hole 3508. After assembly, the connection holes 3508 align with the connection hole 3506 of the cam 3110, described above. The connection holes 3508 are similarly sized and shaped to connection holes 3406 of the cam 3110, and are configured to receive a pin (not shown) that couples the cam 3110 to a rod 3118. Stated another way, a plurality of pins are utilized to couple the cam 3110 to the rods 3118, with each pin passing through the connection hole 3406 of the cam 3110 and passing through connection holes 3508 of the rods 3118. For example, the pin can be a dowel pin, a bolt, and the like. The pin can be formed to a diameter to maintain the corresponding circular openings and cause the pin to operate as a fulcrum. When the cam 3110 rotates clockwise or counter-clockwise, the combination of the pin and the connection holes 3508 allow the rod 3118 to rotate about the pin, with movement of the rod 3118 being limited by the rod channel 3111 of the cam 3110. Thus, the rod channels 3111 of the cam 3110 are configured to provide clearance and permit rotational movement of the of the rods 3118 relative to the cam 3110. When assembled to the cam 3110, the cam 3110 is disposed within the space between the legs 3504 of the rod 3118 and the connection holes 3508 of the legs 3504 are aligned with the connection hole 3406 of the cam 3110.

The base 3502 may include a rounded end 3506A that is formed in a semi-cylindrical shape. The rounded end 3506A includes a connection hole 3506 formed or extending therethrough. Each connection hole 3506 is configured to receive a pin (not shown) that couples the rod 3118 to a crimper element 3114. Stated another way, a plurality of pins are utilized to couple the rod 3118 to the crimper element 3114, with each pin passing through the connection hole 3506 and passing through a similar connection hole formed through the crimper element 3114 For example, the pin can be a dowel pin, a bolt, and the like. After assembly, the connection hole 3506 aligns with the connection holes of the crimper element 3114 and the aligned connection holes and a pin disposed therethrough operate to moveably couple a crimper element 3114 to a rod 3118.

Each rod 3118 is a relatively rigid element with minimal or no bend and/or deformation during operation of the crimper 3100. Because each rod 3118 is fixed at one end to the cam 3110 and at the opposite end to one of the crimper elements 3114, when the cam 3110 is rotated, the distance between the connection of the rod 3118 to the cam 3110 and the connection of the rod 3118 to the crimper element 3114 must remain the same. However, as the cam 3110 is rotated, that distance can only remain the same if the crimper element 3114 is pushed radially inward by the rods 3118. Thus, rotation of the cam 3110 forces the crimper elements 3114 inward via the rods 3118. In particular, the crimper elements 3114 move radially inward generally towards the center of the crimper chamber 3116.

Figure 29A:
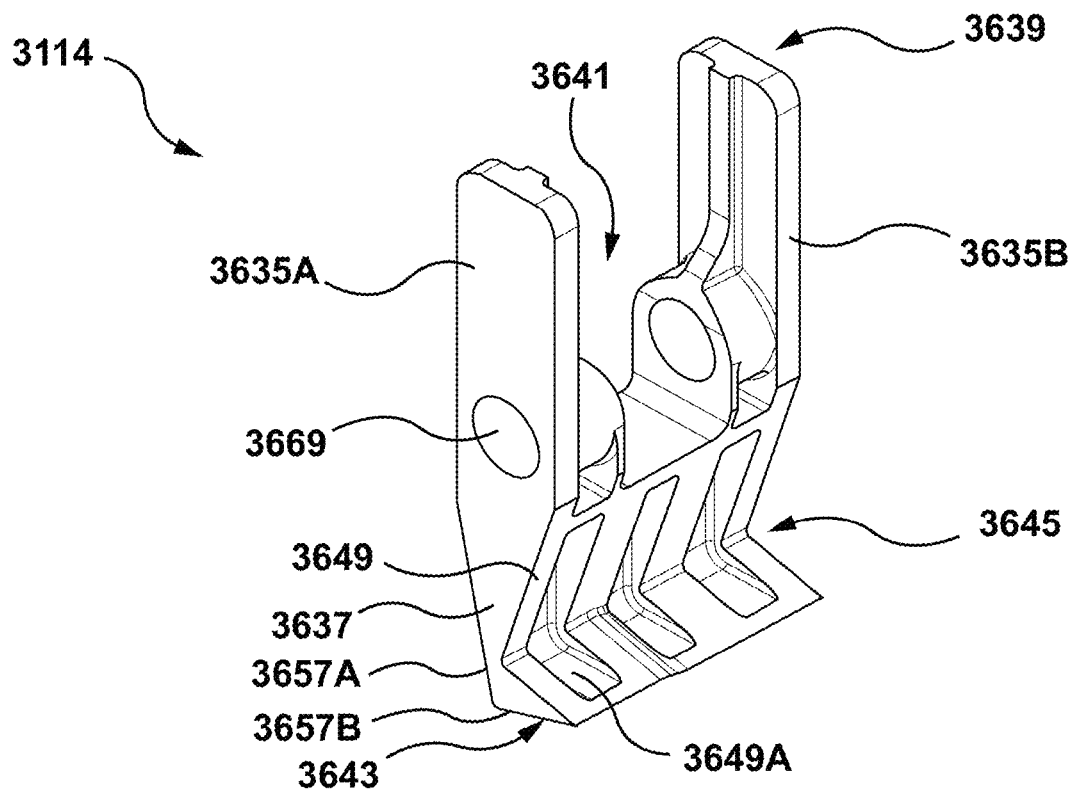
FIGS. 29A, 29B, and 29C depict different views of a crimper element of the crimper of FIGS. 24A and 24B, according to an embodiment hereof.
Figure 29B:
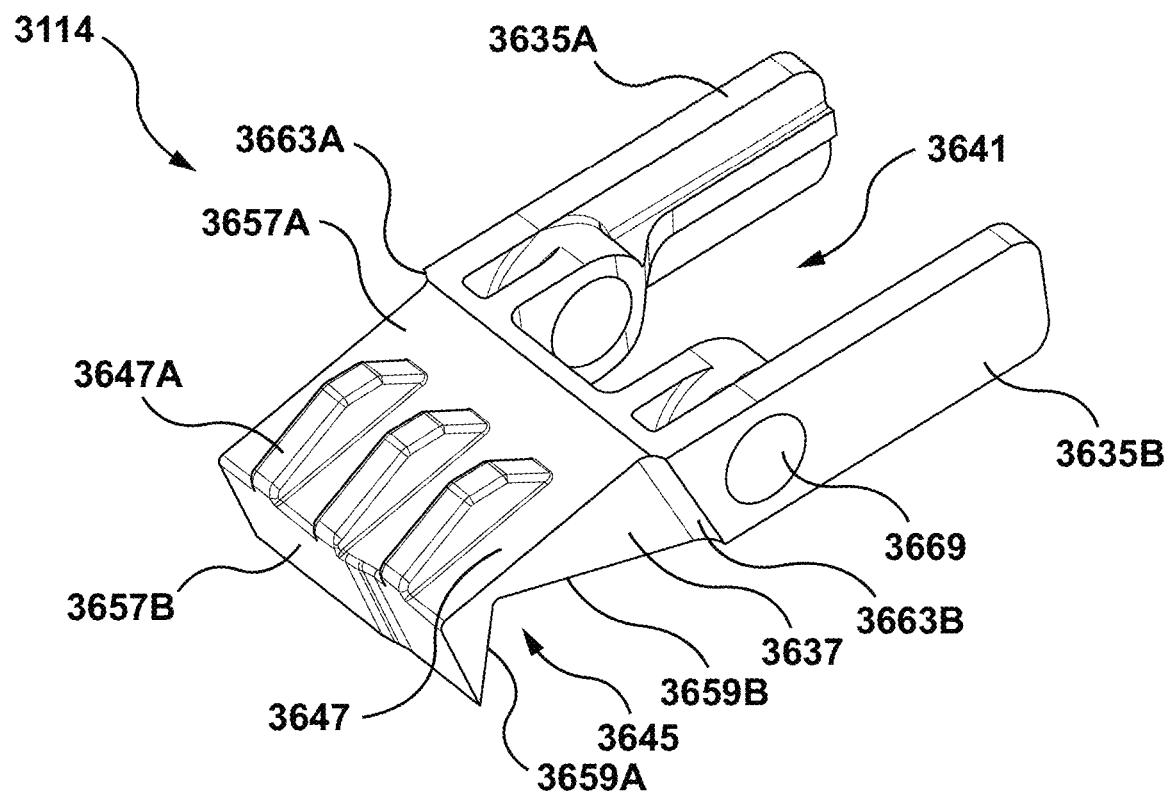
Figure 29C:
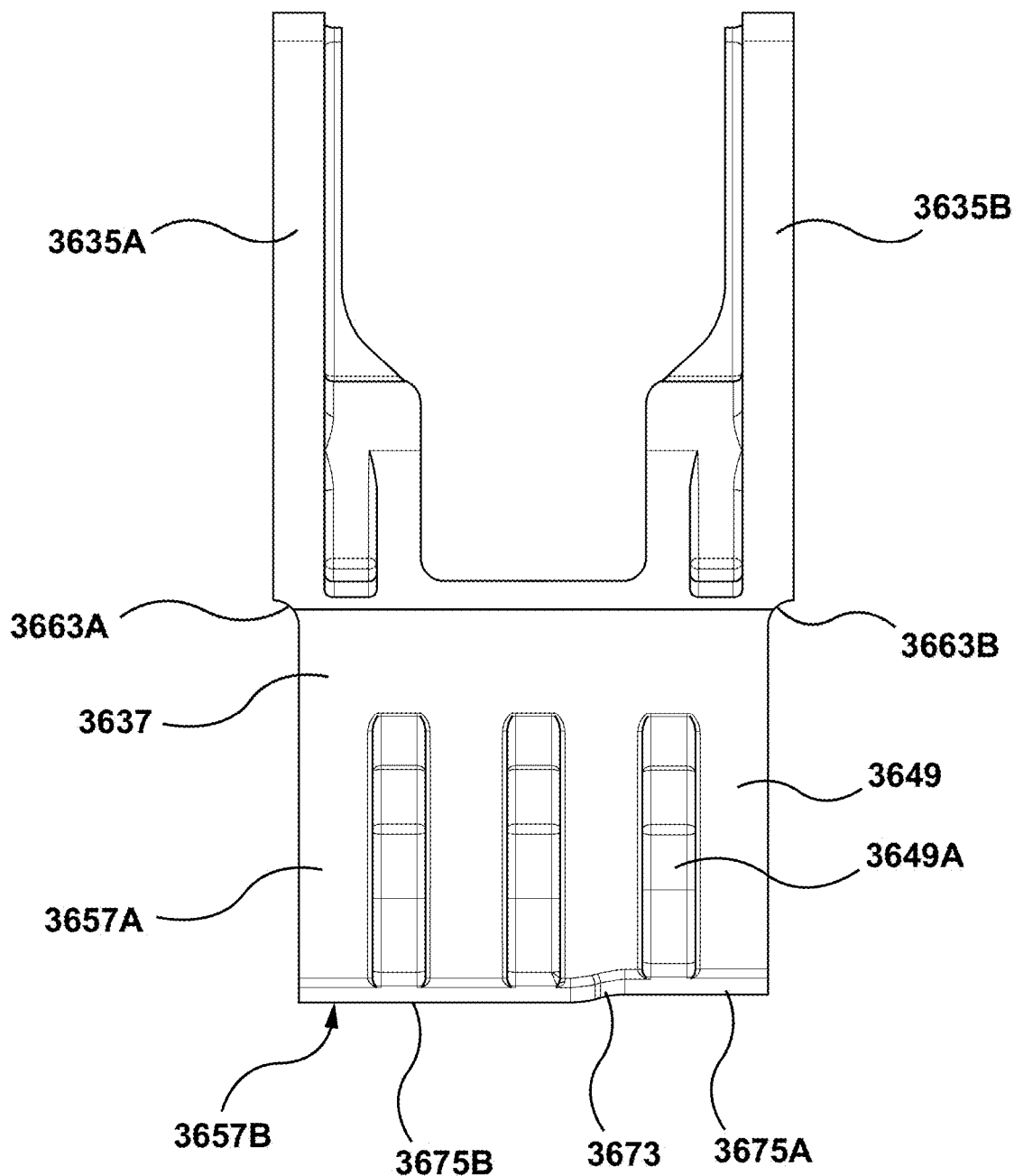

FIGS. 29A-29C illustrate a different views of a crimper element 3114, according to an embodiment hereof. One skilled in the art will realize that FIGS. 29A-29C illustrate one example of a crimper element and that existing components illustrated in FIGS. 29A-29C may be removed and/or additional components may be added to the crimper element 3114. While only one crimper element 3114 is discussed, one skilled in the art will realize that all of the crimper elements 3114 of the crimper 3100 have the same configuration and include the same components as the crimper element 3114 described in FIGS. 29A-29C. In operation, the crimper elements 3114 are displaced by the movement of the handle 3102. That is, as the handle 3102 is moved, the cam 3110 rotates and functions to translate or transform the rotational motion of the handle 3102 into linear motion of the crimper elements 3114 via the rods 3118. As such, the crimper elements 3114 function as an iris to decrease or increase the volume of the crimper chamber 3116 through the movement of the handle 3102.

Each crimper element 3114 has a first leg 3635A, a second leg 3635B, and a crimper lobe 3637 coupled to and extending between the first leg 3635A and the second leg 3635B. The first leg 3635A and the second leg 3635B extend parallel to a long axis of the crimper element 3114, from a proximal end 3639 of the crimper element 3114 to the crimper lobe 3637. The first leg 3635A and the second leg 3635B are spaced apart and define a rod channel 3641 therebetween. A connection hole 3669 is formed in each of the first leg 3635A and the second leg 3635B such that the crimper element 3114 includes a total of two connection holes. In embodiments, the connection holes 3112 can be configured to receive a pin that passes through the two connection holes 3669 and the connection hole 3506 of the rod 3118. For example, the pin can be a dowel pin, a bolt, and the like. The pin can be formed to a diameter to maintain the corresponding circular openings and cause the pin to operate as a fulcrum. The connection holes 3669 operate to moveably couple the crimper elements 3114 to the rod 3118. The rods 3118 are disposed between the legs 3635A, 3635B of the crimper element 3114, within the rod channel 3641 of the crimper element 3114 and with the connection hole 3506 of the rod 3118 aligned with the connection holes 3669 of the crimper element 3114. The rod channel 3641 is sized to permit the rods 3118 to rotate relative to the crimper elements 3114 during operation of the crimper 3100.

In an embodiment, the crimper element 3114 can include a sloped shoulder 3663A, 3663B formed on each of the first leg 3635A and the second leg 3635B, respectively, at the intersection of the leg and the crimper lobe 3637. The sloped shoulders 3663A, 3663B operate to maintain the first leg 3635A and the second leg 3635B within a corresponding crimper element channel 3306 on the interior surface 3302 of the second side 3105 of the crimper housing 3104. That is, the sloped shoulders 3663A, 3663B are formed on the first leg 3635A and the second leg 3635B to extend a width of the crimper element 3114 thereby engaging one or the corresponding crimper element channel 3306. In an embodiment, a width of the crimper element 3114 can be specific to a size of the implantable medical device being crimped. As such, the sloped shoulders 3663A, 3663B may vary in size based on a size of the implantable medical device being crimped.

The crimper lobe 3637 extends from the first leg 3635A and the second leg 3635B to a distal end 3643 of the crimper element 3114. The crimper lobe 3637 defines a crimper space 3645, or stated another way, includes the crimper space 3645 defined therein. The crimper space 3645 is configured to accommodate or receive an adjacent or neighboring crimper element 3114 when the crimper 3100 is operated and the crimper chamber 3116 decreases in size or volume. More particularly, the crimper element 3114 includes a first side or exterior surface 3647 and a second side or interior surface 3649 formed on the opposing side thereof. When assembled into the crimper 3100, the exterior surface 3647 of a crimper element 3114 is disposed adjacent to the interior surface 3649 of a neighboring crimper element such that the crimper element 3114 is received into the crimper space 3645 of the neighboring crimper element. The exterior surface 3647 may include one or more shaped protrusions 3647A that are sized and shaped to be received within one or more corresponding recesses 3649A formed on the interior surface 3649 of the neighboring crimper element. The mating protrusions 3647A and recesses 3649A guide or assist the sliding relative motion between the neighboring crimper elements during operation of the crimper 3100.

Along the exterior surface 3647 of the crimper lobe 3637, the crimper lobe 3637 includes a first exterior ramp 3657A and a second exterior ramp 3657B. The first exterior ramp 3657A and the second exterior ramp 3657B are angled surfaces relative to a long axis of the crimper element 3114. Along the interior surface 3649 of the crimper lobe 3637, the crimper lobe 3637 includes a first interior ramp 3659A and a second interior ramp 3659B. The first interior ramp 3659A and the second interior ramp 3659B define the crimper space 3645, and thus are configured to contact a neighboring crimper element to generate the iris effect when the crimper elements are displaced. The first interior ramp 3659A and the second interior ramp 3659B can be formed at angles to relative to a long axis of the crimper element 3114.

The dimensions of the crimper element 3114 can be governed by a size of the object being crimped. In an embodiment, the axial length of the crimper chamber 3116 can range from approximately 20 mm to approximately 50 mm and the diameter thereof can range from approximately 1 mm to approximately 40 mm. In an embodiment, the angle formed between the second exterior ramp 3657B and the first interior ramp 3659A depends on the crimper elements included in the crimper 3100. More particularly, the angle formed between the second exterior ramp 3657B and the first interior ramp 3659A may be determined by dividing 360 degrees by the number of crimper elements 3114 in the crimper 3100. In an embodiment, the number of crimper elements can range from 8 to 16. In another embodiment, the number of crimper elements can range from 10 to 12. The angle or slope of each of the first exterior ramp 3657A and the second interior ramp 3659B are set or configured to allow the crimper elements 3114 to clear each other during operation of the crimper 3100.

Crimper elements 3114 are configured to apply non-uniform radial compression along a length of the implantable medical device. More particularly, during operation of the crimper 3100, at least a portion of the second exterior ramp 3657B of the crimper element 3114 contacts the implantable medical device that is disposed within the crimper chamber 3116. The second exterior ramp 3657B is a non-planar surface that applies non-uniform radial compression along a length of the implantable medical device. As used herein, "non-planar" includes a surface that includes two or more integral portions that do not lie in the same plane, with the integral portions being disposed at different distances from a centerline or longitudinal axis of the crimper chamber. In the embodiment of FIGS. 29A-29C, the second exterior ramp 3657B includes a ridge 3673 formed thereon that effectively segments the second exterior ramp 3657B into a first longitudinal portion 3675A and a second longitudinal portion 3675B. In an embodiment, the first longitudinal portion 3675A is between 35% and 45% of the total length of the crimper chamber 3116 and the second longitudinal portion 3675B is between 55% and 65% of the total length of the crimper chamber 3116. The ridge 3673 is a curved surface extending between the first longitudinal portion 3675A and the second longitudinal portion 3675B such that the first longitudinal portion 3675A and the second longitudinal portion 3675B are disposed at different radial positions within the crimper chamber 3116. In the depicted embodiment, the second longitudinal portion 3675B is disposed closer to the centerline or longitudinal axis of the crimper chamber 3116 than the first longitudinal portion 3675A. As a result of the different radial positions, the second longitudinal portion 3675B is configured to apply more radial force to the implantable medical device during crimping thereof than the first longitudinal portion 3675A. Stated another way, a first radial force is applied onto a first section of the implantable medical device by the first longitudinal portion 3675A of the non-planar surface of the second exterior ramp 3657B and a second radial force is applied onto a second section of the implantable medical device by the second longitudinal portion 3675B of the non-planar surface of the second exterior ramp 3657B, the second radial force being greater than the first radial force.

Figure 30A:
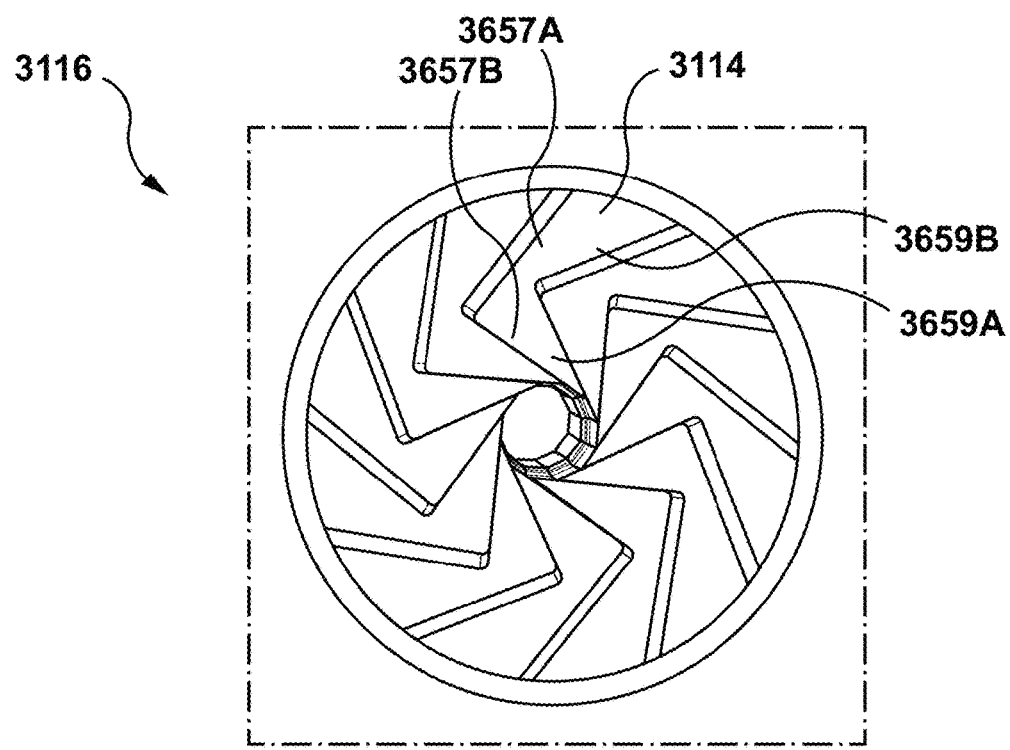
FIGS. 30A and 30B depict end and side views of a crimper chamber formed by the crimper elements of FIGS. 29A, 29B, and 29C, according to an embodiment hereof.
Figure 30B:
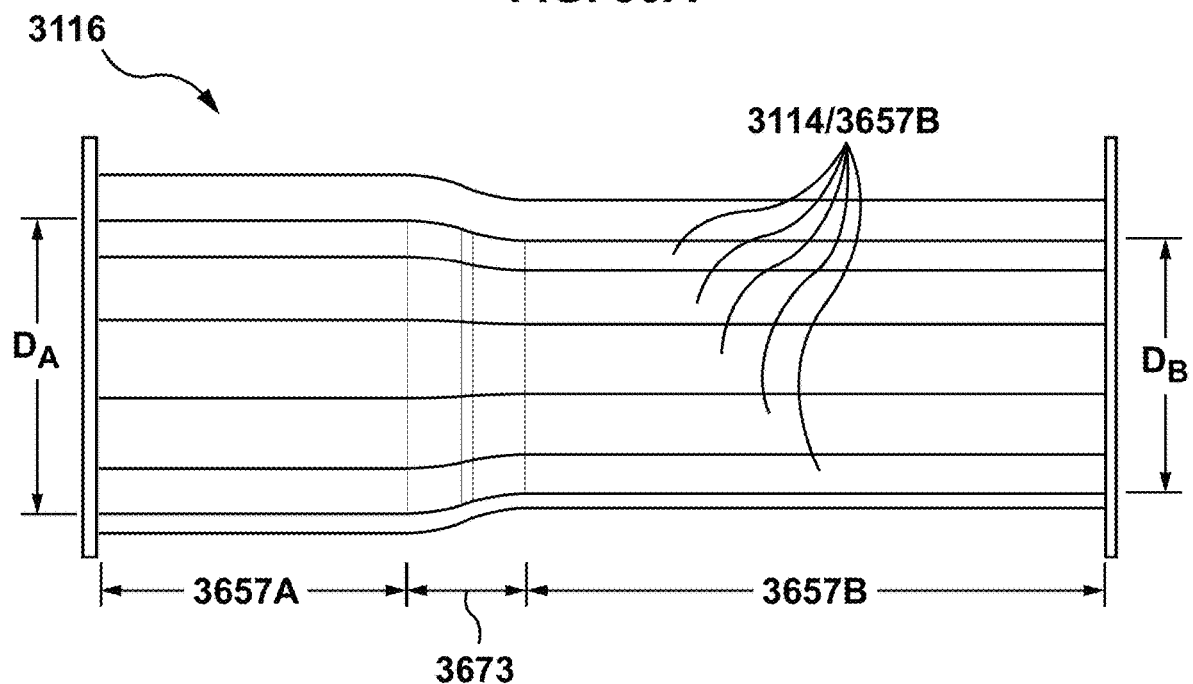

FIGS. 30A and 30B depict end and side views of the crimper chamber 3116 formed by the crimper elements 3114. At a first end of the crimper chamber 3116, the crimper chamber 3116 has a first diameter DA that is formed collectively by the first longitudinal portions 3675A of the crimper elements 3114. At a second end of the crimper chamber 3116, the crimper chamber 3116 has a second diameter DB that is formed collectively by the second longitudinal portions 3675B of the crimper elements 3114. Due to the different radial positions of the first and second longitudinal portions 3675A, 3675B, the first diameter DA is greater than the second diameter DB. Since the first longitudinal portions 3675A of the crimper elements 3114 are disposed further away from the centerline or longitudinal axis of the crimper chamber 3116 than the second longitudinal portions 3675B of the crimper elements 3114, the diameter of the crimper chamber 3116 is larger along the first longitudinal portions 3675A. Conversely, since the second longitudinal portions 3675B of the crimper elements 3114 are disposed closer from the centerline or longitudinal axis of the crimper chamber 3116 than the first longitudinal portions 3675A of the crimper elements 3114, the diameter of the crimper chamber 3116 is smaller along the second longitudinal portions 3675B. This smaller diameter, i.e., second diameter DB, results in a higher or greater radial force being applied to the implantable medical device along the second longitudinal portions 3675B of the crimper elements 3114 as compared to the radial force being applied to the implantable medical device along the first longitudinal portions 3675A of the crimper elements 3114. Application of higher radial force along only a portion of the implantable medical device is beneficial when the implantable medical device includes sections of denser materials, such as the portion of an implantable medical device that includes a valve. In this instance, the non-uniform radial compression results in a substantially uniform profile in the compressed state of the implantable medical device because more radial force is applied by the second longitudinal portions 3675B of the crimper elements 3114 over the denser portions of the implantable medical device. Less radial force is applied by the first longitudinal portions 3675A of the crimper elements 3114 over the less dense, or sensitive, portions of the implantable medical device to avoid damage thereto. Once crimped via non-uniform radial compression applied by the crimper elements 3114, the implantable medical device has a more uniform or consistent crimped profile along a length thereof as compared to the profile that would be achieved with uniform radial compression.

Figure 31A:
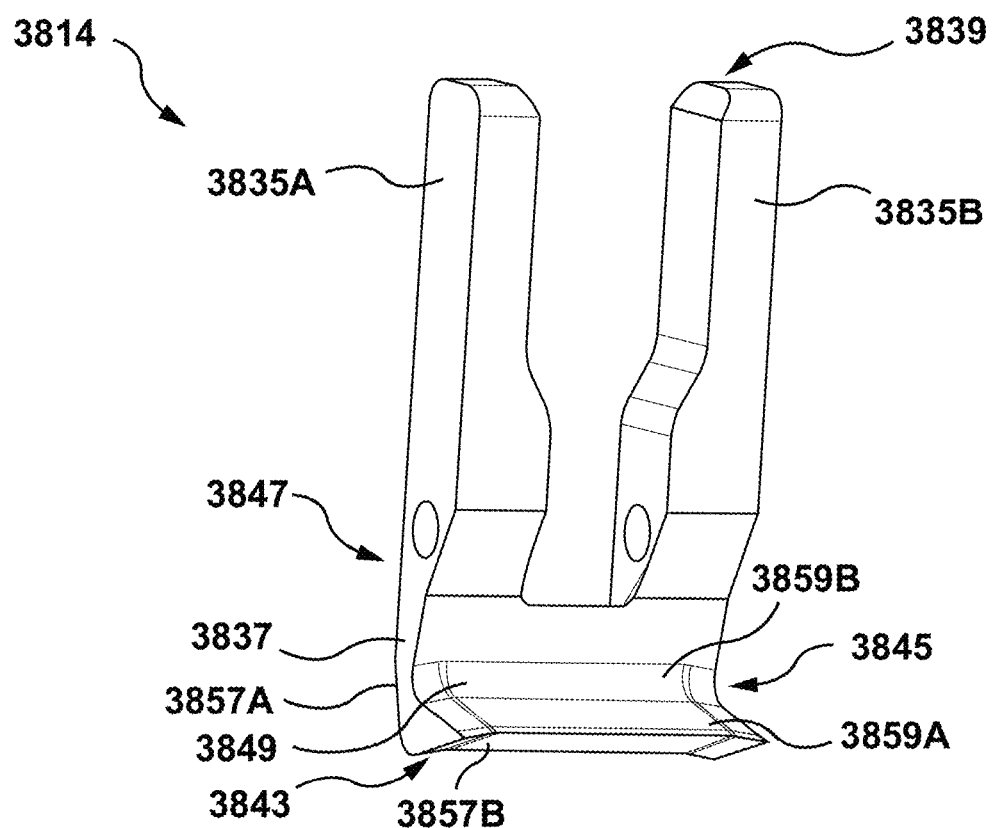
FIGS. 31A and 31B depict perspective and front views of a crimper element for use in the crimper of FIGS. 24A and 24B, according to another embodiment hereof.
Figure 31B:
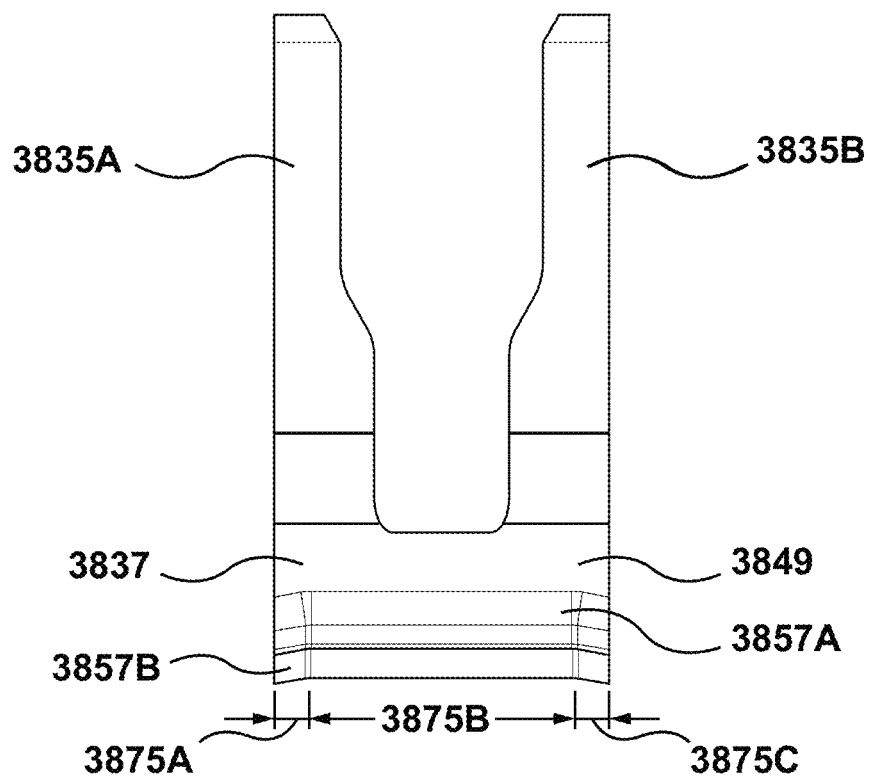

FIGS. 31A-31B illustrate a different views of a crimper element 3814, according to another embodiment hereof, that may be utilized in the crimper 3100 or other crimper described herein. One skilled in the art will realize that FIGS. 31A-31B illustrate one example of a crimper element and that existing components illustrated in FIGS. 31A-31B may be removed and/or additional components may be added to the crimper element 3814. While only one crimper element 3814 is discussed, one skilled in the art will realize that all of the crimper elements 3814 of the crimper 3100 have the same configuration and include the same components as the crimper element 3814 described in FIGS. 31A-31B.

Similar to crimper elements 3114, each crimper element 3814 has a first leg 3835A, a second leg 3835B, and a crimper lobe 3837 coupled to and extending between the first leg 3835A and the second leg 3835B. The first leg 3835A and the second leg 3835B extend parallel to a long axis of the crimper element 3814, from a proximal end 3839 of the crimper element 3814 to the crimper lobe 3837. The crimper lobe 3837 extends from the first leg 3835A and the second leg 3835B to a distal end 3843 of the crimper element 3814. The crimper lobe 3837 defines a crimper space 3845, or stated another way, includes the crimper space 3845 defined therein. The crimper space 3845 is configured to accommodate or receive an adjacent or neighboring crimper element 3814 when the crimper 3100 is operated and the crimper chamber 3816 decreases in size or volume. More particularly, the crimper element 3814 includes a first side or exterior surface 3847 and a second side or interior surface 3849 formed on the opposing side thereof. When assembled into the crimper 3100, the exterior surface 3847 of a crimper element 3814 is disposed adjacent to the interior surface 3849 of a neighboring crimper element such that the crimper element 3814 is received into the crimper space 3845 of the neighboring crimper element. The first exterior ramp 3857A and the second exterior ramp 3857B are angled surfaces relative to a long axis of the crimper element 3814. Along the interior surface 3849 of the crimper lobe 3837, the crimper lobe 3837 includes a first interior ramp 3859A and a second interior ramp 3859B. The first interior ramp 3859A and the second interior ramp 3859B define the crimper space 3845, and thus are configured to contact a neighboring crimper element to generate the iris effect when the crimper elements are displaced. The first interior ramp 3859A and the second interior ramp 3859B are angled surfaces relative to a long axis of the crimper element 3814.

Similar to crimper elements 3114, crimper elements 3814 are also configured to apply non-uniform radial compression along a length of the implantable medical device. More particularly, during operation of the crimper 3100, at least a portion of the second exterior ramp 3857B of the crimper element 3814 contacts the implantable medical device that is disposed within the crimper chamber 3816. The second exterior ramp 3857B is a non-planar surface that applies non-uniform radial compression along a length of the implantable medical device. In the embodiment of FIGS. 31A-31B, the second exterior ramp 3857B includes three longitudinal portions disposed at different radial positions within the crimper chamber 3816, particularly a first longitudinal portion 3875A, a second longitudinal portion 3875B, and a third longitudinal portion 3875C. The second longitudinal portion 3875B is disposed between the first and third longitudinal portions 3875A, 3875C. In the depicted embodiment, each of the first and third longitudinal portions 3875A, 3875C taper along its length to the second longitudinal portion 3875B. Each of the first and third longitudinal portions 3875A, 3875C is disposed closer to the centerline or longitudinal axis of the crimper chamber 3816 than the second longitudinal portion 3875B. As a result of the different radial positions, the first and third longitudinal portions 3875A, 3875C are configured to apply more radial force to the implantable medical device during crimping thereof than the second longitudinal portion 3875B.

Figure 32A:
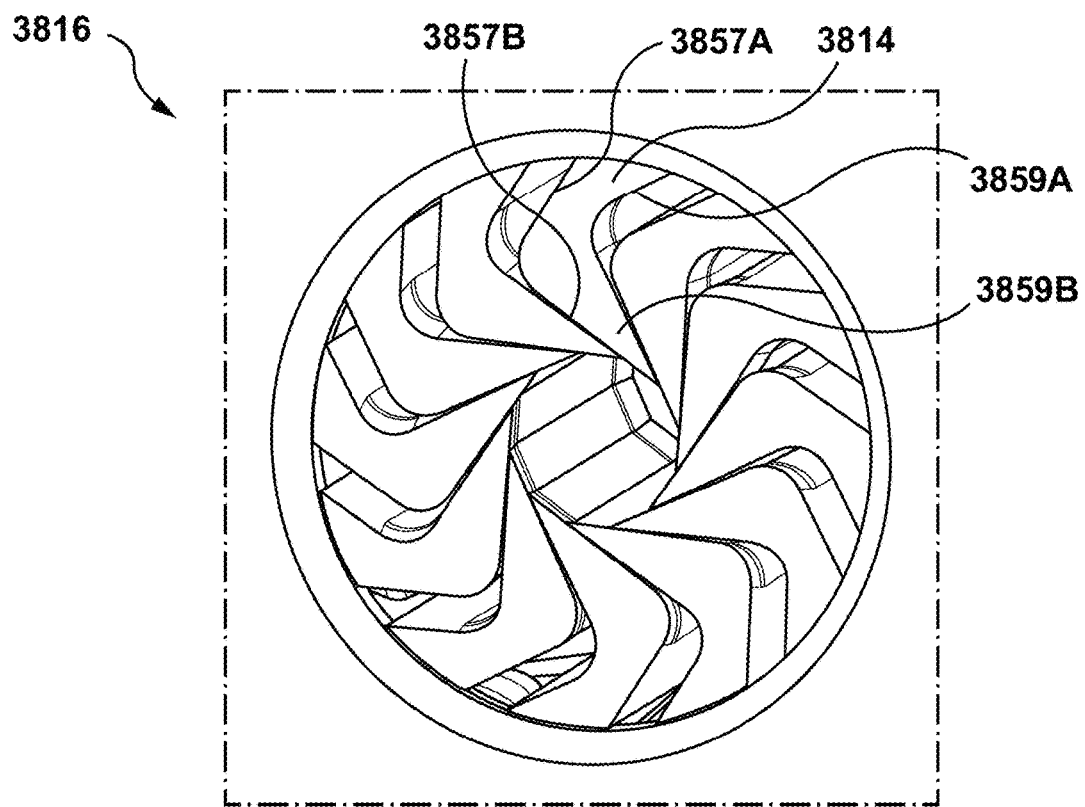
FIGS. 32A and 32B depict end and side views of a crimper chamber formed by the crimper elements of FIGS. 31A and 31B, according to an embodiment hereof.
Figure 32B:
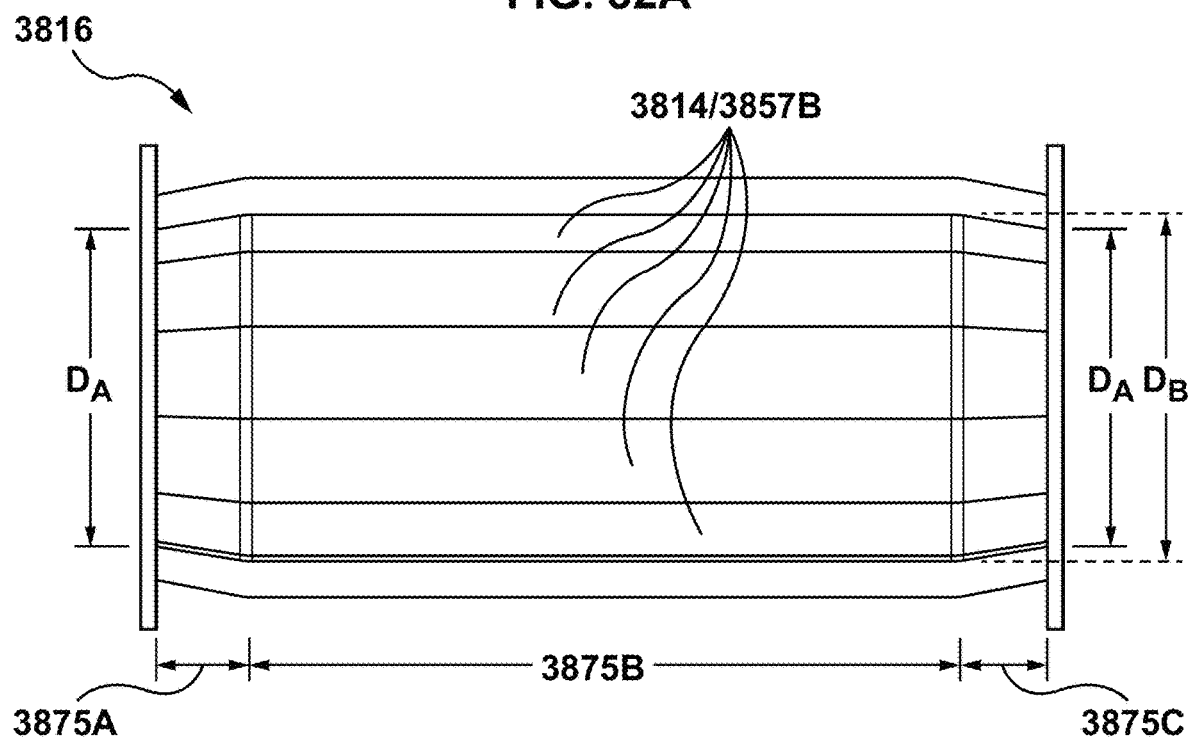

FIGS. 32A and 32B depict end and side views of the crimper chamber 3816 formed by the crimper elements 3814. At the first end of the crimper chamber 3816, the crimper chamber 3816 has a first diameter DA that is formed collectively by the first longitudinal portions 3875A of the crimper elements 3814. Similarly, at the second end of the crimper chamber 3816, the crimper chamber 3816 also has the diameter DA that is formed collectively by the third longitudinal portions 3875C of the crimper elements 3814. At a midportion of the crimper chamber 3816, along the second longitudinal portion 3875B, the crimper chamber 3816 has a second diameter DB that is formed collectively by the second longitudinal portions 3875B of the crimper elements 3814. Due to the different radial positions of the first, second, and third longitudinal portions 3875A, 3875B, 3875C, the first diameter DA is less than the second diameter DB. Since the second longitudinal portions 3875B of the crimper elements 3814 are disposed further away from the centerline or longitudinal axis of the crimper chamber 3816 than the first and third longitudinal portions 3875A, 3875C of the crimper elements 3814, the diameter of the crimper chamber 3816 is larger along the second longitudinal portions 3875B. Conversely, since the first and third longitudinal portions 3875A, C of the crimper elements 3814 are disposed closer from the centerline or longitudinal axis of the crimper chamber 3816 than the second longitudinal portions 3875B of the crimper elements 3814, the diameter of the crimper chamber 3816 is smaller along the first and third longitudinal portions 3875A, C. This smaller diameter, i.e., the first diameter DA, results in a higher or greater radial force being applied to the implantable medical device along the first and third longitudinal portions 3875A, 3875C of the crimper elements 3814 as compared to the radial force being applied to the implantable medical device along the second longitudinal portions 3875B of the crimper elements 3814. Application of higher radial force along only the ends of the implantable medical device is beneficial to increase the retention of the implantable medical device on the delivery system. More radial force is applied to the end portions of the implantable medical device to preferably crimp the ends of the implantable medical device on the delivery system.

Figure 33A:
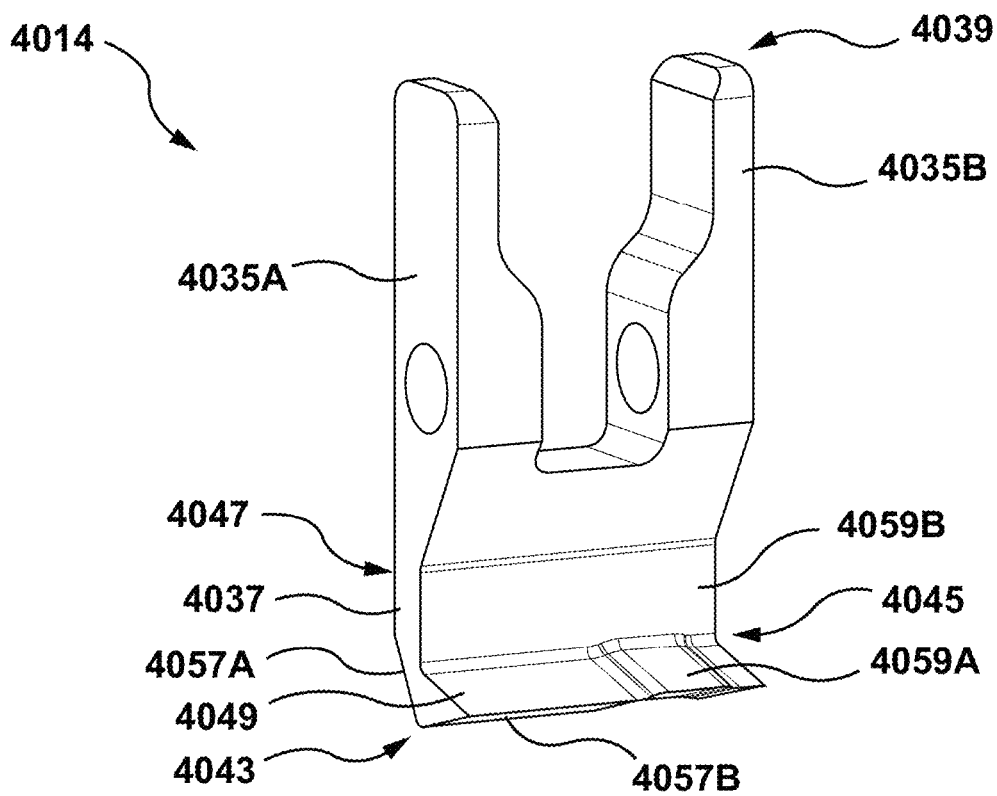
FIGS. 33A and 33B depict perspective and front views of a crimper element for use in the crimper of FIGS. 24A and 24B, according to another embodiment hereof.
Figure 33B:
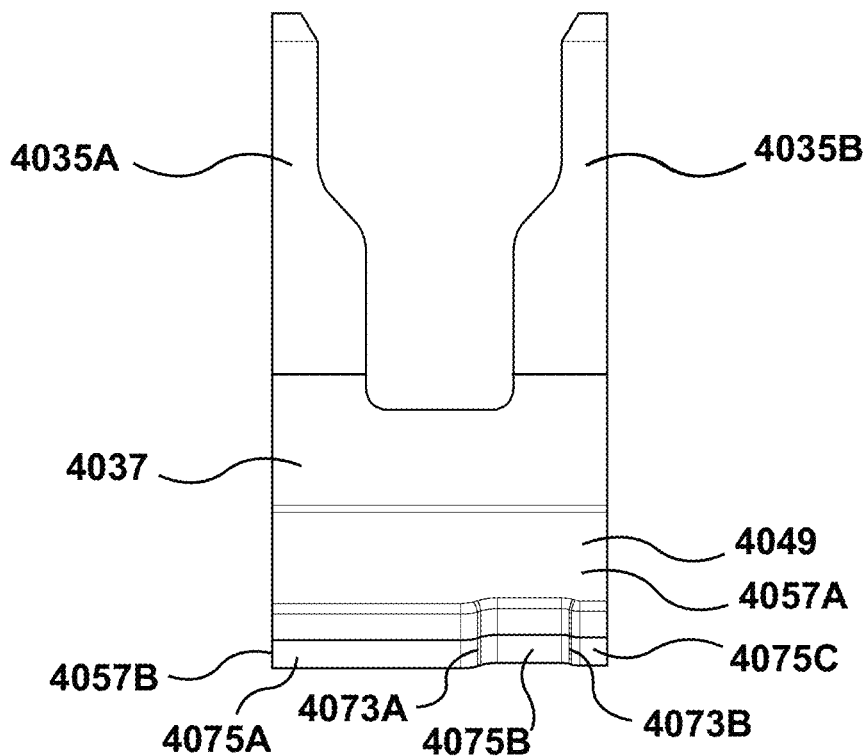

FIGS. 33A-33B illustrate a different views of a crimper element 4014, according to another embodiment hereof, that may be utilized in the crimper 3100 or other crimper described herein. One skilled in the art will realize that FIGS. 33A-33B illustrate one example of a crimper element and that existing components illustrated in FIGS. 33A-33B may be removed and/or additional components may be added to the crimper element 4014. While only one crimper element 4014 is discussed, one skilled in the art will realize that all of the crimper elements 4014 of the crimper 3100 have the same configuration and include the same components as the crimper element 4014 described in FIGS. 33A-33B.

Similar to crimper elements 3114, each crimper element 4014 has a first leg 4035A, a second leg 4035B, and a crimper lobe 4037 coupled to and extending between the first leg 4035A and the second leg 4035B. The first leg 4035A and the second leg 4035B extend parallel to a long axis of the crimper element 4014, from a proximal end 4039 of the crimper element 4014 to the crimper lobe 4037. The crimper lobe 4037 extends from the first leg 4035A and the second leg 4035B to a distal end 4043 of the crimper element 4014. The crimper lobe 4037 defines a crimper space 4045, or stated another way, includes the crimper space 4045 defined therein. The crimper space 4045 is configured to accommodate or receive an adjacent or neighboring crimper element 4014 when the crimper 3100 is operated and the crimper chamber 4016 decreases in size or volume. More particularly, the crimper element 4014 includes a first side or exterior surface 4047 and a second side or interior surface 4049 formed on the opposing side thereof. When assembled into the crimper 3100, the exterior surface 4047 of a crimper element 4014 is disposed adjacent to the interior surface 4049 of a neighboring crimper element such that the crimper element 4014 is received into the crimper space 4045 of the neighboring crimper element. The first exterior ramp 4057A and the second exterior ramp 4057B are angled surfaces relative to a long axis of the crimper element 4014. Along the interior surface 4049 of the crimper lobe 4037, the crimper lobe 4037 includes a first interior ramp 4059A and a second interior ramp 4059B. The first interior ramp 4059A and the second interior ramp 4059B define the crimper space 4045, and thus are configured to contact a neighboring crimper element to generate the iris effect when the crimper elements are displaced. The first interior ramp 4059A and the second interior ramp 4059B are angled surfaces relative to a long axis of the crimper element 4014.

Similar to crimper elements 3114, crimper elements 4014 are also configured to apply non-uniform radial compression along a length of the implantable medical device. More particularly, during operation of the crimper 3100, at least a portion of the second exterior ramp 4057B of the crimper element 4014 contacts the implantable medical device that is disposed within the crimper chamber 4016. The second exterior ramp 4057B is a non-planar surface that applies non-uniform radial compression along a length of the implantable medical device. In the embodiment of FIGS. 33A-33B, the second exterior ramp 4057B includes three longitudinal portions disposed at different radial positions within the crimper chamber 4016, particularly a first longitudinal portion 4075A, a second longitudinal portion 4075B, and a third longitudinal portion 4075C. The second longitudinal portion 4075B is disposed between the first and third longitudinal portions 4075A, 4075C. In the embodiment of FIGS. 33A-33B, the second exterior ramp 4057B includes a first ridge 4073A formed thereon that bridges or extends between the first longitudinal portion 4075A and the second longitudinal portion 4075B and a second ridge 4073B formed thereon that bridges or extends between the second longitudinal portion 4075B and the third longitudinal portion 4075C. Each of the first and second ridges 4073A, 4073B is a curved surface extending between the respective longitudinal portions such that the respective longitudinal portions are disposed at different radial positions within the crimper chamber 4016.

Figure 34A:
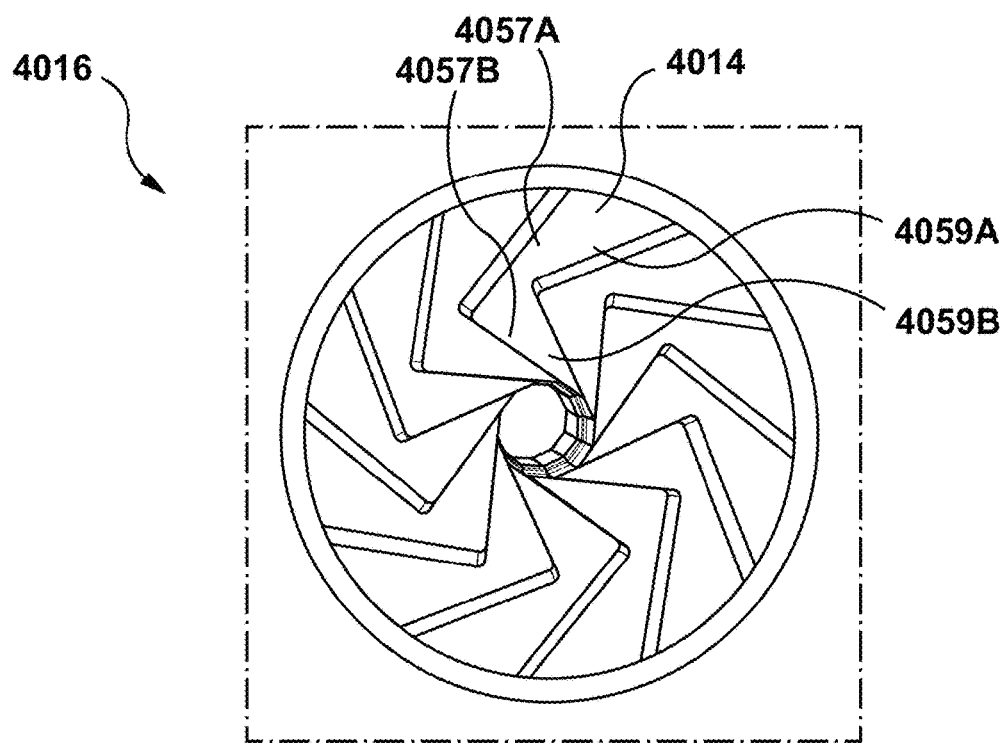
FIGS. 34A and 34B depict end and side views of a crimper chamber formed by the crimper elements of FIGS. 33A and 33B, according to an embodiment hereof.
Figure 34B:
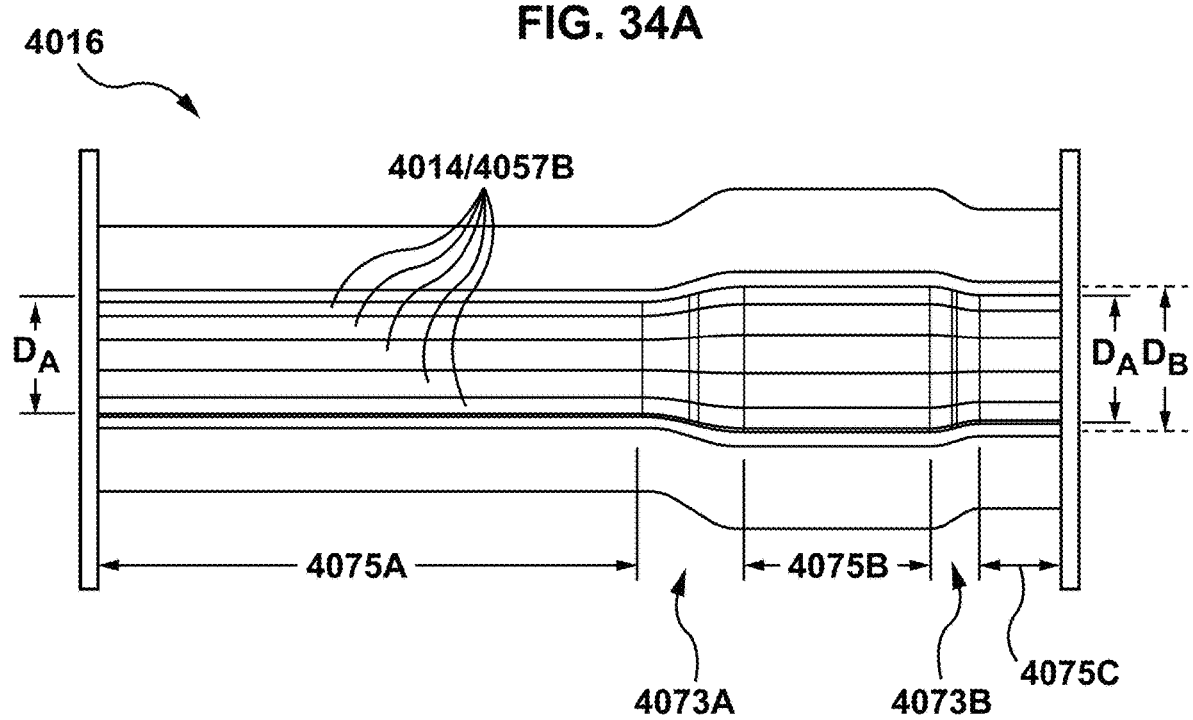

FIGS. 34A and 34B depict end and side views of the crimper chamber 4016 formed by the crimper elements 4014. At the first end of the crimper chamber 4016, the crimper chamber 4016 has a first diameter DA that is formed collectively by the first longitudinal portions 4075A of the crimper elements 4014. Similarly, at the second end of the crimper chamber 4016, the crimper chamber 4016 also has the diameter DA that is formed collectively by the third longitudinal portions 4075C of the crimper elements 4014. Along the second longitudinal portion 4075B, the crimper chamber 4016 has a second diameter DB that is formed collectively by the second longitudinal portions 4075B of the crimper elements 4014. Due to the different radial positions of the first, second, and third longitudinal portions 4075A, 4075B, 4075C, the first diameter DA is less than the second diameter DB. Since the second longitudinal portions 4075B of the crimper elements 4014 are disposed further away from the centerline or longitudinal axis of the crimper chamber 4016 than the first and third longitudinal portions 4075A, 4075C of the crimper elements 4014, the diameter of the crimper chamber 4016 is larger along the second longitudinal portions 4075B. Conversely, since the first and third longitudinal portions 4075A, C of the crimper elements 4014 are disposed closer from the centerline or longitudinal axis of the crimper chamber 4016 than the second longitudinal portions 4075B of the crimper elements 4014, the diameter of the crimper chamber 4016 is smaller along the first and third longitudinal portions 4075A, 4075C. This smaller diameter, i.e., the first diameter DA, results in a higher or greater radial force being applied to the implantable medical device along the first and third longitudinal portions 4075A, C of the crimper elements 4014 as compared to the radial force being applied to the implantable medical device along the second longitudinal portions 4075B of the crimper elements 4014.

Figure 40A:
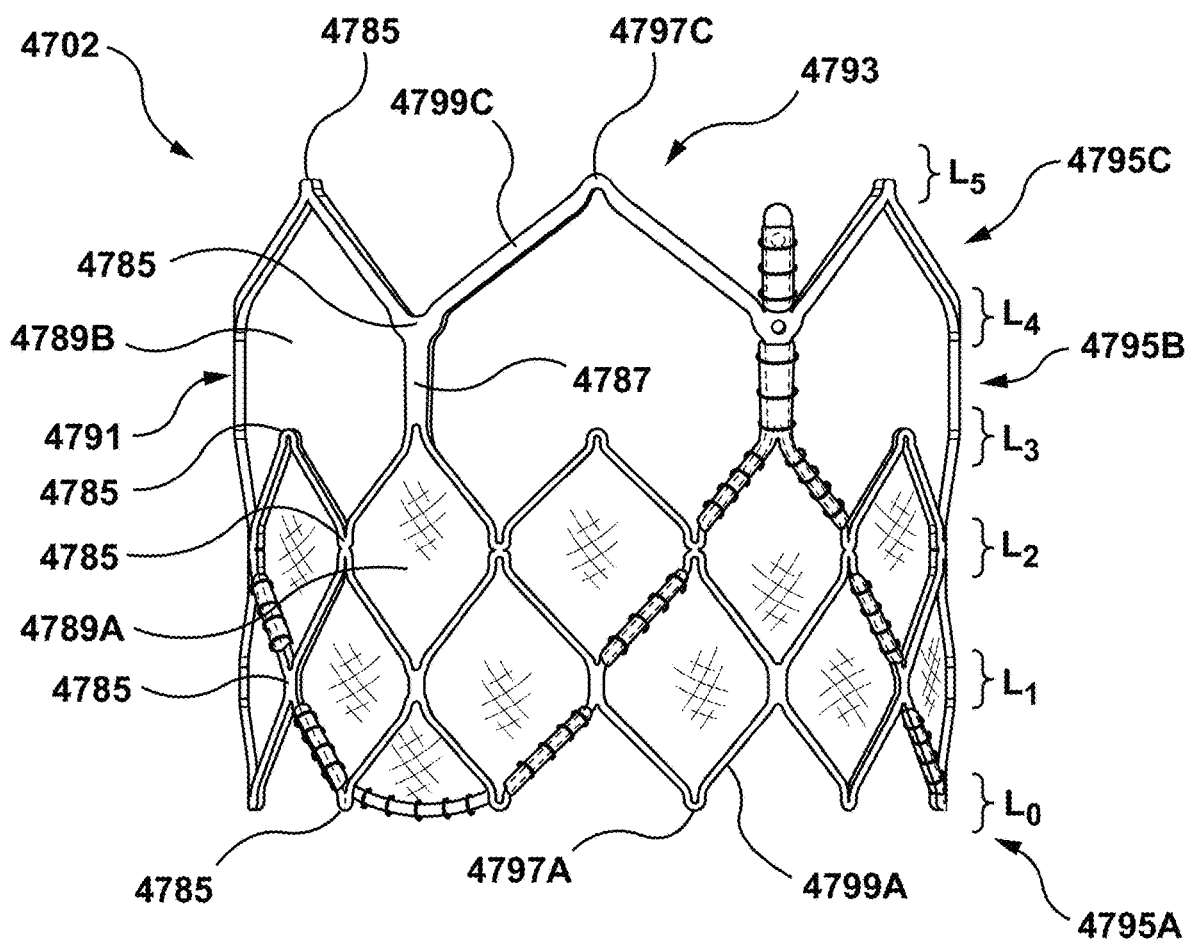
FIG. 40A depicts a side view of a prosthetic heart valve for use with the crimper of FIGS. 24A and 24B, according to an embodiment hereof.

In the embodiment of FIGS. 33A-33B, the first longitudinal portion 4075A is the longest longitudinal portion and extends between 55-65% of the total length of the crimper chamber 4016. The second longitudinal portion 4075B extends between 25-35% of the total length of the crimper chamber 4016 and the third longitudinal portion 4075C extends between 5-15% of the total length of the crimper chamber 4016. With reference to FIG. 40A, the first longitudinal portion 4075A is configured to contact level $L_0$ of nodes 4785, level $L_1$ of nodes 4785, level $L_2$ of nodes 4785, and level $L_3$ of nodes 4785 of the prosthetic heart valve 4702. The second longitudinal portion 4075B is configured to contact level $L_4$ of nodes 4785 of the prosthetic heart valve 4702, and the third longitudinal portion 4075C is configured to contact level $L_5$ of nodes 4785 of the prosthetic heart valve 4702.

In the depicted embodiment, each of the first and third longitudinal portions 4075A, 4075C is disposed closer to the centerline or longitudinal axis of the crimper chamber 4016 than the second longitudinal portion 3675B. As a result of the different radial positions, the first and third longitudinal portions 4075A, 4075C are configured to apply more radial force to the implantable medical device during crimping thereof than the second longitudinal portion 4075B. Thus, when utilized with the prosthetic heart valve 4702, more radial force is applied to level $L_0$ of nodes 4785, level $L_1$ of nodes 4785, level $L_2$ of nodes 4785, level $L_3$ of nodes 4785, and level $L_5$ of nodes 4785 via the first and third longitudinal portions 4075A, 4075C while less radial force is applied to level $L_4$ of nodes 4785 of the prosthetic heart valve 4702. It is desirable to apply less radial force to level $L_4$ of nodes 4785 of the prosthetic heart valve 4702 because level $L_4$ of nodes 4785 is positioned adjacent to endmost outflow side openings 4789B, which are less dense compared to other portions of the prosthetic heart valve 4702 and do not require as much radial force applied thereto in order to achieve a desired crimped profile. More particularly, the first longitudinal portions 4075A of the crimper elements 4014 are configured to apply a higher radial force along a section of the prosthetic heart valve 4702 of denser materials. In this instance, the non-uniform radial compression results in a substantially uniform profile in the compressed state of the implantable medical device because more radial force is applied by the first longitudinal portions 3675A of the crimper elements 3114 over the denser portions of the prosthetic heart valve 4702. Less radial force is applied by the second longitudinal portions 3675B of the crimper elements 3114 over the less dense, or sensitive, portions of the prosthetic heart valve 4702 to avoid damage thereto. Once crimped via non-uniform radial compression applied by the crimper elements 3114, the implantable medical device has a more uniform or consistent crimped profile along a length thereof as compared to the profile that would be achieved with uniform radial compression. In this embodiment, the third longitudinal portions 4075C of the crimper elements 4014 are configured to apply a higher radial force at the outflow end of the prosthetic heart valve 4702 to increase the retention of the prosthetic heart valve 4702 on the delivery system at the outflow end.

Figure 35A:
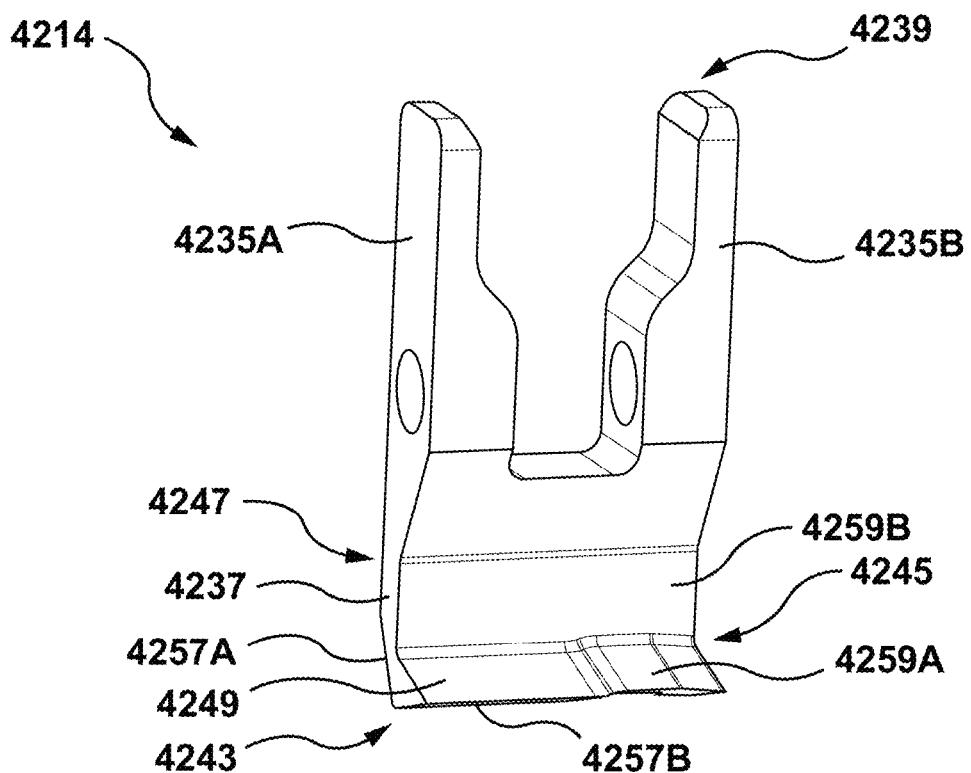
FIGS. 35A and 35B depict perspective and front views of a crimper element for use in the crimper of FIGS. 24A and 24B, according to another embodiment hereof.
Figure 35B:
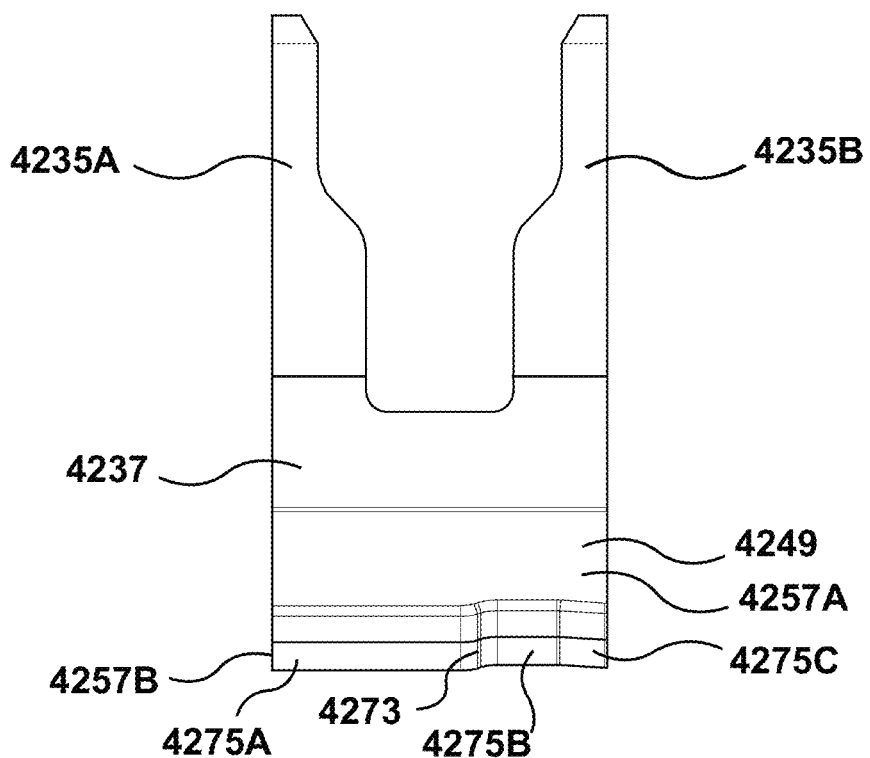

FIGS. 35A-35B illustrate a different views of a crimper element 4214, according to another embodiment hereof, that may be utilized in the crimper 3100 or other crimper described herein. One skilled in the art will realize that FIGS. 35A-35B illustrate one example of a crimper element and that existing components illustrated in FIGS. 35A-35B may be removed and/or additional components may be added to the crimper element 4214. While only one crimper element 4214 is discussed, one skilled in the art will realize that all of the crimper elements 4214 of the crimper 3100 have the same configuration and include the same components as the crimper element 4214 described in FIGS. 35A-35B.

Similar to crimper elements 3114, each crimper element 4214 has a first leg 4235A, a second leg 4235B, and a crimper lobe 4237 coupled to and extending between the first leg 4235A and the second leg 4235B. The first leg 4235A and the second leg 4235B extend parallel to a long axis of the crimper element 4214, from a proximal end 4239 of the crimper element 4214 to the crimper lobe 4237. The crimper lobe 4237 extends from the first leg 4235A and the second leg 4235B to a distal end 4243 of the crimper element 4214. The crimper lobe 4237 defines a crimper space 4245, or stated another way, includes the crimper space 4245 defined therein. The crimper space 4245 is configured to accommodate or receive an adjacent or neighboring crimper element 4214 when the crimper 3100 is operated and the crimper chamber 4216 decreases in size or volume. More particularly, the crimper element 4214 includes a first side or exterior surface 4247 and a second side or interior surface 4249 formed on the opposing side thereof. When assembled into the crimper 3100, the exterior surface 4247 of a crimper element 4214 is disposed adjacent to the interior surface 4249 of a neighboring crimper element such that the crimper element 4214 is received into the crimper space 4245 of the neighboring crimper element. Along the exterior surface 4247 of the crimper lobe 4237, the crimper lobe 4237 includes a first exterior ramp 4257A and a second exterior ramp 4257B. The first exterior ramp 4257A and the second exterior ramp 4257B are angled surfaces relative to a long axis of the crimper element 4214. Along the interior surface 4249 of the crimper lobe 4237, the crimper lobe 4237 includes a first interior ramp 4259A and a second interior ramp 4259B. The first interior ramp 4259A and the second interior ramp 4259B define the crimper space 4245, and thus are configured to contact a neighboring crimper element to generate the iris effect when the crimper elements are displaced. The first interior ramp 4259A and the second interior ramp 4259B are angled surfaces relative to a long axis of the crimper element 4214.

Similar to crimper elements 3114, crimper elements 4214 are also configured to apply non-uniform radial compression along a length of the implantable medical device. More particularly, during operation of the crimper 3100, at least a portion of the second exterior ramp 4257B of the crimper element 4214 contacts the implantable medical device that is disposed within the crimper chamber 4216. The second exterior ramp 4257B is a non-planar surface that applies non-uniform radial compression along a length of the implantable medical device. In the embodiment of FIGS. 35A-35B, the second exterior ramp 4257B includes three longitudinal portions disposed at different radial positions within the crimper chamber 4216, particularly a first longitudinal portion 4275A, a second longitudinal portion 4275B, and a third longitudinal portion 4275C. The second longitudinal portion 4275B is disposed between the first and third longitudinal portions 4275A, 4275C. The second exterior ramp 4257B includes a ridge 4273 formed thereon that bridges or extends between the first longitudinal portion 4275A and the second longitudinal portion 4275B. The ridge 4273 is a curved surface extending between the first longitudinal portion 4275A and the second longitudinal portion 4275B such that the respective longitudinal portions are disposed at different radial positions within the crimper chamber 4216. In this embodiment, the third longitudinal portion 4275C tapers along its length to the second longitudinal portion 4275B.

Figure 36A:
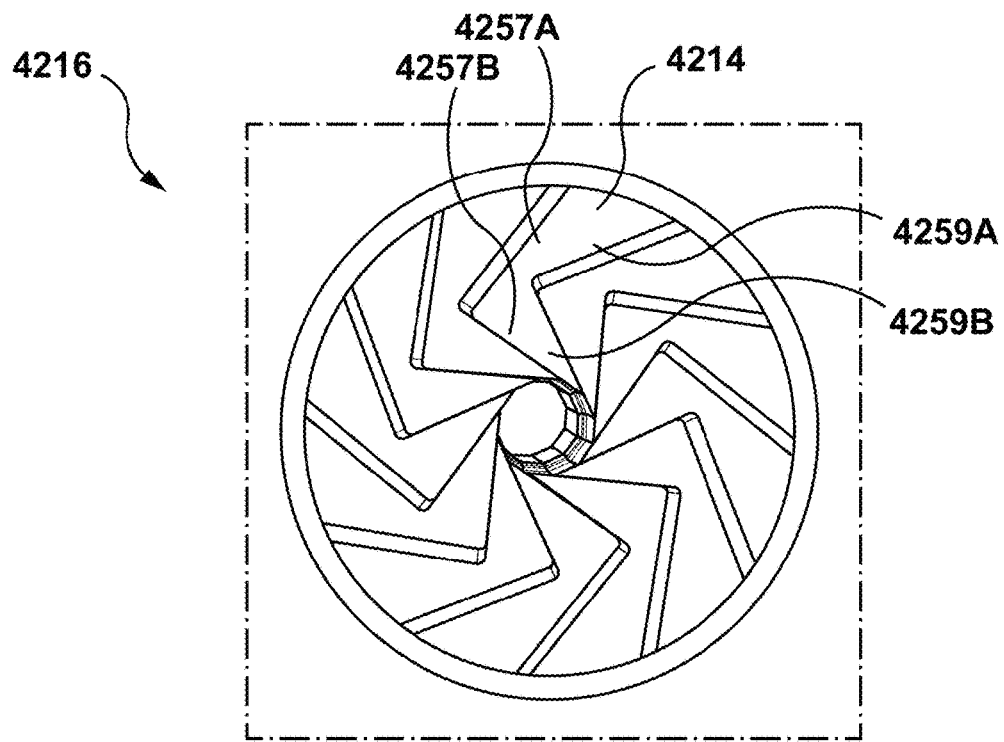
FIGS. 36A and 36B depict end and side views of a crimper chamber formed by the crimper elements of FIGS. 42A and 42B, according to an embodiment hereof.
Figure 36B:
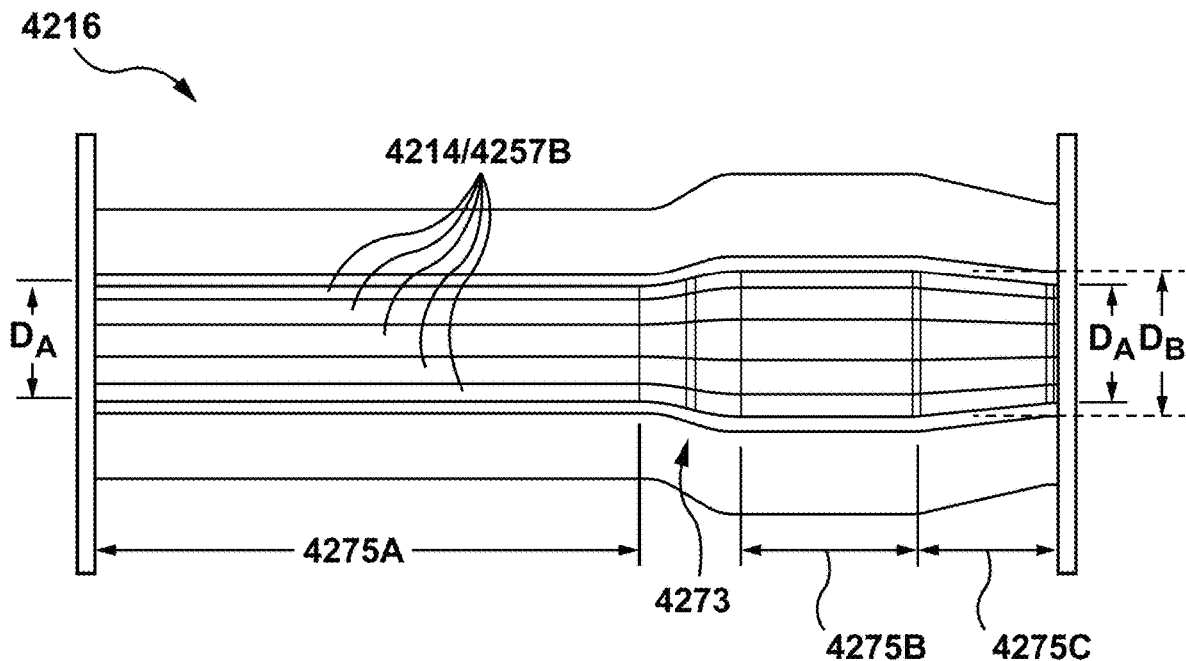

FIGS. 36A and 36B depict end and side views of the crimper chamber 4216 formed by the crimper elements 4214. At the first end of the crimper chamber 4216, the crimper chamber 4216 has a first diameter DA that is formed collectively by the first longitudinal portions 4275A of the crimper elements 4214. Similarly, at the second end of the crimper chamber 4216, the crimper chamber 4216 also has the diameter DA that is formed collectively by the third longitudinal portions 4275C of the crimper elements 4214. Along the second longitudinal portion 4275B, the crimper chamber 4216 has a second diameter DB that is formed collectively by the second longitudinal portions 4275B of the crimper elements 4214. Due to the different radial positions of the first, second, and third longitudinal portions 4275A, 4275B, 4275C, the first diameter DA is less than the second diameter DB. Since the second longitudinal portions 4275B of the crimper elements 4214 are disposed further away from the centerline or longitudinal axis of the crimper chamber 4216 than the first and third longitudinal portions 4275A, 4275C of the crimper elements 4214, the diameter of the crimper chamber 4216 is larger along the second longitudinal portions 4275B. Conversely, since the first and third longitudinal portions 4275A, C of the crimper elements 4214 are disposed closer from the centerline or longitudinal axis of the crimper chamber 4216 than the second longitudinal portions 4275B of the crimper elements 4214, the diameter of the crimper chamber 4216 is smaller along the first and third longitudinal portions 4275A, C. This smaller diameter, i.e., first diameter DA, results in a higher or greater radial force being applied to the implantable medical device along the first and third longitudinal portions 4275A, C of the crimper elements 4214 as compared to the radial force being applied to the implantable medical device along the second longitudinal portions 4275B of the crimper elements 4214. In this embodiment, along the third longitudinal section 4275C, the diameter of the crimper chamber 4216 tapers from the first diameter DA at the end of the crimper chamber 4216 to the second diameter DB at the point of intersection between the first and second longitudinal sections 4275A, 4275B.

In the embodiment of FIGS. 35A-35B, the first longitudinal portion 4275A is the longest longitudinal portion and extends between 55-65% of the total length of the crimper chamber 4216. The second longitudinal portion 4275B extends between 25-35% of the total length of the crimper chamber 4216 and the third longitudinal portion 4275C extends between 5-15% of the total length of the crimper chamber 4216. With reference to FIG. 40A, the first longitudinal portion 4275A is configured to contact level $L_0$ of nodes 4785, level $L_1$ of nodes 4785, level $L_2$ of nodes 4785, and level $L_3$ of nodes 4785 of the prosthetic heart valve 4702. The second longitudinal portion 4275B is configured to contact level $L_4$ of nodes 4785 of the prosthetic heart valve 4702, and the third longitudinal portion 4275C is configured to contact level $L_5$ of nodes 4785 of the prosthetic heart valve 4702.

In the depicted embodiment, each of the first and third longitudinal portions 4275A, 4275C is disposed closer to the centerline or longitudinal axis of the crimper chamber 4216 than the second longitudinal portion 3675B. As a result of the different radial positions, the first and third longitudinal portions 4275A, 4275C are configured to apply more radial force to the implantable medical device during crimping thereof than the second longitudinal portion 4275B. Thus, when utilized with the prosthetic heart valve 4702, more radial force is applied to level $L_0$ of nodes 4785, level $L_1$ of nodes 4785, level $L_2$ of nodes 4785, level $L_3$ of nodes 4785, and level $L_5$ of nodes 4785 via the first and third longitudinal portions 4075A, 4075C while less radial force is applied to level $L_4$ of nodes 4785 of the prosthetic heart valve 4702. It is desirable to apply less radial force to level $L_4$ of nodes 4785 of the prosthetic heart valve 4702 because level $L_4$ of nodes 4785 is positioned adjacent to endmost outflow side openings 4789B, which are less dense compared to other portions of the prosthetic heart valve 4702 and do not require as much radial force applied thereto in order to achieve a desired crimped profile. More particularly, the first longitudinal portions 4275A of the crimper elements 4214 are configured to apply a higher radial force along a section of denser materials, such as the portion of an implantable medical device that includes a valve. In this instance, the non-uniform radial compression results in a substantially uniform profile in the compressed state of the implantable medical device because more radial force is applied by the first longitudinal portions 4275A of the crimper elements 4214 over the denser portions of the prosthetic heart valve 4702. Less radial force is applied by the second longitudinal portions 4275B of the crimper elements 4214 over the less dense, or sensitive, portions of the prosthetic heart valve 4702 to avoid damage thereto. Once crimped via non-uniform radial compression applied by the crimper elements 4214, the implantable medical device has a more uniform or consistent crimped profile along a length thereof as compared to the profile that would be achieved with uniform radial compression. In this embodiment, the third longitudinal portions 4275C of the crimper elements 4214 are configured to apply a higher radial force at the outflow end of the prosthetic heart valve 4702 to increase the retention of the prosthetic heart valve 4702 on the delivery system at the outflow end. Due to the tapering diameter along the third longitudinal sections 4275C of the crimper elements 4214, the profile of the implantable medical device is tapered at the outflow end thereof.

Figure 37A:
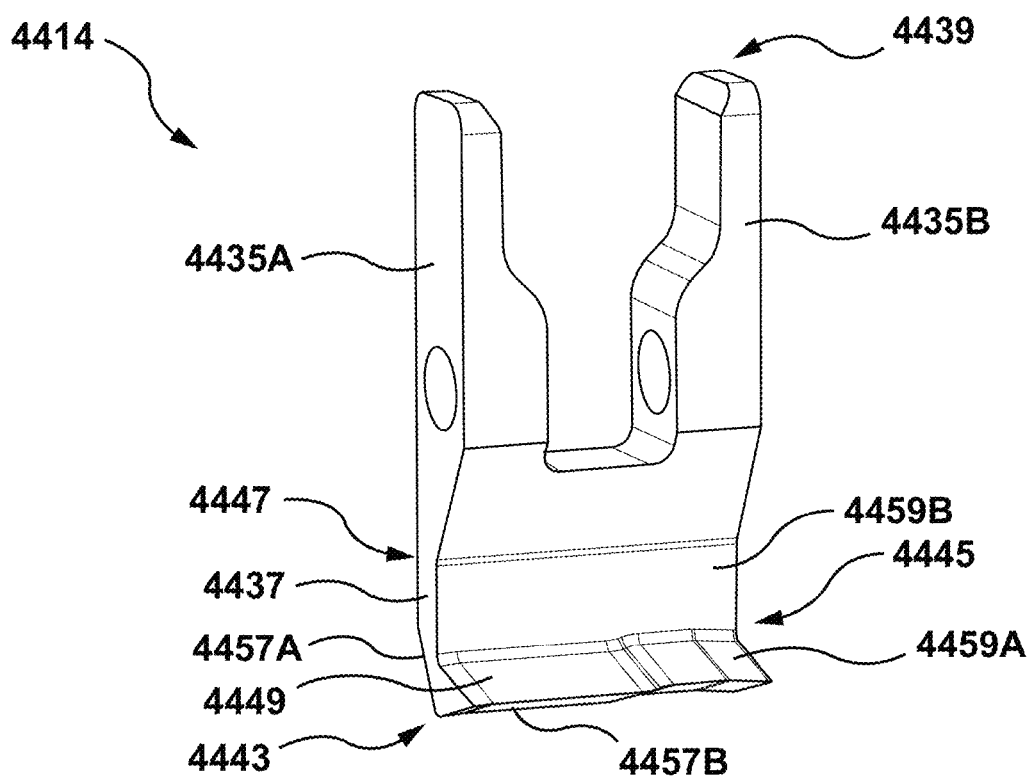
FIGS. 37A and 37B depict perspective and front views of a crimper element for use in the crimper of FIGS. 24A and 24B, according to another embodiment hereof.
Figure 37B:
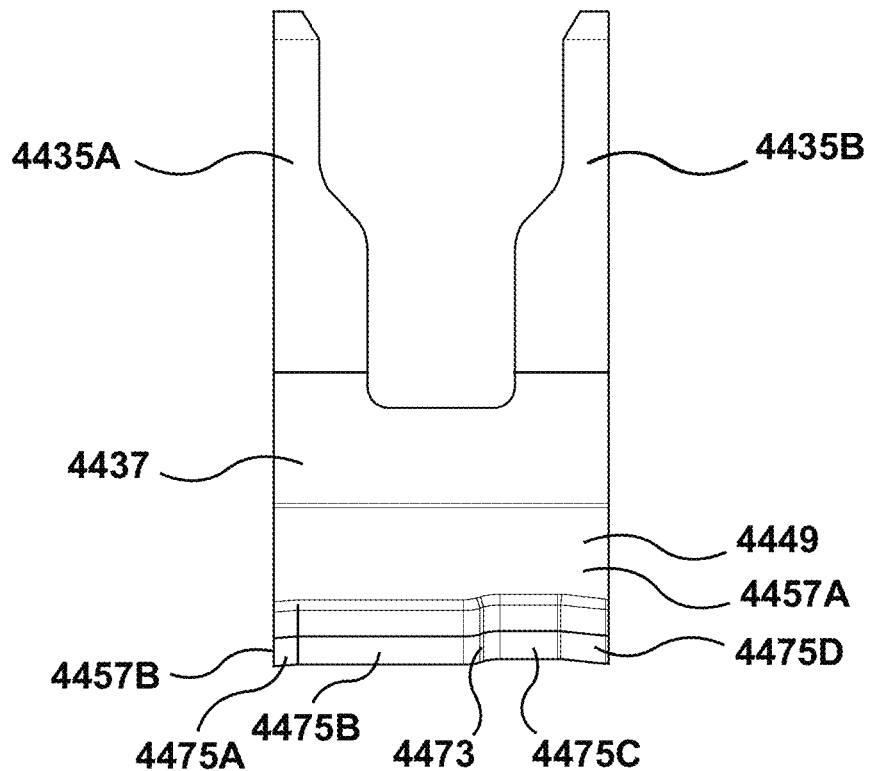

FIGS. 37A-37B illustrate a different views of a crimper element 4414, according to another embodiment hereof, that may be utilized in the crimper 3100 or other crimper described herein. One skilled in the art will realize that FIGS. 37A-37B illustrate one example of a crimper element and that existing components illustrated in FIGS. 37A-37B may be removed and/or additional components may be added to the crimper element 4414. While only one crimper element 4414 is discussed, one skilled in the art will realize that all of the crimper elements 4414 of the crimper 4400 have the same configuration and include the same components as the crimper element 4414 described in FIGS. 37A-37B.

Similar to crimper elements 3114, each crimper element 4414 has a first leg 4435A, a second leg 4435B, and a crimper lobe 4437 coupled to and extending between the first leg 4435A and the second leg 4435B. The first leg 4435A and the second leg 4435B extend parallel to a long axis of the crimper element 4414, from a proximal end 4439 of the crimper element 4414 to the crimper lobe 4437. The crimper lobe 4437 extends from the first leg 4435A and the second leg 4435B to a distal end 4443 of the crimper element 4414. The crimper lobe 4437 defines a crimper space 4445, or stated another way, includes the crimper space 4445 defined therein. The crimper space 4445 is configured to accommodate or receive an adjacent or neighboring crimper element 4414 when the crimper 4400 is operated and the crimper chamber 4416 decreases in size or volume. More particularly, the crimper element 4414 includes a first side or exterior surface 4447 and a second side or interior surface 4449 formed on the opposing side thereof. When assembled into the crimper 4400, the exterior surface 4447 of a crimper element 4414 is disposed adjacent to the interior surface 4449 of a neighboring crimper element such that the crimper element 4414 is received into the crimper space 4445 of the neighboring crimper element. Along the exterior surface 4447 of the crimper lobe 4437, the crimper lobe 4437 includes a first exterior ramp 4457A and a second exterior ramp 4457B. The first exterior ramp 4457A and the second exterior ramp 4457B are angled surfaces relative to a long axis of the crimper element 4414. Along the interior surface 4449 of the crimper lobe 4437, the crimper lobe 4437 includes a first interior ramp 4459A and a second interior ramp 4459B. The first interior ramp 4459A and the second interior ramp 4459B define the crimper space 4445, and thus are configured to contact a neighboring crimper element to generate the iris effect when the crimper elements are displaced. The first interior ramp 4459A and the second interior ramp 4459B are angled surfaces relative to a long axis of the crimper element 4414.

Similar to crimper elements 3114, crimper elements 4414 are also configured to apply non-uniform radial compression along a length of the implantable medical device. More particularly, during operation of the crimper 3100, at least a portion of the second exterior ramp 4457B of the crimper element 4414 contacts the implantable medical device that is disposed within the crimper chamber 4416. The second exterior ramp 4457B is a non-planar surface that applies non-uniform radial compression along a length of the implantable medical device. In the embodiment of FIGS. 37A-37B, the second exterior ramp 4457B includes four longitudinal portions disposed at different radial positions within the crimper chamber 4416, particularly a first longitudinal portion 4475A, a second longitudinal portion 4475B, a third longitudinal portion 4475C, and a fourth longitudinal portion 4475D. The second longitudinal portion 4475B is disposed between the first and third longitudinal portions 4475A, 4475C. The third longitudinal portion 4475C is disposed between the second and fourth longitudinal portions 4475B, 4475D. The second exterior ramp 4457B includes a ridge 4473 formed thereon that bridges or extends between the second longitudinal portion 4475B and the third longitudinal portion 4475C. The ridge 4473 is a curved surface extending between the second longitudinal portion 4475B and the third longitudinal portion 4475C such that the respective longitudinal portions are disposed at different radial positions within the crimper chamber 4416. In this embodiment, the first longitudinal portion 4475A tapers along its length to the second longitudinal portion 4275B and the fourth longitudinal portion 4475D tapers along its length to the third longitudinal portion 4275C.

Figure 38A:
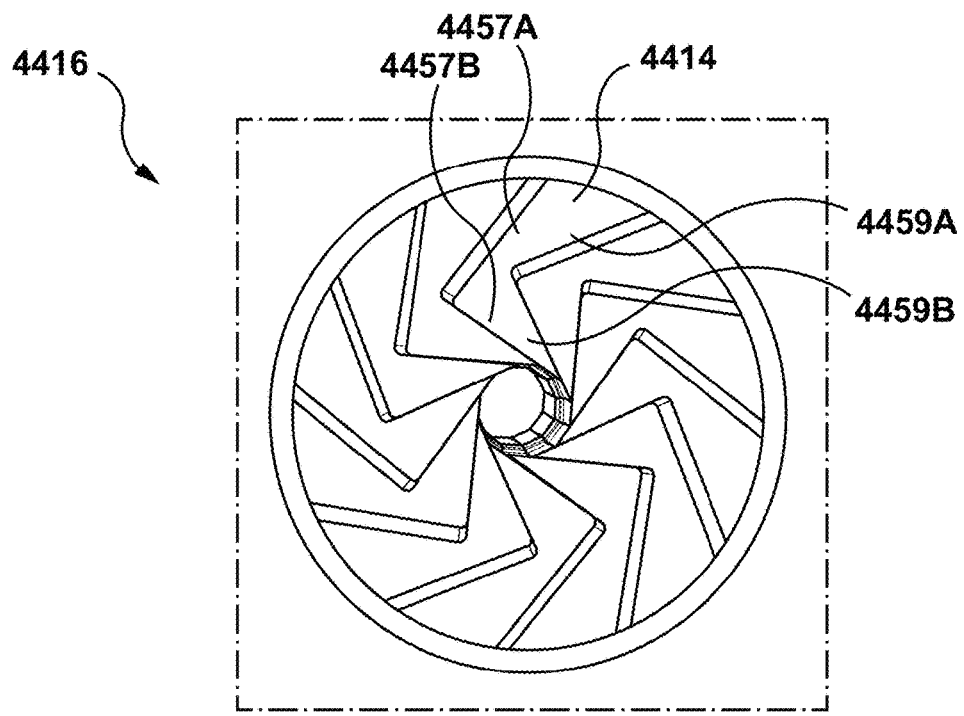
FIGS. 38A and 38B depict end and side views of a crimper chamber formed by the crimper elements of FIGS. 44A and 44B, according to an embodiment hereof.
Figure 38B:
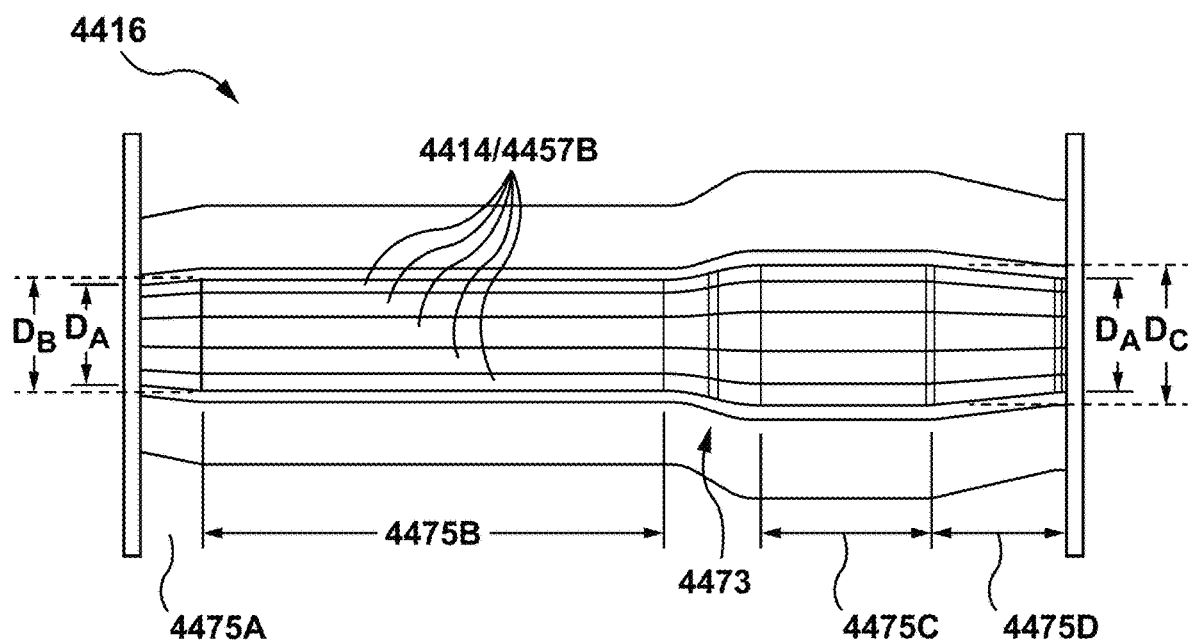

FIGS. 38A and 38B depict end and side views of the crimper chamber 4416 formed by the crimper elements 4414. At the first end of the crimper chamber 4416, the crimper chamber 4416 has a first diameter DA that is formed collectively by the first longitudinal portions 4475A of the crimper elements 4414. Similarly, at the second end of the crimper chamber 4416, the crimper chamber 4416 also has the diameter DA that is formed collectively by the fourth longitudinal portions 4475D of the crimper elements 4414. Along the second longitudinal portion 4475B, the crimper chamber 4416 has a second diameter DB that is formed collectively by the second longitudinal portions 4475B of the crimper elements 4414. Similarly, along the third longitudinal portion 4475C, the crimper chamber 4416 has a third diameter Dc that is formed collectively by the third longitudinal portions 4475C of the crimper elements 4414. Due to the different radial positions of the first, second, third, and fourth longitudinal portions 4475A, 4475B, 4475C, 4475D, the first diameter DA is less than each of the second diameter DB and the third diameter Dc. Further, due to the different radial positions of the second and third longitudinal portions 4475B, 4475C, the second diameter DB is less than the third diameter Dc. Since the third longitudinal portions 4475C of the crimper elements 4414 are disposed the furthest away from the centerline or longitudinal axis of the crimper chamber 4416, the diameter of the crimper chamber 4416 is largest along the third longitudinal portions 4475C. Conversely, since the first and fourth longitudinal portions 4475A, 4475D of the crimper elements 4414 are disposed closest from the centerline or longitudinal axis of the crimper chamber 4416, the diameter of the crimper chamber 4416 is smallest along the first and fourth longitudinal portions 4475A, 4475D. This smallest diameter, i.e., first diameter DA, results in a highest or greatest radial force being applied to the implantable medical device along the first and fourth longitudinal portions 4475A, 4475D of the crimper elements 4414 as compared to the radial force being applied to the implantable medical device along the second and third longitudinal portions 4475B, 4475C of the crimper elements 4414. In this embodiment, along the first longitudinal section 4475A, the diameter of the crimper chamber 4416 tapers from the first diameter DA at the end of the crimper chamber 4416 to the second diameter DB at the point of intersection between the first and second longitudinal sections 4475A, 4475B. In addition, in this embodiment along the fourth longitudinal section 4475D, the diameter of the crimper chamber 4416 tapers from the first diameter DA at the end of the crimper chamber 4416 to the third diameter Dc at the point of intersection between the fourth and third longitudinal sections 4475D, 4475C.

In the embodiment of FIGS. 37A-37B, the second longitudinal portion 4475B is the longest longitudinal portion and extends between 50-60% of the total length of the crimper chamber 4416. The first longitudinal portion 4475 extends between 2-8% of the total length of the crimper chamber 4416, the third longitudinal portion 4475C extends between 25-35% of the total length of the crimper chamber 4416 and the fourth longitudinal portion 4475D extends between 5-15% of the total length of the crimper chamber 4416. With reference to FIG. 40A, the first longitudinal portion 4475A is configured to contact level $L_0$ of nodes 4785 of the prosthetic heart valve 4702, while the second longitudinal portion 4475B is configured to contact level $L_1$ of nodes 4785, level $L_2$ of nodes 4785, and level $L_3$ of nodes 4785 of the prosthetic heart valve 4702. The third longitudinal portion 4475C is configured to contact level $L_4$ of nodes 4785 of the prosthetic heart valve 4702, and the fourth longitudinal portion 4475D is configured to contact level $L_5$ of nodes 4785 of the prosthetic heart valve 4702.

Each of the first and fourth longitudinal portions 4475A, 4475D is disposed closer to the centerline or longitudinal axis of the crimper chamber 4416 than the second and third longitudinal portions 4475B, 4475C. Further, the second longitudinal portions 4475B are disposed closer to the centerline or longitudinal axis of the crimper chamber 4416 than the third longitudinal portions 4475C. As a result of the different radial positions, the first and fourth longitudinal portions 4475A, 4475D are configured to apply more radial force to the implantable medical device during crimping thereof than the second and third longitudinal portions 4475B, 4475C. In addition, the second longitudinal portions 4475B are configured to apply more radial force to the implantable medical device during crimping thereof than the third longitudinal portions 4475C. Thus, when utilized with the prosthetic heart valve 4702, the highest amount of radial force is applied to level $L_0$ of nodes 4785 at the inflow end of the prosthetic heart valve 4702 and level $L_5$ of nodes 4785 at the outflow end of the prosthetic heart valve. Similarly, relatively more radial force is applied to level $L_1$ of nodes 4785, level $L_2$ of nodes 4785, and level $L_3$ of nodes 4785, via the second longitudinal portions 4475B while less radial force is applied to level $L_4$ of nodes 4785 of the prosthetic heart valve 4702 via the third longitudinal portions 4475C. It is desirable to apply less radial force to level $L_4$ of nodes 4785 of the prosthetic heart valve 4702 because level $L_4$ of nodes 4785 is positioned adjacent to endmost outflow side openings 4789B, which are less dense compared to other portions of the prosthetic heart valve 4702 and do not require as much radial force applied thereto in order to achieve a desired crimped profile. More particularly, the second longitudinal portions 4475B of the crimper elements 4414 are configured to apply a higher radial force along a section of the prosthetic heart valve 4702 of denser materials as compared to the third longitudinal portions 4475C of the crimper elements 4414. In this instance, the non-uniform radial compression results in a substantially uniform profile in the compressed state of the implantable medical device because more radial force is applied by the second longitudinal portions 3675B of the crimper elements 4414 over the denser portions of the prosthetic heart valve 4702. Less radial force is applied by the third longitudinal portions 4475C of the crimper elements 4414 over the less dense, or sensitive, portions of the prosthetic heart valve 4702 to avoid damage thereto. Once crimped via non-uniform radial compression applied by the crimper elements 4414, the implantable medical device has a more uniform or consistent crimped profile along a length thereof as compared to the profile that would be achieved with uniform radial compression. In this embodiment, each of the first and fourth longitudinal portions 4475A, 4475D of the crimper elements 4414 are configured to apply a higher radial force at the inflow and outflow ends, respectively, of the prosthetic heart valve 4702 to increase the retention of the prosthetic heart valve 4702 on the delivery system at the outflow end. Due to the tapering diameter along the first and fourth longitudinal sections 4475A, 4475D of the crimper elements 4414, the profile of the implantable medical device is tapered at the inflow and outflow ends thereof.

FIGS. 39A-39D illustrate an example of the operation of the crimper 3100 in accordance with an embodiment hereof. One skilled in the art will realize that FIGS. 39A-39D illustrate only a few operating states in order to illustrate the operation of the crimper 3100, and will realize that the crimper 3100 can assume other operational states without departing from the scope of the present invention.

Figure 39A:
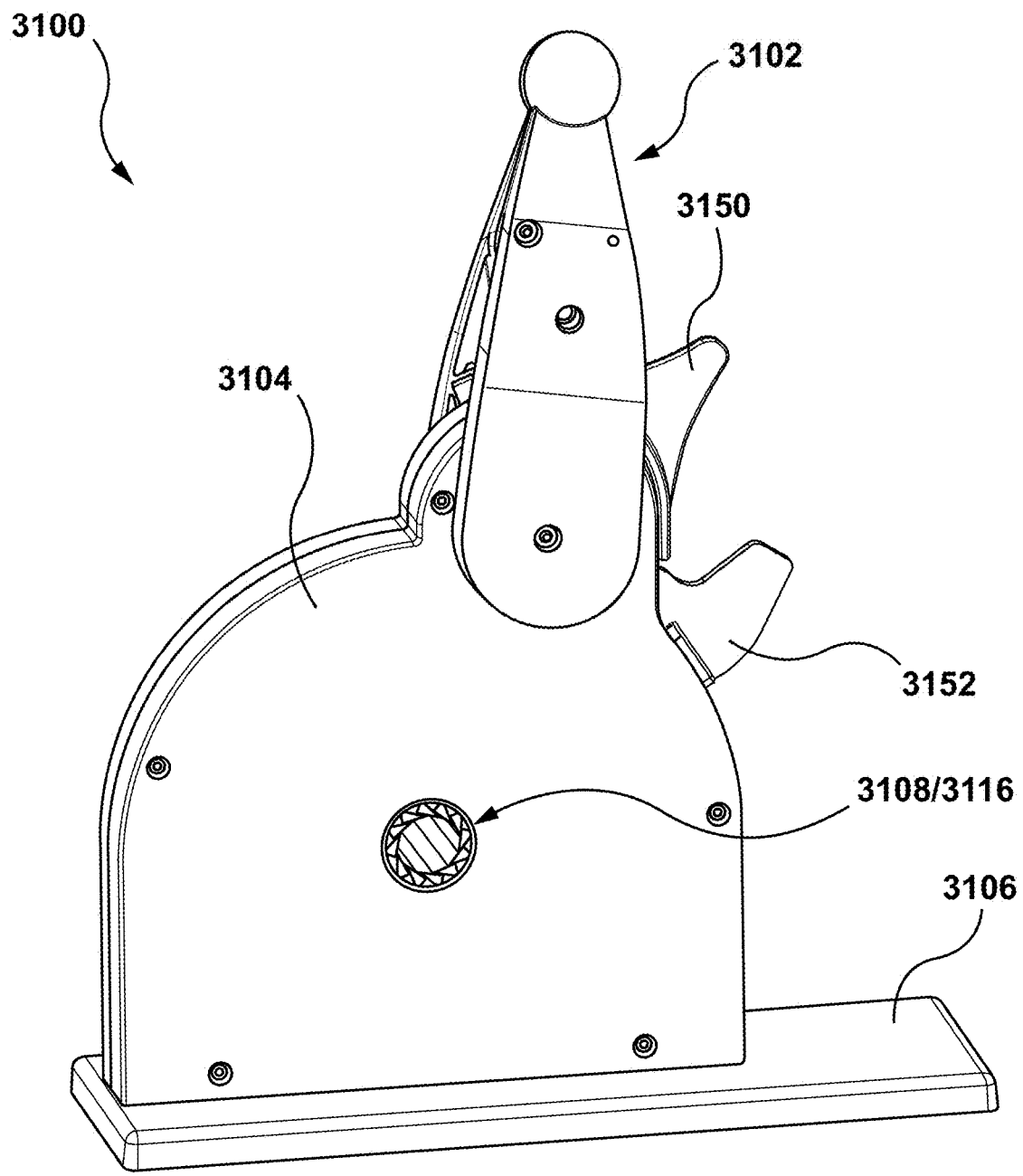
FIGS. 39A-39D depict an operation of the crimper of FIGS. 24A and 24B, according to an embodiment hereof.
Figure 39B:
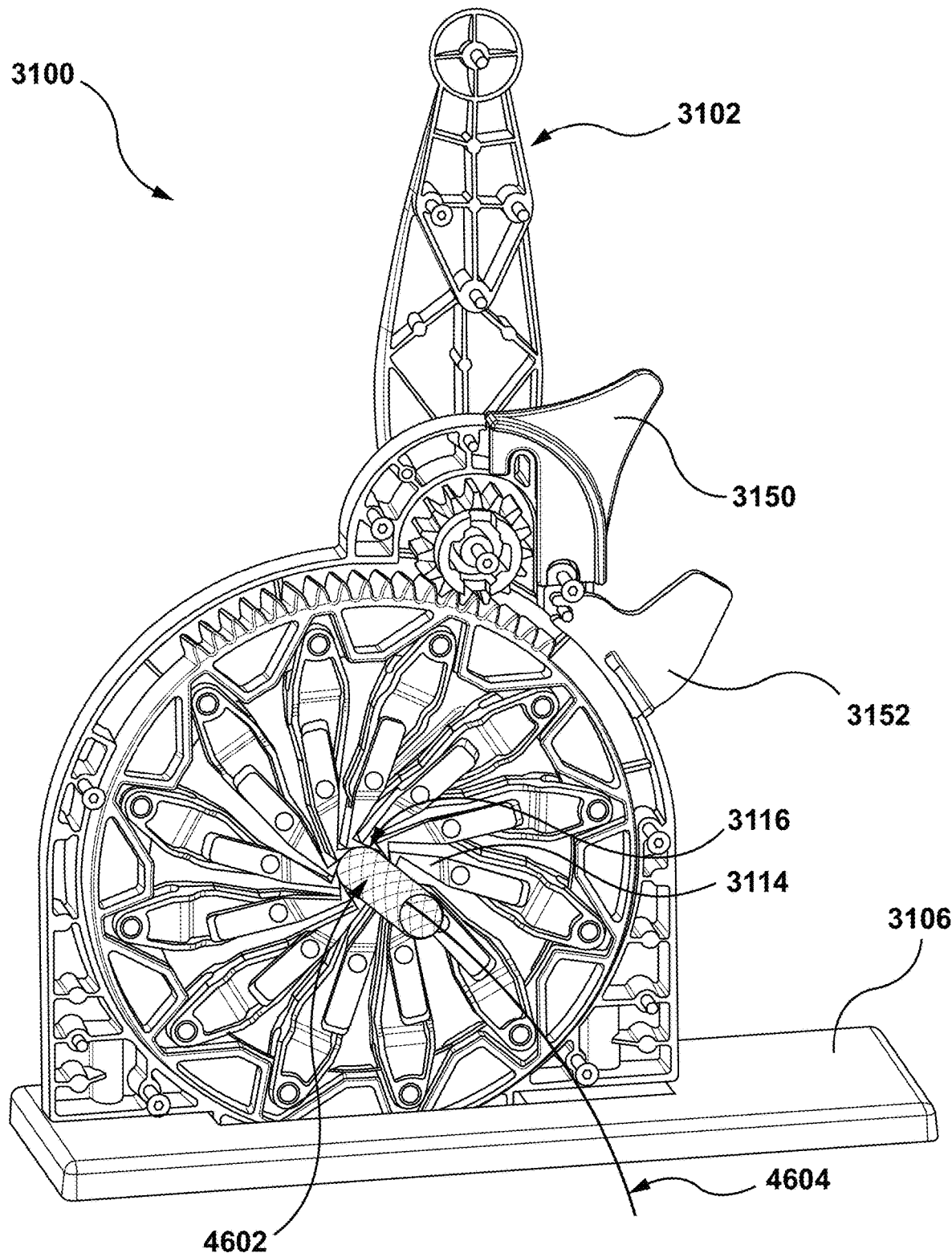
Figure 39C:
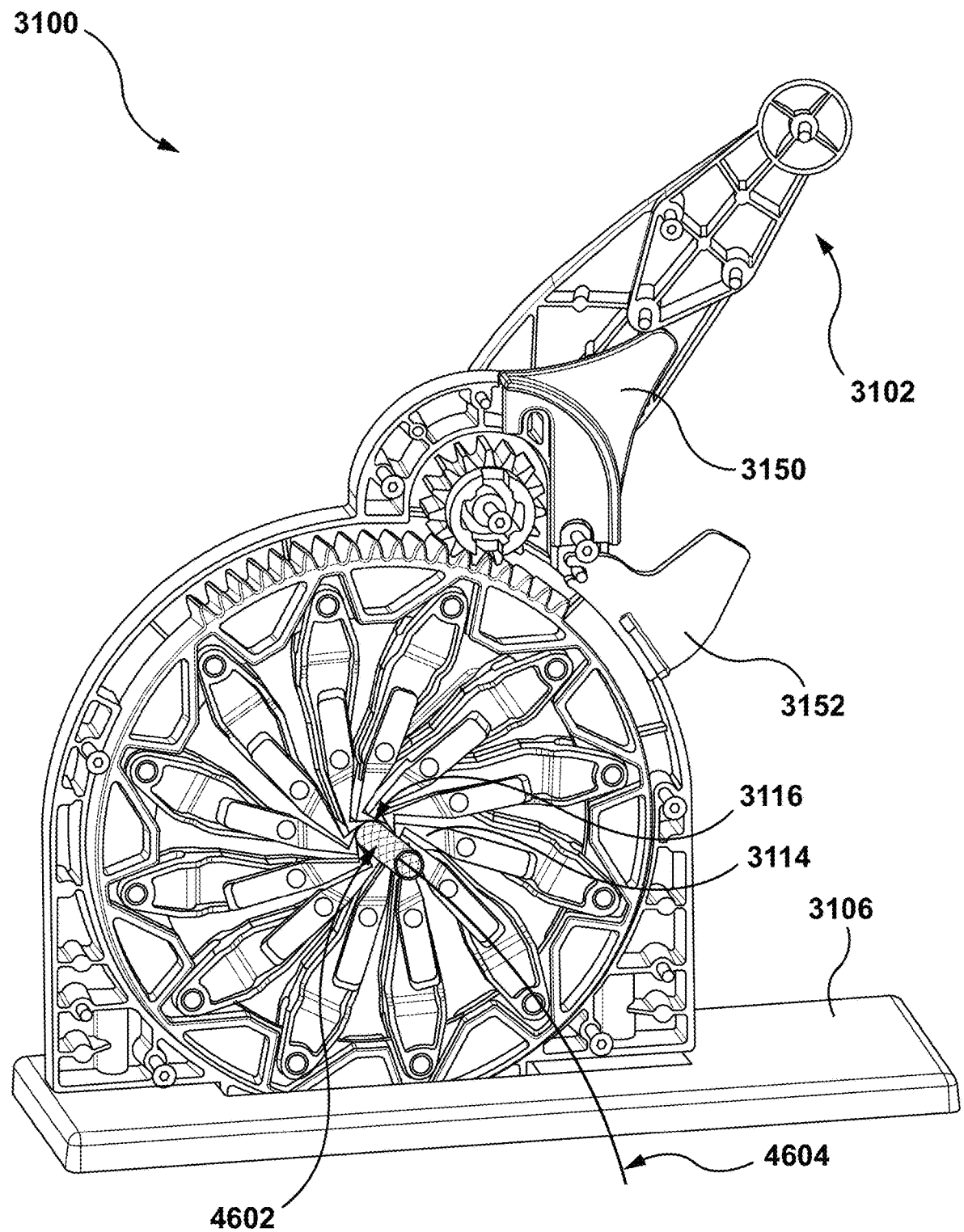
Figure 39D:
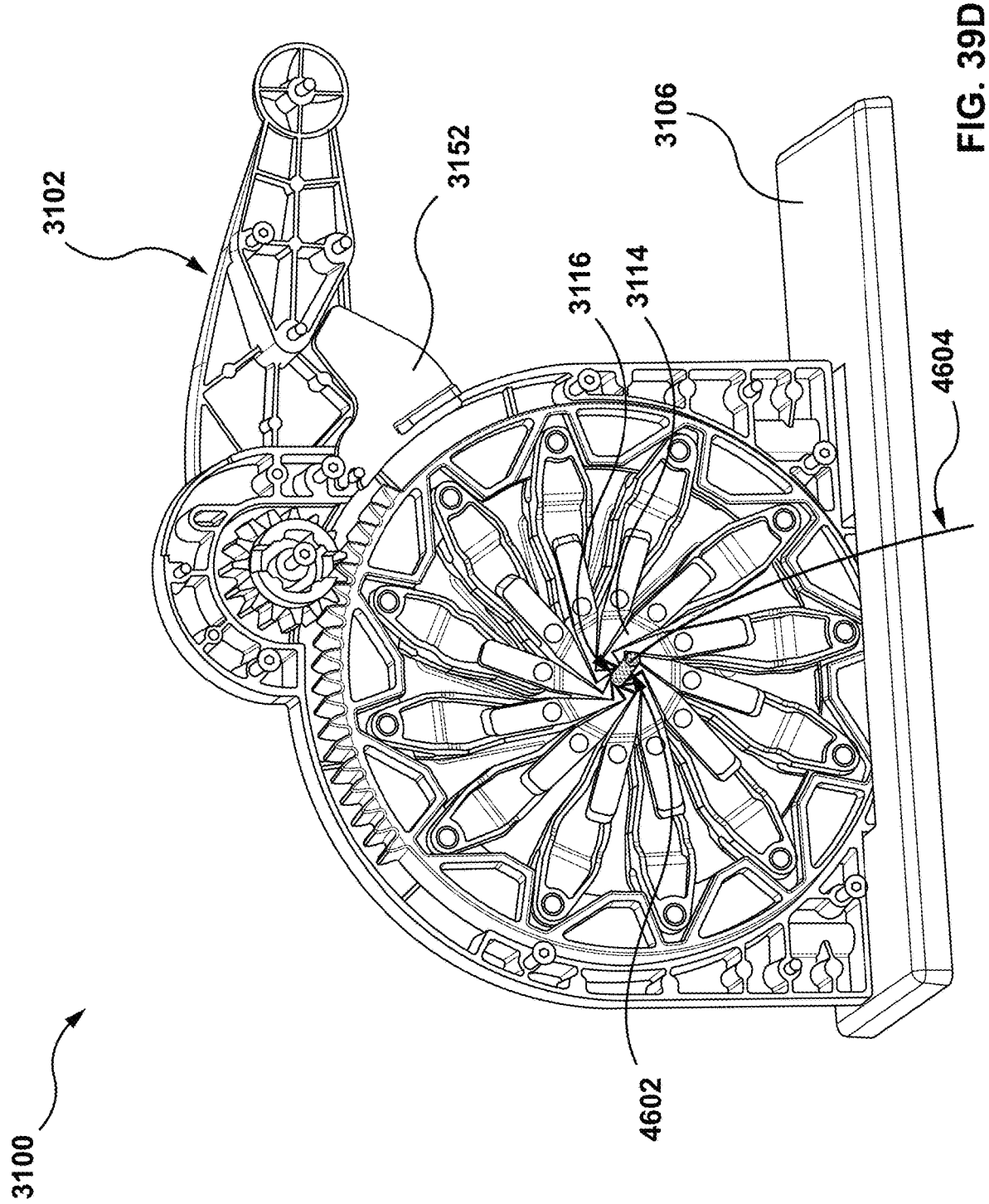

As illustrated in FIG. 39A and FIG. 39B, an implantable medical device 4602 and a delivery device 4604 is loaded or placed into the crimper chamber 3116 of the crimper housing 3104. As described above, the crimper elements 3114 form the crimper chamber 3116. As illustrated in FIG. 39C-39D, to compress the implantable medical device 4602, a force is applied to the handle 3102 in the direction of the base 3106 in a clockwise direction. The force applied to the handle 3102 is transferred to the cam 3110 via the gear 3112, and the cam 3110 rotates in an opposing direction from the handle 3102, i.e., a counter-clockwise direction. Rotation of the cam 3110 causes the crimper elements 3112 to move radially inward via the rods 3118. More particularly, as described above, as the handle 3102 moves, the cam 3110 rotates and translates or transforms the rotational motion of the handle 3102 into linear motion of the crimper elements 3114 via the rods 3118.

As the crimper elements 3114 move radially inward, the space available for the crimper elements 3114 to occupy is reduced. As such, the volume of the crimper chamber 3116 decreases and the crimper elements 3114 apply a compression force to external surfaces of the implantable medical device 4602 to crimp the implantable medical device 4602 from an uncompressed or radially expanded state to a radially compressed state. For example, if the implantable medical device 4602 is generally cylindrical in shape, the crimper elements apply a force on the surface of the implantable medical device from various directions as force is applied to the handle 3102 thereby compressing the implantable medical device.

As illustrated in FIG. 39C, the handle 3102 can be moved downward until the handle 3102 abuts the first stop 3150, thereby partially compressing the implantable medical device 4602 to a predetermined diameter. If the implantable medical device 4602 requires only a partial compression, the handle 3102 can be moved upward and the implantable medical device 4602 removed from the crimper chamber 3116.

If the implantable medical device 4602 is to be fully compressed, the first stop 3150 is removed from the crimper 3104 and the handle 3102 is further actuated or moved until the handle 3102 abuts the second stop 3152 as illustrated in FIG. 39D. The further movement of the handle 3102 causes additional radial compression of the implantable medical device 4602.

Crimper elements 3114 are configured to apply non-uniform radial compression along a length of the implantable medical device. As described above, the second longitudinal portions 3675B of the crimper elements 3114 are configured to apply more radial force to the implantable medical device during crimping thereof than the first longitudinal portions 3675A of the crimper elements 3114. In an embodiment in which the implantable medical device 4602 includes a valve disposed thereon, the second longitudinal portions 3675B of the crimper elements 3114 are configured to be disposed over a first portion of the implantable medical device 4602 including the valve while the first longitudinal portions 3675A of the crimper elements 3114 are configured to be disposed over a second portion of the implantable medical device 4602 which does not include the valve. In this embodiment, the non-uniform radial compression of the results in a substantially uniform profile in the compressed state of the implantable medical device because more radial force is applied by the second longitudinal portions 3675B of the crimper elements 3114 over the denser portions of the implantable medical device. Less radial force is applied by the first longitudinal portions 3675A of the crimper elements 3114 over the less dense, or sensitive, portions of the implantable medical device to avoid damage thereto. Once crimped via non-uniform radial compression applied by the crimper elements 3114, the implantable medical device has a more uniform or consistent crimped profile along a length thereof as compared to the profile that would be achieved with uniform radial compression.

In another embodiment hereof, the implantable medical device 4602 does not include a valve and the density thereof is generally uniform along a length thereof. In this embodiment, the crimped profile of the implantable medical device 4602 is stepped such that a first longitudinal portion thereof, which is crimped by the second longitudinal portions 3675B, has a smaller crimped diameter than a second longitudinal portion thereof, which is crimped by the first longitudinal portions 3675A.

The crimper 3100 can be utilized on any type of implantable medical device that requires a conversion from an uncompressed state to a compressed state. In an embodiment, the crimper can be applied to any implantable medical device that requires onsite crimping of the implanted medical device onto a catheter, e.g., organic tissue containing valve repair devices. In an embodiment, the crimper 3100 can be used with balloon-expandable medical devices and/or mechanically expandable medical devices. For example, the crimper 3100 can be utilized on implantable medical devices that are to be delivered transluminally, e.g., via a catheter, and need to be loaded onto or into a catheter. In this example, the implantable medical device can include a heart valve prosthesis, which includes a stent or frame, and a prosthetic valve attached to the interior of the frame. The stent/frame may be crimped to have a low profile such that the prosthesis can be delivery through the vessels to a target location in a compressed state, and then expanded at the target location, by a balloon of the delivery device, for instance, to replace the native heart valve.

Figure 40B:
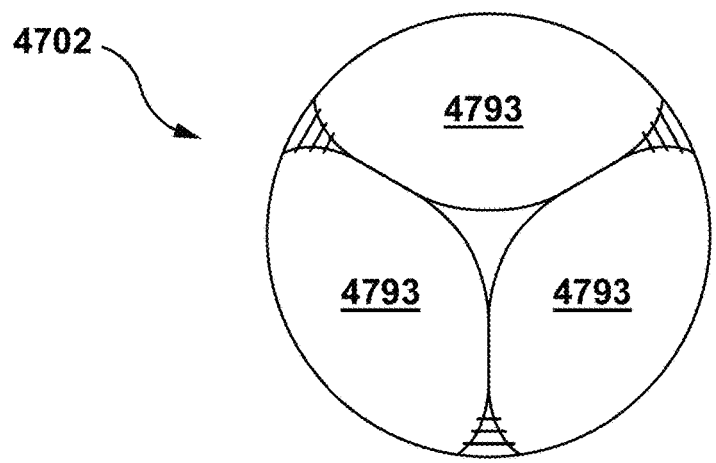
FIG. 40B depicts a top view of the prosthetic heart valve of FIG. 40A.

An exemplary implantable medical device including a valve disposed therein for use with the crimper 3100 is shown in FIGS. 40A and 40B. FIGS. 40A and 40B illustrate a prosthetic heart valve 4702 having a radially-expandable stent 4791 and a prosthetic valve 4793. The prosthetic heart valve 4702 is only exemplary, and it will be apparent to one of ordinary skill in the art that the crimper 3100 may be utilized any type of radially compressible implantable medical device. The prosthetic heart valve 4702 is more fully described in U.S. patent application Ser. No. 17/186,485, filed Feb. 26, 2021, which is herein incorporated by reference in its entirety. The stent 4791 of the prosthetic heart valve 4702 is a unitary frame or scaffold that supports the prosthetic valve 4793 including one or more valve leaflets within the interior of the stent 4791. The prosthetic valve 4793 is capable of blocking flow in one direction to regulate flow there-through via the valve leaflets that may form a bicuspid or tricuspid replacement valve. The stent 4791 includes an inflow portion 4795A, an outflow portion 4795C, and a transition portion 4795B bridging, connecting, or otherwise extending between the inflow portion 4795A and the outflow portion 4795C.

The inflow portion 4795A includes a plurality of crowns 4797A and a plurality of struts 4799A with each crown 4797A being formed between a pair of opposing struts 4799A. Each crown 4797A is a curved segment or bend extending between opposing struts 4799A. The inflow portion 4795A is tubular, with a plurality of side openings 4789A being defined by the plurality of crowns 4797A and the plurality of struts 4799A. In an embodiment, the plurality of side openings 4789A may be diamond-shaped.

The outflow portion 4795C includes a plurality of crowns 4797C and a plurality of struts 4799C with each crown 4797C being formed between a pair of opposing struts 4799C. Each crown 4797C is a curved segment or bend extending between opposing struts 4799C. The outflow portion 4795C can be configured in a shape that forms a central lumen or passageway, for example, a ring.

The three leaflets of the prosthetic valve 4793 are attached to the stent 4791 along a margin of attachment that follows struts 4799A and nodes 4785 of the inflow portion 4795A of the stent 4791. A node 4785 is defined as a region where two crowns of the plurality of crowns 4797A within the inflow portion 4795A connect or where two crowns of the plurality of crowns 4797C within the outflow portion 4795C connect. As shown on FIG. 40A, the prosthetic heart valve 4702 includes five levels of nodes, i.e., level $L_0$ of nodes 4785 at the inflow end of the prosthetic valve device 4702, level $L_1$ of nodes 4785 directly adjacent to level $L_0$, level $L_2$ of nodes 4785 directly adjacent to level $L_1$, level $L_3$ of nodes 4785 directly adjacent to level $L_2$, level $L_4$ of nodes 4785 directly adjacent to level $L_3$, and level $L_5$ of nodes 4785 at the outflow end of the prosthetic valve device 4702.

The transition portion 4795B bridges, connects, or otherwise extends between the inflow portion 4795A and the outflow portion 4795C. The transition portion 4795B includes a total of six axial frame members 4787, each axial frame member 4787 extending between a crown 4797C of the outflow portion 4795C and a crown 4797A of the inflow portion 4795A. The axial frame members 4787 are substantially parallel to the central longitudinal axis of the stent 4791. Three of the six axial frame members 4787 are commissure posts and aligned with and attached to a respective commissure of the three leaflets of the prosthetic valve 4793. Three of the axial frame members 4787 are axial struts and are disposed between adjacent commissure posts.

The stent 4791 includes a plurality of endmost outflow side openings or cells 4789B. The endmost outflow side openings 4789B of the outflow portion 4795C are relatively larger than the plurality of side openings 4789A of the inflow portion 4795A to improve access to the coronary arteries. More particularly, the endmost outflow side openings 4789B of the outflow portion 4795C are configured to be of sufficient size to be easily crossed with a coronary guide catheter into either the right coronary artery or the left main coronary artery once the prosthetic heart valve 4702 is deployed in situ.

Although described herein for use in the crimper 3100, it will be apparent to one of ordinary skill in the art that the non-planar surfaces of the crimper elements 3114, 3814, 4014, 4214, 4414 may be incorporated into the crimper elements of the crimpers 800, 1500, 1900, 2600 described herein to apply non-uniform radial compression to an implantable medical device.

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components associated with, for example, a medical device.

What is claimed is:

1. A clamshell crimper for altering an implantable medical device from an uncompressed state to a compressed state, the crimper comprising:
    a top shell comprising a top cam, a top crimper element housing, and a first plurality of crimper elements, the first plurality of crimper elements defining a top channel;
    a base shell comprising a base cam, a base crimper element housing, and a second plurality of crimper elements, the second plurality of crimper elements defining a bottom channel, wherein:
        the top shell and the base shell are coupled at a pivot connection,
        the top shell is configured to rotate about the pivot connection relative to the base shell from an open state to a closed state,
        when in the open state, the bottom channel is exposed for loading the implantable medical device, and
        when in the closed state, the top channel and the bottom channel define a crimper chamber;
    a handle configured to operate the clamshell crimper and coupled to at least the top cam of the top shell;
        when in the closed state, movement of the handle rotates the top cam and the base cam thereby displacing the first plurality of crimper elements and the second plurality of crimper elements, and
        the displacement of the first plurality of crimper elements and the second plurality of crimper elements decreases a volume of the crimper chamber to transition the implantable medical device from the uncompressed state to the compressed state.

2. The clamshell crimper of claim 1, wherein the handle comprises:
    a handle bar; and
    a handle base coupled to the handle bar and configured to couple to at least one of the top cam or the base cam.

3. The clamshell crimper of claim 1, further comprising one or more stops configured to limit the movement of the handle.

4. The clamshell crimper of claim 1, wherein the first plurality of crimper elements is movably coupled within the top crimper element housing and the base crimper element housing.

5. The clamshell crimper of claim 4, wherein one of the top crimper element housing or the base crimper element housing comprises:
    a side plate comprising an interior surface and an exterior surface, wherein:
        one or more crimper channels are formed within the interior surface of the side plate, and
        the one or more crimper channels are configured to allow the displacement of the first plurality of crimper elements or the second plurality of crimper elements.

6. The clamshell crimper of claim 1, wherein the top shell further comprises a first locking mechanism, wherein the first locking mechanism prevents movement of the handle to enable movement of the top shell from the closed state to the open state.

7. The clamshell crimper of claim 6, wherein at least one of the top shell or the base shell further comprises a second locking mechanism, wherein the second locking mechanism locks the top shell and the base shell into the closed state.

8. The clamshell crimper of claim 1, wherein a crimper element from the first plurality of crimper elements or the second plurality of crimper elements comprises:
   a crimper lobe, wherein a surface of the crimper lobe forms a portion of the crimper chamber,
   a crimper body coupled to the crimper lobe, and
   at least one pin coupled to the crimper body, wherein the at least one pin is configured to moveably couple the crimper element to one of the top cam or the base cam.

9. The clamshell crimper of claim 8, wherein the crimper lobe comprises a crimper space defined by one or more ramps, and
   wherein at least one of the one or more ramps contacts an adjacent crimper lobe from an adjacent crimper element from the first plurality of crimper elements or the second plurality of crimper elements.

10. The clamshell crimper of claim 9, wherein at least one of the top cam or the base cam comprises:
    at least one pin channel formed within a surface of the top cam or the base cam, wherein the pin channel is configured to receive the at least one pin of the crimper element.

11. The clamshell crimper of claim 10, wherein the at least one pin channel comprises a plurality of pin channels formed in a spiral pattern.

12. A clamshell crimper for altering an implantable medical device from an uncompressed state to a compressed state, the crimper comprising:
    a top iris shell comprising a first plurality of crimper elements that define a top iris channel;
    a base iris shell coupled to the top iris shell at a pivot connection, the base iris shell comprising a second plurality of crimper elements that define a base iris channel, wherein:
      the top iris shell is configured to rotate about the pivot connection relative to the base shell from an open state to a closed state,
      when in the open state, the base iris channel is exposed for loading the implantable medical device, and
      when in the closed state, the top iris channel and the base iris channel define a crimper chamber; and
    a handle configured to operate the clamshell crimper, wherein actuation of the handle decreases a volume of the crimper chamber to transition the implantable medical device from the uncompressed state to the compressed state.

13. The clamshell crimper of claim 12, wherein the first plurality of crimper elements is movably coupled within the top iris shell and the second plurality of crimper elements is movably coupled within the base iris shell.

14. The clamshell crimper of claim 12, further comprising one or more stops configured to limit movement of the handle.

15. The clamshell crimper of claim 12, wherein the top iris shell further comprises a first locking mechanism, wherein the first locking mechanism prevents movement of the handle to enable movement of the top iris shell from the closed state to the open state.

16. The clamshell crimper of claim 15, wherein at least one of the top iris shell or the base iris shell further comprises a second locking mechanism, wherein the second locking mechanism locks the top iris shell and the base iris shell into the closed state.

17. The clamshell crimper of claim 12, wherein a crimper element from the first plurality of crimper elements or the second plurality of crimper elements comprises:
    a crimper lobe, wherein a surface of the crimper lobe forms a portion of the crimper chamber,
    a crimper body coupled to the crimper lobe, and
    at least one pin coupled to the crimper body, wherein the at least one pin is configured to moveably couple the crimper element to one of at least one cam of the top iris shell or the base iris shell.

18. The clamshell crimper of claim 17, wherein the crimper lobe comprises a crimper space defined by one or more ramps, and
    wherein at least one of the one or more ramps contacts an adjacent crimper lobe from an adjacent crimper element from the first plurality of crimper elements or the second plurality of crimper elements.

19. The clamshell crimper of claim 17, wherein the at least one cam comprises:
    at least one pin channel formed within a surface of the at least one cam, wherein the at least one pin channel is configured to receive the at least one pin of the crimper element.

20. The clamshell crimper of claim 19, wherein the at least one pin channel comprises a plurality of pin channels formed in a spiral pattern.

* * * * *